(12) United States Patent
Vidlund et al.

(10) Patent No.: US 11,786,366 B2
(45) Date of Patent: Oct. 17, 2023

(54) DEVICES AND METHODS FOR ANCHORING TRANSCATHETER HEART VALVE

(71) Applicant: VDyne, Inc., Maple Grove, MN (US)

(72) Inventors: Robert Vidlund, Forest Lake, MN (US); Mark Christianson, Plymouth, MN (US); David Holtan, Eden Prairie, MN (US)

(73) Assignee: VDyne, Inc., Maple Grove, MN (US)

( * ) Notice: Subject to any disclaimer, the term of this patent is extended or adjusted under 35 U.S.C. 154(b) by 242 days.

(21) Appl. No.: 17/062,080

(22) Filed: Oct. 2, 2020

(65) Prior Publication Data

US 2021/0228349 A1 Jul. 29, 2021

Related U.S. Application Data

(63) Continuation of application No. PCT/US2019/028822, filed on Apr. 24, 2019.

(60) Provisional application No. 62/695,614, filed on Jul. 9, 2018, provisional application No. 62/694,444, filed on Jul. 6, 2018, provisional application No. 62/668,813, filed on May 8, 2018, provisional application No. 62/652,898, filed on Apr. 4, 2018.

(51) Int. Cl.
*A61F 2/24* (2006.01)

(52) U.S. Cl.
CPC .......... *A61F 2/2418* (2013.01); *A61F 2/2409* (2013.01); *A61F 2/2433* (2013.01); *A61F 2220/0016* (2013.01); *A61F 2220/0075* (2013.01)

(58) Field of Classification Search
CPC .................................................. A61F 2/2418
See application file for complete search history.

(56) References Cited

U.S. PATENT DOCUMENTS

| | | | |
|---|---|---|---|
| 3,744,060 A | 7/1973 | Bellhouse et al. |
| 4,079,468 A | 3/1978 | Liotta et al. |
| 5,397,351 A | 3/1995 | Pavcnik et al. |
| 5,509,428 A | 4/1996 | Dunlop |
| 5,554,185 A | 9/1996 | Block et al. |
| 6,006,134 A | 12/1999 | Hill et al. |
| 6,197,013 B1 | 3/2001 | Reed et al. |
| 6,290,719 B1 | 9/2001 | Garberoglio |
| 6,312,464 B1 | 11/2001 | Navia |
| 6,449,507 B1 | 9/2002 | Hill et al. |

(Continued)

FOREIGN PATENT DOCUMENTS

| AU | 2006203686 B2 | 11/2008 |
|---|---|---|
| AU | 2009219415 A1 | 9/2009 |

(Continued)

OTHER PUBLICATIONS

International Search Report and Written Opinion for International Application No. PCT/US2019/028822, dated Oct. 24, 2019, 14 pages.

(Continued)

*Primary Examiner* — Suba Ganesan
(74) *Attorney, Agent, or Firm* — COOLEY LLP

(57) ABSTRACT

The invention relates to methods and devices for a transcatheter heart valve replacement (A61F2/2412), and in particular a device and method for percutaneously anchoring a transcatheter heart valve.

4 Claims, 60 Drawing Sheets

(56) References Cited

U.S. PATENT DOCUMENTS

| | | |
|---|---|---|
| 6,458,153 B1 | 10/2002 | Bailey et al. |
| 6,532,388 B1 | 3/2003 | Hill et al. |
| 6,582,467 B1 | 6/2003 | Teitelbaum et al. |
| 6,628,987 B1 | 9/2003 | Hill et al. |
| 6,669,724 B2 | 12/2003 | Park et al. |
| 6,718,208 B2 | 4/2004 | Hill et al. |
| 6,769,434 B2 | 8/2004 | Liddicoat et al. |
| 6,890,330 B2 | 5/2005 | Streeter et al. |
| 6,896,690 B1 | 5/2005 | Lambrecht et al. |
| 6,904,318 B2 | 6/2005 | Hill et al. |
| 6,929,653 B2 | 8/2005 | Streeter |
| 7,074,189 B1 | 7/2006 | Montegrande |
| 7,125,418 B2 | 10/2006 | Duran et al. |
| 7,175,660 B2 | 2/2007 | Cartledge et al. |
| 7,201,761 B2 | 4/2007 | Woolfson et al. |
| 7,225,019 B2 | 5/2007 | Jahns et al. |
| 7,269,457 B2 | 9/2007 | Shafer et al. |
| 7,331,991 B2 | 2/2008 | Kheradvar et al. |
| 7,361,189 B2 | 4/2008 | Case et al. |
| 7,374,571 B2 | 5/2008 | Pease et al. |
| 7,442,204 B2 | 10/2008 | Schwammenthal et al. |
| 7,449,027 B2 | 11/2008 | Hunt et al. |
| 7,621,948 B2 | 11/2009 | Herrmann et al. |
| 7,648,527 B2 | 1/2010 | Agnew |
| 7,717,952 B2 | 5/2010 | Case et al. |
| 7,749,245 B2 | 7/2010 | Cohn et al. |
| 7,753,949 B2 | 7/2010 | Lamphere et al. |
| 7,811,316 B2 | 10/2010 | Kalmann et al. |
| 7,828,840 B2 | 11/2010 | Biggs et al. |
| 7,846,199 B2 | 12/2010 | Paul, Jr. et al. |
| 8,303,648 B2 | 11/2012 | Grewe et al. |
| 8,366,768 B2 | 2/2013 | Zhang |
| 8,491,650 B2 | 7/2013 | Wiemeyer et al. |
| 8,568,474 B2 | 10/2013 | Yeung et al. |
| 8,628,571 B1 | 1/2014 | Hacohen et al. |
| 8,641,752 B1 | 2/2014 | Holm et al. |
| 8,696,743 B2 | 4/2014 | Holecek et al. |
| 8,728,153 B2 | 5/2014 | Bishop et al. |
| 8,758,395 B2 | 6/2014 | Kleshinski et al. |
| 8,846,390 B2 | 9/2014 | Dove et al. |
| 8,876,892 B2 | 11/2014 | Tran et al. |
| 8,900,295 B2 | 12/2014 | Migliazza et al. |
| 8,915,958 B2 | 12/2014 | Braido |
| 8,926,690 B2 | 1/2015 | Kovalsky |
| 8,926,692 B2 | 1/2015 | Dwork |
| 8,926,694 B2 | 1/2015 | Costello |
| 8,940,044 B2 | 1/2015 | Hammer et al. |
| 8,956,404 B2 | 2/2015 | Bortlein et al. |
| 8,986,370 B2 | 3/2015 | Annest et al. |
| 9,011,524 B2 | 4/2015 | Eberhardt |
| 9,017,399 B2 | 4/2015 | Gross et al. |
| 9,050,188 B2 | 6/2015 | Schweich, Jr. et al. |
| 9,072,604 B1 | 7/2015 | Melnick et al. |
| 9,119,714 B2 | 9/2015 | Shandas et al. |
| 9,216,076 B2 | 12/2015 | Mitra et al. |
| 9,232,995 B2 | 1/2016 | Kovalsky et al. |
| 9,241,792 B2 | 1/2016 | Benichou et al. |
| 9,248,016 B2 | 2/2016 | Oba et al. |
| 9,259,215 B2 | 2/2016 | Chou et al. |
| 9,277,990 B2 | 3/2016 | Klima et al. |
| 9,289,282 B2 | 3/2016 | Olson et al. |
| 9,289,296 B2 | 3/2016 | Braido et al. |
| 9,295,547 B2 | 3/2016 | Costello et al. |
| 9,301,839 B2 | 4/2016 | Stante et al. |
| 9,308,086 B2 | 4/2016 | Ho |
| 9,339,367 B2 | 5/2016 | Carpenter et al. |
| 9,370,418 B2 | 6/2016 | Pintor et al. |
| 9,381,083 B2 | 7/2016 | Costello |
| 9,387,075 B2 | 7/2016 | Bortlein et al. |
| 9,393,111 B2 | 7/2016 | Ma et al. |
| 9,414,915 B2 | 8/2016 | Lombardi et al. |
| 9,433,500 B2 | 9/2016 | Chau et al. |
| 9,440,054 B2 | 9/2016 | Bishop et al. |
| 9,456,899 B2 | 10/2016 | Yeung et al. |
| 9,468,525 B2 | 10/2016 | Kovalsky et al. |
| 9,474,604 B2 | 10/2016 | Centola et al. |
| 9,486,306 B2 | 11/2016 | Tegels et al. |
| 9,510,941 B2 | 12/2016 | Bishop et al. |
| 9,554,902 B2 | 1/2017 | Braido et al. |
| 9,579,196 B2 | 2/2017 | Morriss et al. |
| 9,579,200 B2 | 2/2017 | Lederman et al. |
| 9,597,181 B2 | 3/2017 | Christianson et al. |
| 9,610,159 B2 | 4/2017 | Christianson et al. |
| 9,615,925 B2 | 4/2017 | Subramanian et al. |
| 9,629,719 B2 | 4/2017 | Rothstein |
| 9,636,222 B2 | 5/2017 | Oslund |
| 9,649,191 B2 | 5/2017 | Savage et al. |
| 9,662,202 B2 | 5/2017 | Quill et al. |
| 9,662,203 B2 | 5/2017 | Sheahan et al. |
| 9,662,209 B2 | 5/2017 | Gross et al. |
| 9,675,454 B2 | 6/2017 | Vidlund et al. |
| 9,675,485 B2 | 6/2017 | Essinger et al. |
| 9,687,343 B2 | 6/2017 | Bortlein et al. |
| 9,707,076 B2 | 7/2017 | Stack et al. |
| 9,713,530 B2 | 7/2017 | Cabiri et al. |
| 9,750,607 B2 | 9/2017 | Ganesan et al. |
| 9,763,778 B2 | 9/2017 | Eidenschink et al. |
| 9,763,779 B2 | 9/2017 | Bortlein et al. |
| 9,788,946 B2 | 10/2017 | Bobo, Jr. et al. |
| 9,839,511 B2 | 12/2017 | Ma et al. |
| 9,849,011 B2 | 12/2017 | Zimmerman et al. |
| 9,855,384 B2 | 1/2018 | Cohen et al. |
| 9,861,464 B2 | 1/2018 | Azimpour et al. |
| 9,895,219 B2 | 2/2018 | Costello et al. |
| 9,901,330 B2 | 2/2018 | Akpinar |
| 9,918,838 B2 | 3/2018 | Ring |
| 9,943,409 B2 | 4/2018 | Kim et al. |
| 9,949,825 B2 | 4/2018 | Braido et al. |
| 9,968,444 B2 | 5/2018 | Millwee et al. |
| 9,968,445 B2 | 5/2018 | Kheradvar |
| 9,980,815 B2 | 5/2018 | Nitzan et al. |
| 9,987,121 B2 | 6/2018 | Blanzy |
| 10,010,411 B2 | 7/2018 | Peter |
| 10,010,412 B2 | 7/2018 | Taft et al. |
| 10,022,054 B2 | 7/2018 | Najafi et al. |
| 10,022,222 B2 | 7/2018 | Groothuis et al. |
| 10,022,223 B2 | 7/2018 | Bruchman |
| 10,028,821 B2 | 7/2018 | Centola et al. |
| 10,028,831 B2 | 7/2018 | Morin et al. |
| 10,034,667 B2 | 7/2018 | Morris et al. |
| 10,034,747 B2 | 7/2018 | Harewood |
| 10,039,638 B2 | 8/2018 | Bruchman et al. |
| 10,058,315 B2 | 8/2018 | Rafiee et al. |
| 10,058,411 B2 | 8/2018 | Fifer et al. |
| 10,058,421 B2 | 8/2018 | Eberhardt et al. |
| 10,058,426 B2 | 8/2018 | Barbarino |
| 10,064,405 B2 | 9/2018 | Dale et al. |
| 10,080,653 B2 | 9/2018 | Conklin et al. |
| 10,085,835 B2 | 10/2018 | Thambar et al. |
| 10,105,224 B2 | 10/2018 | Buchbinder et al. |
| 10,117,741 B2 | 11/2018 | Schweich, Jr. et al. |
| 10,123,874 B2 | 11/2018 | Khairkhahan et al. |
| 10,130,331 B2 | 11/2018 | Stigall et al. |
| 10,130,467 B2 | 11/2018 | Braido et al. |
| 10,149,685 B2 | 12/2018 | Kizuka |
| 10,154,905 B2 | 12/2018 | Duffy |
| 10,179,043 B2 | 1/2019 | Cohen-Tzemach et al. |
| 10,182,908 B2 | 1/2019 | Tubishevitz et al. |
| 10,182,911 B2 | 1/2019 | Hillukka |
| 10,206,775 B2 | 2/2019 | Kovalsky et al. |
| 10,219,895 B2 | 3/2019 | Wagner et al. |
| 10,219,896 B2 | 3/2019 | Sandstrom et al. |
| 10,220,192 B2 | 3/2019 | Drasler et al. |
| 10,226,178 B2 | 3/2019 | Cohen et al. |
| 10,226,335 B2 | 3/2019 | Cartledge et al. |
| 10,245,142 B2 | 4/2019 | Bonhoeffer |
| 10,258,467 B2 | 4/2019 | Hou et al. |
| 10,265,173 B2 | 4/2019 | Griffin et al. |
| 10,321,987 B2 | 6/2019 | Wang et al. |
| 10,321,995 B1 | 6/2019 | Christianson et al. |
| 10,327,895 B2 | 6/2019 | Lozonschi et al. |
| 10,327,899 B2 | 6/2019 | Sandstrom et al. |
| 10,329,066 B2 | 6/2019 | Kruetzfeldt et al. |
| 10,350,047 B2 | 7/2019 | Rajpara et al. |

(56) References Cited

U.S. PATENT DOCUMENTS

| | | |
|---|---|---|
| 10,357,361 B2 | 7/2019 | Rafi et al. |
| 10,368,989 B2 | 8/2019 | Duffy et al. |
| 10,398,550 B2 | 9/2019 | Chalekian et al. |
| 10,426,611 B2 | 10/2019 | Hariton et al. |
| 10,433,957 B2 | 10/2019 | Khouengboua et al. |
| 10,433,960 B1 | 10/2019 | Sutherland et al. |
| 10,463,489 B2 | 11/2019 | Christianson et al. |
| 10,485,976 B2 | 11/2019 | Streeter et al. |
| 10,595,994 B1 | 3/2020 | Christianson et al. |
| 10,631,983 B1 | 4/2020 | Christianson et al. |
| 10,653,522 B1 | 5/2020 | Vidlund et al. |
| 10,758,346 B1 | 9/2020 | Christianson et al. |
| 10,761,511 B2 | 9/2020 | Chen et al. |
| 10,779,937 B2 | 9/2020 | Vidlund et al. |
| 11,071,627 B2 | 7/2021 | Saikrishnan et al. |
| 11,076,956 B2 | 8/2021 | Christianson et al. |
| 11,109,969 B2 | 9/2021 | Vidlund et al. |
| 11,166,814 B2 | 11/2021 | Vidlund, I et al. |
| 11,173,027 B2 | 11/2021 | Christianson et al. |
| 11,179,239 B2 | 11/2021 | Vidlund et al. |
| 11,185,409 B2 | 11/2021 | Christianson et al. |
| 11,202,706 B2 | 12/2021 | Christianson et al. |
| 11,234,813 B2 | 2/2022 | Perrin |
| 11,253,359 B2 | 2/2022 | Vidlund et al. |
| 11,273,032 B2 | 3/2022 | Christianson et al. |
| 11,273,033 B2 | 3/2022 | Christianson et al. |
| 11,278,437 B2 | 3/2022 | Christianson et al. |
| 11,298,227 B2 | 4/2022 | Vidlund et al. |
| 11,331,186 B2 | 5/2022 | Christianson et al. |
| 11,337,807 B2 | 5/2022 | Christianson et al. |
| 11,344,412 B2 | 5/2022 | Vidlund et al. |
| 11,344,413 B2 | 5/2022 | Christianson et al. |
| 2003/0040772 A1 | 2/2003 | Hyodoh et al. |
| 2003/0040808 A1 | 2/2003 | Stack et al. |
| 2003/0153901 A1 | 8/2003 | Herweck et al. |
| 2003/0166990 A1 | 9/2003 | Trauthen et al. |
| 2003/0171801 A1 | 9/2003 | Bates |
| 2004/0049207 A1 | 3/2004 | Goldfarb et al. |
| 2004/0088047 A1 | 5/2004 | Spence et al. |
| 2004/0093060 A1 | 5/2004 | Seguin et al. |
| 2004/0116996 A1 | 6/2004 | Freitag |
| 2004/0117009 A1 | 6/2004 | Cali et al. |
| 2004/0199209 A1 | 10/2004 | Hill et al. |
| 2004/0225352 A1 | 11/2004 | Osborne et al. |
| 2005/0010246 A1 | 1/2005 | Streeter et al. |
| 2005/0075659 A1 | 4/2005 | Realyvasquez et al. |
| 2005/0075725 A1 | 4/2005 | Rowe |
| 2005/0107811 A1 | 5/2005 | Starksen et al. |
| 2005/0137686 A1 | 6/2005 | Salahieh et al. |
| 2005/0228472 A1 | 10/2005 | Case et al. |
| 2005/0228495 A1 | 10/2005 | Macoviak |
| 2006/0015167 A1 | 1/2006 | Armstrong et al. |
| 2006/0190075 A1 | 8/2006 | Jordan et al. |
| 2006/0195180 A1 | 8/2006 | Kheradvar et al. |
| 2006/0195183 A1 * | 8/2006 | Navia .................. A61F 2/2418 623/2.11 |
| 2006/0229708 A1 | 10/2006 | Powell et al. |
| 2006/0241745 A1 | 10/2006 | Solem |
| 2006/0271098 A1 | 11/2006 | Peacock, III |
| 2006/0276887 A1 | 12/2006 | Brady et al. |
| 2007/0016286 A1 | 1/2007 | Herrmann et al. |
| 2007/0027535 A1 | 2/2007 | Purdy, Jr. et al. |
| 2007/0032850 A1 | 2/2007 | Ruiz et al. |
| 2007/0038295 A1 | 2/2007 | Case et al. |
| 2007/0100427 A1 | 5/2007 | Perouse |
| 2007/0162102 A1 | 7/2007 | Ryan et al. |
| 2007/0208417 A1 | 9/2007 | Agnew |
| 2007/0213805 A1 | 9/2007 | Schaeffer et al. |
| 2007/0233176 A1 | 10/2007 | Gilson et al. |
| 2007/0233228 A1 | 10/2007 | Eberhardt et al. |
| 2007/0239271 A1 | 10/2007 | Nguyen |
| 2007/0288087 A1 | 12/2007 | Fearnot et al. |
| 2008/0004686 A1 | 1/2008 | Hunt et al. |
| 2008/0020013 A1 | 1/2008 | Reyes et al. |
| 2008/0065204 A1 | 3/2008 | Macoviak et al. |
| 2008/0071287 A1 | 3/2008 | Goto |
| 2008/0132999 A1 | 6/2008 | Mericle et al. |
| 2008/0140181 A1 | 6/2008 | Reynolds et al. |
| 2008/0154355 A1 | 6/2008 | Benichou et al. |
| 2008/0183279 A1 | 7/2008 | Bailey et al. |
| 2008/0200977 A1 | 8/2008 | Paul et al. |
| 2008/0200980 A1 | 8/2008 | Robin et al. |
| 2008/0208332 A1 | 8/2008 | Lamphere et al. |
| 2008/0221672 A1 | 9/2008 | Lamphere et al. |
| 2008/0262592 A1 | 10/2008 | Jordan et al. |
| 2008/0262609 A1 | 10/2008 | Gross et al. |
| 2008/0275550 A1 | 11/2008 | Kheradvar et al. |
| 2009/0005863 A1 | 1/2009 | Goetz et al. |
| 2009/0054976 A1 | 2/2009 | Tuval et al. |
| 2009/0094189 A1 | 4/2009 | Stephens |
| 2009/0192586 A1 | 7/2009 | Tabor et al. |
| 2009/0192601 A1 | 7/2009 | Rafiee et al. |
| 2009/0254174 A1 | 10/2009 | Case et al. |
| 2009/0264991 A1 | 10/2009 | Paul, Jr. et al. |
| 2009/0287290 A1 | 11/2009 | Macaulay et al. |
| 2010/0049294 A1 | 2/2010 | Zukowski et al. |
| 2010/0049313 A1 | 2/2010 | Alon et al. |
| 2010/0087918 A1 | 4/2010 | Vesely et al. |
| 2010/0121434 A1 | 5/2010 | Paul et al. |
| 2010/0160773 A1 | 6/2010 | Cohen et al. |
| 2010/0161043 A1 | 6/2010 | Maisano et al. |
| 2010/0168844 A1 | 7/2010 | Toomes et al. |
| 2010/0174363 A1 | 7/2010 | Castro |
| 2010/0179583 A1 | 7/2010 | Carpenter et al. |
| 2010/0179584 A1 | 7/2010 | Carpenter et al. |
| 2010/0179647 A1 | 7/2010 | Carpenter et al. |
| 2010/0280591 A1 | 11/2010 | Shin et al. |
| 2010/0298929 A1 | 11/2010 | Thornton et al. |
| 2010/0305685 A1 | 12/2010 | Millwee et al. |
| 2011/0004237 A1 | 1/2011 | Schneider et al. |
| 2011/0029071 A1 | 2/2011 | Zlotnick et al. |
| 2011/0029072 A1 | 2/2011 | Gabbay |
| 2011/0066233 A1 | 3/2011 | Thornton et al. |
| 2011/0071613 A1 | 3/2011 | Wood et al. |
| 2011/0098804 A1 | 4/2011 | Yeung et al. |
| 2011/0125145 A1 | 5/2011 | Mody et al. |
| 2011/0137397 A1 | 6/2011 | Chau et al. |
| 2011/0160836 A1 | 6/2011 | Behan |
| 2011/0172764 A1 | 7/2011 | Badhwar |
| 2011/0172784 A1 | 7/2011 | Richter et al. |
| 2011/0224785 A1 | 9/2011 | Hacohen et al. |
| 2011/0245911 A1 | 10/2011 | Quill et al. |
| 2011/0245917 A1 | 10/2011 | Savage et al. |
| 2011/0251675 A1 | 10/2011 | Dwork |
| 2011/0257721 A1 | 10/2011 | Tabor |
| 2011/0264191 A1 | 10/2011 | Rothstein |
| 2012/0022605 A1 | 1/2012 | Jahns et al. |
| 2012/0022633 A1 | 1/2012 | Olson et al. |
| 2012/0022639 A1 | 1/2012 | Hacohen et al. |
| 2012/0022640 A1 | 1/2012 | Gross et al. |
| 2012/0022644 A1 | 1/2012 | Reich et al. |
| 2012/0035701 A1 | 2/2012 | To |
| 2012/0065723 A1 | 3/2012 | Drasler et al. |
| 2012/0083874 A1 | 4/2012 | Dale et al. |
| 2012/0123531 A1 | 5/2012 | Tsukashima et al. |
| 2012/0137521 A1 | 6/2012 | Millwee et al. |
| 2012/0165928 A1 | 6/2012 | Nitzan et al. |
| 2012/0172981 A1 | 7/2012 | Dumontelle |
| 2012/0203336 A1 | 8/2012 | Annest |
| 2012/0209375 A1 | 8/2012 | Madrid et al. |
| 2012/0232574 A1 | 9/2012 | Kim et al. |
| 2012/0277853 A1 | 11/2012 | Rothstein |
| 2012/0310327 A1 | 12/2012 | McHugo |
| 2012/0310328 A1 | 12/2012 | Olson et al. |
| 2013/0035759 A1 | 2/2013 | Gross et al. |
| 2013/0055941 A1 | 3/2013 | Holecek et al. |
| 2013/0131714 A1 | 5/2013 | Wang et al. |
| 2013/0131792 A1 | 5/2013 | Miller et al. |
| 2013/0166017 A1 | 6/2013 | Cartledge et al. |
| 2013/0178931 A1 | 7/2013 | Fargahi |
| 2013/0184742 A1 | 7/2013 | Ganesan et al. |
| 2013/0190857 A1 | 7/2013 | Mitra et al. |
| 2013/0190861 A1 | 7/2013 | Chau et al. |
| 2013/0197621 A1 | 8/2013 | Ryan et al. |

(56) References Cited

U.S. PATENT DOCUMENTS

| | | |
|---|---|---|
| 2013/0226289 A1 | 8/2013 | Shaolian et al. |
| 2013/0238010 A1 | 9/2013 | Johnson et al. |
| 2013/0238089 A1 | 9/2013 | Lichtenstein et al. |
| 2013/0253570 A1 | 9/2013 | Bates |
| 2013/0274618 A1 | 10/2013 | Hou et al. |
| 2013/0274855 A1 | 10/2013 | Stante et al. |
| 2013/0282110 A1 | 10/2013 | Schweich, Jr. et al. |
| 2013/0297010 A1 | 11/2013 | Bishop et al. |
| 2013/0304197 A1 | 11/2013 | Buchbinder et al. |
| 2013/0304200 A1 | 11/2013 | McLean et al. |
| 2013/0331929 A1 | 12/2013 | Mitra et al. |
| 2013/0338764 A1 | 12/2013 | Thornton et al. |
| 2014/0000112 A1 | 1/2014 | Braido et al. |
| 2014/0005540 A1 | 1/2014 | Merhi |
| 2014/0005768 A1 | 1/2014 | Thomas et al. |
| 2014/0005778 A1 | 1/2014 | Buchbinder et al. |
| 2014/0012372 A1 | 1/2014 | Chau et al. |
| 2014/0018915 A1 | 1/2014 | Baidillah et al. |
| 2014/0039511 A1 | 2/2014 | Morris et al. |
| 2014/0039611 A1 | 2/2014 | Lane et al. |
| 2014/0052237 A1 | 2/2014 | Lane et al. |
| 2014/0081383 A1 | 3/2014 | Eberhardt et al. |
| 2014/0088680 A1 | 3/2014 | Costello et al. |
| 2014/0107758 A1 | 4/2014 | Glazier |
| 2014/0110279 A1 | 4/2014 | Kruetzfeldt et al. |
| 2014/0114403 A1 | 4/2014 | Dale et al. |
| 2014/0121763 A1 | 5/2014 | Duffy et al. |
| 2014/0135895 A1 | 5/2014 | Andress et al. |
| 2014/0135908 A1 | 5/2014 | Glozman et al. |
| 2014/0142695 A1 | 5/2014 | Gross et al. |
| 2014/0172070 A1 | 6/2014 | Seguin |
| 2014/0180069 A1 | 6/2014 | Millett |
| 2014/0180070 A1 | 6/2014 | Millett et al. |
| 2014/0194704 A1 | 7/2014 | Millett et al. |
| 2014/0194983 A1 | 7/2014 | Kovalsky et al. |
| 2014/0207231 A1 | 7/2014 | Hacohen et al. |
| 2014/0214069 A1 | 7/2014 | Franklin |
| 2014/0214159 A1 | 7/2014 | Vidlund et al. |
| 2014/0222136 A1 | 8/2014 | Geist et al. |
| 2014/0222137 A1 | 8/2014 | Miller et al. |
| 2014/0222142 A1 | 8/2014 | Kovalsky et al. |
| 2014/0249566 A1 | 9/2014 | Quinn et al. |
| 2014/0257466 A1 | 9/2014 | Board et al. |
| 2014/0257467 A1 | 9/2014 | Lane et al. |
| 2014/0276616 A1 | 9/2014 | Smith et al. |
| 2014/0276971 A1 | 9/2014 | Kovach |
| 2014/0277342 A1 | 9/2014 | Roeder et al. |
| 2014/0277388 A1 | 9/2014 | Skemp |
| 2014/0277408 A1 | 9/2014 | Folan |
| 2014/0277563 A1 | 9/2014 | White |
| 2014/0288480 A1 | 9/2014 | Zimmerman et al. |
| 2014/0296962 A1 | 10/2014 | Cartledge et al. |
| 2014/0296969 A1 | 10/2014 | Tegels et al. |
| 2014/0296975 A1 | 10/2014 | Tegels et al. |
| 2014/0303718 A1 | 10/2014 | Tegels et al. |
| 2014/0303724 A1 | 10/2014 | Bluestein et al. |
| 2014/0309732 A1 | 10/2014 | Solem |
| 2014/0324161 A1 | 10/2014 | Tegels et al. |
| 2014/0350662 A1 | 11/2014 | Vaturi |
| 2014/0358224 A1 | 12/2014 | Tegels et al. |
| 2014/0371789 A1 | 12/2014 | Hariton et al. |
| 2014/0379076 A1 | 12/2014 | Vidlund et al. |
| 2015/0005808 A1 | 1/2015 | Chouinard et al. |
| 2015/0005874 A1 | 1/2015 | Vidlund et al. |
| 2015/0039081 A1 | 2/2015 | Costello |
| 2015/0045880 A1 | 2/2015 | Hacohen |
| 2015/0051687 A1 | 2/2015 | Dickerhoff et al. |
| 2015/0094802 A1 | 4/2015 | Buchbinder et al. |
| 2015/0112188 A1 | 4/2015 | Stigall et al. |
| 2015/0119982 A1 | 4/2015 | Quill et al. |
| 2015/0127093 A1 | 5/2015 | Hosmer et al. |
| 2015/0142103 A1 | 5/2015 | Vidlund |
| 2015/0157457 A1 | 6/2015 | Hacohen |
| 2015/0173898 A1 | 6/2015 | Drasler et al. |
| 2015/0196390 A1 | 7/2015 | Ma et al. |
| 2015/0196391 A1 | 7/2015 | Dwork |
| 2015/0202044 A1 | 7/2015 | Chau et al. |
| 2015/0216661 A1* | 8/2015 | Hacohen ............... A61F 2/2409 623/2.37 |
| 2015/0230919 A1 | 8/2015 | Chau et al. |
| 2015/0245934 A1 | 9/2015 | Lombardi et al. |
| 2015/0257878 A1 | 9/2015 | Lane et al. |
| 2015/0257880 A1 | 9/2015 | Bortlein et al. |
| 2015/0257882 A1 | 9/2015 | Bortlein et al. |
| 2015/0265400 A1 | 9/2015 | Eidenschink et al. |
| 2015/0272731 A1 | 10/2015 | Racchini et al. |
| 2015/0282922 A1 | 10/2015 | Hingston et al. |
| 2015/0282931 A1 | 10/2015 | Brunnett et al. |
| 2015/0289971 A1 | 10/2015 | Costello et al. |
| 2015/0289975 A1 | 10/2015 | Costello |
| 2015/0297241 A1 | 10/2015 | Yodfat et al. |
| 2015/0305867 A1 | 10/2015 | Liu et al. |
| 2015/0313701 A1 | 11/2015 | Krahbichler |
| 2015/0335424 A1 | 11/2015 | McLean et al. |
| 2015/0342717 A1 | 12/2015 | O'Donnell et al. |
| 2015/0351904 A1 | 12/2015 | Cooper et al. |
| 2015/0351906 A1 | 12/2015 | Hammer et al. |
| 2015/0351910 A1 | 12/2015 | Gilmore et al. |
| 2015/0359629 A1 | 12/2015 | Ganesan et al. |
| 2016/0008130 A1 | 1/2016 | Hasin |
| 2016/0008131 A1 | 1/2016 | Christianson et al. |
| 2016/0022417 A1 | 1/2016 | Karapetian et al. |
| 2016/0030165 A1 | 2/2016 | Mitra et al. |
| 2016/0030167 A1 | 2/2016 | Delaloye et al. |
| 2016/0038280 A1 | 2/2016 | Morriss et al. |
| 2016/0038283 A1 | 2/2016 | Divekar et al. |
| 2016/0045165 A1 | 2/2016 | Braido et al. |
| 2016/0045306 A1 | 2/2016 | Agrawal et al. |
| 2016/0045309 A1 | 2/2016 | Valdez et al. |
| 2016/0067031 A1 | 3/2016 | Kassab et al. |
| 2016/0081799 A1 | 3/2016 | Leo et al. |
| 2016/0095703 A1 | 4/2016 | Thomas et al. |
| 2016/0095704 A1 | 4/2016 | Whitman |
| 2016/0113764 A1 | 4/2016 | Sheahan et al. |
| 2016/0113766 A1 | 4/2016 | Ganesan et al. |
| 2016/0113768 A1 | 4/2016 | Ganesan et al. |
| 2016/0143721 A1 | 5/2016 | Rosenbluth et al. |
| 2016/0143730 A1 | 5/2016 | Kheradvar |
| 2016/0143735 A1 | 5/2016 | Subramanian et al. |
| 2016/0143739 A1 | 5/2016 | Horgan et al. |
| 2016/0158004 A1 | 6/2016 | Kumar et al. |
| 2016/0158007 A1 | 6/2016 | Centola et al. |
| 2016/0158008 A1 | 6/2016 | Miller et al. |
| 2016/0166382 A1 | 6/2016 | Nguyen |
| 2016/0184488 A1 | 6/2016 | Toyoda et al. |
| 2016/0194425 A1 | 7/2016 | Mitra et al. |
| 2016/0213470 A1 | 7/2016 | Ahlberg et al. |
| 2016/0213473 A1 | 7/2016 | Hacohen et al. |
| 2016/0220367 A1 | 8/2016 | Barrett |
| 2016/0220372 A1 | 8/2016 | Medema et al. |
| 2016/0220734 A1 | 8/2016 | Dyamenahalli et al. |
| 2016/0228250 A1 | 8/2016 | Casley et al. |
| 2016/0235530 A1 | 8/2016 | Thomas et al. |
| 2016/0256269 A1 | 9/2016 | Cahalane et al. |
| 2016/0256270 A1 | 9/2016 | Folan et al. |
| 2016/0270911 A1 | 9/2016 | Ganesan et al. |
| 2016/0303804 A1 | 10/2016 | Grbic et al. |
| 2016/0310274 A1 | 10/2016 | Gross et al. |
| 2016/0317301 A1 | 11/2016 | Quadri et al. |
| 2016/0324633 A1 | 11/2016 | Gross et al. |
| 2016/0324639 A1 | 11/2016 | Nguyen et al. |
| 2016/0331534 A1 | 11/2016 | Buchbinder et al. |
| 2016/0354201 A1 | 12/2016 | Keogh |
| 2016/0361169 A1 | 12/2016 | Gross et al. |
| 2016/0361184 A1 | 12/2016 | Tabor et al. |
| 2016/0367360 A1 | 12/2016 | Cartledge et al. |
| 2016/0367364 A1 | 12/2016 | Torrianni et al. |
| 2017/0000603 A1 | 1/2017 | Conklin et al. |
| 2017/0000604 A1 | 1/2017 | Conklin et al. |
| 2017/0020670 A1 | 1/2017 | Murray et al. |
| 2017/0035562 A1 | 2/2017 | Quadri et al. |
| 2017/0035568 A1 | 2/2017 | Lombardi et al. |
| 2017/0056166 A1 | 3/2017 | Ratz et al. |
| 2017/0056171 A1 | 3/2017 | Cooper et al. |

(56) References Cited

U.S. PATENT DOCUMENTS

| | | |
|---|---|---|
| 2017/0071733 A1 | 3/2017 | Ghione et al. |
| 2017/0071736 A1 | 3/2017 | Zhu et al. |
| 2017/0076014 A1 | 3/2017 | Bressloff |
| 2017/0079786 A1 | 3/2017 | Li et al. |
| 2017/0079795 A1 | 3/2017 | Morrissey |
| 2017/0100236 A1 | 4/2017 | Robertson et al. |
| 2017/0100246 A1 | 4/2017 | Rust et al. |
| 2017/0112620 A1 | 4/2017 | Curley et al. |
| 2017/0128208 A1 | 5/2017 | Christianson et al. |
| 2017/0143488 A1 | 5/2017 | Lashinski |
| 2017/0143489 A1 | 5/2017 | Lashinski |
| 2017/0165065 A1 | 6/2017 | Rothstein et al. |
| 2017/0172737 A1 | 6/2017 | Kuetting et al. |
| 2017/0172738 A1 | 6/2017 | Kassas |
| 2017/0181851 A1 | 6/2017 | Annest |
| 2017/0181852 A1 | 6/2017 | Kassas |
| 2017/0189177 A1 | 7/2017 | Schweich, Jr. et al. |
| 2017/0196690 A1 | 7/2017 | Racchini et al. |
| 2017/0209266 A1 | 7/2017 | Lane et al. |
| 2017/0209268 A1 | 7/2017 | Cunningham et al. |
| 2017/0216023 A1 | 8/2017 | Lane et al. |
| 2017/0216026 A1 | 8/2017 | Quill et al. |
| 2017/0216030 A1 | 8/2017 | Jonsson |
| 2017/0224480 A1 | 8/2017 | Garde et al. |
| 2017/0224486 A1 | 8/2017 | Delaloye et al. |
| 2017/0231755 A1 | 8/2017 | Gloss et al. |
| 2017/0231760 A1 | 8/2017 | Lane et al. |
| 2017/0239047 A1 | 8/2017 | Quill et al. |
| 2017/0245993 A1 | 8/2017 | Gross et al. |
| 2017/0245994 A1 | 8/2017 | Khairkhahan et al. |
| 2017/0252163 A1 | 9/2017 | Kheradvar |
| 2017/0258584 A1 | 9/2017 | Chang et al. |
| 2017/0258585 A1 | 9/2017 | Marquez et al. |
| 2017/0273784 A1 | 9/2017 | Racchini et al. |
| 2017/0281337 A1 | 10/2017 | Campbell |
| 2017/0281341 A1 | 10/2017 | Lim et al. |
| 2017/0296340 A1 | 10/2017 | Gross et al. |
| 2017/0319333 A1* | 11/2017 | Tegels ............... A61B 17/0401 |
| 2017/0325943 A1 | 11/2017 | Robin et al. |
| 2017/0325948 A1 | 11/2017 | Wallace et al. |
| 2017/0325976 A1 | 11/2017 | Nguyen et al. |
| 2017/0333184 A1 | 11/2017 | Ryan |
| 2017/0333240 A1 | 11/2017 | Stangenes et al. |
| 2017/0348099 A1 | 12/2017 | Mendelson et al. |
| 2017/0348100 A1 | 12/2017 | Lane et al. |
| 2017/0360557 A1 | 12/2017 | Kheradvar et al. |
| 2017/0360558 A1 | 12/2017 | Ma |
| 2017/0360561 A1 | 12/2017 | Bell et al. |
| 2018/0014932 A1 | 1/2018 | Hammer et al. |
| 2018/0021130 A1 | 1/2018 | Danino |
| 2018/0035971 A1 | 2/2018 | Brenner et al. |
| 2018/0042549 A1 | 2/2018 | Ho et al. |
| 2018/0042723 A1 | 2/2018 | Yellin et al. |
| 2018/0043133 A1 | 2/2018 | Wong |
| 2018/0049875 A1 | 2/2018 | Iflah et al. |
| 2018/0049876 A1 | 2/2018 | Miraki |
| 2018/0055628 A1 | 3/2018 | Patel et al. |
| 2018/0055633 A1 | 3/2018 | Costello et al. |
| 2018/0056045 A1 | 3/2018 | Donoghue et al. |
| 2018/0056046 A1 | 3/2018 | Kiersey et al. |
| 2018/0071088 A1 | 3/2018 | Badhwar et al. |
| 2018/0078367 A1 | 3/2018 | Saar et al. |
| 2018/0078368 A1 | 3/2018 | Vidlund et al. |
| 2018/0078370 A1 | 3/2018 | Kovalsky et al. |
| 2018/0085219 A1 | 3/2018 | Krivoruchko |
| 2018/0098837 A1 | 4/2018 | Shahriari |
| 2018/0099124 A1 | 4/2018 | McLoughlin et al. |
| 2018/0116793 A1 | 5/2018 | Salahieh et al. |
| 2018/0116843 A1 | 5/2018 | Schreck et al. |
| 2018/0125642 A1 | 5/2018 | White et al. |
| 2018/0125654 A1 | 5/2018 | Duffy |
| 2018/0126127 A1 | 5/2018 | Devereux et al. |
| 2018/0133000 A1 | 5/2018 | Scheinblum et al. |
| 2018/0133006 A1 | 5/2018 | Jones et al. |
| 2018/0133011 A1 | 5/2018 | Perouse |
| 2018/0140417 A1 | 5/2018 | Sciscio et al. |
| 2018/0147041 A1 | 5/2018 | Chouinard et al. |
| 2018/0147055 A1 | 5/2018 | Vidlund et al. |
| 2018/0153689 A1 | 6/2018 | Maimon et al. |
| 2018/0161158 A1 | 6/2018 | Kovalsky et al. |
| 2018/0161161 A1 | 6/2018 | Yellin et al. |
| 2018/0168793 A1 | 6/2018 | Lees et al. |
| 2018/0177580 A9 | 6/2018 | Shemesh et al. |
| 2018/0177594 A1 | 6/2018 | Patel et al. |
| 2018/0185153 A1 | 7/2018 | Bishop et al. |
| 2018/0193138 A1 | 7/2018 | Vidlund |
| 2018/0200049 A1 | 7/2018 | Chambers et al. |
| 2018/0206983 A1 | 7/2018 | Noe et al. |
| 2018/0214141 A1 | 8/2018 | Mendez |
| 2018/0221016 A1 | 8/2018 | Conklin et al. |
| 2018/0243071 A1 | 8/2018 | Eigler et al. |
| 2018/0243532 A1 | 8/2018 | Willard et al. |
| 2018/0256322 A1 | 9/2018 | Zhang et al. |
| 2018/0256327 A1 | 9/2018 | Perszyk et al. |
| 2018/0256329 A1 | 9/2018 | Chambers et al. |
| 2018/0263767 A1 | 9/2018 | Chau et al. |
| 2018/0263773 A1 | 9/2018 | Poppe et al. |
| 2018/0280174 A1 | 10/2018 | Dwork |
| 2018/0289474 A1 | 10/2018 | Rajagopal et al. |
| 2018/0289475 A1 | 10/2018 | Chung et al. |
| 2018/0289485 A1 | 10/2018 | Rajagopal et al. |
| 2018/0296325 A1 | 10/2018 | McLean |
| 2018/0296335 A1 | 10/2018 | Miyashiro |
| 2018/0296337 A1 | 10/2018 | Duhay et al. |
| 2018/0296341 A1 | 10/2018 | Noe et al. |
| 2018/0303488 A1 | 10/2018 | Hill |
| 2018/0303612 A1 | 10/2018 | Pasquino et al. |
| 2018/0311037 A1 | 11/2018 | Morriss et al. |
| 2018/0311041 A1 | 11/2018 | Tyler, II et al. |
| 2018/0318071 A1* | 11/2018 | Lozonschi ............ A61F 2/2412 |
| 2018/0318073 A1 | 11/2018 | Tseng et al. |
| 2018/0318078 A1 | 11/2018 | Willard |
| 2018/0325665 A1 | 11/2018 | Gurovich et al. |
| 2018/0325671 A1 | 11/2018 | Abunassar et al. |
| 2018/0333259 A1 | 11/2018 | Dibie |
| 2018/0338832 A1 | 11/2018 | Ganesan et al. |
| 2018/0344456 A1 | 12/2018 | Barash et al. |
| 2018/0353293 A1 | 12/2018 | Colavito et al. |
| 2018/0353295 A1 | 12/2018 | Cooper et al. |
| 2018/0360439 A1 | 12/2018 | Niland et al. |
| 2018/0360599 A1 | 12/2018 | Drasler et al. |
| 2019/0000619 A1 | 1/2019 | Quijano et al. |
| 2019/0008636 A1 | 1/2019 | Francis et al. |
| 2019/0008640 A1 | 1/2019 | Cooper et al. |
| 2019/0015188 A1 | 1/2019 | Eigler et al. |
| 2019/0021834 A1 | 1/2019 | Nir et al. |
| 2019/0029819 A1 | 1/2019 | Huber |
| 2019/0029823 A1 | 1/2019 | Nguyen et al. |
| 2019/0038404 A1 | 2/2019 | Iamberger et al. |
| 2019/0038405 A1 | 2/2019 | Iamberger et al. |
| 2019/0053894 A1 | 2/2019 | Levi et al. |
| 2019/0053895 A1 | 2/2019 | Levi |
| 2019/0053897 A1 | 2/2019 | Levi et al. |
| 2019/0053898 A1 | 2/2019 | Maimon et al. |
| 2019/0053899 A1 | 2/2019 | Levi |
| 2019/0060051 A1 | 2/2019 | Scheeff et al. |
| 2019/0060057 A1 | 2/2019 | Cohen et al. |
| 2019/0060059 A1 | 2/2019 | Delgado et al. |
| 2019/0060069 A1 | 2/2019 | Maimon et al. |
| 2019/0060071 A1 | 2/2019 | Lane et al. |
| 2019/0069995 A1 | 3/2019 | Levi et al. |
| 2019/0070003 A1 | 3/2019 | Siegel et al. |
| 2019/0076233 A1 | 3/2019 | Fish |
| 2019/0076249 A1 | 3/2019 | Khairkhahan et al. |
| 2019/0083085 A1 | 3/2019 | Gilmore et al. |
| 2019/0091005 A1 | 3/2019 | Fifer et al. |
| 2019/0091015 A1 | 3/2019 | Dienno et al. |
| 2019/0091018 A1 | 3/2019 | Hariton et al. |
| 2019/0091022 A1 | 3/2019 | Yellin et al. |
| 2019/0099265 A1 | 4/2019 | Braido et al. |
| 2019/0099270 A1 | 4/2019 | Morrissey et al. |
| 2019/0105153 A1 | 4/2019 | Barash et al. |
| 2019/0117223 A1 | 4/2019 | Abunassar et al. |
| 2019/0117387 A1 | 4/2019 | Li et al. |

(56) References Cited

U.S. PATENT DOCUMENTS

| | | |
|---|---|---|
| 2019/0117391 A1 | 4/2019 | Humair |
| 2019/0117400 A1 | 4/2019 | Medema et al. |
| 2019/0117401 A1 | 4/2019 | Cortez, Jr. et al. |
| 2019/0125287 A1 | 5/2019 | Itou et al. |
| 2019/0125536 A1 | 5/2019 | Prabhu et al. |
| 2019/0133528 A1 | 5/2019 | Kassab et al. |
| 2019/0133756 A1 | 5/2019 | Zhang et al. |
| 2019/0133757 A1 | 5/2019 | Zhang et al. |
| 2019/0133765 A1 | 5/2019 | Yellin et al. |
| 2019/0142566 A1 | 5/2019 | Lansky et al. |
| 2019/0142582 A1 | 5/2019 | Drasler et al. |
| 2019/0150867 A1 | 5/2019 | Itou et al. |
| 2019/0151509 A1 | 5/2019 | Kheradvar et al. |
| 2019/0167423 A1 | 6/2019 | Hariton et al. |
| 2019/0167429 A1 | 6/2019 | Stearns et al. |
| 2019/0175338 A1 | 6/2019 | White et al. |
| 2019/0175339 A1 | 6/2019 | Vidlund |
| 2019/0175344 A1 | 6/2019 | Khairkhahan |
| 2019/0183639 A1 | 6/2019 | Moore |
| 2019/0183644 A1 | 6/2019 | Hacohen |
| 2019/0183648 A1 | 6/2019 | Trapp et al. |
| 2019/0192287 A1 | 6/2019 | Sandstrom et al. |
| 2019/0192296 A1 | 6/2019 | Schwartz et al. |
| 2019/0209317 A1 | 7/2019 | Zhang et al. |
| 2019/0209320 A1 | 7/2019 | Drasler et al. |
| 2019/0231523 A1 | 8/2019 | Lombardi et al. |
| 2019/0240020 A1 | 8/2019 | Rafiee et al. |
| 2019/0240022 A1 | 8/2019 | Rafiee et al. |
| 2019/0247050 A1 | 8/2019 | Goldsmith |
| 2019/0254815 A1 | 8/2019 | Bruchman et al. |
| 2019/0254816 A1 | 8/2019 | Anderson et al. |
| 2019/0262118 A1 | 8/2019 | Eigler et al. |
| 2019/0262129 A1 | 8/2019 | Cooper et al. |
| 2019/0269413 A1 | 9/2019 | Yodfat et al. |
| 2019/0269504 A1 | 9/2019 | Wang et al. |
| 2019/0269839 A1 | 9/2019 | Wilson et al. |
| 2019/0282360 A1 | 9/2019 | Colavito et al. |
| 2019/0290426 A1 | 9/2019 | Maimon et al. |
| 2019/0290427 A1 | 9/2019 | Mantanus et al. |
| 2019/0307563 A1 | 10/2019 | Sandstrom et al. |
| 2019/0307589 A1 | 10/2019 | Goldberg et al. |
| 2019/0365538 A1 | 12/2019 | Chambers et al. |
| 2019/0388219 A1 | 12/2019 | Lane et al. |
| 2020/0121452 A1 | 4/2020 | Saikrishnan et al. |
| 2020/0121458 A1 | 4/2020 | Vidlund et al. |
| 2020/0179146 A1 | 6/2020 | Christianson et al. |
| 2020/0188097 A1 | 6/2020 | Perrin et al. |
| 2020/0237506 A1 | 7/2020 | Christianson et al. |
| 2020/0289259 A1 | 9/2020 | Christianson et al. |
| 2020/0289263 A1 | 9/2020 | Christianson et al. |
| 2021/0000592 A1 | 1/2021 | Christianson et al. |
| 2021/0137677 A1 | 5/2021 | Christianson et al. |
| 2021/0154011 A1 | 5/2021 | Christianson et al. |
| 2021/0186693 A1 | 6/2021 | Vidlund, I et al. |
| 2021/0220126 A1 | 7/2021 | Perrin |
| 2021/0220127 A1 | 7/2021 | Vidlund et al. |
| 2021/0220134 A1 | 7/2021 | Christianson et al. |
| 2021/0236280 A1 | 8/2021 | Christianson et al. |
| 2021/0244533 A1 | 8/2021 | Vidlund et al. |
| 2021/0244535 A1 | 8/2021 | Iyer et al. |
| 2021/0244536 A1 | 8/2021 | Christianson et al. |
| 2021/0290381 A1 | 9/2021 | Vidlund et al. |
| 2021/0290385 A1 | 9/2021 | Christianson et al. |
| 2021/0315694 A1 | 10/2021 | Vidlund et al. |
| 2021/0330459 A1 | 10/2021 | Christianson et al. |
| 2021/0353412 A1 | 11/2021 | Christianson et al. |
| 2022/0000614 A1 | 1/2022 | Vidlund et al. |
| 2022/0096226 A1 | 3/2022 | Christianson et al. |
| 2022/0160504 A1 | 5/2022 | Vidlund et al. |
| 2022/0249228 A1 | 8/2022 | Vidlund et al. |
| 2022/0280292 A1 | 9/2022 | Vidlund et al. |
| 2022/0280296 A1 | 9/2022 | Christianson et al. |
| 2022/0323212 A1 | 10/2022 | Vidlund et al. |
| 2022/0395370 A1 | 12/2022 | Vidlund et al. |
| 2022/0409369 A1 | 12/2022 | Christianson et al. |

FOREIGN PATENT DOCUMENTS

| | | |
|---|---|---|
| AU | 2011238752 A1 | 10/2012 |
| AU | 2011240940 A1 | 10/2012 |
| AU | 2012272855 A1 | 1/2014 |
| AU | 2011236036 B2 | 6/2014 |
| AU | 2011248657 B2 | 12/2014 |
| AU | 2016228261 A1 | 4/2017 |
| AU | 2017210659 A1 | 8/2017 |
| AU | 2013245201 B2 | 10/2017 |
| AU | 2014360294 B2 | 10/2017 |
| AU | 2016249819 A1 | 11/2017 |
| AU | 2016371525 A1 | 5/2018 |
| AU | 2016366783 A1 | 6/2018 |
| AU | 2017214672 B2 | 10/2018 |
| AU | 2017285993 A1 | 1/2019 |
| AU | 2014201920 B2 | 2/2019 |
| AU | 2015411406 B2 | 2/2019 |
| AU | 2019202290 A1 | 4/2019 |
| AU | 2017388857 A1 | 8/2019 |
| BR | PI0909379 B1 | 9/2019 |
| CA | 2531528 A1 | 1/2005 |
| CA | 2609800 A1 | 1/2007 |
| CA | 2822636 A1 | 10/2008 |
| CA | 2398948 C | 8/2009 |
| CA | 2813419 A1 | 4/2012 |
| CA | 2856088 A1 | 5/2013 |
| CA | 2866315 A1 | 9/2013 |
| CA | 2922123 A1 | 4/2015 |
| CA | 2504258 C | 6/2015 |
| CA | 2677648 C | 10/2015 |
| CA | 2815331 C | 10/2015 |
| CA | 2986584 A1 | 11/2015 |
| CA | 2975294 A1 | 8/2016 |
| CA | 2995603 A1 | 2/2017 |
| CA | 2753853 C | 4/2017 |
| CA | 2702615 C | 6/2017 |
| CA | 2744395 C | 8/2017 |
| CA | 3020238 A1 | 11/2017 |
| CA | 3033666 A1 | 2/2018 |
| CA | 3031572 A1 | 3/2018 |
| CA | 3022641 A1 | 5/2018 |
| CA | 3044062 A1 | 6/2018 |
| CA | 3048893 A1 | 7/2018 |
| CA | 3049792 A1 | 7/2018 |
| CA | 3046693 A1 | 8/2018 |
| CA | 2778944 C | 8/2019 |
| CN | 2855366 Y | 1/2007 |
| CN | 100584292 C | 1/2010 |
| CN | 101677820 A | 3/2010 |
| CN | 101677851 A | 3/2010 |
| CN | 102858272 A | 1/2013 |
| CN | 102869320 A | 1/2013 |
| CN | 102892384 A | 1/2013 |
| CN | 103118630 A | 5/2013 |
| CN | 103189015 A | 7/2013 |
| CN | 103228231 A | 7/2013 |
| CN | 103298426 A | 9/2013 |
| CN | 103370035 A | 10/2013 |
| CN | 103391756 A | 11/2013 |
| CN | 102245120 B | 8/2014 |
| CN | 104220027 A | 12/2014 |
| CN | 102917668 B | 1/2015 |
| CN | 104394803 A | 3/2015 |
| CN | 104582637 A | 4/2015 |
| CN | 102905647 B | 7/2015 |
| CN | 103648570 B | 9/2015 |
| CN | 104884000 A | 9/2015 |
| CN | 104160076 B | 12/2015 |
| CN | 105380730 A | 3/2016 |
| CN | 105451687 A | 3/2016 |
| CN | 105520792 A | 4/2016 |
| CN | 105530893 A | 4/2016 |
| CN | 102458309 B | 5/2016 |
| CN | 103200900 B | 5/2016 |
| CN | 105555232 A | 5/2016 |
| CN | 105578992 A | 5/2016 |
| CN | 103338709 B | 6/2016 |
| CN | 105658178 A | 6/2016 |

(56) References Cited

FOREIGN PATENT DOCUMENTS

| | | |
|---|---|---|
| CN | 105792780 A | 7/2016 |
| CN | 103347467 B | 8/2016 |
| CN | 103648439 B | 8/2016 |
| CN | 103889472 B | 8/2016 |
| CN | 105899150 A | 8/2016 |
| CN | 103153232 B | 9/2016 |
| CN | 106061437 A | 10/2016 |
| CN | 106068109 A | 11/2016 |
| CN | 106073946 A | 11/2016 |
| CN | 106255475 A | 12/2016 |
| CN | 103917194 B | 2/2017 |
| CN | 106456324 A | 2/2017 |
| CN | 106456325 A | 2/2017 |
| CN | 105073068 B | 3/2017 |
| CN | 106470641 A | 3/2017 |
| CN | 105451684 B | 4/2017 |
| CN | 106573129 A | 4/2017 |
| CN | 103945792 B | 5/2017 |
| CN | 106659394 A | 5/2017 |
| CN | 106716098 A | 5/2017 |
| CN | 106794063 A | 5/2017 |
| CN | 106890035 A | 6/2017 |
| CN | 106943207 A | 7/2017 |
| CN | 106999054 A | 8/2017 |
| CN | 106999281 A | 8/2017 |
| CN | 104114127 B | 9/2017 |
| CN | 107115161 A | 9/2017 |
| CN | 107249482 A | 10/2017 |
| CN | 107260366 A | 10/2017 |
| CN | 104918582 B | 11/2017 |
| CN | 107374783 A | 11/2017 |
| CN | 107427364 A | 12/2017 |
| CN | 106255476 B | 1/2018 |
| CN | 107530157 A | 1/2018 |
| CN | 107530167 A | 1/2018 |
| CN | 107530177 A | 1/2018 |
| CN | 107613908 A | 1/2018 |
| CN | 104869948 B | 2/2018 |
| CN | 107714240 A | 2/2018 |
| CN | 107920897 A | 4/2018 |
| CN | 104853696 B | 6/2018 |
| CN | 108135696 A | 6/2018 |
| CN | 108430392 A | 8/2018 |
| CN | 108472142 A | 8/2018 |
| CN | 106726007 B | 11/2018 |
| CN | 109124829 A | 1/2019 |
| CN | 109199641 A | 1/2019 |
| CN | 109561962 A | 4/2019 |
| CN | 109567991 A | 4/2019 |
| CN | 109862835 A | 6/2019 |
| CN | 109906063 A | 6/2019 |
| CN | 109996581 A | 7/2019 |
| CN | 110013358 A | 7/2019 |
| CN | 110290764 A | 9/2019 |
| DE | 102014102648 A1 | 9/2015 |
| DE | 102014102650 A1 | 9/2015 |
| DE | 102014102718 A1 | 9/2015 |
| DE | 102014102722 A1 | 9/2015 |
| DE | 202017104793 U1 | 11/2018 |
| DE | 202016008737 U1 | 4/2019 |
| DK | 2549953 T3 | 2/2017 |
| DK | 2254514 T3 | 12/2018 |
| EA | 027348 B1 | 7/2017 |
| EP | 0902704 A4 | 3/1999 |
| EP | 1301225 A2 | 4/2003 |
| EP | 1684666 A2 | 8/2006 |
| EP | 1996246 A2 | 12/2008 |
| EP | 2211779 A1 | 8/2010 |
| EP | 2254513 A1 | 12/2010 |
| EP | 2263605 A1 | 12/2010 |
| EP | 2273947 A1 | 1/2011 |
| EP | 2296744 A1 | 3/2011 |
| EP | 2379008 A2 | 10/2011 |
| EP | 2400926 A2 | 1/2012 |
| EP | 2427145 A2 | 3/2012 |
| EP | 1582178 B1 | 9/2012 |
| EP | 2542186 A2 | 1/2013 |
| EP | 2558030 A1 | 2/2013 |
| EP | 2560579 A1 | 2/2013 |
| EP | 2575681 A1 | 4/2013 |
| EP | 2603172 A2 | 6/2013 |
| EP | 2637607 A1 | 9/2013 |
| EP | 2651337 A2 | 10/2013 |
| EP | 2658476 A1 | 11/2013 |
| EP | 2699201 A1 | 2/2014 |
| EP | 2405966 B1 | 4/2014 |
| EP | 2055263 B1 | 6/2014 |
| EP | 2741711 A2 | 6/2014 |
| EP | 2793763 A1 | 10/2014 |
| EP | 2822503 A2 | 1/2015 |
| EP | 2538879 B1 | 4/2015 |
| EP | 2444031 B1 | 7/2015 |
| EP | 1702247 B1 | 8/2015 |
| EP | 2772228 B1 | 11/2015 |
| EP | 2943160 A2 | 11/2015 |
| EP | 2470098 B1 | 12/2015 |
| EP | 1991168 B1 | 1/2016 |
| EP | 2254512 B1 | 1/2016 |
| EP | 2964152 A1 | 1/2016 |
| EP | 2967853 A1 | 1/2016 |
| EP | 2967860 A1 | 1/2016 |
| EP | 2994073 A1 | 3/2016 |
| EP | 3001978 A1 | 4/2016 |
| EP | 3003187 A1 | 4/2016 |
| EP | 3007649 A1 | 4/2016 |
| EP | 3010447 A1 | 4/2016 |
| EP | 3017792 A1 | 5/2016 |
| EP | 3019092 A1 | 5/2016 |
| EP | 2563236 B1 | 6/2016 |
| EP | 3027143 A1 | 6/2016 |
| EP | 3037064 A1 | 6/2016 |
| EP | 2211758 B1 | 7/2016 |
| EP | 3052053 A1 | 8/2016 |
| EP | 3060140 A1 | 8/2016 |
| EP | 3062745 A1 | 9/2016 |
| EP | 3071149 A1 | 9/2016 |
| EP | 2282700 B1 | 11/2016 |
| EP | 2967854 B1 | 11/2016 |
| EP | 1998713 B1 | 12/2016 |
| EP | 3099271 A1 | 12/2016 |
| EP | 3100701 A1 | 12/2016 |
| EP | 3141219 A1 | 3/2017 |
| EP | 3157469 A1 | 4/2017 |
| EP | 2538880 B1 | 5/2017 |
| EP | 2967852 B1 | 6/2017 |
| EP | 3174503 A1 | 6/2017 |
| EP | 3182931 A1 | 6/2017 |
| EP | 2830536 B1 | 8/2017 |
| EP | 2830537 B1 | 9/2017 |
| EP | 2720642 B1 | 10/2017 |
| EP | 3232941 A1 | 10/2017 |
| EP | 3256076 A1 | 12/2017 |
| EP | 3281608 A1 | 2/2018 |
| EP | 2608815 B1 | 3/2018 |
| EP | 3310302 A1 | 4/2018 |
| EP | 3311778 A1 | 4/2018 |
| EP | 3337412 A1 | 6/2018 |
| EP | 3340931 A1 | 7/2018 |
| EP | 3344188 A1 | 7/2018 |
| EP | 3344197 A1 | 7/2018 |
| EP | 3345573 A1 | 7/2018 |
| EP | 2822473 B1 | 8/2018 |
| EP | 3354208 A1 | 8/2018 |
| EP | 3370649 A1 | 9/2018 |
| EP | 3372198 A1 | 9/2018 |
| EP | 3372199 A1 | 9/2018 |
| EP | 3375411 A1 | 9/2018 |
| EP | 2928538 B1 | 11/2018 |
| EP | 3399947 A1 | 11/2018 |
| EP | 3400913 A1 | 11/2018 |
| EP | 3406224 A1 | 11/2018 |
| EP | 2555709 B1 | 12/2018 |
| EP | 3417813 A1 | 12/2018 |
| EP | 3426188 A1 | 1/2019 |

(56) References Cited

FOREIGN PATENT DOCUMENTS

| | | |
|---|---|---|
| EP | 3429507 A1 | 1/2019 |
| EP | 3431040 A1 | 1/2019 |
| EP | 3432825 A1 | 1/2019 |
| EP | 3432834 A1 | 1/2019 |
| EP | 3437669 A1 | 2/2019 |
| EP | 3448312 A1 | 3/2019 |
| EP | 3454787 A1 | 3/2019 |
| EP | 2663259 B1 | 5/2019 |
| EP | 3302364 B1 | 5/2019 |
| EP | 3478224 A1 | 5/2019 |
| EP | 3484411 A1 | 5/2019 |
| EP | 3487420 A1 | 5/2019 |
| EP | 2560580 B1 | 6/2019 |
| EP | 3508113 A1 | 7/2019 |
| EP | 3518748 A1 | 8/2019 |
| EP | 3522830 A1 | 8/2019 |
| EP | 3528749 A1 | 8/2019 |
| EP | 3288495 B1 | 9/2019 |
| EP | 3538024 A1 | 9/2019 |
| EP | 3538025 A1 | 9/2019 |
| EP | 3019123 B1 | 10/2019 |
| EP | 3552584 A1 | 10/2019 |
| EP | 3552655 A1 | 10/2019 |
| ES | 2369241 T3 | 11/2011 |
| ES | 2647777 T3 | 12/2017 |
| ES | 2664243 T3 | 4/2018 |
| ES | 2675726 T3 | 7/2018 |
| GB | 2539444 A | 12/2016 |
| JP | 2003530956 A | 10/2003 |
| JP | 2005521513 A | 7/2005 |
| JP | 2008506459 A | 3/2008 |
| JP | 2008512211 A | 4/2008 |
| JP | 2009148579 A | 7/2009 |
| JP | 2009525138 A | 7/2009 |
| JP | 2009527316 A | 7/2009 |
| JP | 2009254864 A | 11/2009 |
| JP | 4426182 B2 | 3/2010 |
| JP | 2010518947 A | 6/2010 |
| JP | 2010537680 A | 12/2010 |
| JP | 2011510797 A | 4/2011 |
| JP | 2013503009 A | 1/2013 |
| JP | 2013505082 A | 2/2013 |
| JP | 2013508027 A | 3/2013 |
| JP | 2013512765 A | 4/2013 |
| JP | 2013523261 A | 6/2013 |
| JP | 2013527010 A | 6/2013 |
| JP | 2013543399 A | 12/2013 |
| JP | 2014501563 A | 1/2014 |
| JP | 2014505537 A | 3/2014 |
| JP | 5527850 B2 | 6/2014 |
| JP | 2014518697 A | 8/2014 |
| JP | 2014522678 A | 9/2014 |
| JP | 2015503948 A | 2/2015 |
| JP | 2015510819 A | 4/2015 |
| JP | 2015517854 A | 6/2015 |
| JP | 5767764 B2 | 8/2015 |
| JP | 5803010 B2 | 11/2015 |
| JP | 2015531283 A | 11/2015 |
| JP | 2015534887 A | 12/2015 |
| JP | 2016503710 A | 2/2016 |
| JP | 2016506794 A | 3/2016 |
| JP | 2016508858 A | 3/2016 |
| JP | 2016517748 A | 6/2016 |
| JP | 2016520391 A | 7/2016 |
| JP | 2016526438 A | 9/2016 |
| JP | 2016530046 A | 9/2016 |
| JP | 2016533787 A | 11/2016 |
| JP | 2016540617 A | 12/2016 |
| JP | 2017000729 A | 1/2017 |
| JP | 2017504410 A | 2/2017 |
| JP | 2017515609 A | 6/2017 |
| JP | 2017516536 A | 6/2017 |
| JP | 2017516609 A | 6/2017 |
| JP | 2017131738 A | 8/2017 |
| JP | 2017159055 A | 9/2017 |
| JP | 2017529908 A | 10/2017 |
| JP | 2018501001 A | 1/2018 |
| JP | 2018501901 A | 1/2018 |
| JP | 2018506412 A | 3/2018 |
| JP | 6329570 B2 | 5/2018 |
| JP | 2018515306 A | 6/2018 |
| JP | 2018118136 A | 8/2018 |
| JP | 2018532556 A | 11/2018 |
| JP | 2018535074 A | 11/2018 |
| JP | 2019500952 A | 1/2019 |
| JP | 2019501696 A | 1/2019 |
| JP | 2019501712 A | 1/2019 |
| JP | 6466853 B2 | 2/2019 |
| JP | 6480343 B2 | 3/2019 |
| JP | 2019507664 A | 3/2019 |
| JP | 6506813 B2 | 4/2019 |
| JP | 6526043 B2 | 6/2019 |
| JP | 2019103821 A | 6/2019 |
| JP | 2019514490 A | 6/2019 |
| JP | 2019516527 A | 6/2019 |
| JP | 2019517346 A | 6/2019 |
| JP | 6568213 B2 | 8/2019 |
| JP | 2019134972 A | 8/2019 |
| JP | 2019523090 A | 8/2019 |
| JP | 2019155178 A | 9/2019 |
| JP | 2019526303 A | 9/2019 |
| KR | 20010013991 A | 2/2001 |
| KR | 20120101625 A | 9/2012 |
| KR | 101223313 B1 | 1/2013 |
| KR | 101354189 B1 | 1/2014 |
| KR | 20140139060 A | 12/2014 |
| KR | 20150097757 A | 8/2015 |
| KR | 20160024992 A | 3/2016 |
| RU | 177405 U1 | 2/2018 |
| WO | WO-0044308 A2 | 8/2000 |
| WO | WO-03072287 A1 | 9/2003 |
| WO | WO-2004093728 A2 | 11/2004 |
| WO | WO-2006029062 A1 | 3/2006 |
| WO | WO-2006066150 A2 | 6/2006 |
| WO | WO-2007047945 A2 | 4/2007 |
| WO | WO-2007054015 A1 | 5/2007 |
| WO | WO-2007095233 A2 | 8/2007 |
| WO | WO-2007129220 A2 | 11/2007 |
| WO | WO-2008013915 A2 | 1/2008 |
| WO | WO-2008091925 A2 | 7/2008 |
| WO | WO-2008103280 A2 | 8/2008 |
| WO | WO-2009081396 A2 | 7/2009 |
| WO | WO-2009094188 A2 | 7/2009 |
| WO | WO-2009094189 A1 | 7/2009 |
| WO | WO-2009094197 A1 | 7/2009 |
| WO | WO-2009094501 A1 | 7/2009 |
| WO | WO-2009100242 A2 | 8/2009 |
| WO | WO-2010029190 A1 | 3/2010 |
| WO | WO-2010079427 A1 | 7/2010 |
| WO | WO-2010119110 A1 | 10/2010 |
| WO | WO-2011112706 A2 | 9/2011 |
| WO | WO-2011137531 A1 | 11/2011 |
| WO | WO-2012009558 A2 | 1/2012 |
| WO | WO 2012/035279 | 3/2012 |
| WO | WO-2012063228 A1 | 5/2012 |
| WO | WO-2012063242 A1 | 5/2012 |
| WO | WO-2012112469 A2 | 8/2012 |
| WO | WO-2012145545 A1 | 10/2012 |
| WO | WO-2012161786 A1 | 11/2012 |
| WO | WO-2012175483 A1 | 12/2012 |
| WO | WO-2012178115 A2 | 12/2012 |
| WO | WO-2013021375 A2 | 2/2013 |
| WO | WO-2013085719 A1 | 6/2013 |
| WO | WO-2013103612 A1 | 7/2013 |
| WO | WO-2013116785 A1 | 8/2013 |
| WO | WO-2013128436 A1 | 9/2013 |
| WO | WO-2013148019 A1 | 10/2013 |
| WO | WO-2013166356 A2 | 11/2013 |
| WO | WO-2013177684 A1 | 12/2013 |
| WO | WO-2013184945 A1 | 12/2013 |
| WO | WO-2014011330 A1 | 1/2014 |
| WO | WO-2014064695 A2 | 5/2014 |
| WO | WO-2014121042 A1 | 8/2014 |
| WO | WO-2014133667 A1 | 9/2014 |

(56) References Cited

FOREIGN PATENT DOCUMENTS

| | | |
|---|---|---|
| WO | WO-2014137805 A1 | 9/2014 |
| WO | WO-2014140230 A1 | 9/2014 |
| WO | WO-2014162306 A2 | 10/2014 |
| WO | WO-2014164151 A1 | 10/2014 |
| WO | WO-2014168655 A1 | 10/2014 |
| WO | WO-2015004173 A1 | 1/2015 |
| WO | WO-2015014960 A1 | 2/2015 |
| WO | WO-2015017075 A1 | 2/2015 |
| WO | WO-2015055605 A1 | 4/2015 |
| WO | WO-2015057735 A1 | 4/2015 |
| WO | WO-2015058039 A1 | 4/2015 |
| WO | WO-2015061021 A1 | 4/2015 |
| WO | WO-2015117025 A1 | 8/2015 |
| WO | WO-2015120122 A2 | 8/2015 |
| WO | WO-2015123607 A2 | 8/2015 |
| WO | WO-2015127264 A1 | 8/2015 |
| WO | WO-2015142834 A1 | 9/2015 |
| WO | WO-2015153755 A2 | 10/2015 |
| WO | WO-2016011267 A1 | 1/2016 |
| WO | WO-2016025733 A1 | 2/2016 |
| WO | WO-2016083351 A1 | 6/2016 |
| WO | WO-2016097337 A1 | 6/2016 |
| WO | WO-2016100799 A1 | 6/2016 |
| WO | WO-2016118851 A1 | 7/2016 |
| WO | WO-2016130913 A1 | 8/2016 |
| WO | WO-2016148777 A1 | 9/2016 |
| WO | WO-2016149083 A1 | 9/2016 |
| WO | WO-2016150806 A1 | 9/2016 |
| WO | WO-2016189391 A2 | 12/2016 |
| WO | WO-2017040684 A1 | 3/2017 |
| WO | WO-2017096157 A1 | 6/2017 |
| WO | WO-2017114928 A1 | 7/2017 |
| WO | WO-2017120404 A1 | 7/2017 |
| WO | WO-2017121193 A1 | 7/2017 |
| WO | WO-2017121194 A1 | 7/2017 |
| WO | WO-2017121195 A1 | 7/2017 |
| WO | WO-2017123802 A1 | 7/2017 |
| WO | WO-2017136596 A1 | 8/2017 |
| WO | WO-2017151292 A1 | 9/2017 |
| WO | WO-2017155892 A1 | 9/2017 |
| WO | WO-2017156352 A1 | 9/2017 |
| WO | WO-2017161204 A1 | 9/2017 |
| WO | WO-2017165842 A1 | 9/2017 |
| WO | WO-2017196511 A1 | 11/2017 |
| WO | WO-2017201082 A1 | 11/2017 |
| WO | WO-2017202042 A1 | 11/2017 |
| WO | WO-2017210356 A1 | 12/2017 |
| WO | WO-2017218375 A1 | 12/2017 |
| WO | WO-2018008019 A2 | 1/2018 |
| WO | WO-2018026445 A1 | 2/2018 |
| WO | WO-2018026904 A1 | 2/2018 |
| WO | WO-2018035105 A1 | 2/2018 |
| WO | WO-2018040244 A1 | 3/2018 |
| WO | WO-2018042439 A1 | 3/2018 |
| WO | WO-2018045156 A2 | 3/2018 |
| WO | WO-2018071115 A1 | 4/2018 |
| WO | WO-2018077143 A1 | 5/2018 |
| WO | WO-2018077146 A1 | 5/2018 |
| WO | WO-2018080328 A1 | 5/2018 |
| WO | WO-2018083493 A1 | 5/2018 |
| WO | WO-2018090576 A1 | 5/2018 |
| WO | WO-2018098032 A1 | 5/2018 |
| WO | WO-2018106460 A1 | 6/2018 |
| WO | WO-2018119304 A1 | 6/2018 |
| WO | WO-2018136726 A1 | 7/2018 |
| WO | WO-2018138658 A1 | 8/2018 |
| WO | WO-2018145055 A1 | 8/2018 |
| WO | WO-2018156767 A1 | 8/2018 |
| WO | WO-2018156922 A1 | 8/2018 |
| WO | WO-2018158747 A1 | 9/2018 |
| WO | WO-2018160790 A1 | 9/2018 |
| WO | WO-2018165358 A1 | 9/2018 |
| WO | WO-2018170149 A1 | 9/2018 |
| WO | WO-2018175220 A1 | 9/2018 |
| WO | WO-2018175619 A1 | 9/2018 |
| WO | WO-2018178208 A1 | 10/2018 |
| WO | WO-2018178977 A1 | 10/2018 |
| WO | WO-2018183832 A1 | 10/2018 |
| WO | WO-2018184225 A1 | 10/2018 |
| WO | WO-2018184226 A1 | 10/2018 |
| WO | WO-2018187495 A1 | 10/2018 |
| WO | WO-2018187753 A1 | 10/2018 |
| WO | WO-2018191681 A1 | 10/2018 |
| WO | WO-2018200531 A1 | 11/2018 |
| WO | WO-2018200942 A2 | 11/2018 |
| WO | WO-2018201111 A2 | 11/2018 |
| WO | WO-2018201212 A1 | 11/2018 |
| WO | WO-2018204106 A1 | 11/2018 |
| WO | WO-2018209302 A1 | 11/2018 |
| WO | WO-2018213209 A1 | 11/2018 |
| WO | WO-2018217525 A1 | 11/2018 |
| WO | WO-2018222799 A1 | 12/2018 |
| WO | WO-2018226628 A1 | 12/2018 |
| WO | WO-2019003221 A1 | 1/2019 |
| WO | WO-2019006383 A2 | 1/2019 |
| WO | WO-2019010458 A1 | 1/2019 |
| WO | WO-2019014473 A1 | 1/2019 |
| WO | WO-2019018319 A1 | 1/2019 |
| WO | WO-2019023385 A1 | 1/2019 |
| WO | WO-2019026059 A1 | 2/2019 |
| WO | WO-2019032992 A2 | 2/2019 |
| WO | WO-2019037579 A1 | 2/2019 |
| WO | WO-2019040357 A1 | 2/2019 |
| WO | WO-2019042472 A1 | 3/2019 |
| WO | WO-2019046099 A1 | 3/2019 |
| WO | WO-2019046205 A1 | 3/2019 |
| WO | WO-2019051168 A2 | 3/2019 |
| WO | WO-2019051180 A2 | 3/2019 |
| WO | WO-2019051587 A1 | 3/2019 |
| WO | WO-2019055577 A1 | 3/2019 |
| WO | WO-2019058178 A1 | 3/2019 |
| WO | WO-2019067219 A1 | 4/2019 |
| WO | WO-2019081689 A1 | 5/2019 |
| WO | WO-2019081985 A2 | 5/2019 |
| WO | WO-2019086958 A1 | 5/2019 |
| WO | WO-2019089136 A1 | 5/2019 |
| WO | WO-2019089821 A1 | 5/2019 |
| WO | WO-2019093387 A1 | 5/2019 |
| WO | WO-2019095049 A1 | 5/2019 |
| WO | WO-2019096033 A1 | 5/2019 |
| WO | WO-2019099722 A2 | 5/2019 |
| WO | WO-2019116322 A1 | 6/2019 |
| WO | WO-2019119674 A1 | 6/2019 |
| WO | WO-2019126518 A1 | 6/2019 |
| WO | WO-2019131148 A1 | 7/2019 |
| WO | WO-2019136162 A1 | 7/2019 |
| WO | WO-2019140293 A1 | 7/2019 |
| WO | WO-2019143775 A1 | 7/2019 |
| WO | WO-2019144036 A1 | 7/2019 |
| WO | WO-2019147585 A1 | 8/2019 |
| WO | WO-2019165213 A1 | 8/2019 |
| WO | WO-2019173475 A1 | 9/2019 |
| WO | WO 2019/195860 | 10/2019 |
| WO | WO-2019190800 A1 | 10/2019 |
| WO | WO-2019191102 A1 | 10/2019 |
| WO | WO-2020061124 A1 | 3/2020 |
| WO | WO-2020061331 A2 | 3/2020 |
| WO | WO-2020131978 A1 | 6/2020 |
| WO | WO-2020154735 A1 | 7/2020 |
| WO | WO-2020181154 A2 | 9/2020 |
| WO | WO-2020186251 A1 | 9/2020 |
| WO | WO-2020227249 A1 | 11/2020 |
| WO | WO-2021035032 A1 | 2/2021 |
| WO | WO-2021040996 A1 | 3/2021 |
| WO | WO-2021146515 A1 | 7/2021 |

OTHER PUBLICATIONS

Office Action for U.S. Appl. No. 16/435,687, dated Aug. 7, 2019, 19 pages.
International Search Report and Written Opinion for International Application No. PCT/US2019/051615, dated Mar. 2, 2020, 14 pages.

(56) References Cited

OTHER PUBLICATIONS

Office Action for U.S. Appl. No. 17/167,983, dated Apr. 13, 2021, 20 pages.
International Search Report and Written Opinion for International Application No. PCT/US2019/051957, dated Apr. 30, 2020, 16 pages.
Office Action for U.S. Appl. No. 16/155,890, dated Feb. 8, 2019, 13 pages.
Office Action for U.S. Appl. No. 16/448,108, dated Jan. 21, 2020, 14 pages.
Office Action for U.S. Appl. No. 16/448,108, dated Sep. 1, 2020, 14 pages.
Office Action for U.S. Appl. No. 16/448,108, dated Mar. 8, 2021, 8 pages.
Office Action for U.S. Appl. No. 16/163,577, dated Mar. 8, 2021, 10 pages.
Office Action for U.S. Appl. No. 16/455,417, dated Sep. 23, 2019, 11 pages.
International Search Report and Written Opinion for International Application No. PCT/US2019/067010, dated Mar. 10, 2020, 17 pages.
Office Action for U.S. Appl. No. 16/455,740, dated Jul. 24, 2020, 7 pages.
International Search Report and Written Opinion for International Application No. PCT/US2020/015231, dated Apr. 23, 2020, 10 pages.
International Search Report and Written Opinion for International Application No. PCT/US2020/021300, dated Oct. 7, 2020, 6 pages.
International Search Report and Written Opinion for International Application No. PCT/US2020/031390, dated Aug. 3, 2020, 10 pages.
International Search Report and Written Opinion for International Application No. PCT/US2020/013240, dated Jun. 3, 2020, 7 pages.
International Search Report and Written Opinion for International Application No. PCT/US2020/022828, dated May 19, 2020, 12 pages.
Office Action for U.S. Appl. No. 17/154,227, dated Mar. 29, 2021, 6 pages.
Office Action for U.S. Appl. No. 16/442,504, dated Jan. 14, 2020, 11 pages.
Office Action for U.S. Appl. No. 16/445,210, dated Jan. 28, 2021, 7 pages.
Office Action for U.S. Appl. No. 17/154,438, dated May 3, 2021, 16 pages.
International Search Report and Written Opinion for International Application No. PCT/US2021/013570, dated Apr. 1, 2021, 9 pages.
International Search Report and Written Opinion for International Application No. PCT/US2020/045195, dated Jan. 8, 2021, 18 pages.
Office Action for U.S. Appl. No. 17/193,936, dated May 27, 2021, 6 pages.
International Search Report and Written Opinion for International Application No. PCT/US2020/047162, dated Dec. 30, 2020, 9 pages.
Extended European Search Report for European Application No. 19863898.3, dated Apr. 29, 2022, 13 pages.
Extended European Search Report for European Application No. 19897707.6, dated Sep. 6, 2022, 7 pages.
Extended European Search Report for European Application No. 20745513.0, dated Sep. 20, 2022, 9 pages.
Extended European Search Report for European Application No. 20767325.2, dated Oct. 25, 2022, 5 pages.
Extended European Search Report for European Application No. 20769769.9, dated Oct. 17, 2022, 6 pages.
Extended European Search Report for European Application No. 20801681.6, dated Jan. 18, 2023, 13 pages.
Office Action for U.S. Appl. No. 16/443,862, dated Nov. 12, 2021, 9 pages.
Office Action for U.S. Appl. No. 16/449,420, dated Sep. 1, 2021, 16 pages.
Office Action for U.S. Appl. No. 16/711,415, dated Jan. 18, 2022, 7 pages.
Office Action for U.S. Appl. No. 17/154,227, dated Jun. 18, 2021, 8 pages.
Office Action for U.S. Appl. No. 17/167,988, dated Sep. 22, 2021, 19 pages.
Office Action for U.S. Appl. No. 17/221,547, dated Aug. 4, 2021, 11 pages.
Office Action for U.S. Appl. No. 17/221,547, dated Oct. 21, 2021, 9 pages.
Office Action for U.S. Appl. No. 17/222,182, dated Sep. 2, 2021, 23 pages.
Office Action for U.S. Appl. No. 17/222,430, dated Oct. 7, 2021, 17 pages.
Office Action for U.S. Appl. No. 17/236,219, dated Aug. 4, 2021, 17 pages.
Office Action for U.S. Appl. No. 17/388,983, dated Jan. 6, 2022, 11 pages.

* cited by examiner

FIG. 71

| | | dia. | Circ. $2\pi r$ | size after plications | | |
|---|---|---|---|---|---|---|
| | | | | 2 plications (20mm) | 3 plications (30mm) | 4 plications (40mm) |
| tricuspid valve diameter, circumference, and repaired size | Normal 28±5 mm | 23 | 72 | | | |
| | | 33 | 103 | | | |
| | | 40 | 125 | 105 | 95 | 85 |
| | | 50 | 157 | 137 | 127 | 117 |
| | | 60 | 188 | 168 | 158 | 148 |
| | | 70 | 220 | 200 | 190 | 180 |

FIG. 72A    FIG. 72B    FIG. 72C
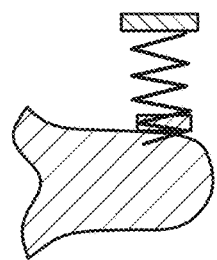 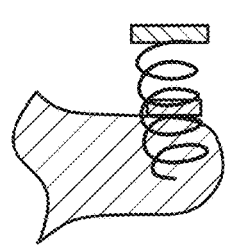 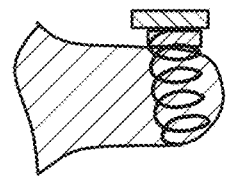
FIG. 73    FIG. 74    FIG. 75    FIG. 76
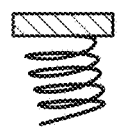 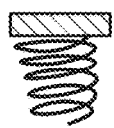 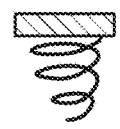 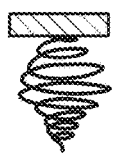

Deltoid  Rhomboid  Ovate  Cordate

DEVICES AND METHODS FOR ANCHORING TRANSCATHETER HEART VALVE

CROSS-REFERENCE TO RELATED APPLICATIONS

This application is a continuation of International Patent Application Serial No. PCT/US2019/028822, filed Apr. 24, 2019, entitled "Devices and Methods for Anchoring Transcatheter Heart Valve," which claims priority to and the benefit of U.S. Provisional patent Application Ser. Nos. 62/695,614, filed Jul. 9, 2018, entitled "Transcatheter Heart Valve Having Plication Sleeve and Compressible Wire Cell with Tissue Anchors;" 62/694,444, filed Jul. 6, 2018, entitled "Transcatheter Heart Valve with Folding Tabs;" 62/668,813, filed May 8, 2018, entitled "Pin Alignment Method for Heart Valve Prosthesis;" and 62/652,898, filed Apr. 4, 2018, entitled "Pinning Method for Heart Valve Prosthesis," the disclosure of each of which is incorporated herein by reference in its entirety.

BACKGROUND OF THE INVENTION

The invention relates to devices and methods for anchoring a transcatheter heart valve replacement (A61F2/2412), and in particular devices and methods for anchoring a percutaneously (transcatheter) deployed heart valve prosthesis that has an atrial annular flange or cuff having one or more integral tissue anchors for engaging annular tissue.

The human heart has four chambers, two upper collection chambers are called atrium, and two lower pumping chambers called ventricles. The right-side atrium receives blood from the body and has a trapdoor opening, called a tricuspid valve, that delivers blood to the right-side ventricle. The right ventricle then pumps the blood a short distance, through a one-way valve called a pulmonary valve, to the lungs where the blood is oxygenated. When the oxygenated blood is returned to the left side of the heart from the lungs, the blood reaches the left upper, collection chamber, called the left atrium. Here, the blood is released through a second trapdoor opening, called a mitral valve, into the large, muscular left ventricle, which pumps the blood at high pressure through a one-way valve called an aortic valve to return the oxygenated blood back to the body.

Heart valve disease, such as those caused by damage or a defect, can include stenosis and valvular insufficiency or regurgitation. Valvular stenosis causes the valve to become narrowed and hardened which can prevent blood flow to a downstream heart chamber or structure (e.g., aorta) to occur at the proper flow rate and cause the heart to work harder to pump the blood through the diseased valve. Diseased or damaged valves, which can be congenital, age-related, drug induced, or caused by infection, can result in an enlarged, thickened heart that loses elasticity and efficiency.

Prosthetic heart valves have been developed for repair and replacement of diseased and/or damaged heart valves. Such valves can be percutaneously delivered and deployed at the site of the diseased heart valve through catheter-based systems. Such prosthetic heart valves can be delivered while in a low-profile or compressed/contracted arrangement so that the prosthetic valves can be contained within a sheath component of a delivery catheter and advanced through the patient's vasculature. Once positioned at the treatment site, the prosthetic valves can be expanded to engage tissue at the diseased heart valve region to, for instance, hold the prosthetic valve in position. While these prosthetic valves offer minimally invasive methods for heart valve repair and/or replacement, challenges remain to provide prosthetic valves that prevent leakage between the implanted prosthetic valve and the surrounding tissue (paravalvular leakage) and for preventing movement and/or migration of the prosthetic valve that could occur during the cardiac cycle.

For example, the repair or replacement of a valve can present numerous challenges due to differing anatomies and etiologies presented by individual patients, including varying sizes and topologies associated with an abnormal or unhealthy aortic valve that prevents proper alignment of the replacement (e.g., prosthetic) valve which can cause leakage, valve impingement or dislodgement of the prosthesis. Additionally, stenosis of a valve can deform the valvular area which can result in paravalvular leakage around an implanted replacement valve. Additional challenges can include providing a prosthetic valve that can be adjusted or repositioned during or after implantation and/or for replacing a previously implanted prosthetic valve.

In 1952 surgeons implanted the first mechanical heart valve. This first valve was a ball valve and it was designed by Dr. Charles Hufnagel. The recipient of this valve was a 30-year-old woman who could lead a normal life after the surgery. However, one downside of this design was that it could only be placed in the descending aorta instead of the heart itself. For this reason, it did not fully correct the valve problem, only alleviate the symptoms. However, it was a significant achievement because it proved that synthetic materials could be used to create heart valves.

In 1960, a new type of valve was invented and was successfully implanted. This valve is the Starr-Edwards ball valve, named after its originators. This valve was a modification of Hufnagel's original valve. The ball of the valve was slightly smaller and caged from both sides so it could be inserted into the heart itself.

The next development was tilting disc technology which was introduced in the late 1960s. These valves were a great improvement over the ball designs. The tilting disc technology allowed blood to flow in a more natural way while reducing damage to blood cells from mechanical forces. However, the struts of these valves tended to fracture from fatigue over time. As of 2003, more than 100,000 Omniscience and 300,000 Hall-Kaster/Medtronic-Hall tilting disc valves were implanted with essentially no mechanical failure.

In 1977, bi-leaflet heart valves were introduced by St. Jude. Similar to a native heart valve, blood flows directly through the center of the annulus of pyrolytic carbon valves mounted within nickel-titanium housing which makes these valves superior to other designs. However, a downside of this design is that it allows some regurgitation. A vast majority of mechanical heart valves used today have this design. As of 2003, more than 1.3 million St. Jude valves were deployed and over 500,000 Carbomedics valves with no failures to leaflets or housing. It should be noted that the human heart beats about 31 million times per year.

Development continues with compressible valves that are delivered via a catheter instead of requiring the trauma and complications of open heart surgery. This means that a cardiologist trained in endoscopy can, in theory, deploy a heart valve replacement during an outpatient procedure. However, transcatheter valves are often delivered by perforating the apex of the heart to access the ventricle, and the perforation is often used to anchor an annular valve replacement.

Additionally, a problem with stent-style replacement valves is that they often continue to have the regurgitation or leakage problems of prior generations of valves, as well as require expensive materials engineering in order to cope with the 100's of millions of cycles encountered during just a few years of normal heart function. Accordingly, there is still a need for alternative and simpler solutions to addressing valve-related heart pathologies.

BRIEF SUMMARY OF THE INVENTION

The invention provides numerous advantages over prior designs. One problem is the difficulty of fitting a large prosthetic valve inside the deliverable space of a transcatheter delivery catheter. Another problem stems from each patient requiring a different sized valve. Another problem involves the stenosis and/or calcification that occurs with existing heart valves. Another problem involves the difficulty of anchoring a transcatheter valve to heart tissue, as well as the difficulty of placing tissue anchors in the correct locations, and avoiding sensitive, electrically conductive heart tissue.

In one non-limiting embodiment, a biocompatible mesh disk can be deployed sequentially after the valve has been positioned in the valve annulus, allowing a larger sealing mesh disk to be used for greater sealing. By delivering the mesh disk separately, the circumference of the opening of the atrial flange can be uniform across patient types. This also allows a valve to have a diameter of, for example, 40 mm, while delivering a sealing disk having a diameter of, e.g. 60 mm. This significantly reduces the amount of material that is required to be delivered down a transcatheter delivery catheter.

In another non-limiting embodiment, the valve uses a flow control sleeve instead of a traditional leaflet valve to reduce stenosis and other hemodynamic problems, e.g. blood flow directionality.

In another non-limiting embodiment, the valve has Nitinol folding tabs attached to the atrial flange which are used to secure the mesh disk against the atrial flange and to provide a mounting platform for tissue anchors.

In another non-limiting embodiment, the heat-treated Nitinol folding tabs are able to be elongated away from the main body of the valve during the compression of the valve into the delivery catheter, which accommodates the limited delivery space within the transcatheter delivery catheter. This is especially important for a valve repair or replacement for a valve such as the tricuspid valve, which requires the delivery of a very large valve in pathological conditions. By staging, or segmenting, the inventive valve herein, the problem of fitting a large valve in a small transcatheter delivery catheter is addressed.

In another non-limiting embodiment, the valve body is asymmetric having a flat, septal side and channeled, flanged sides for the anterior and posterior annulus faces of the valve body.

In another non-limiting embodiment, the problems are addressed by providing a transcatheter delivered prosthetic valve having an asymmetric pericardial tissue covered wire frame with an upper angled collar of scalloped diamond-shapes forming an atrial flange, the atrial flange connected to a middle ring of longitudinally vertical diamond-shapes that is used to mount a reciprocating flow control conduit/tube, wherein the upper flange has a steep angle of inclination at the septal region, a shallower angle of inclination around the anterior and posterior annular regions, and an indent or cutout area near the coronary sinus region, wherein the septal region of the flange is contemplated as angled between 30-90 degrees to the horizontal plane of the annulus, and having a polyester material covering to promote tissue in-growth, and a non-leaflet containing reciprocating tube disposed with a lumen of the wire frame to reduce stenosis and calcification, and a plurality of folding wire tabs mounted on the wire frame, each of the plurality of folding wire tabs having at least one tissue anchor connected thereto for engaging annular tissue.

In some embodiments, there is a second lower angled collar of scalloped diamond shapes forming a sub-annular ventricular flange.

Accordingly, the present invention is directed in one preferred embodiment to a transcatheter heart valve replacement, comprising: (i) an asymmetric cylindrical wire frame with a septal wall of substantially vertical diamond-shaped cells, an axial lumen, and an annular channel opposite the septal wall where the annular channel is connected to an atrial flange on a proximal edge and is connected to a ventricular flange on a distal edge, and wherein the atrial flange has a coronary sinus cutout area from the wire frame, wherein the wire frame has an inner covering of pericardial tissue, and an outer covering of a polyester material; (ii) a reciprocating flow control sleeve mounted on a support member and disposed within the axial lumen of the asymmetric cylindrical wire frame; at least one folding wire tab mounted on and extending proximally from a circumferential edge of the atrial flange of the asymmetric cylindrical wire frame, each of the folding wire tabs having at least one tissue anchor connected thereto for engaging annular tissue; and (iii) a biocompatible mesh ring covering the atrial flange of the asymmetric cylindrical wire frame and covering a portion of the folding wire tab.

In another preferred embodiment, there is provided a transcatheter heart valve replacement wherein the reciprocating flow control sleeve is a three-panel collapsible tube valve mounted on a three-arch wire frame forming a lumen that has a triangular cross section.

In another preferred embodiment, there is provided a transcatheter heart valve replacement comprising: (i) an asymmetric wire frame with an atrial flange and an annular collar, said atrial flange having a plurality of angled substantially horizontal diamond-shape cells, and said annular collar having a plurality of substantially vertical diamond-shape cells defining a lumen; (ii) a reciprocating flow control sleeve mounted on the annular collar and disposed within the lumen; and (iii) a plurality of folding wire tabs mounted on the wire frame, each of the plurality of folding wire tabs having at least one tissue anchor connected thereto for engaging annular tissue; wherein the atrial flange has a steep angle of inclination at a septal region of the wire frame, and a shallower angle of inclination around anterior and posterior annular regions of the wire frame, and wherein the atrial flange has a coronary sinus cutout area from the wire frame; wherein the wire frame has an inner covering of pericardial tissue, and an outer covering of a polyester material.

In another preferred embodiment, there is provided a transcatheter heart valve replacement wherein there is a ventricular flange having substantially horizontal diamond-shape cells, said ventricular flange attached on a distal circumferential edge of said annular collar.

In another preferred embodiment, there is provided a transcatheter heart valve replacement comprising: an atrial sealing cuff frame, said cuff frame connected to a collapsible flow control sleeve that provides a reciprocating closable channel from a heart atrium to a heart ventricle, said cuff frame comprised of a braided or laser-cut wire frame having a substantially circular central aperture, said cuff frame partially covered with a biocompatible material, said collapsible flow control sleeve connected at an upper end to an inner perimeter of the central aperture of the cuff frame, and the collapsible flow control sleeve extending beyond the central aperture of the cuff frame and having a lower end positioned with the ventricle of the heart, and a plurality of folding wire tabs mounted on the wire frame, each of the plurality of folding wire tabs having at least one tissue anchor connected thereto for engaging annular tissue.

In another preferred embodiment, the invention comprises a transcatheter heart valve replacement as described and claimed herein, wherein the tissue anchor comprises a floating radiopaque marker threaded onto the tissue anchor, wherein advancing the tissue anchor through tissue moves the floating radiopaque marker from an initial distal lower thread position on the anchor to a secondary position on a higher thread.

In another preferred embodiment, the invention comprises a transcatheter heart valve replacement as described and claimed herein, wherein one or more of the tissue anchors are selected from the group consisting of: a straight thread constant pitch fastener, a tapered thread constant pitch fastener, a straight thread variable pitch fastener, a tapered thread variable pitch fastener, and a sunken taper thread variable pitch fastener.

In another preferred embodiment, the invention comprises a transcatheter heart valve replacement as described and claimed herein, wherein the cuff frame is configured as a flat cone shape having a diameter R of 50-70 mm, a diameter r of 20-30 mm, and a height of 20-40 mm.

In another preferred embodiment, the invention comprises a transcatheter heart valve replacement as described and claimed herein, wherein the cuff frame has an inner wall and an outer wall, said inner wall having a biocompatible material comprising pericardial tissue, and said outer wall having a biocompatible material comprising a woven synthetic polyester material.

In another preferred embodiment, the invention comprises a transcatheter heart valve replacement as described and claimed herein, wherein the cuff frame is configured as an hourglass flat conical shape having a top diameter R1 of 50-70 mm, a bottom diameter R2 of 50-70 mm, an internal diameter r of 20-30 mm, and a height of 20-50 mm.

In another preferred embodiment, the invention comprises a transcatheter heart valve replacement as described and claimed herein, wherein the collapsible flow control sleeve has an internal diameter of 20-30 mm and a height of 30-80 mm, said sleeve comprising three substantially flat rectangular panels of pericardial material joined to form a rounded triangular cylinder.

In another preferred embodiment, the invention comprises a transcatheter heart valve replacement as described and claimed herein, wherein the transcatheter heart valve replacement is compressible and fits when compressed within the internal diameter of a transcatheter implantation catheter having an internal diameter less than 22 Fr (7.33 mm) to 34 Fr (9.33 mm).

In another preferred embodiment, the invention comprises a transcatheter heart valve replacement as described and claimed herein, wherein the collapsible flow control sleeve is supported with one or more longitudinal supports integrated into a fabric or material of the collapsible flow control sleeve, the one or more longitudinal supports selected from rigid or semi-rigid ribs, rigid or semi-rigid battens, rigid or semi-rigid panels, and combination thereof.

In another preferred embodiment, the invention comprises a transcatheter heart valve replacement as described and claimed herein, wherein one or more of the tissue anchors or secondary tissue anchors are selected from the group consisting of: a helical coil, a screw, a dart, a pin, and a fastener means.

In another preferred embodiment, the invention comprises a method for securing a transcatheter heart valve prosthesis within a heart, the method comprising the steps: (i) advancing a procedure guide wire into a ventricle of a heart; (ii) advancing a 22 Fr-34 Fr steerable catheter over the procedure guide wire to deliver a compressed transcatheter heart valve prosthesis described herein to an atrium of the ventricle of the heart; (iii) advancing the catheter to the valve annulus and releasing the self-expanding atrial sealing collar from within the catheter; (iv) folding one or more wire tabs mounted on the wire frame from a vertical position to a horizontal position to align a tissue anchor on the one or more wire tabs with a tissue target using a transcatheter tissue anchor tool; (v) anchoring a tissue anchor through the wire frame and into the annular tissue using the transcatheter tissue anchor tool; and (vi) releasing said transcatheter tissue anchor tool from attachment to tissue anchor by actuating a release mechanism, and withdrawing the transcatheter tissue anchor tool, guide wire, and steerable catheter from the heart.

Accordingly, the present invention is directed to a method of using a radiopaque alignment device for delivering a surgical anchor, comprising the steps: (i) advancing an anchor-delivery lumen down a first transcatheter guide wire, said anchor-delivery lumen having a radiopaque ball at a distal end of the lumen, and having a radiopaque ring attached to the anchor-delivery lumen proximally to the radiopaque ball; (ii) using an imaging procedure, aligning the radiopaque ring with the radiopaque ball to establish an anchor target location; and (iii) advancing an anchor from within the aligned anchor-delivery lumen to the anchor target location and attaching the anchor to the target location, wherein the target location is selected from tissue or an anchorable surface of a medical device.

In another preferred embodiment, the invention provides a method for securing a transcatheter heart valve prosthesis within a heart, the method comprising the steps: (i) advancing a procedure guide wire into a ventricle of a heart; (ii) advancing a 22 Fr-34 Fr steerable catheter over the procedure guide wire to deliver a compressed transcatheter heart valve prosthesis to an atrium of the ventricle of the heart, the catheter having an extensible nosecone that houses at least a portion of the compressed transcatheter heart valve prosthesis, the transcatheter heart valve prosthesis comprising a self-expanding atrial sealing collar and a self-expanding ventricular sealing collar, each of said collars connected to a collapsible flow control sleeve that provides a reciprocating closable channel from heart atrium to heart ventricle, each of said collars comprised of a substantially flat braided or laser-cut wire frame covered with a biocompatible material and each having a central aperture, the collapsible flow control sleeve connected at an upper end to an inner perimeter of the central aperture of the self-expanding atrial sealing collar, the collapsible flow control sleeve connected at a middle section to an inner perimeter of the central aperture of the self-expanding ventricular sealing collar, and the collapsible flow control sleeve extending beyond the central aperture of the self-expanding ventricular sealing collar and having a lower end positioned within the ventricle of the heart; (iii) advancing the catheter to the valve annulus and extending the extensible nosecone away from the catheter to release the self-expanding atrial sealing collar, wherein the nosecone extends to a first intermediate position using a nosecone torque cable, wherein the extensible nosecone is extended distance d=1 as a partial extension along a central axis of the annulus in the direction from atrium to ventricle, wherein the extending to a first intermediate position to distance d=1 of the extensible nosecone from the catheter releases the self-expanding atrial sealing collar, said self-expanding atrial sealing collar having from 3-10 releasable spoke members releasably attached at a distal end to the atrial sealing collar, each of said releasable spoke members connected at a proximal end to a spoke torque cable disposed within the catheter, and each of said releasable spoke members paired with a spoke-release guide wire; and optionally step (iii) includes torqueing the atrial sealing collar into a aligned position; (iv) advancing the catheter nosecone to the ventricle and extending the extensible nosecone away from the catheter using a nosecone torque cable, wherein the extensible nosecone is extended distance d=2 as a full extension along a central axis of the annulus in the direction from atrium to ventricle, wherein the full extending of the extensible nosecone from the catheter releases the self-expanding ventricular sealing collar; (v) torqueing the transcatheter heart valve prosthesis to align the self-expanding atrial sealing collar with heart anatomy, the self-expanding atrial sealing collar having an irregular circumference defined by a narrow septal collar section, a wide anterior collar section adjacent one side of the narrow septal collar section, and a wide posterior collar section adjacent another side of the narrow septal collar section, wherein said torqueing aligns the narrow septal collar section with annular septal region; (vi) advancing a dart-delivery lumen down a first spoke-release guide wire, said dart-delivery lumen having a radiopaque ball at a distal end of the lumen, and having a radiopaque atrial ring attached to the lumen proximally to the radiopaque ball; (vii) using an imaging procedure, aligning the radiopaque atrial ring with the radiopaque ball, and aligning the radiopaque atrial ring and the radiopaque ball with a radiopaque target ring affixed to the ventricular sealing collar; (viii) anchoring two or more darts to the ventricular sealing collar by advancing each dart from the aligned dart-delivery lumen, through the atrial sealing collar to a radiopaque target ring affixed to the ventricular sealing collar; and (ix) releasing said 3-10 spoke members from attachment to the atrial sealing collar by actuating said spoke-release guide wires and withdrawing the steerable catheter from the heart.

In another preferred embodiment, the transcatheter heart valve replacement method includes wherein the dart has a pointed end and a groove with a flanged shoulder for inserting into an aperture in the ventricular sealing collar, said aperture having a diameter equal to or smaller than the diameter of the flanged shoulder, whereby inserting the pointed end of the pin into the aperture temporarily elastically expands the diameter of the aperture and locks the aperture around the groove securing the pin to the ventricular sealing collar.

In another preferred embodiment, the transcatheter heart valve replacement method includes wherein the step of (iv) tensioning the securement wire comprises pulling the securement wire through a cammed locking mechanism.

In another preferred embodiment, there is provided a transcatheter heart valve replacement system, comprising: (i) a 22 Fr-34 Fr steerable catheter; (ii) a procedure guide wire for deployment within the catheter; (iii) an extensible nose cone at a distal end of the catheter, and a nose cone torque cable attached to the nose cone and configured for deployment within the catheter; (iv) a transcatheter heart valve replacement having an atrial sealing collar and a ventricular sealing collar, each of said collars connected to a collapsible flow control sleeve that provides a reciprocating closable channel from a heart atrium to a heart ventricle, each of said collars comprised of a substantially flat braided or laser-cut wire frame covered with a biocompatible material and each having a central aperture, the collapsible flow control sleeve connected at an upper end to an inner perimeter of the central aperture of the atrial sealing collar, the collapsible flow control sleeve connected at a middle section to an inner perimeter of the central aperture of the ventricular sealing collar, and the collapsible flow control sleeve extending beyond the central aperture of the ventricular sealing collar and having a lower end positioned with the ventricle of the heart, and from 3-10 anchoring darts, said darts configured to connect the ventricular sealing collar and the atrial sealing collar; (v) at least three (3) spoke members attached to the atrial collar, said spoke members each having a spoke-release guide wire, said spoke members connected to a spoke torque cable, the self-expanding atrial sealing collar having an irregular circumference defined by a narrow septal collar section, a wide anterior collar section adjacent one side of the narrow septal collar section, and a wide posterior collar section adjacent another side of the narrow septal collar section, wherein said torqueing aligns the narrow septal collar section with annular septal region; and (vi) a dart-delivery catheter/lumen configured to be deployed using a spoke-release guide wire, said dart-delivery lumen having a radiopaque ball at a distal end of the lumen, a radiopaque atrial ring attached to the lumen proximally to the radiopaque ball, and a radiopaque target ring affixed to the ventricular sealing collar, wherein the radiopaque atrial ring, ball, and ventricular ring are configured to align dart delivery during an imaging procedure.

In another preferred embodiment, the transcatheter heart valve replacement system includes a secondary open framed annular collar attached to the atrial sealing collar, said open frame annular collar having 2-12 radial bracket supports and connecting the open framed annular collar to a central mounting hub, an elongated axial post having a proximal end attached to and extending away from the central mounting hub, and the elongated axial post disposed within a lumen of the collapsible flow control sleeve.

In another preferred embodiment, the transcatheter heart valve replacement system includes wherein the elongated axial post has a distal end that is fastened to a moderator band anchor.

In another preferred embodiment, the transcatheter heart valve replacement system includes wherein the transcatheter heart valve replacement is compressible and fits when compressed within the internal diameter of a transcatheter implantation catheter having an internal diameter less than 22 Fr (7.33 mm) to 34 Fr (9.33 mm).

In another preferred embodiment, the transcatheter heart valve replacement system includes wherein the collapsible flow control sleeve is attached at the distal end to 2-8 flexible sleeve tethers, the flexible sleeve tethers attached to the distal end of the elongated axial post.

In another preferred embodiment, the transcatheter heart valve replacement system includes wherein the collapsible flow control sleeve is attached at the distal end to 2-8 flexible sleeve tethers, the flexible sleeve tethers attached to a floating ring anchor, the floating ring anchor having a diameter slightly larger than the elongated axial post and the floating ring anchor circumscribing a distal end of the elongated axial post.

In another preferred embodiment, the transcatheter heart valve replacement system includes wherein the collapsible flow control sleeve is supported with one or more longitudinal supports integrated into a fabric or material of the collapsible flow control sleeve, the one or more longitudinal supports selected from rigid or semi-rigid ribs, rigid or semi-rigid batons, rigid or semi-rigid panels, and combination thereof.

In another preferred embodiment, the transcatheter heart valve replacement system includes wherein said darts are elongated with detent stops, or have securement wires, wherein the modified darts tension the atrial collar and the ventricular collar to compress native heart annular tissue between the collars to function as a securement and mounting mechanism.

In another preferred embodiment, the transcatheter heart valve replacement includes wherein the elongated axial post has a distal end that is fastened to a moderator band anchor.

In another preferred embodiment, the transcatheter heart valve replacement includes wherein the transcatheter heart valve replacement is compressible and fits when compressed within the internal diameter of a transcatheter implantation catheter having an internal diameter less than 34 Fr, or less than 32 Fr, or less than 30 Fr, or less than 28 Fr (9.33), or less than 26 Fr (8.67 mm), or less than 24 Fr (8.0 mm), or less than 22 Fr (7.33 mm).

In another preferred embodiment, the transcatheter heart valve replacement includes wherein the collapsible flow control sleeve is attached at the distal end to 2-8 flexible sleeve tethers, the flexible sleeve tethers attached to the distal end of the elongated axial post.

In another preferred embodiment, the transcatheter heart valve replacement includes wherein the collapsible flow control sleeve is attached at the distal end to 2-8 flexible sleeve tethers, the flexible sleeve tethers attached to a floating ring anchor, the floating ring anchor having a diameter slightly larger than the elongated axial post and the floating ring anchor circumscribing a distal end of the elongated axial post.

In another preferred embodiment, the transcatheter heart valve replacement includes wherein the collapsible flow control sleeve is supported with one or more longitudinal supports integrated into a fabric or material of the collapsible flow control sleeve, the one or more longitudinal supports selected from rigid or semirigid ribs, rigid or semi-rigid batons, rigid or semi-rigid panels, and combination thereof.

The invention provides numerous advantages over prior designs. Specifically, the problems are addressed by providing a transcatheter delivered prosthetic valve having an asymmetric pericardial tissue covered wire frame with an upper angled collar of scalloped diamond-shapes forming an atrial flange, the atrial flange connected to a middle ring of longitudinally vertical diamond-shapes that is used to mount a reciprocating flow control conduit/tube, wherein the upper flange has a steep angle of inclination at the septal region, a shallower angle of inclination around the anterior and posterior annular regions, and an indent or cutout area near the coronary sinus region, wherein the septal region of the flange is contemplated as angled between 30-90 degrees to the horizontal plane of the annulus, and having a polyester material covering to promote tissue in-growth, and a non-leaflet containing reciprocating tube disposed with a lumen of the wire frame to reduce stenosis and calcification, and a plurality of plication tissue anchors mounted on the wire frame for engaging annular tissue.

In some embodiments, there is a second lower angled collar of scalloped diamond shapes forming a sub-annular ventricular flange.

Accordingly, the present invention is directed to a transcatheter heart valve replacement comprising: (i) an asymmetric cylindrical wire frame with an upper angled collar of diamond-shaped cells forming an atrial flange, the cylindrical wire frame having a lumen, and the cylindrical wire frame having a biocompatible material covering the scalloped diamond-shaped cells; (ii) a reciprocating flow control sleeve mounted within the lumen of the cylindrical wire frame; and (iii) a plurality of wire plication cells, each plication cell comprised of a first wire arm and a second wire arm, said wire arms each attached to the atrial flange at a proximal end, and joined together to form a point at a distal end; at least one plication tissue anchor mounted on each wire arm for engaging annular tissue; and (iv) a plicator device operably associated with each wire plication cell, wherein the plicator device is movable from a distal position to a proximal position, and wherein said wire arms and said mounted plication tissue anchors are separated a maximum distance when the plicator device is at the distal position, and wherein moving the plicator device to a proximal position folds the wire arms together bringing the mounted plication tissue anchors together; wherein the atrial flange has a steep angle of inclination at a septal region of the wire frame, and a shallower angle of inclination around anterior and posterior annular regions of the wire frame, and wherein the atrial flange has a coronary sinus cutout area from the wire frame; wherein the wire frame has an inner covering of pericardial tissue, and an outer covering of a polyester material.

In another preferred embodiment, the invention comprises a transcatheter heart valve replacement comprising: (i) an atrial sealing cuff frame defining a lumen; (ii) a collapsible flow control sleeve connected to the cuff frame and disposed within the lumen, said flow control sleeve comprising a reciprocating closable channel from a heart atrium to a heart ventricle; said cuff frame comprised of a braided or laser-cut wire frame having a substantially circular central aperture, said cuff frame partially covered with a biocompatible material; said collapsible flow control sleeve connected at an upper end to an inner perimeter of the central aperture of the cuff frame, and the collapsible flow control sleeve extending beyond the central aperture of the cuff frame and having a lower end extending beyond the cuff frame; (iii) one or more wire plication cells extending from a circumferential edge of the cuff frame, each wire plication cell attached to the atrial flange at a proximal end, and joined together to form a point at a distal end, each wire plication cell having a circumferential shape selected from the group consisting of: a deltoid shape, a rhomboid shape, an ovate shape, and a cordate shape; (iv) a pair of plication tissue anchors mounted on each wire plication cell, said pair of plication tissue anchors separated by a pre-determined distance and mounted to engage annular tissue; and (v) a plicator device operably associated with each wire plication cell, wherein the plicator device is movable from a distal position to a proximal position, and wherein said wire arms and said mounted plication tissue anchors are separated a maximum distance when the plicator device is at the distal position, and wherein moving the plicator device to a proximal position folds the wire arms together bringing the mounted plication tissue anchors together; wherein the atrial flange has a steep angle of inclination at a septal region of the wire frame, and a shallower angle of inclination around anterior and posterior annular regions of the wire frame, and wherein the atrial flange has a coronary sinus cutout area from the wire frame; wherein the wire frame has an inner covering of pericardial tissue, and an outer covering of a polyester material.

In another preferred embodiment, the invention includes wherein the plicator device is a sleeve or a coil that advances over the compressible wire plication cell.

In another preferred embodiment, the invention includes wherein each compressible wire plication cell has a locking element on one of the first or second wire arms, and each plicator device is a sleeve or a coil that advances over the compressible wire plication cell, and has a detent element configured to cooperatively engage the locking element.

In another preferred embodiment, the invention includes wherein there is a second lower angled collar of diamond shaped cells forming a sub-annular ventricular flange.

In another preferred embodiment, the invention includes wherein the steep angle is between 30-90 degrees to the horizontal plane of the annulus.

In another preferred embodiment, the invention comprises a transcatheter heart valve replacement as described and claimed herein, wherein the plication tissue anchor comprises a floating radiopaque marker threaded onto the plication tissue anchor, wherein advancing the plication tissue anchor through tissue moves the floating radiopaque marker from an initial distal lower thread position on the anchor to a secondary position on a higher thread.

In another preferred embodiment, the invention comprises a transcatheter heart valve replacement as described and claimed herein, wherein one or more of the plication tissue anchors are selected from the group consisting of: a straight thread constant pitch fastener, a tapered thread constant pitch fastener, a straight thread variable pitch fastener, a tapered thread variable pitch fastener, and a sunken taper thread variable pitch fastener.

In another preferred embodiment, the invention comprises a transcatheter heart valve replacement as described and claimed herein, wherein the cuff frame is configured as a flat cone shape having a diameter R of 50-70 mm, a diameter r of 20-30 mm, and a height of 20-40 mm.

In another preferred embodiment, the invention comprises a transcatheter heart valve replacement as described and claimed herein, wherein the cuff frame has an inner wall and an outer wall, said inner wall having a biocompatible material comprising pericardial tissue, and said outer wall having a biocompatible material comprising a woven synthetic polyester material.

In another preferred embodiment, the invention comprises a transcatheter heart valve replacement as described and claimed herein, wherein the cuff frame is configured as an hourglass flat conical shape having a top diameter R1 of 50-70 mm, a bottom diameter R2 of 50-70 mm, an internal diameter r of 20-30 mm, and a height of 20-50 mm.

In another preferred embodiment, the invention comprises a transcatheter heart valve replacement as described and claimed herein, wherein the collapsible flow control sleeve has an internal diameter of 20-30 mm and a height of 30-80 mm, said sleeve comprising three substantially flat rectangular panels of pericardial material joined to form a rounded triangular cylinder.

In another preferred embodiment, the invention comprises a transcatheter heart valve replacement as described and claimed herein, wherein the transcatheter heart valve replacement is compressible and fits when compressed within the internal diameter of a transcatheter implantation catheter having an internal diameter less than 22 Fr (7.33 mm) to 34 Fr (9.33 mm).

In another preferred embodiment, the invention comprises a transcatheter heart valve replacement as described and claimed herein, wherein the collapsible flow control sleeve is supported with one or more longitudinal supports integrated into a fabric or material of the collapsible flow control sleeve, the one or more longitudinal supports selected from rigid or semi-rigid ribs, rigid or semi-rigid batons, rigid or semi-rigid panels, and combination thereof.

In another preferred embodiment, the invention comprises a transcatheter heart valve replacement as described and claimed herein, wherein one or more of the plication tissue anchors or secondary tissue anchors are selected from the group consisting of: a helical coil, a screw, a dart, a pin, and a fastener means.

In another preferred embodiment, the invention comprises a method for securing a transcatheter heart valve prosthesis within a heart, the method comprising the steps: (i) advancing a procedure guide wire into a ventricle of a heart; (ii) advancing a 22 Fr-34 Fr steerable catheter over the procedure guide wire to deliver a compressed transcatheter heart valve prosthesis to an atrium of the ventricle of the heart; (iii) advancing the catheter to the valve annulus and releasing the self-expanding atrial sealing collar from within the catheter; (iv) anchoring at least one wire plication cell to the annular tissue, wherein said anchoring comprises fastening a pair of plication tissue anchors to tissue one or near a native annulus or leaflet, wherein the plication tissue anchors are fastened at least 5 mm apart; and, (v) advancing the plicator device onto the at least one wire plication cell to fold the wire plication cell into a confined configuration and bring the pair of plication tissue anchors together.

Accordingly, the present invention is directed to a method for securing a transcatheter heart valve prosthesis within a heart, the transcatheter heart valve prosthesis comprising a supra-annular sealing collar and a sub-annular sealing collar, each of said collars connected to a collapsible flow control sleeve that provides a reciprocating closable channel from a heart atrium to a heart ventricle, each of said collars comprised of a substantially flat braided or laser-cut wire frame covered with a biocompatible material and each having a central aperture, the collapsible flow control sleeve connected at an upper end to an inner perimeter of the central aperture of the supra-annular sealing collar, the collapsible flow control sleeve connected at a middle section to an inner perimeter of the central aperture of the sub-annular sealing collar, and the collapsible flow control sleeve extending beyond the central aperture of the sub-annular sealing collar and having a lower end positioned with the ventricle of the heart, the method comprising the steps: (i) piercing the supra-annular sealing collar of the transcatheter heart valve prosthesis using a pin delivery tool; (ii) anchoring a pin into the sub-annular sealing collar of the transcatheter heart valve prosthesis using the pin delivery tool; (iii) detaching the pin from the pin delivery tool and withdrawing the pin delivery tool, said pin having a securement wire attached thereto, the securement wire disposed within an inner lumen of the pin delivery tool, wherein the securement wire is revealed by withdrawal of the pin delivery tool, and wherein the pin delivery tool is withdrawn above the supra-annular sealing collar; (iv) tensioning the securement wire to draw the sub-annular sealing collar toward the supra-annular sealing collar by reducing the length of the securement wire between the sealing collars; (v) fastening the securement wire to the supra-annular sealing collar and trimming the securement wire to disconnect the securement wire from the pin delivery tool; and (vi) repeating steps (i)-(v) to deploy from 2-12 pins and securement wires in the transcatheter heart valve prosthesis.

In another preferred embodiment, the method includes the step of (ii) anchoring comprises inserting a pin having a pointed end and a groove with a flanged shoulder into an aperture in the sub-annular sealing collar, said aperture having a diameter equal to or smaller than the diameter of the flanged shoulder, whereby inserting the pointed end of the pin into the aperture temporarily elastically expands the diameter of the aperture and locks the aperture around the groove securing the pin to the sub-annular sealing collar.

In another preferred embodiment, the method includes wherein the step of (iv) tensioning the securement wire comprises pulling the securement wire through a cammed locking mechanism.

The invention is also directed to a transcatheter heart valve replacement, comprising: (i) a supra-annular sealing collar and (ii) a sub-annular sealing collar, each of said collars connected to (iii) a collapsible flow control sleeve that provides a reciprocating closable channel from a heart atrium to a heart ventricle, each of said collars comprised of a substantially flat braided or laser-cut wire frame covered with a biocompatible material and each having a central aperture, the collapsible flow control sleeve connected at an upper end to an inner perimeter of the central aperture of the supra-annular sealing collar, the collapsible flow control sleeve connected at a middle section to an inner perimeter of the central aperture of the sub-annular sealing collar, and the collapsible flow control sleeve extending beyond the central aperture of the sub-annular sealing collar and having a lower end positioned with the ventricle of the heart, and (iv) from 2-12 fastening pins with securement wires, said fastening pins attached to the sub-annular sealing collar and said securement wires attached to the supra-annular sealing collar, wherein said fastening pins with securement wires are tensioned to compress native heart annular tissue between the collars to function as a securement and mounting mechanism.

In another preferred embodiment, the transcatheter heart valve replacement includes (v) a secondary open framed annular collar attached to the supra-annular sealing collar, said open frame annular collar having (vi) 2-12 radial bracket supports and connecting the open framed annular collar to (vii) a central mounting hub, (viii) an elongated axial post having a proximal end attached to and extending away from the central mounting hub, and the elongated axial post disposed within a lumen of the collapsible flow control sleeve.

In another preferred embodiment, the transcatheter heart valve replacement includes wherein the elongated axial post has a distal end that is fastened to a moderator band anchor.

In another preferred embodiment, the transcatheter heart valve replacement includes wherein the transcatheter heart valve replacement is compressible and fits when compressed within the internal diameter of a transcatheter implantation catheter having an internal diameter less than 22 Fr (7.33 mm).

In another preferred embodiment, the transcatheter heart valve replacement includes wherein the collapsible flow control sleeve is attached at the distal end to 2-8 flexible sleeve tethers, the flexible sleeve tethers attached to the distal end of the elongated axial post.

In another preferred embodiment, the transcatheter heart valve replacement includes wherein the collapsible flow control sleeve is attached at the distal end to 2-8 flexible sleeve tethers, the flexible sleeve tethers attached to a floating ring anchor, the floating ring anchor having a diameter slightly larger than the elongated axial post and the floating ring anchor circumscribing a distal end of the elongated axial post.

In another preferred embodiment, the transcatheter heart valve replacement includes wherein the collapsible flow control sleeve is supported with one or more longitudinal supports integrated into a fabric or material of the collapsible flow control sleeve, the one or more longitudinal supports selected from rigid or semirigid ribs, rigid or semi-rigid batons, rigid or semi-rigid panels, and combination thereof.

Accordingly, the present invention is directed to a medical implant, comprising a tricuspid pinch valve, having an open framed annular collar having 2-12 radial bracket supports disposed therein and connecting the open framed annular collar to a central mounting hub, an elongated axial tether having a proximal end attached to and extending away from the central mounting hub, and an elongated pliant conduit having a proximal end attached to and extending away from the open framed annular collar, with the elongated axial tether disposed within a lumen of the pliant conduit.

In another preferred embodiment, the elongated axial tether has a distal end that is fastened to a moderator band anchor.

In another preferred embodiment, the pinch valve is compressible and fits when compressed within the internal diameter of a transcatheter implantation catheter having an internal diameter less than 22 Fr (7.33 mm).

In another preferred embodiment, the open framed annular collar is attached to a flange along an external circumferential edge of the open framed annular collar.

In another preferred embodiment, the elongated pliant conduit has, at a distal end, 2-8 flexible conduit tethers, the flexible conduit tethers are connected to a distal end of the elongated axial tether.

In another preferred embodiment, the elongated pliant conduit has, at a distal end, to 2-8 flexible conduit tethers, the flexible conduit tethers are connected to a floating ring anchor, the floating ring anchor having a diameter slightly larger than the elongated axial tether and the floating ring anchor circumscribing a distal end of the elongated axial tether.

In another preferred embodiment, the open framed annular collar is attached to flange structure selected from a sub-annular flange, a supra-annular flange, and a sub-annular flange connected by a spanning stent to a supra-annular flange.

In another preferred embodiment, the tricuspid pinch valve has one or more toroidal sealing collars.

In another preferred embodiment, the elongated pliant conduit is supported with one or more longitudinal supports integrated into a fabric or material of the elongated pliant conduit, the one or more longitudinal supports selected from rigid or semi-rigid ribs, rigid or semi-rigid batons, rigid or semi-rigid panels, and combination thereof.

In another preferred embodiment, the open framed annular collar is an expandable stent.

In another preferred embodiment, the open framed annular collar is attached to an expandable vacuum compression stent, wherein the vacuum compression stent has a top flange, a spanning member, a bottom flange, and a toroidal compression bladder disposed with the circumference of the stent, wherein upon inflating the bladder the stent expands in height, and wherein upon deflating the bladder the stent decreases in height and creates an annular tissue compression between the top flange and the bottom flange.

In another preferred embodiment, the elongated pliant conduit is attached at a distal end to 2-8 flexible conduit tethers, the flexible conduit tethers attached to a ventricular frame, and the ventricular frame anchored to a distal end of the elongated axial tether.

In preferred method, the invention comprises a method for securing and positioning a pinch valve repair device within the right ventricle, comprising the steps: (i) loading a compressed pinch valve device described herein within the lumen of a transcatheter delivery system and percutaneously accessing a right side of a heart; (ii) expelling the compressed pinch valve device into the right atrium and expanding the pinch valve by releasing from a distal end of the transcatheter or by balloon inflating; and (iii) seating and securing the pinch valve into the native annulus, wherein the step of securing is selected from: (a) anchoring the open frame annular collar to the tricuspid annulus tissue; (b) anchoring the distal end of the elongated axial tether to the moderator band; (c) anchoring the proximal end of the elongated axial tether to a secondary stent deployed in an inferior or superior vena cava; and (d) a combination of the above.

BRIEF DESCRIPTION OF THE SEVERAL VIEWS OF DRAWINGS

FIG. 1 shows folding wire tabs having a tissue anchors for accessing annular tissue through the biocompatible material covering the valve frame.

FIG. 2 shows folding wire tabs for mounting tissue anchors to secure the valve to annular tissue, through the biocompatible material covering the valve frame.

FIG. 3 shows tissue anchors accessing annular tissue through the biocompatible material covering the valve frame.

FIG. 4 shows folding tabs having tissue anchors folded over a valve frame encircling a collapsible flow control sleeve.

FIG. 5 shows a valve prosthesis with a valve frame having an atrial cuff and three topologically diverse folding wire tabs with tissue anchors for mounting the heart valve prosthesis to the annular tissue.

FIG. 6 shows a valve prosthesis in a radially compressed configuration where the shape memory folding tabs are in a confined configuration and are elongated out of the main body, or annular portion, of the valve wire frame.

FIG. 7 shows a valve prosthesis in a radially expanded, partially uncompressed, configuration where the shape memory folding tabs are in a partially unconfined configuration and are shown elongated out of the main body, or annular portion, of the valve wire frame.

FIG. 8 shows a valve prosthesis in a radially expanded, fully uncompressed, configuration where the shape memory folding tabs are in a final, unconfined, shape-memory configuration and are shown elongated out of the main body, or annular portion, of the valve wire frame.

Figure 9:
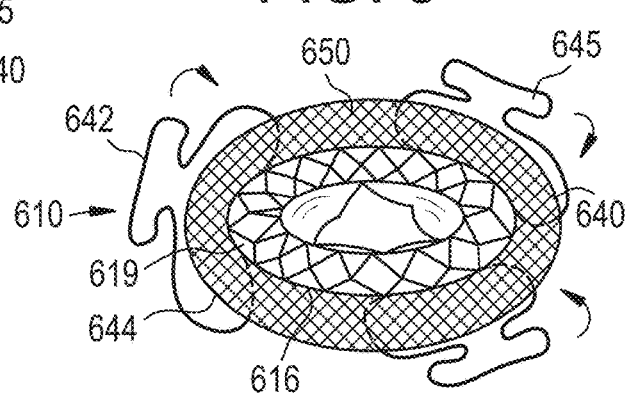

FIG. 9 is an illustration in a plan view of a heart valve prosthesis according to the present invention. FIG. 9 shows a valve prosthesis in a radially expanded, fully uncompressed, configuration where the shape memory folding tabs are in a final, unconfined, shape-memory configuration and are shown elongated out of the main body, or annular portion, of the valve wire frame. FIG. 9 shows biocompatible mesh ring mounted over the valve wire frame to cover the diamond-shaped wire frame and to overlap and cover a lower, bottom portion of the shape memory folding tabs.

Figure 10:
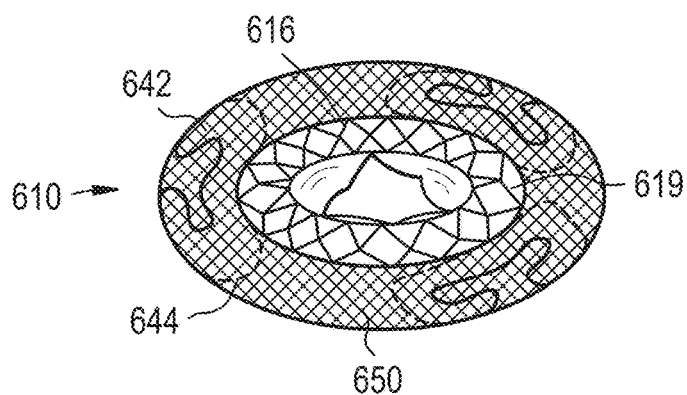

FIG. 10 is an illustration in a plan view of a heart valve prosthesis according to the present invention. FIG. 10 shows a valve prosthesis in a radially expanded, fully uncompressed, configuration where the shape memory folding tabs are in a final, unconfined, shape-memory configuration and are shown with an upper, top portion of the tabs folded inwards towards the main body, or annular portion, of the valve wire frame. FIG. 10 shows biocompatible mesh ring mounted over the valve wire frame to cover the diamond-shaped wire frame and to overlap and cover the lower, bottom portion of the shape memory folding tabs, with the upper, top portion of the shape memory folding tab folded over and sandwiching or covering, a portion of the biocompatible mesh ring.

Figure 11:
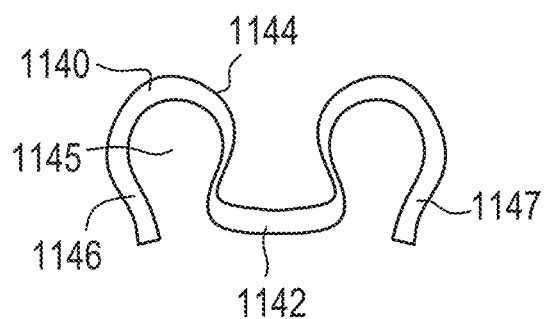

FIG. 11 is an illustration in a top view of a shape memory folding tab in a final, unconfined, shape-memory configuration. FIG. 11 shows folding tab having an upper, top portion in the center, and a lower, bottom portion on the left and right as connecting limbs that attach to the main body or annular portion of the wire frame.

Figure 12:
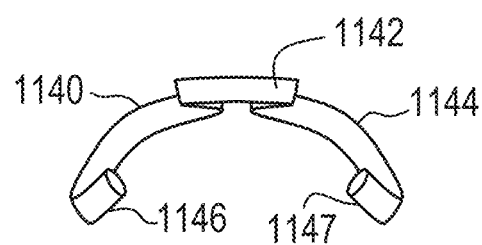

FIG. 12 is an illustration in a front view of a shape memory folding tab in a final, unconfined, shape-memory configuration. FIG. 12 shows folding tab having an upper, top portion in the center, and a lower, bottom portion on the left and right as connecting limbs that attach to the main body or annular portion of the wire frame.

Figure 13:
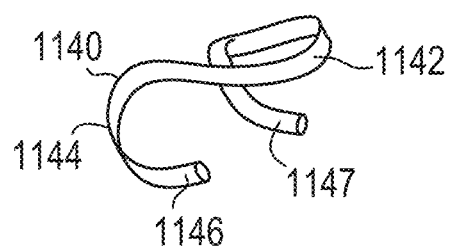

FIG. 13 is an illustration in a perspective view of a shape memory folding tab in a final, unconfined, shape-memory configuration. FIG. 13 shows folding tab having an upper, top portion in the center, and a lower, bottom portion on the left and right as connecting limbs that attach to the main body or annular portion of the wire frame.

Figure 14:
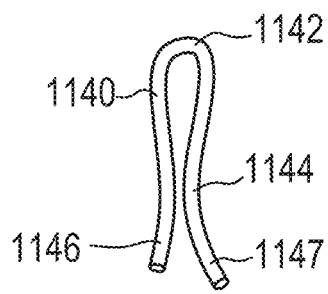

FIG. 14 is an illustration in a plan view of a shape memory folding tab in a compressed and elongated, or confined, shape-memory configuration. FIG. 14 shows folding tab having an upper, top portion in the center, and a lower, bottom portion on the left and right as connecting limbs that attach to the main body or annular portion of the wire frame.

Figure 15:
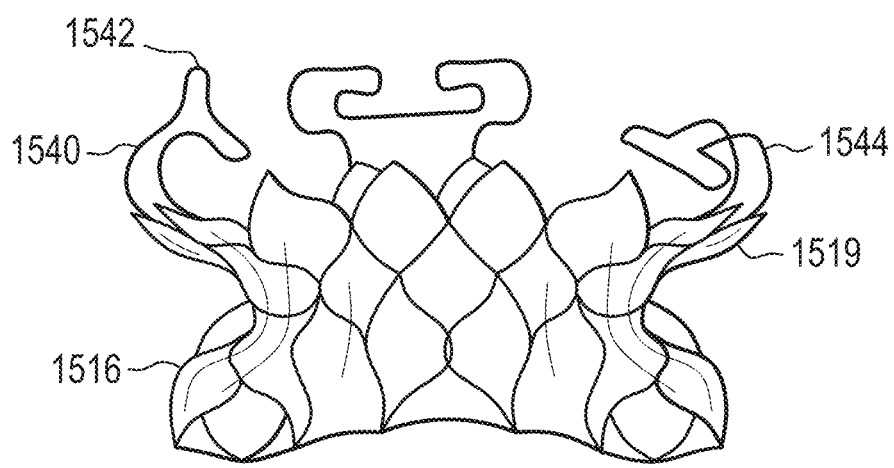

FIG. 15 is an illustration in a plan view of a valve prosthesis wire frame in a radially expanded, fully uncompressed, configuration where the shape memory folding tabs are in a final, unconfined, shape-memory configuration and are shown with an upper, top portion of the tabs folded inwards towards the main body, or annular portion, of the valve wire frame.

Figure 16:
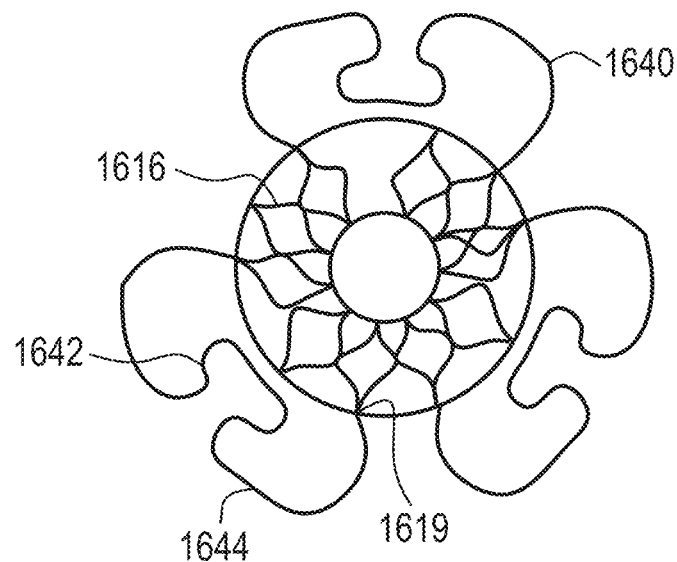

FIG. 16 is an illustration in a top view of another preferred embodiment of a wire-minimized one-diamond valve prosthesis wire frame in a radially expanded, fully uncompressed, configuration where the shape memory folding tabs are in a final, unconfined, shape-memory configuration and are shown with an upper, top portion of the tabs folded inwards towards the main body, or annular portion, of the valve wire frame.

Figure 17:
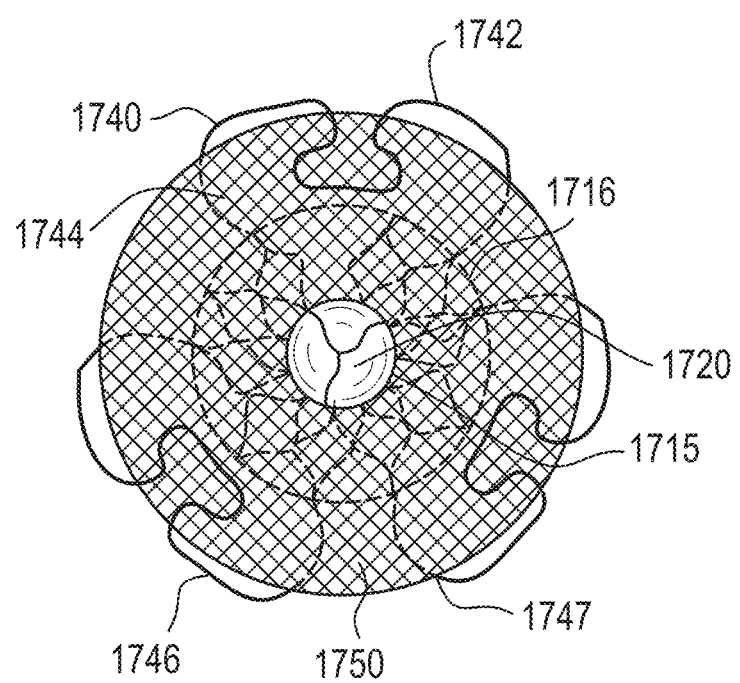

FIG. 17 is an illustration in a top view of another preferred embodiment of a one-diamond-height wire-minimized complete valve prosthesis having (i) a wire frame in a radially expanded, fully uncompressed, configuration where the shape memory folding tabs are in a final, unconfined, shape-memory configuration and are shown with an upper, top portion of the tabs folded inwards towards the main body, or annular portion, of the valve wire frame, (ii) biocompatible mesh disk mounted on the annular portion of the wire frame and across the lower, bottom portion, i.e. across the support arms, of the folding tabs, and under the folded-over upper, top portion of the folding tabs, and (iii) three-panel collapsible tube valve mounted within the axial, center aperture of the wire frame.

Figure 18:
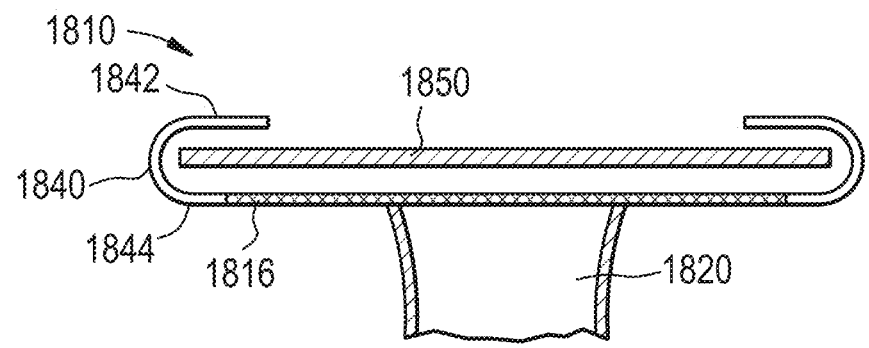

FIG. 18 is an illustration in a plan view of another preferred embodiment of a single flange valve prosthesis having (i) a wire frame in a radially expanded, fully uncompressed, configuration where the shape memory folding tabs are in a final, unconfined, shape-memory configuration and are shown with an upper, top portion of the tabs folded inwards towards the main body, or annular portion, of the valve wire frame, where the wire frame is comprised of an atrial flange only, (ii) biocompatible mesh disk mounted on the annular portion of the wire frame and across the lower, bottom portion, i.e. across the support arms, of the folding tabs, and under the folded-over upper, top portion of the folding tabs, and (iii) a three-panel collapsible tube valve mounted within the axial, center aperture of the wire frame.

Figure 19:
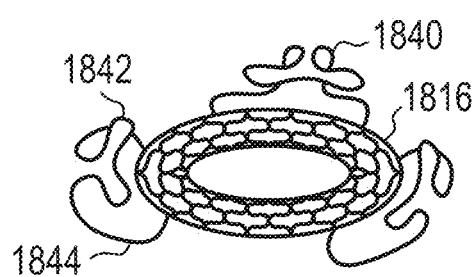

FIG. 19 is an illustration in a perspective view of a wire frame in a radially expanded, fully uncompressed, configuration where the shape memory folding tabs are in a final, unconfined, shape-memory configuration and are shown with an upper, top portion of the tabs folded inwards towards the main body, or annular portion, of the valve wire frame, where the wire frame is comprised of an atrial flange only.

Figure 20:
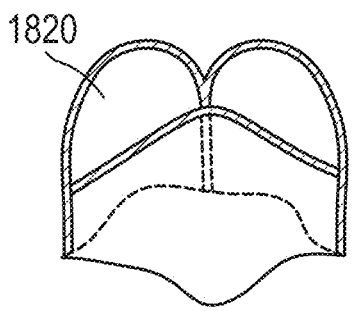

FIG. 20 is an illustration in a perspective view of a biocompatible mesh disk for mounting on the annular portion of the wire frame and across the lower, bottom portion, i.e. across the support arms, of the folding tabs, and under the folded-over upper, top portion of the folding tabs.

Figure 21:
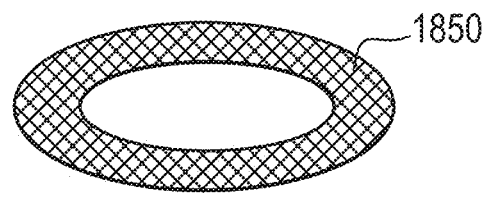

FIG. 21 is an illustration of a three-panel collapsible tube valve for mounting within the axial, center aperture of the wire frame.

Figure 22:
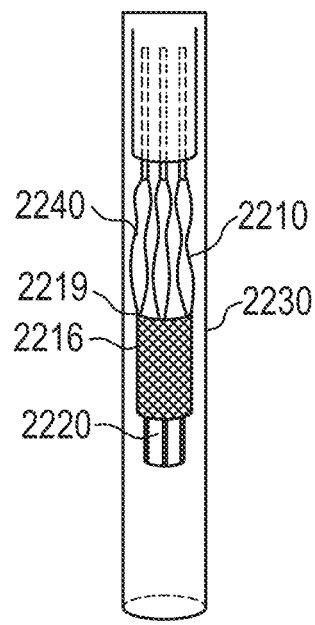

FIG. 22 is an illustration in a plan view of a compressed valve prosthesis within a delivery catheter, having (i) a wire frame in a radially compressed configuration where the shape memory folding tabs are in a confined, elongated shape-memory configuration attached to the main body, or annular portion, of the valve wire frame, which is further connected to the three-panel collapsible tube valve mounted within the axial, center aperture of the wire frame.

Figure 23:
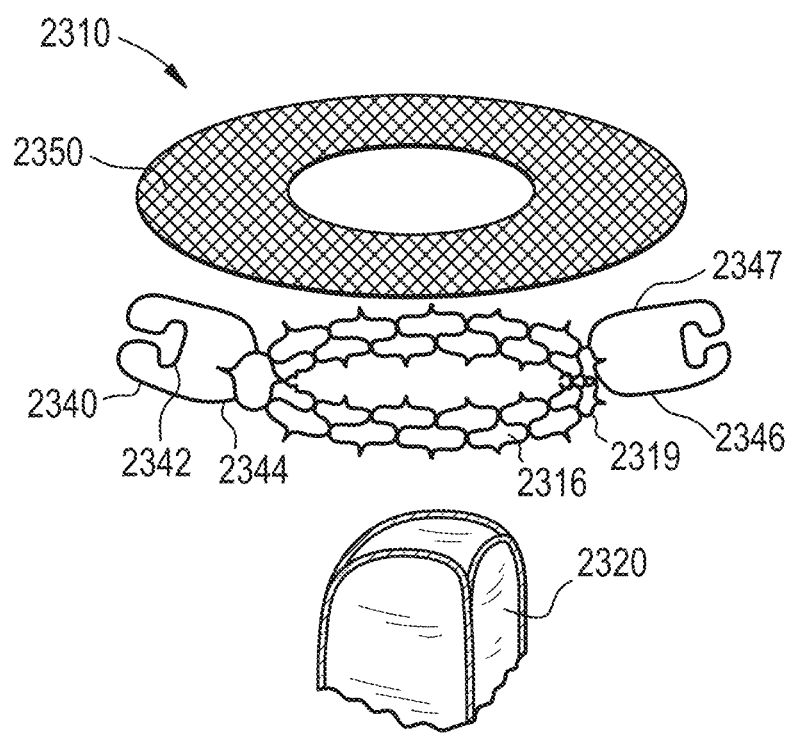

FIG. 23 is an illustration in an exploded view of another preferred embodiment of a single flange valve prosthesis having (i) a wire frame in a radially expanded, fully uncompressed, configuration where the shape memory folding tabs are in a final, unconfined, shape-memory configuration and are shown with an upper, top portion of the tabs folded inwards towards the main body, or annular portion, of the valve wire frame, where the wire frame is comprised of an atrial flange only, (ii) biocompatible mesh disk mounted on the annular portion of the wire frame and across the lower, bottom portion, i.e. across the support arms, of the folding tabs, and under the folded-over upper, top portion of the folding tabs, and (iii) three-panel collapsible tube valve mounted within the axial, center aperture of the wire frame.

Figure 24:
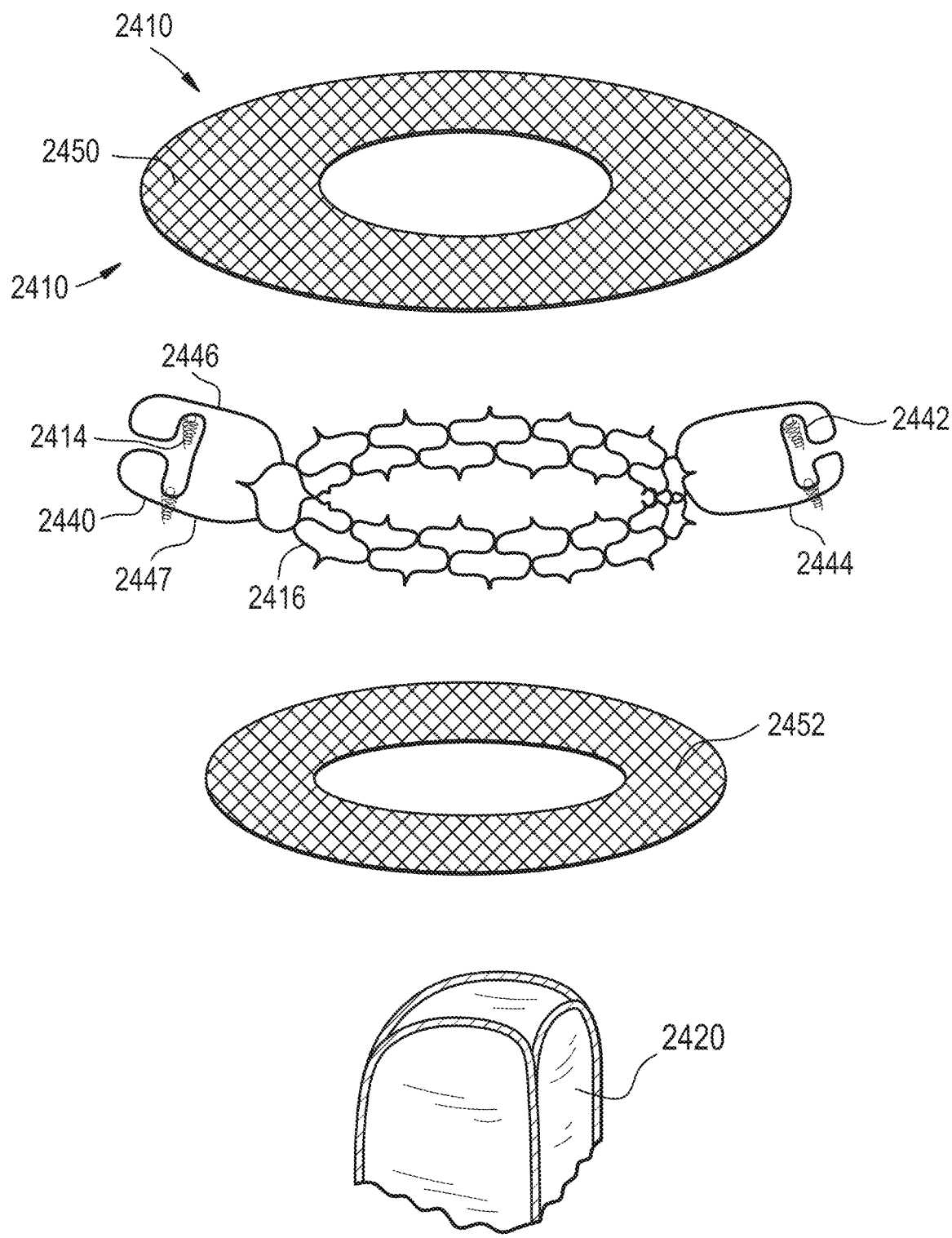

FIG. 24 is an illustration in an exploded view of another preferred embodiment of a single flange valve prosthesis having (i) a wire frame in a radially expanded, fully uncompressed, configuration where the shape memory folding tabs are in a final, unconfined, shape-memory configuration and are shown with an upper, top portion of the tabs folded inwards towards the main body, or annular portion, of the valve wire frame, where the wire frame is comprised of an atrial flange only, (ii) biocompatible mesh disk mounted on the annular portion of the wire frame and across the lower, bottom portion, i.e. across the support arms, of the folding tabs, and under the folded-over upper, top portion of the folding tabs, a (iii) three-panel collapsible tube valve mounted within the axial, center aperture of the wire frame, and (iv) a second biocompatible mesh mounted below the wire frame.

Figure 25A:
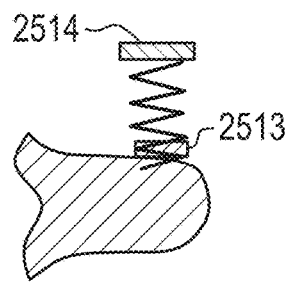
Figure 25B:
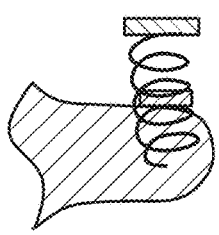
Figure 25C:
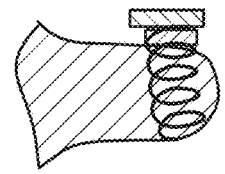

FIGS. 25A to 25C are an illustration of a plan view of a tissue anchor having a floating radiopaque marker. FIG. 25A shows the tissue anchor accessing the annular tissue withe the radiopaque marker at the distal end of the anchor and in contact with the atrial surface of the annular tissue. FIG. 25B shows the tissue anchor advancing into the annular tissue with the radiopaque marker threaded onto the tissue anchor and maintaining position on the atrial surface of the annular tissue. FIG. 25C shows the tissue anchor completely advanced into the annular tissue such that the tissue anchor and the threaded floating marker are now adjacent, indicating the desired depth, tension, and/or plication of the tissue anchor with respect to the annular tissue.

Figure 26:
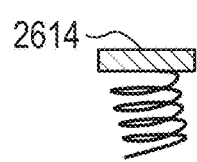

FIG. 26 is an illustration of a plan view of a tissue anchor having a straight thread and a constant pitch.

Figure 27:
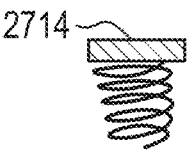

FIG. 27 is an illustration of a plan view of a tissue anchor having a straight thread and a variable pitch.

Figure 28:
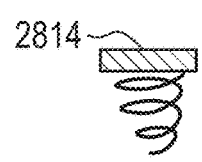

FIG. 28 is an illustration of a plan view of a tissue anchor having a tapered thread and a constant pitch.

Figure 29:
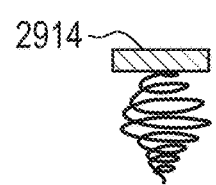

FIG. 29 is an illustration of a plan view of a tissue anchor having a variable taper thread and a constant pitch.

Figure 30:
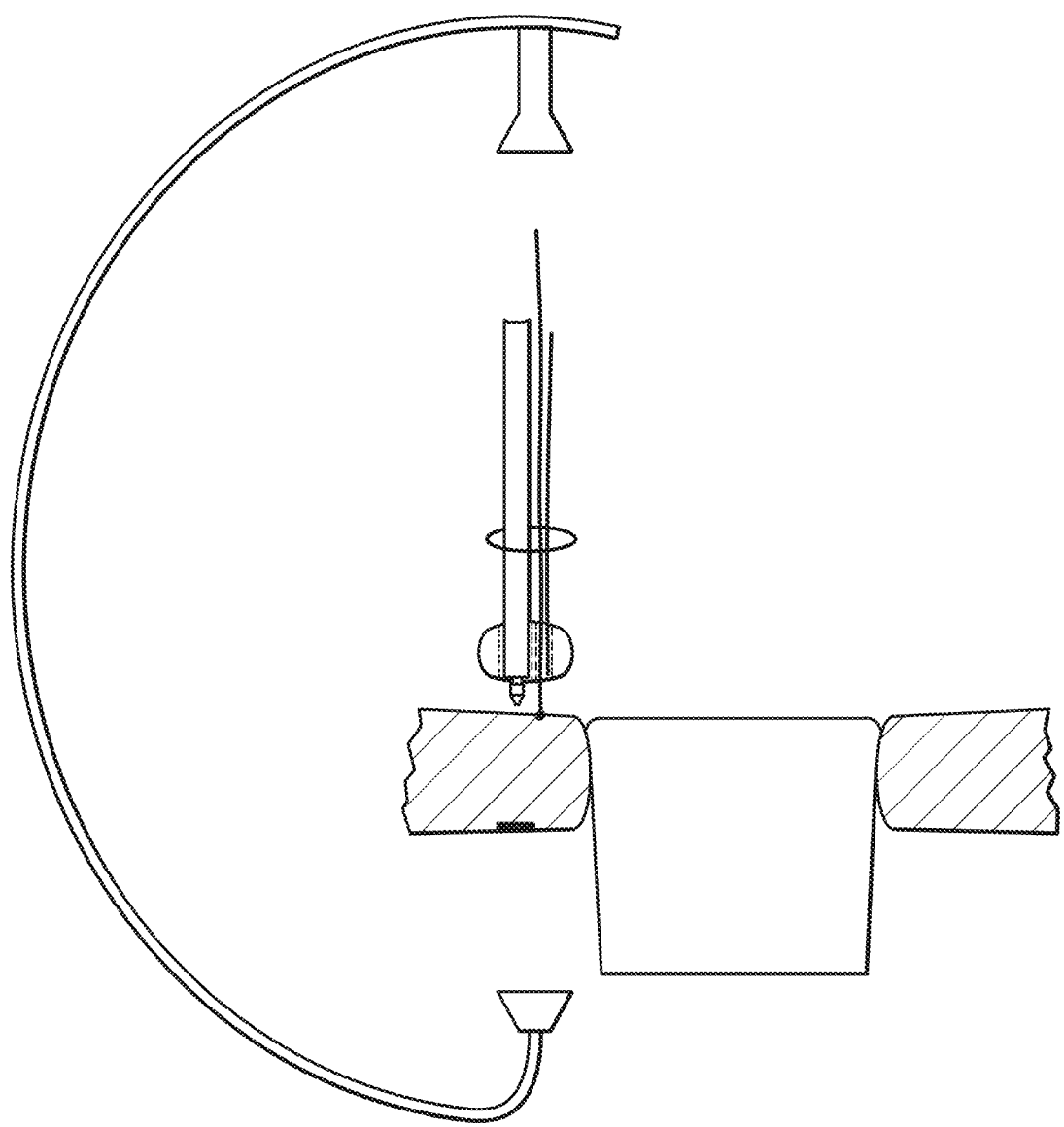

FIG. 30 is an illustration of a plan view of an alignment system according to the present invention. FIG. 30 shows a pair of imaging transceivers, e.g. fluoro, providing illumination along the axis of the dart delivery catheter/lumen with the three radiopaque targeting sights in x and y-axis alignment.

Figure 31:
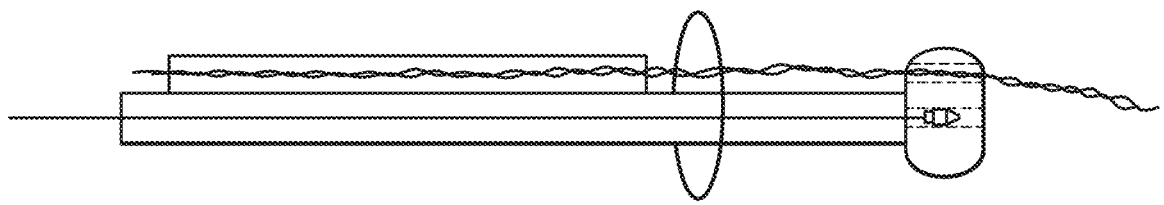
Figure 31:
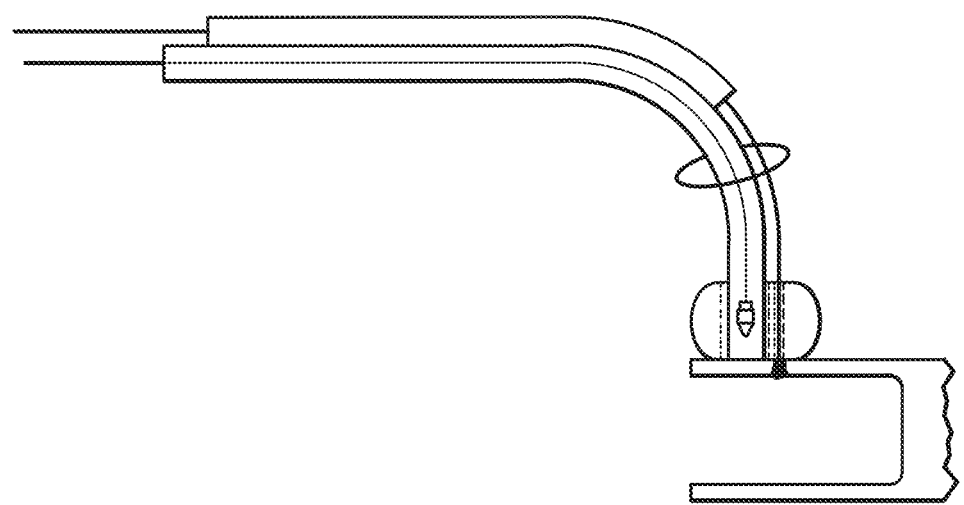

FIG. 31 is an illustration of a plan view of dart delivery catheter of an alignment system according to the present invention. FIG. 31 shows that guide wires and radiopaque markers can be delivered using a single steerable catheter.

Figure 32:
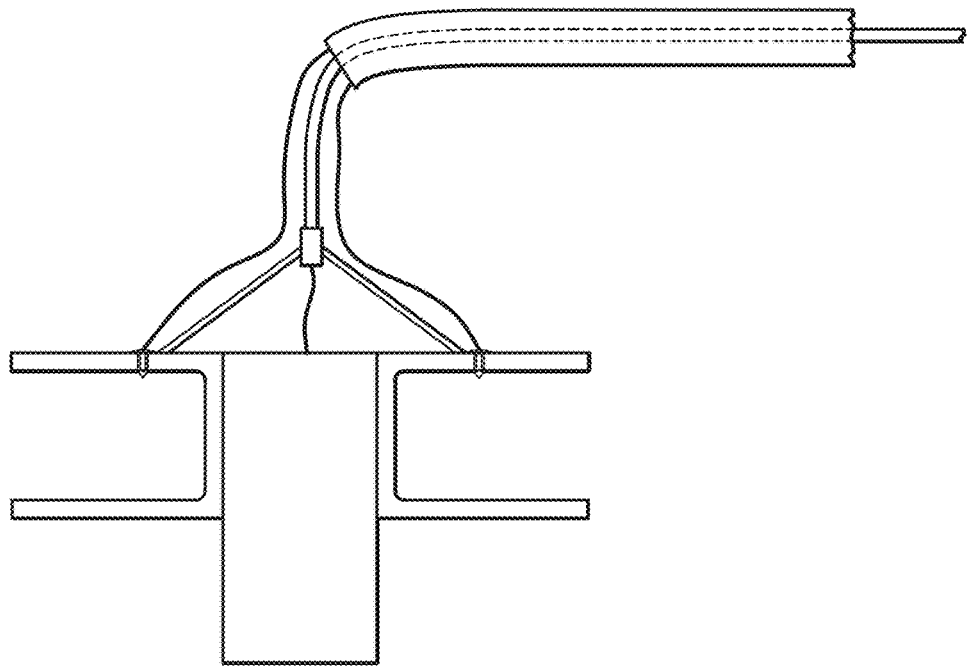

FIG. 32 is an illustration of a plan view of the spoke system with spoke-release guide wires of an alignment system according to the present invention. FIG. 32 shows how the spoke system is used to torque the valve into proper position within the native annulus of a tricuspid or mitral valve.

Figure 33:
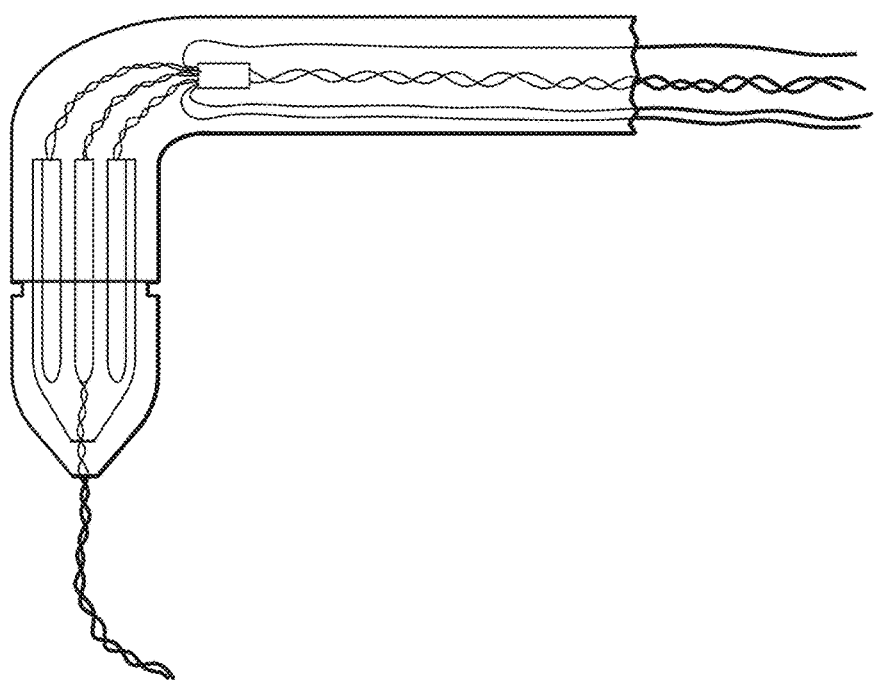

FIG. 33 is an illustration of a plan view of a compressed transcatheter prosthetic valve within the steerable catheter of an alignment system according to the present invention. FIG. 33 shows nose cone housing part of the valve to allow for stepped, section by section delivery of the valve.

Figure 34:
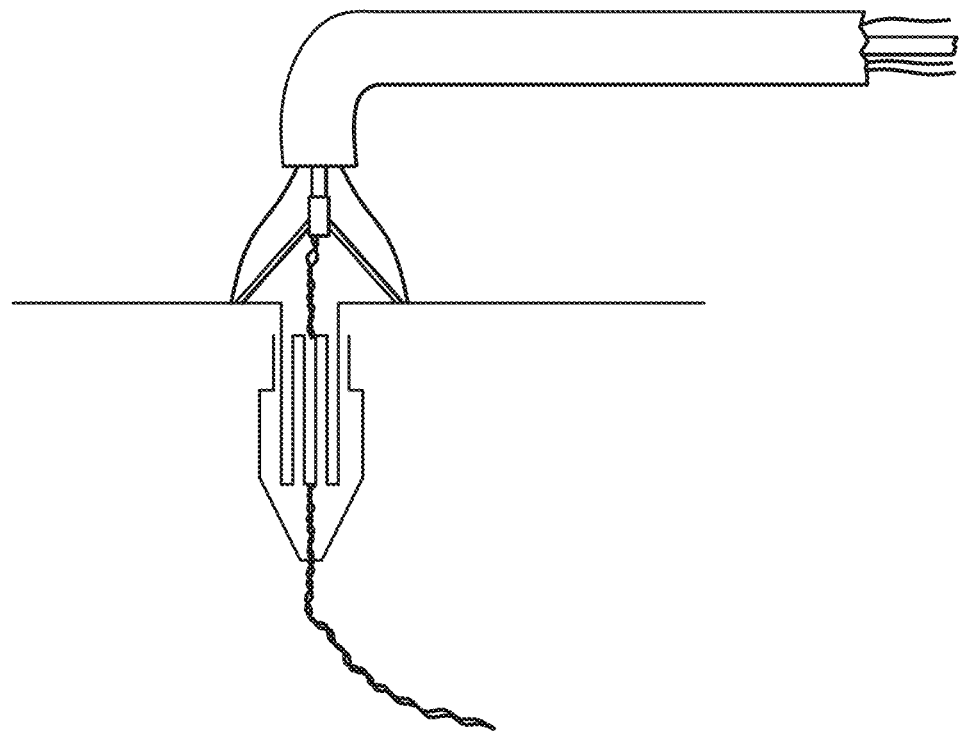

FIG. 34 is an illustration of a plan view of the compressed transcatheter valve partially expelled by extension of the nose cone to release the atrial side collar. FIG. 34 shows spoke attached to the atrial side of the atrial sealing collar.

Figure 35:
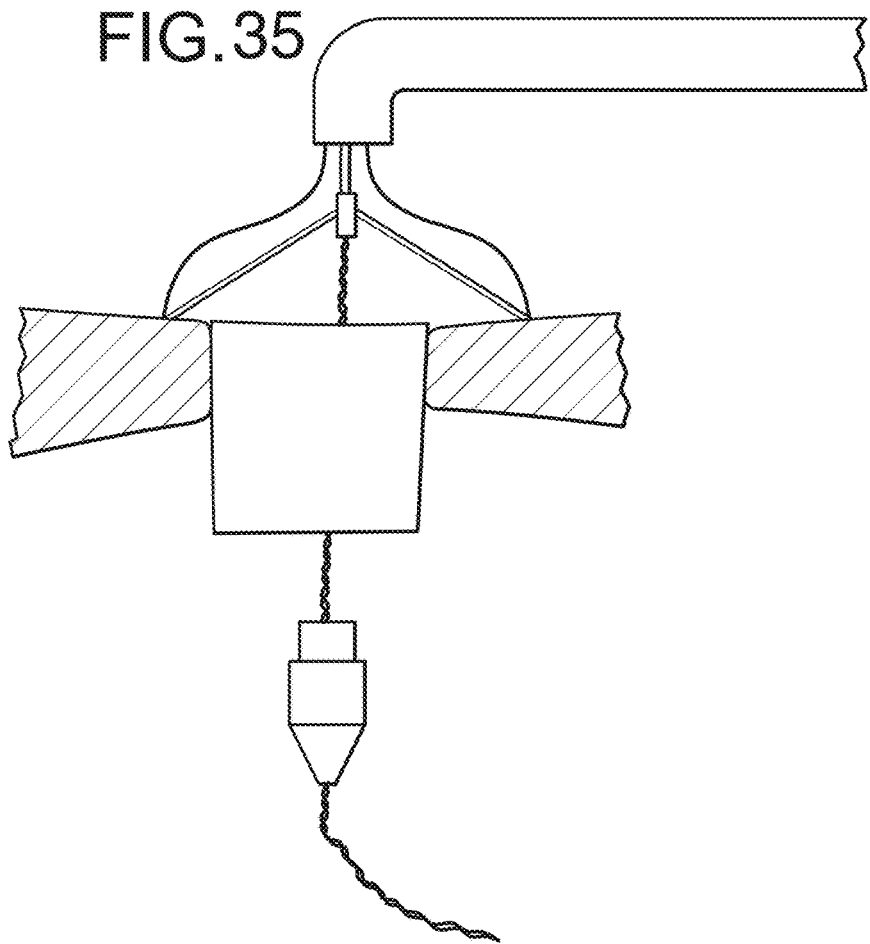

FIG. 35 is an illustration of a plan view of a nose cone fully extended releasing the ventricular sealing collar in the second stage of the staged delivery. FIG. 35 shows how the spokes can be used to torque the valve into proper alignment prior to pin/dart anchoring.

Figure 36:
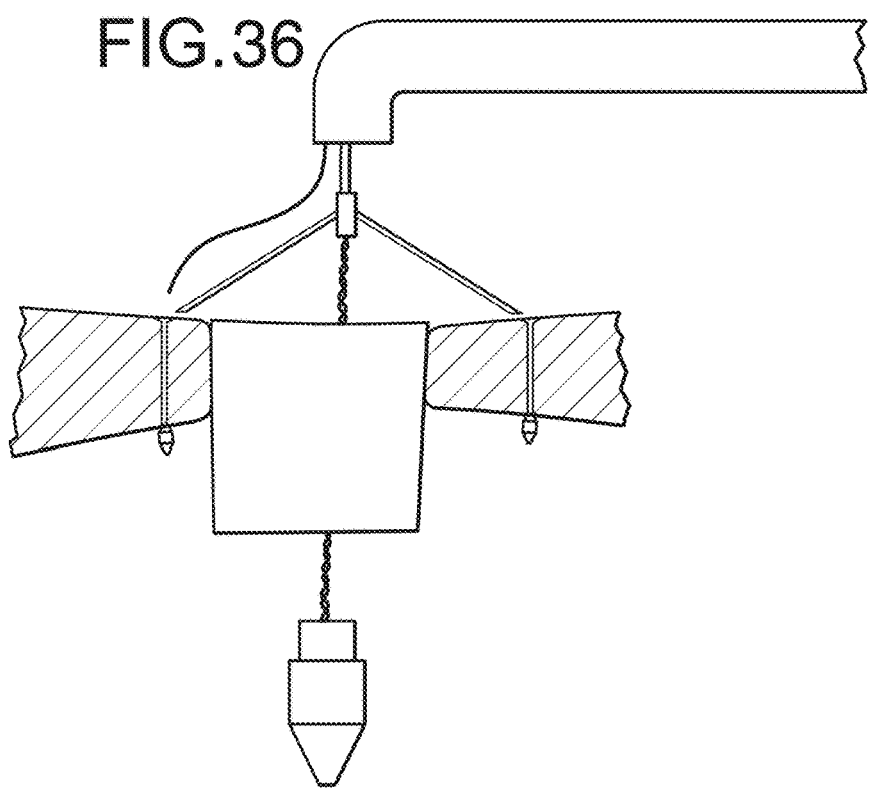

FIG. 36 is an illustration of a plan view of a deployed valve of an alignment system according to the present invention. FIG. 36 shows how release of the spoke guide wire releases the spoke from the atrial sealing collar.

Figure 37:
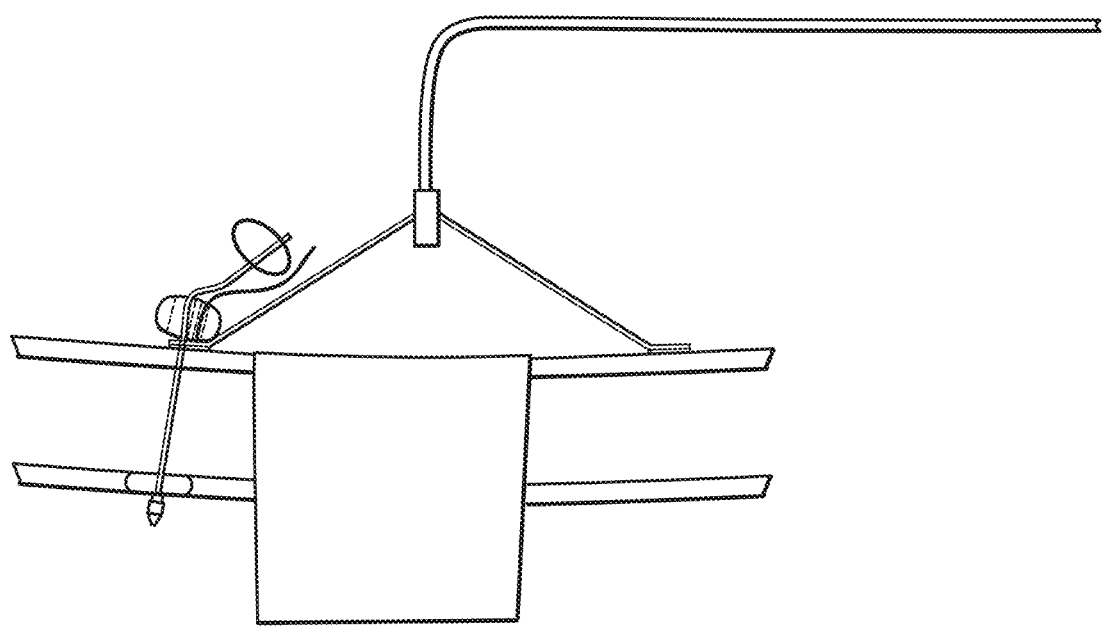

FIG. 37 is an illustration of a plan view of the dart catheter or lumen that is used to deliver the radiopaque markers and the anchoring dart according to the present invention.

Figure 38:
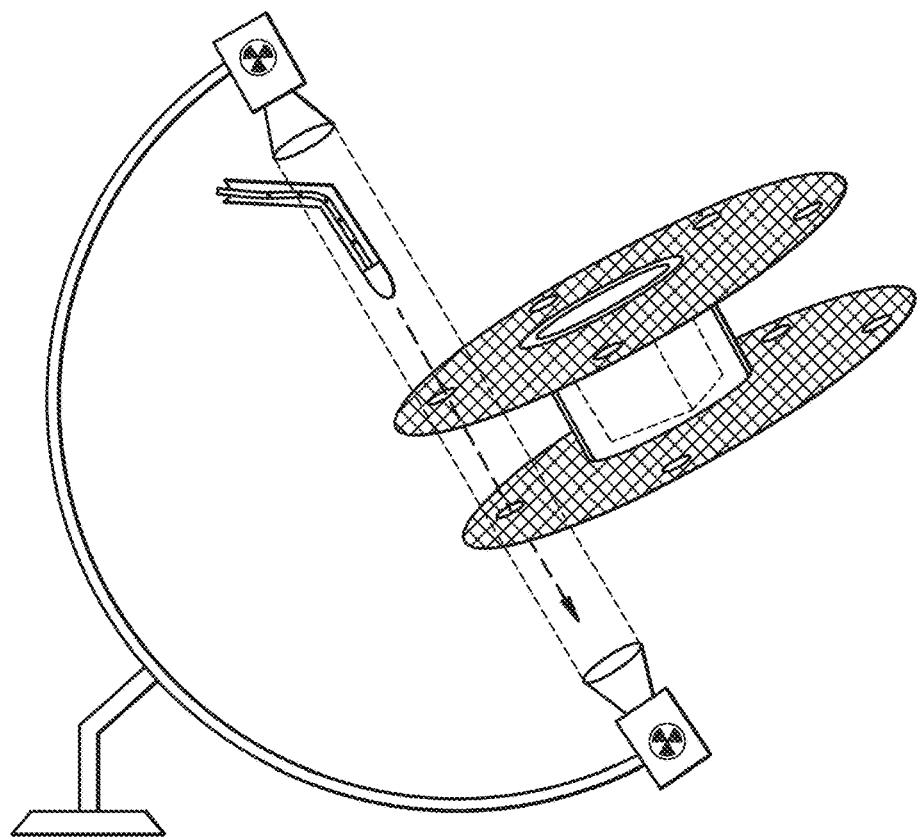

FIG. 38 is an illustration of a perspective view of a valve with alignment system having imaging, radiopaque markers, and catheter dart deployment according to the present invention.

Figure 39A:
Figure 39B:
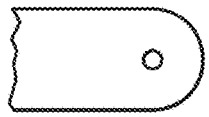
Figure 39C:
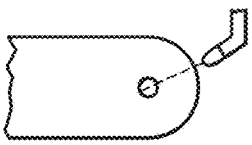

FIGS. 39A-39C are an illustration of a plan view of a time sequence according to the present invention.

Figure 40:
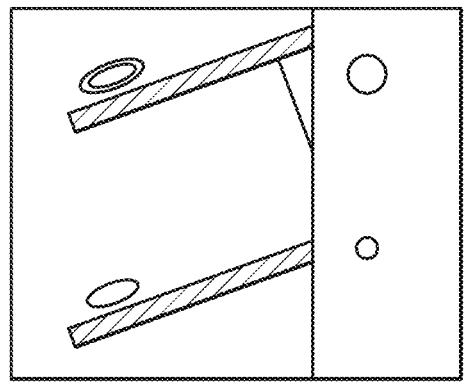
Figure 41:
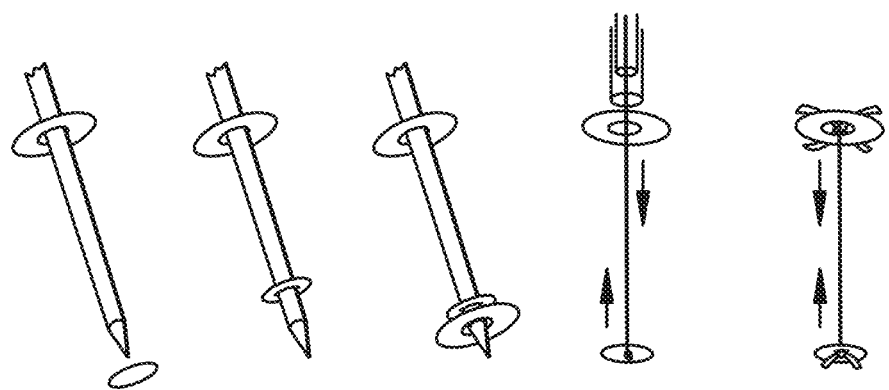

FIG. 40 is an illustration of a plan view of another embodiment of a target sight aligning mechanism according to the present invention FIG. 41 is an illustration of a plan view of a time-sequence of a dart/pin being deployed thru the upper collar, then anchoring into the lower collar/flange according to the present invention.

Figure 42:
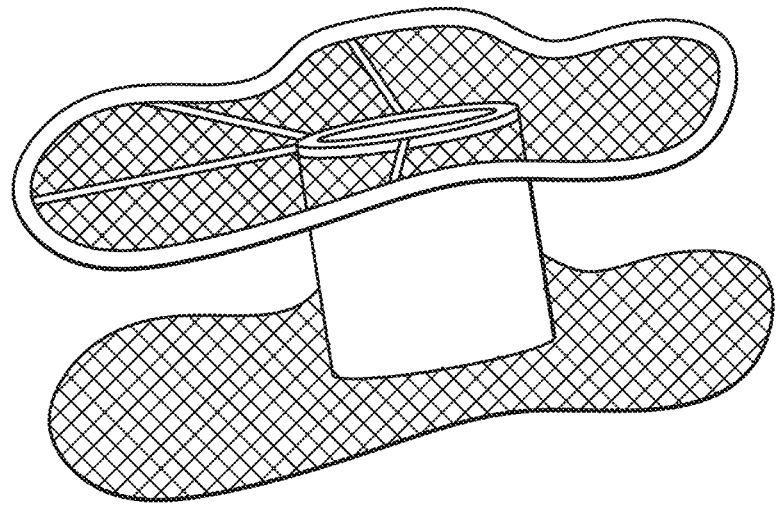

FIG. 42 is an illustration of a perspective view of a valve having an irregular shaped (circumference) tailored to a patient's specific anatomy according to the present invention.

Figure 43:
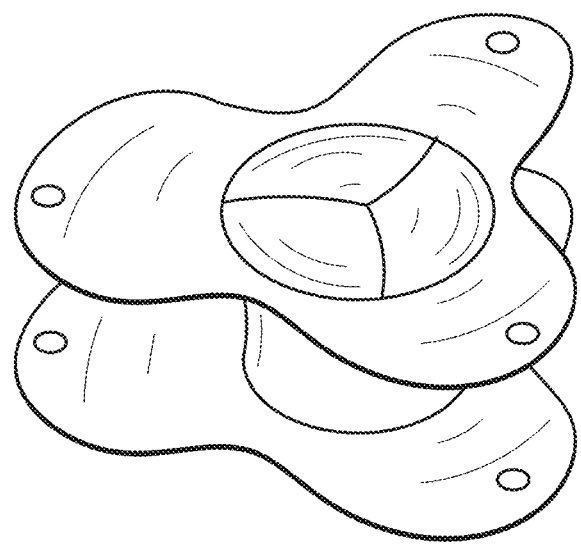
Figure 44:
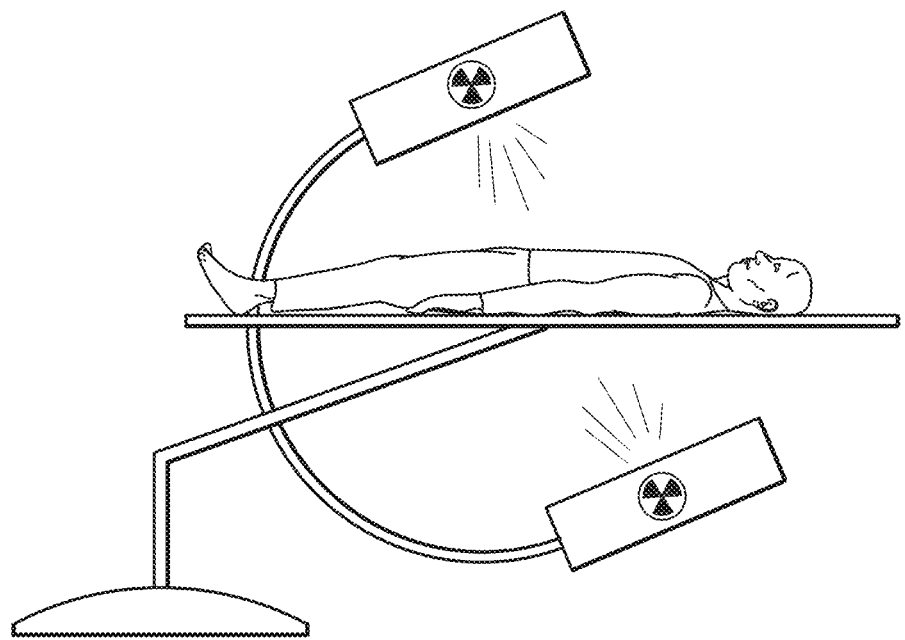
Figure 45:
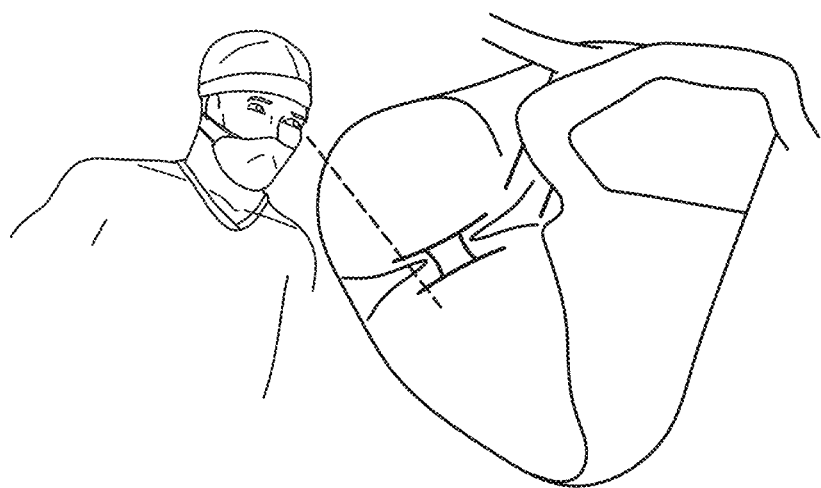

FIG. 43 is an illustration of a perspective view of a three-lobed, double-flanged (collared) annulus spanning valve according to the present invention FIG. 44 is an illustration of a plan view of an example of a radiography apparatus, e.g. fluoro, for performing imaging in real time on a patient who is receiving a transcatheter valve according to the present invention FIG. 45 is an illustration of a plan view of a cardiologist, surgeon, or interventionalist highlighting the difficulty in blind pinning through a first collar, then through captured tissue, and finally affixing to a lower collar according to the present invention.

Figure 46:
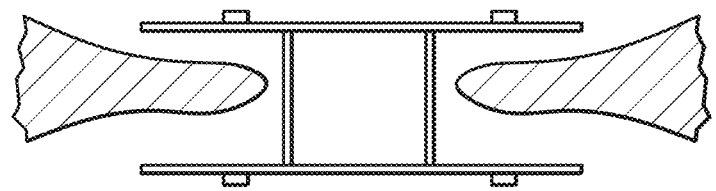
Figure 46:
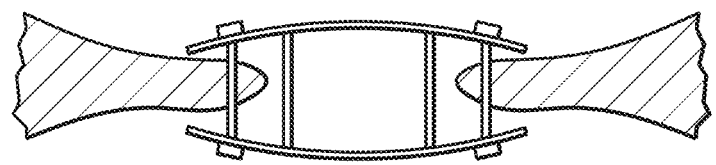

FIG. 46 is an illustration of a plan view of a valve according to the present invention before deployment of the pins/darts, and after installation of the pins/darts.

Figure 47:
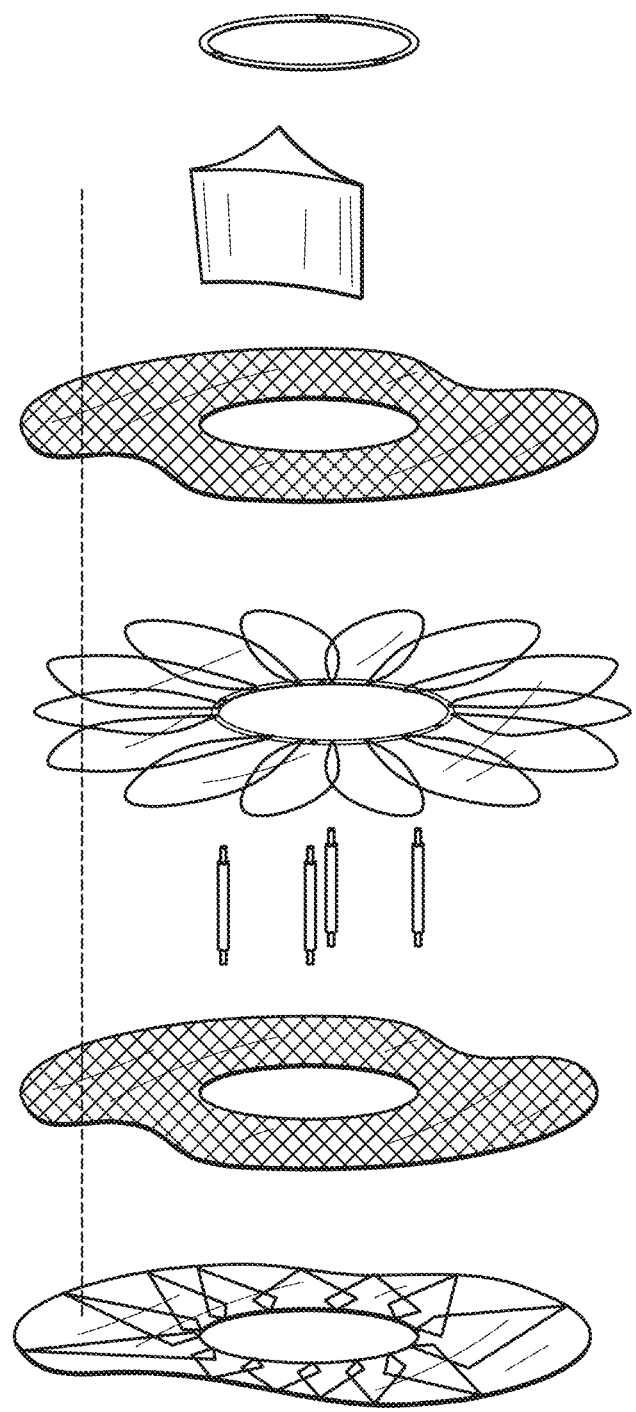

FIG. 47 is an illustration of an exploded view of a transcatheter valve according to the present invention. FIG. 18 shows an example of one of the plurality of pinning paths that are used to secure the atrial collar to the ventricular collar and capture the annular tissue therebetween.

Figure 48:
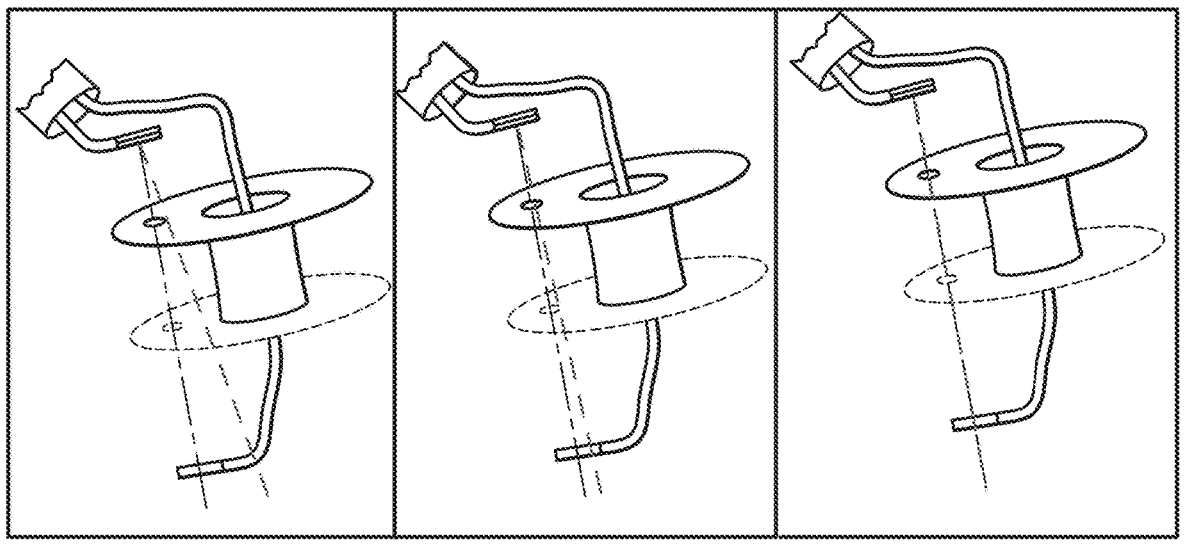
Figure 48:
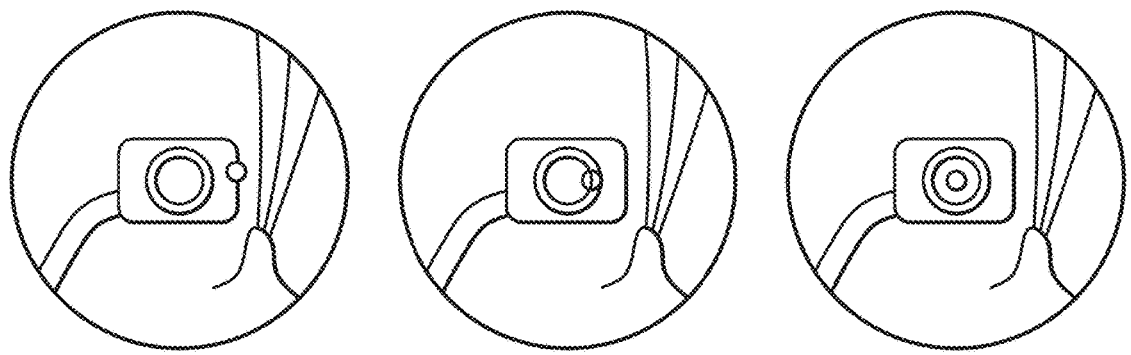

FIG. 48 is an illustration of a series in three parts showing alignment mechanism and method.

Figure 49:
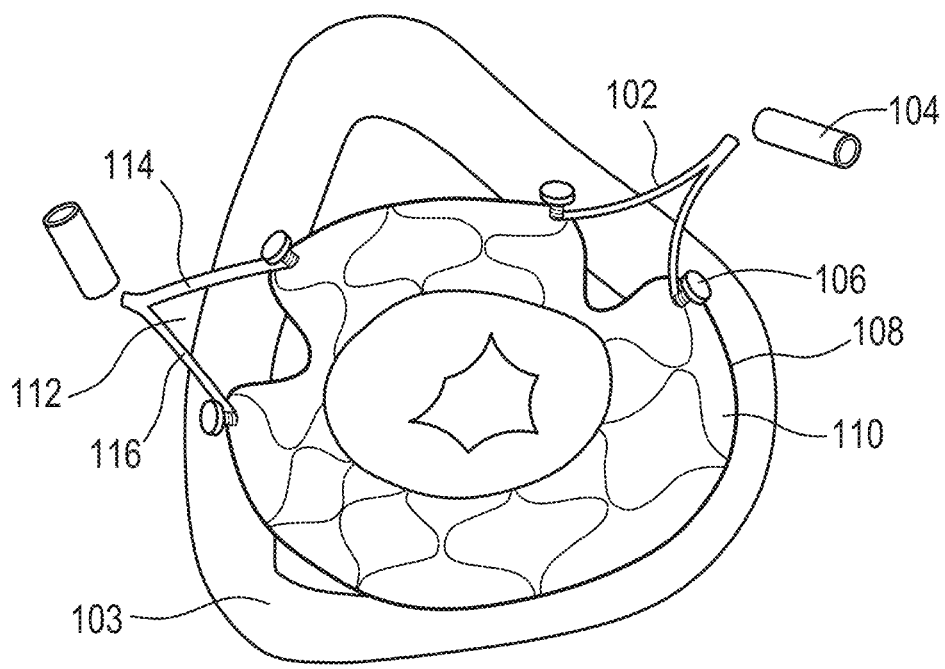

FIG. 49 is an illustration of a perspective top view of a heart valve prosthesis according to the present invention having a flange-integrated plication cell, sleeve plicator, and screw-type tissue anchors. FIG. 49 shows a valve frame having an atrial cuff component, the atrial cuff or flange having a plication gap formed from a plication cell that is integrated with, or integral to, the diamond cells of the flange, and extending from the circumferential edge of the atrial flange, creating an over-sized diamond cell, the plication cell having a first arm and a second arm, with a plication tissue anchor mounted on each arm of the plication cell on either side of the plication gap. FIG. 49 shows a pair of screw-type tissue anchors accessing annular tissue.

Figure 50:
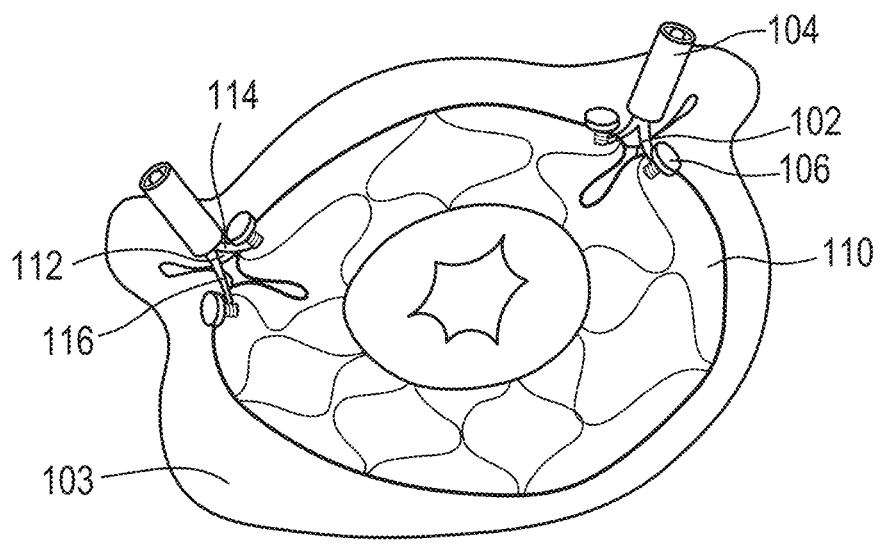

FIG. 50 is an illustration of a perspective top view of a heart valve prosthesis according to the present invention having a flange-integrated plication cell, sleeve plicator, and screw-type tissue anchors. FIG. 50 shows a valve frame having an atrial cuff component, the atrial cuff or flange having a closed plication cell formed from the folding or compression of the plication cell using a plicator device, e.g. a sleeve that confines, compresses, folds the first arm and the second arm of the plication cell together. FIG. 50 shows that by closing the plication gap with the plicator device, the plication tissue anchor that is mounted on each arm of the plication cell on either side of the plication gap cause the annular tissue to fold and plicate, and reduces the circumference of the native annulus. This ability to cinch or plicate the native annular tissue around a limited number of standard sizes of prosthetic valves reduces the problem of fitting each prosthesis to each patient's specific anatomy, simplifying the procedure for the cardiac interventionalist/physician.

Figure 51:
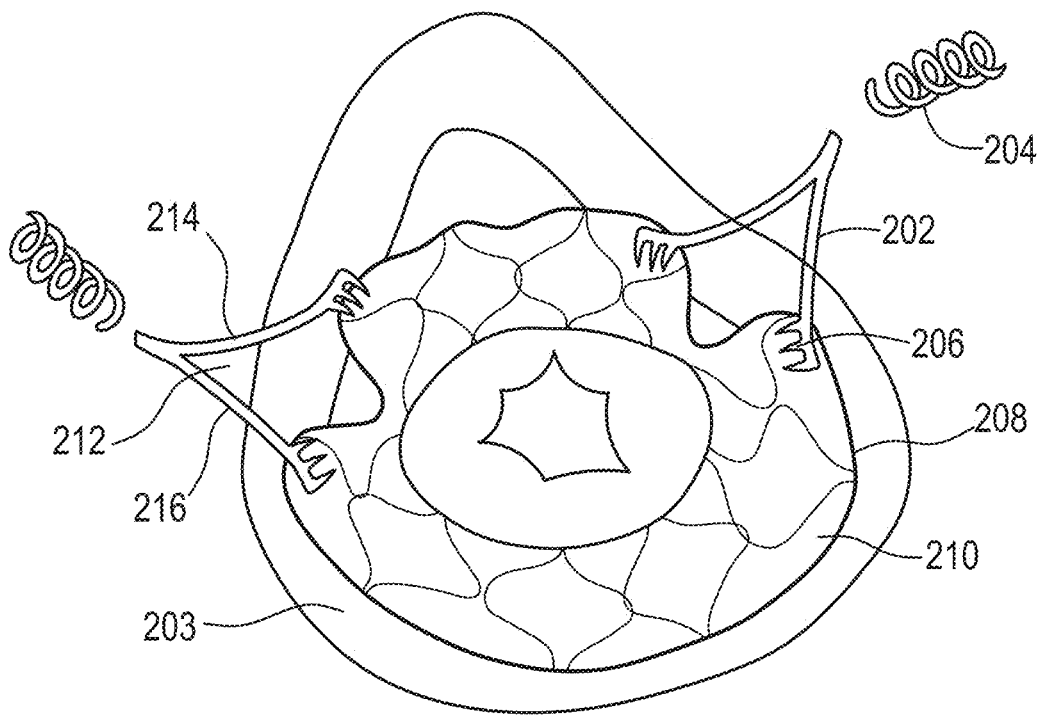

FIG. 51 is an illustration of a perspective top view of a heart valve prosthesis according to the present invention having a flange-integrated plication cell, coil plicator, and post-type tissue anchors. FIG. 51 shows a valve frame having an atrial cuff component, the atrial cuff or flange having a plication gap formed from a plication cell that is integrated with, or integral to, the diamond cells of the flange, and extending from the circumferential edge of the atrial flange, creating an over-sized diamond cell, the plication cell having a first arm and a second arm, with a plication tissue anchor mounted on each arm of the plication cell on either side of the plication gap. FIG. 51 shows post-type tissue anchors accessing and anchoring annular tissue.

Figure 52:
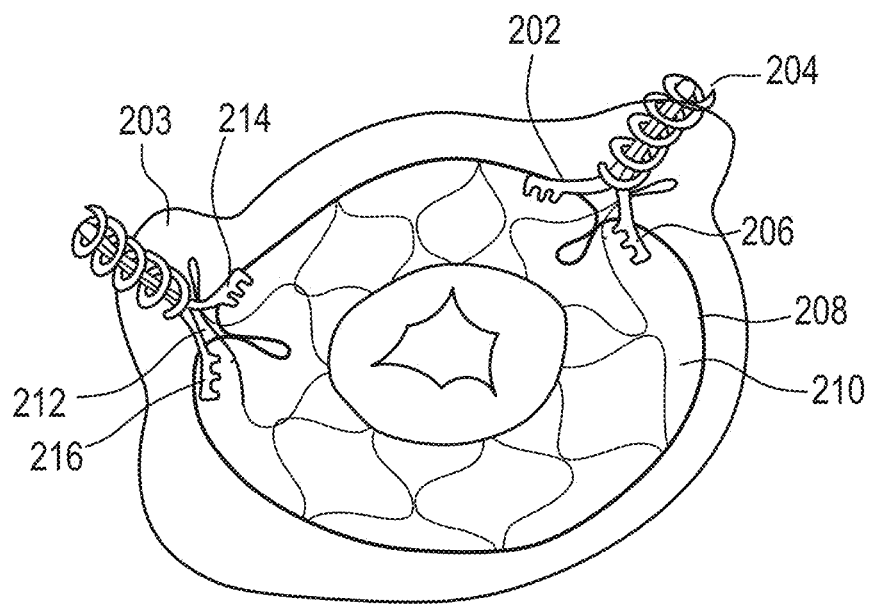

FIG. 52 is an illustration of a perspective top view of a heart valve prosthesis according to the present invention having a flange-integrated plication cell, coil plicator, and post-type tissue anchors. FIG. 52 shows a valve frame having an atrial cuff component, the atrial cuff or flange having a closed plication cell formed from the folding or compression of the plication cell using a plicator, e.g. a coil that confines, compresses, folds the first arm and the second arm of the plication cell together. FIG. 52 shows that by closing the plication gap with the plicator device, the plication tissue anchor that is mounted on each arm of the plication cell on either side of the plication gap cause the annular tissue to fold and plicate, and reduces the circumference of the native annulus. This ability to cinch or plicate the native annular tissue around a limited number of standard sizes of prosthetic valves reduces the problem of fitting each prosthesis to each patient's specific anatomy, simplifying the procedure for the cardiac interventionalist/physician.

Figure 53:
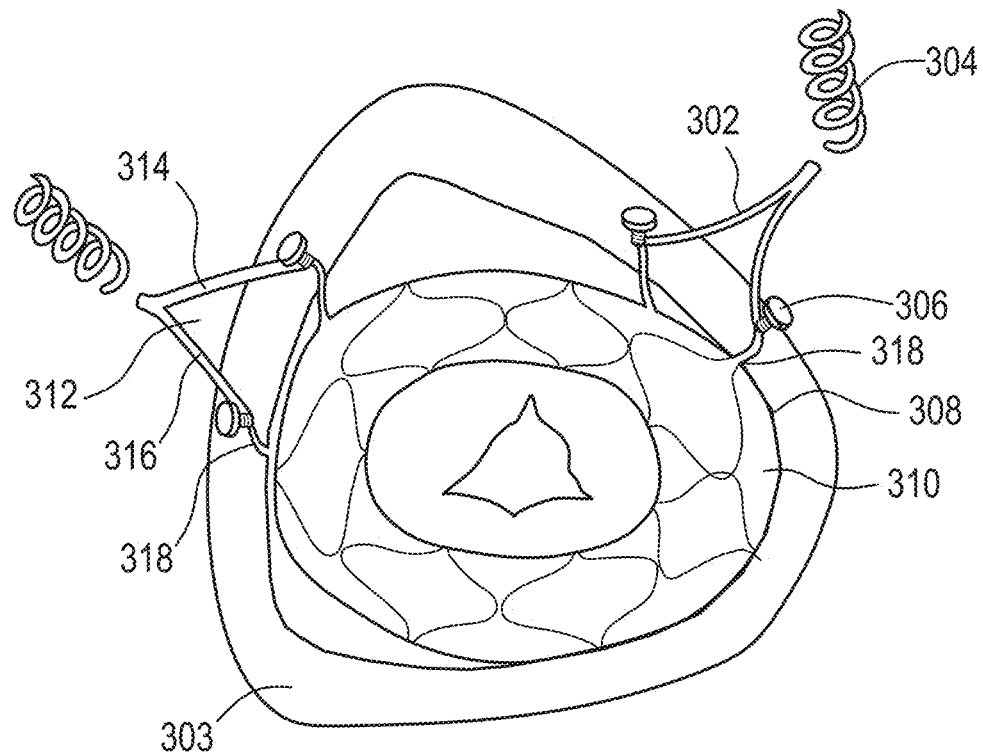

FIG. 53 is an illustration of a perspective top view of a heart valve prosthesis according to the present invention having a peripheral plication cell, coil plicator, and screw-type tissue anchors. FIG. 53 shows a valve frame having an atrial cuff component, the atrial cuff or flange having a plication gap formed from an independent plication cell extending from the peripheral edge of the atrial flange, the independent plication cell having a first arm and a second arm, with a plication tissue anchor mounted on each arm of the plication cell on either side of the plication gap. FIG. 53 shows a pair of screw-type tissue anchors accessing annular tissue.

Figure 54:
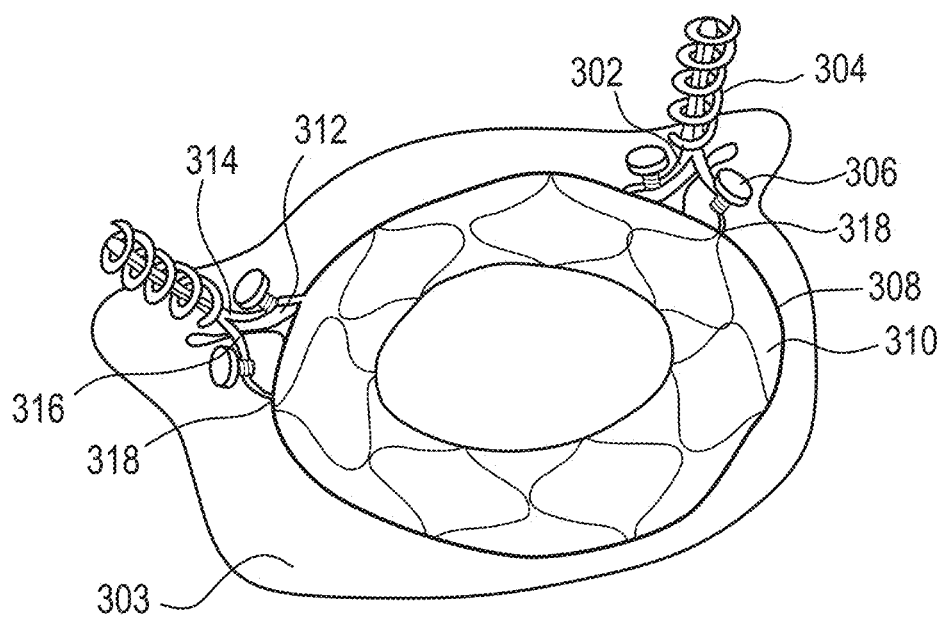

FIG. 54 is an illustration of a perspective top view of a heart valve prosthesis according to the present invention having a peripheral plication cell, coil plicator, and screw-type tissue anchors. FIG. 54 shows a valve frame having an atrial cuff component, the atrial cuff or flange having a closed plication cell formed from the folding or compression of the independent plication cell using a plicator, e.g. a coil or helical member that confines, compresses, folds the first arm and the second arm of the plication cell together. FIG. 54 shows that by closing the plication gap with the plicator device, the plication tissue anchor that is mounted on each arm of the plication cell on either side of the plication gap cause the annular tissue to fold and plicate, and reduces the circumference of the native annulus. This ability to cinch or plicate the native annular tissue around a limited number of standard sizes of prosthetic valves reduces the problem of fitting each prosthesis to each patient's specific anatomy, simplifying the procedure for the cardiac interventionalist/physician.

Figure 55:
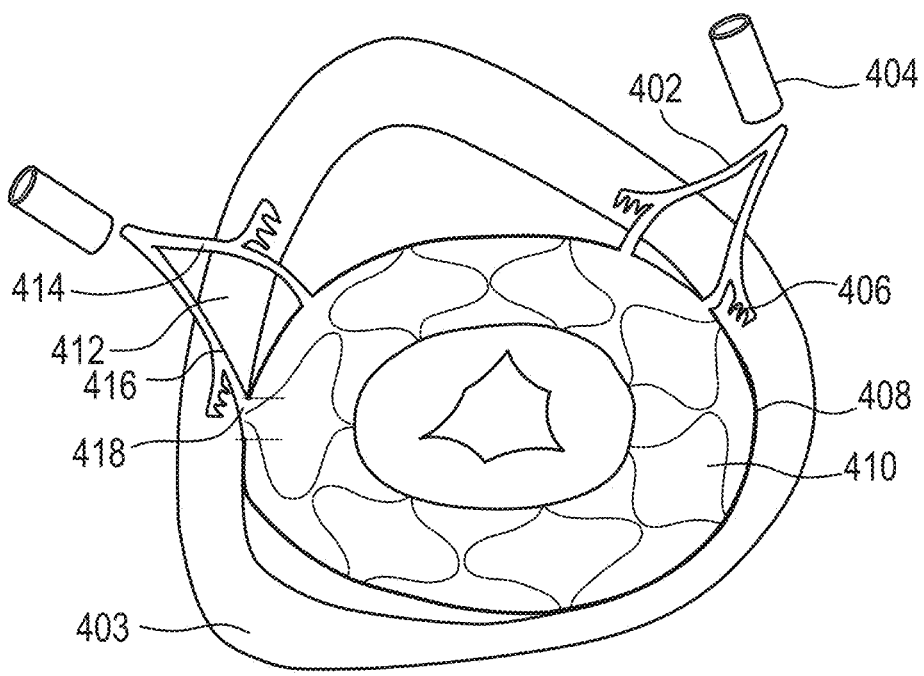

FIG. 55 is an illustration of a perspective top view of a heart valve prosthesis according to the present invention having a peripheral plication cell, sleeve plicator, and post-type tissue anchors. FIG. 55 shows a valve frame having an atrial cuff component, the atrial cuff or flange having a plication gap formed from an independent plication cell extending from the peripheral edge of the atrial flange, the independent plication cell having a first arm and a second arm, with a plication tissue anchor mounted on each arm of the plication cell on either side of the plication gap. FIG. 55 shows post-type tissue anchors accessing and anchoring annular tissue.

Figure 56:
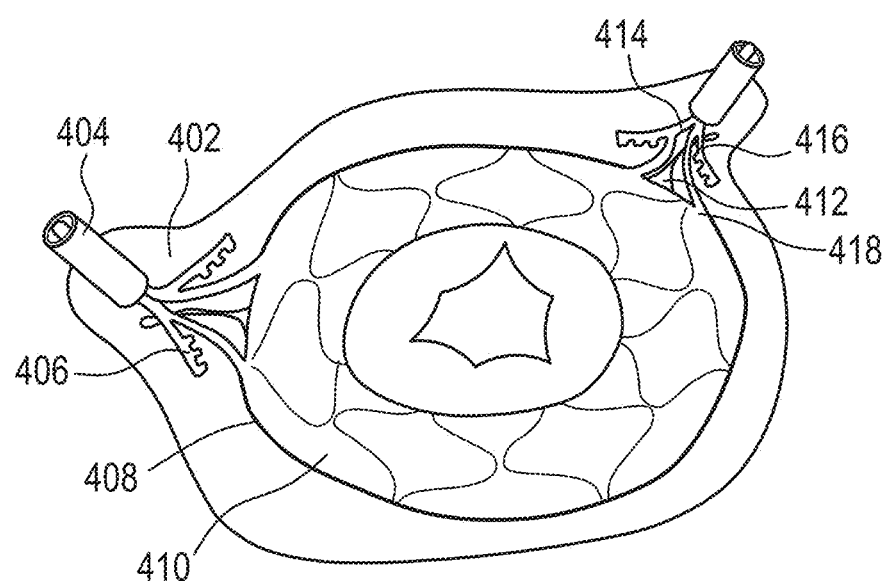

FIG. 56 is an illustration of a perspective top view of a heart valve prosthesis according to the present invention having a peripheral plication cell, sleeve plicator, and post-type tissue anchors. FIG. 56 shows a valve frame having an atrial cuff component, the atrial cuff or flange having a closed plication cell formed from the folding or compression of the independent plication cell using a plicator, e.g. a sleeve that confines, compresses, folds the first arm and the second arm of the plication cell together. FIG. 56 shows that by closing the plication gap with the plicator device, the plication tissue anchor that is mounted on each arm of the plication cell on either side of the plication gap cause the annular tissue to fold and plicate, and reduces the circumference of the native annulus. This ability to cinch or plicate the native annular tissue around a limited number of standard sizes of prosthetic valves reduces the problem of fitting each prosthesis to each patient's specific anatomy, simplifying the procedure for the cardiac interventionalist/physician.

Figure 57:
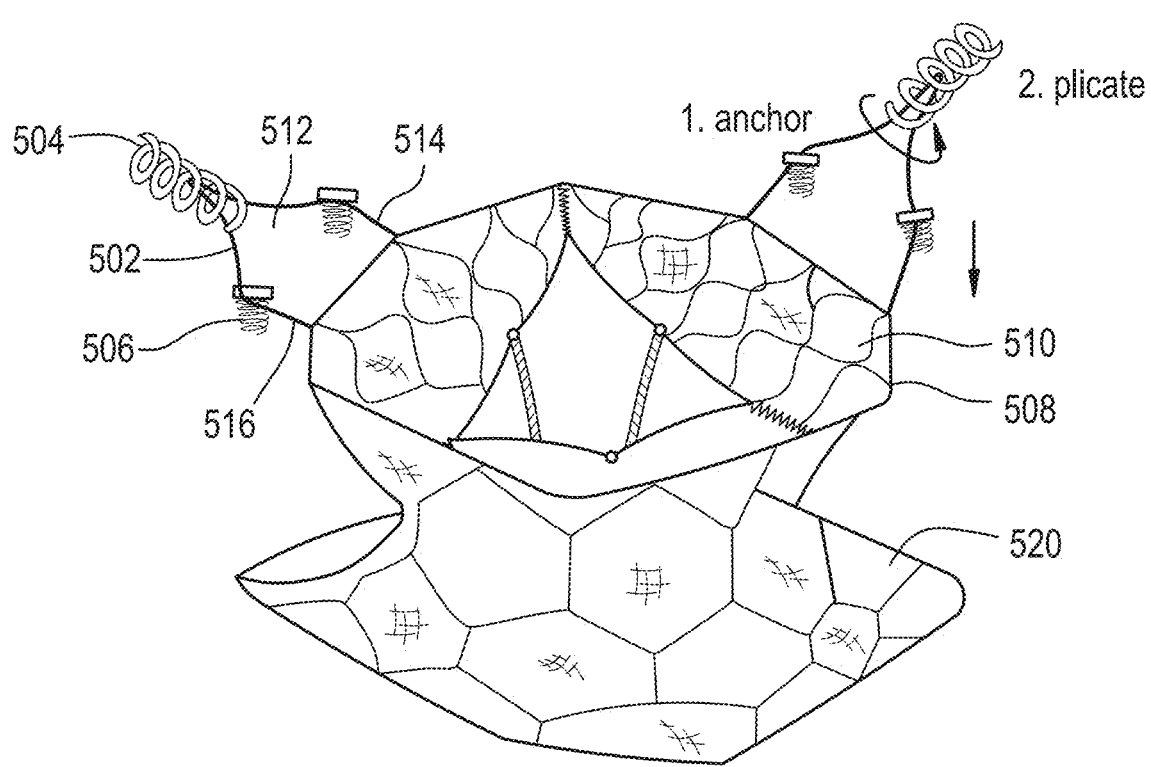

FIG. 57 is an illustration in a perspective view from above of a heart valve prosthesis according to the present invention with a peripheral plication cell, a coil plicator, and screw-type tissue anchors, connected to a valve frame having an atrial cuff component and a ventricular cuff component. FIG. 57 shows plication cell having a first and second arms on which plication tissue anchors are mounted to secure the valve to annular tissue. The tissue anchors may directly engage annular tissue, or optionally, through a biocompatible disk material covering the atrial flange of the valve frame, where the biocompatible disk is different from the biocompatible material covering the diamond cells of the wire frame.

Figure 58:
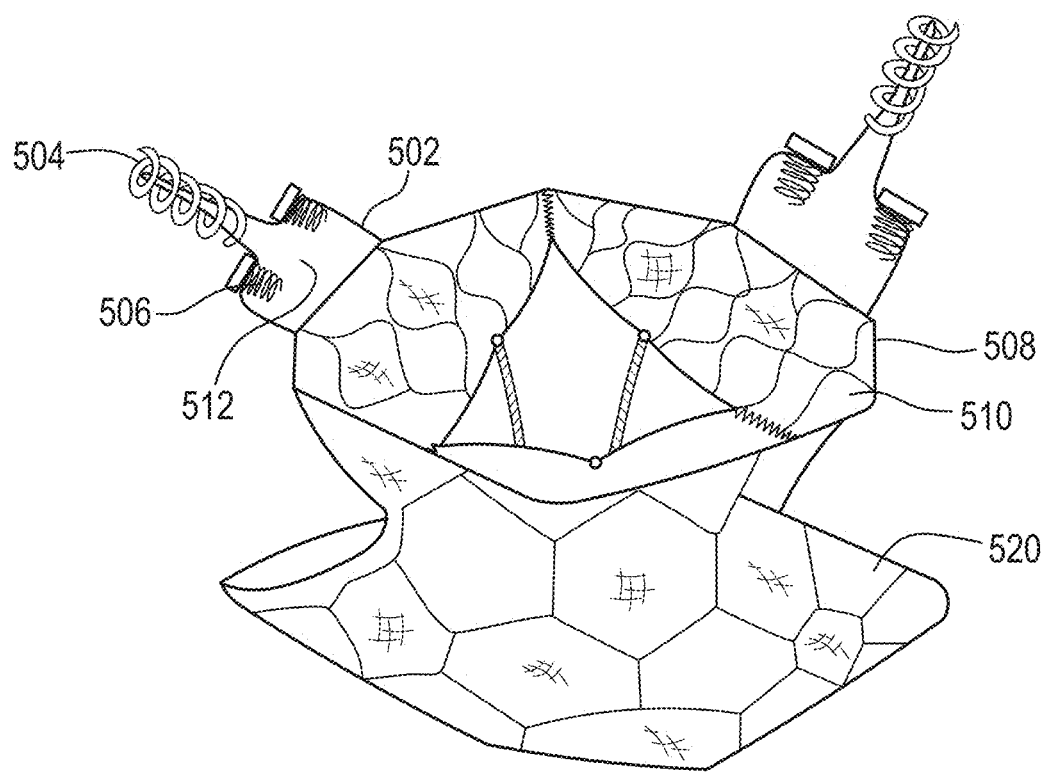

FIG. 58 is an illustration in a perspective view from above of a heart valve prosthesis according to the present invention with a peripheral plication cell, a coil plicator, and screw-type tissue anchors, connected to a valve frame having an atrial cuff component and a ventricular cuff component. FIG. 58 shows the coil plicator folding or compressing the plication cell by winding around the first and second arms. The folding of the arms of the plication cell draws the already-anchored tissue anchors together, which plicates, or pinches together, annular tissue, shortening the annular circumference.

Figure 59:
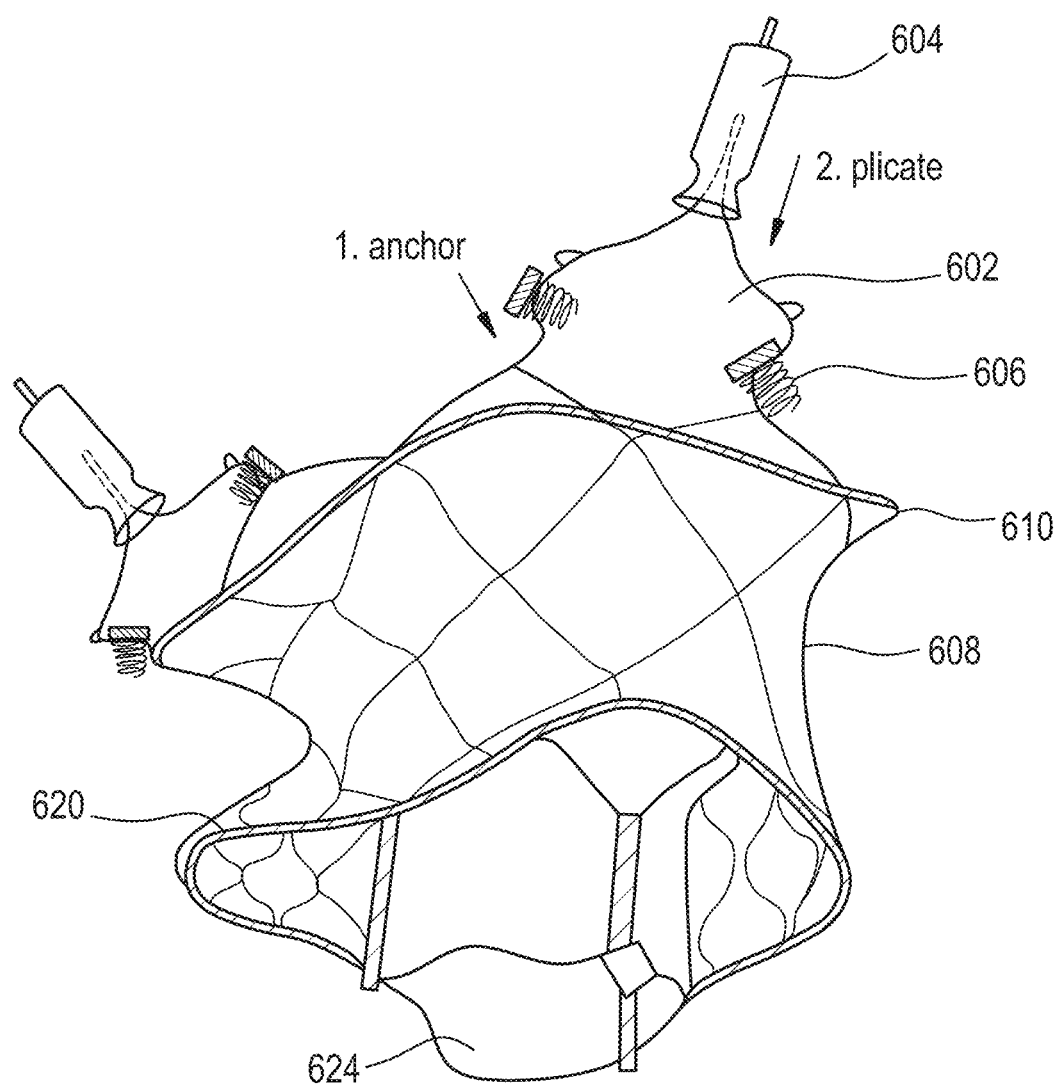

FIG. 59 is an illustration in a perspective view from below of a heart valve prosthesis according to the present invention with a flange-integrated plication cell, a sleeve plicator, and screw-type tissue anchors, connected to a valve frame having an atrial cuff component and a ventricular cuff component. FIG. 59 shows plication cell having a first and second arms on which plication tissue anchors are mounted to secure the valve to annular tissue. The tissue anchors may directly engage annular tissue, or optionally, through a biocompatible disk material covering the atrial flange of the valve frame, where the biocompatible disk is different from the biocompatible material covering the diamond cells of the wire frame.

Figure 60:
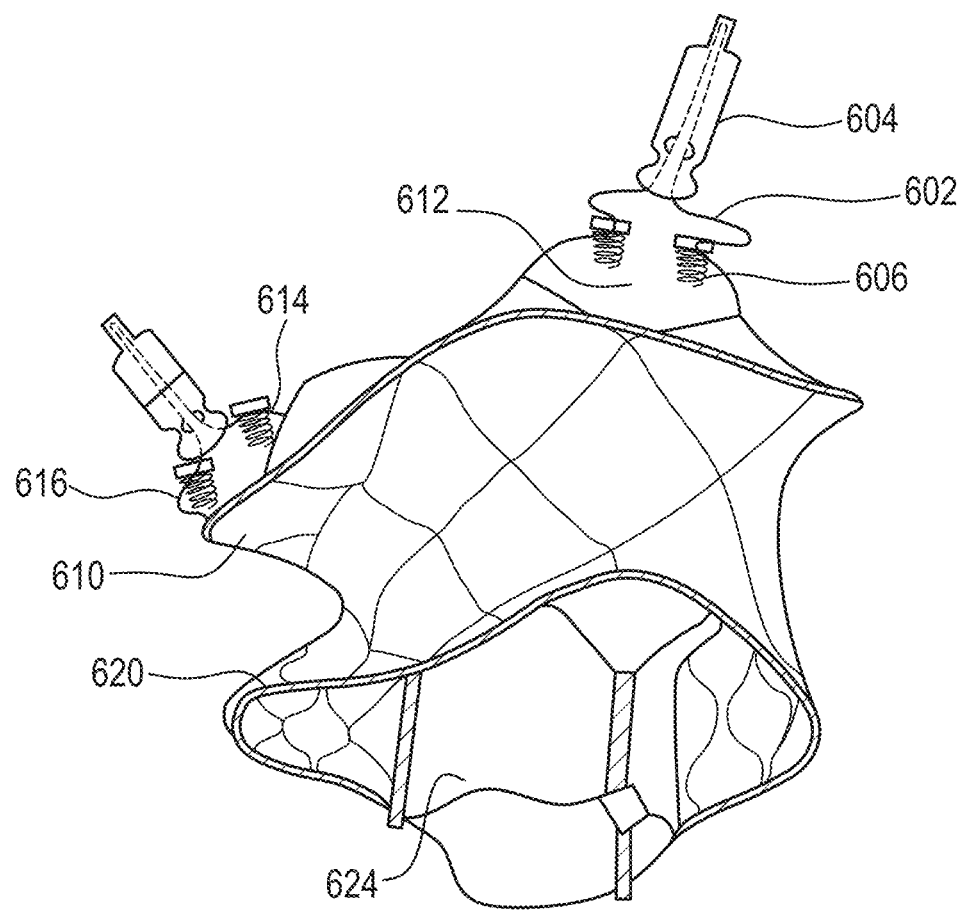

FIG. 60 is an illustration in a perspective view from below of a heart valve prosthesis according to the present invention with a flange-integrated plication cell, a sleeve plicator, and screw-type tissue anchors, connected to a valve frame having an atrial cuff component and a ventricular cuff component. FIG. 60 shows the sleeve plicator folding or compressing the plication cell by sliding down and over the first and second arms to compress the plication cell. The folding of the arms of the plication cell draws the already-anchored tissue anchors together, which plicates, or pinches together, annular tissue, shortening the annular circumference.

Figure 61:
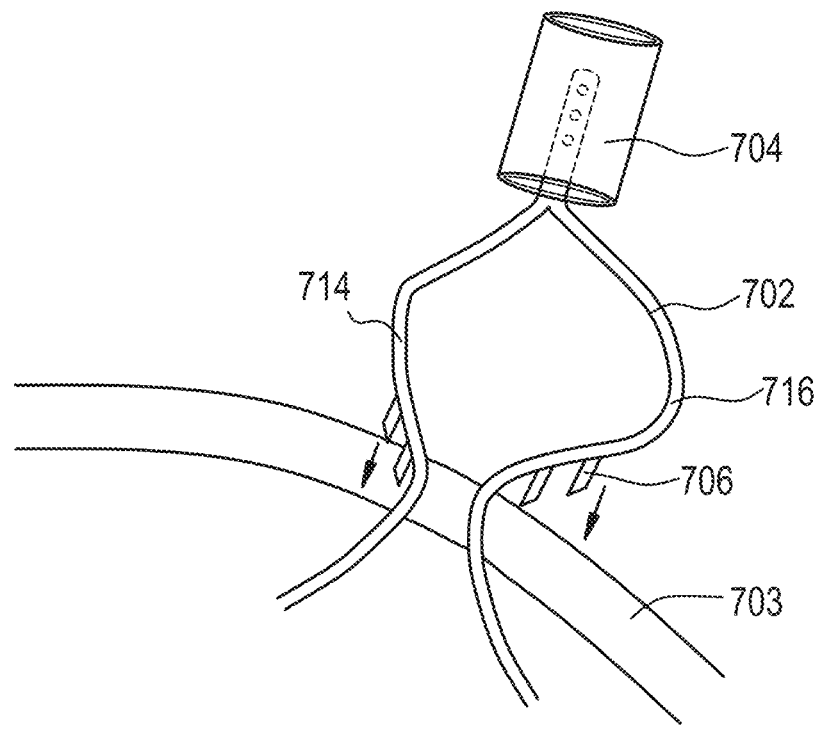

FIG. 61 is an illustration of a detailed view of a plication cell with a sleeve plicator and post-type tissue anchors. FIG. 61 shows the plication cell prior to engagement with the annular tissue, and prior to compression of the plication cell by sliding the sleeve down and over the arms of the plication cell.

Figure 62:
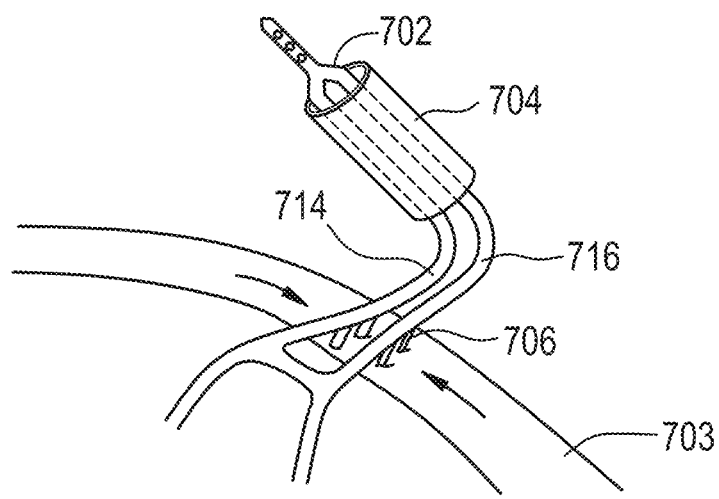

FIG. 62 is an illustration of a detailed view of a plication cell with a sleeve plicator and post-type tissue anchors. FIG. 62 shows the plication cell after engagement of the posts into the annular tissue, and after the compression of the plication cell by sliding the sleeve down and over the arms of the plication cell.

Figure 63:
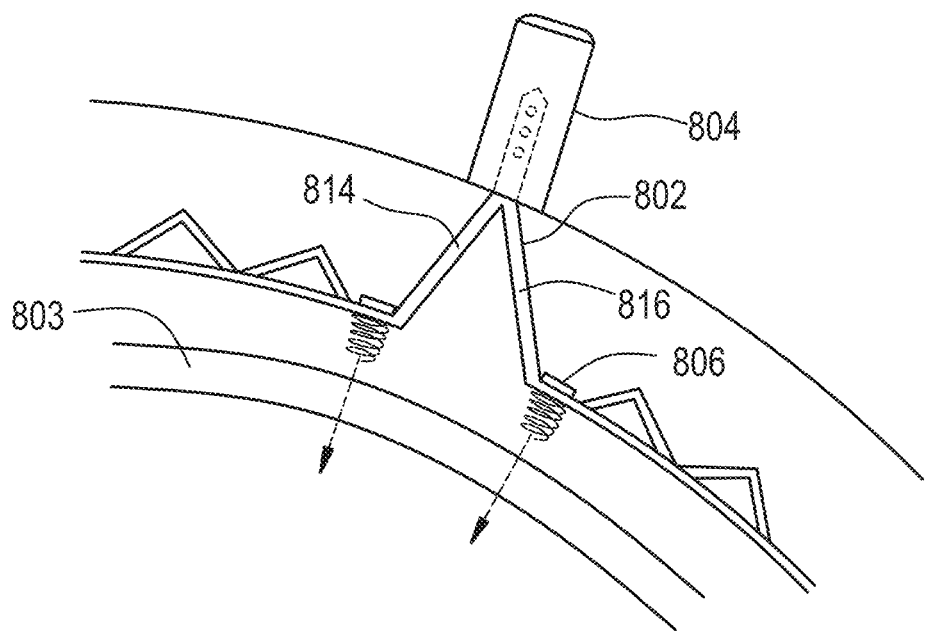

FIG. 63 is an illustration of a detailed view of a plication cell with a sleeve plicator and screw-type tissue anchors. FIG. 63 shows the plication cell prior to engagement with the annular tissue, and prior to compression of the plication cell by sliding the sleeve down and over the arms of the plication cell.

Figure 64:
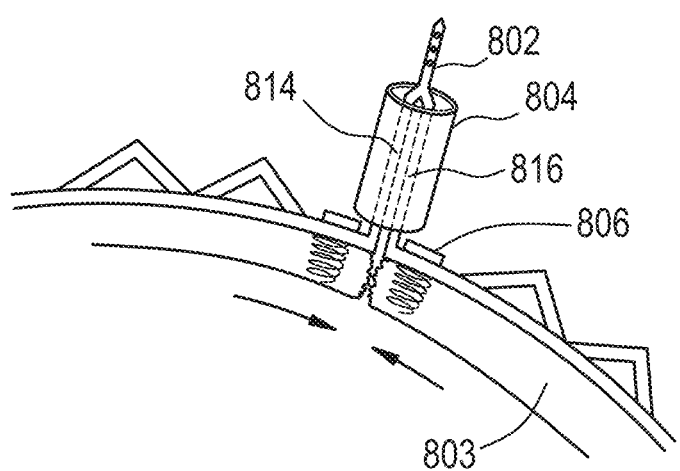

FIG. 64 is an illustration of a detailed view of a plication cell with a sleeve plicator and screw-type tissue anchors. FIG. 64 shows the plication cell after engagement of the screws into the annular tissue, and after the compression of the plication cell by sliding the sleeve down and over the arms of the plication cell.

Figure 65:
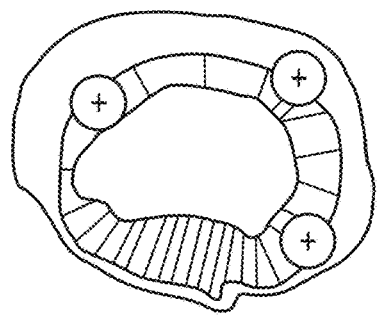

FIG. 65 is an illustration of a top view of a native tricuspid valve. FIG. 65 shows septal region of the annulus at bottom, posterior region of the annulus at right and anterior region of the annulus at left. FIG. 65 shows in a non-limiting preferred embodiment, three preferred locations for plicating and/or for performing tissue anchoring.

Figure 66:
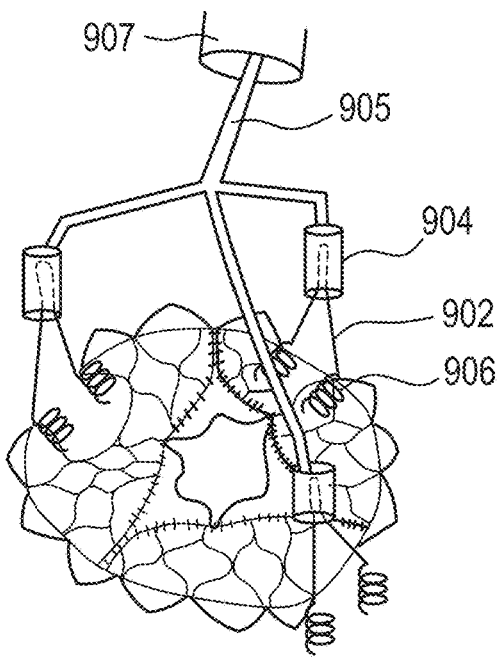

FIG. 66 is an illustration of a perspective view from the top of a plicator delivery tool that is accessing the plication diamond cells of an implanted transcatheter prosthetic valve through a delivery catheter. FIG. 66 shows three plicator sleeves mounted in ready-position on the top of their plication cells. FIG. 66 shows three plication cells framed by screw-type plication tissue anchors.

Figure 67:
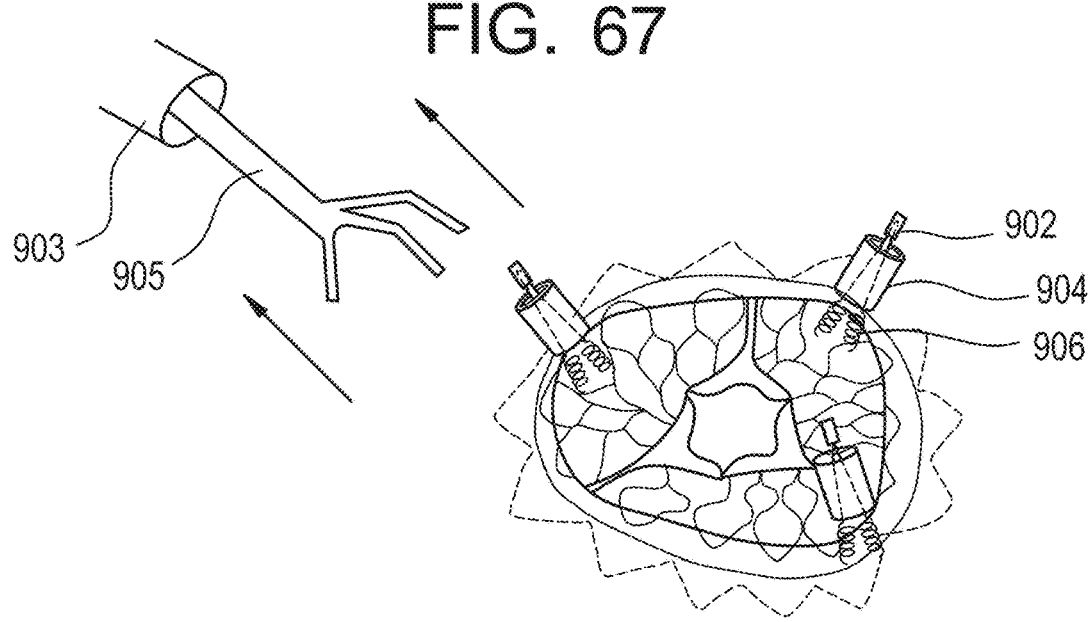

FIG. 67 is an illustration of a perspective view from the top of a plicator delivery tool that has deployed the plication tissue anchors into the annular tissue, and then has compressed the plication cells into the plication sleeves. FIG. 67 shows three plicator sleeves that have been mounted over their plication cells. FIG. 67 shows the closing of the three plication gaps and the plication of the annular tissue by the pairing or merging movement of the fixed screw-type plication tissue anchors. FIG. 67 shows withdrawal of the plicator delivery tool back into the catheter.

Figure 68A:
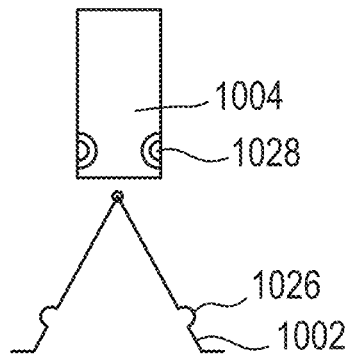
Figure 68B:

FIGS. 68A and 68B are a two-part illustration of a plan view of one preferred embodiment of a plication sleeve and plicator cell combination. FIG. 68A shows plication sleeve having internal detent stops for engaging a matching locking element on the arms of the plication diamond cell. FIG. 68B shows plication sleeve after sliding over the plication cell, causing the plication cell to compress, and locking into place once the locking element of the plication cell arms has passed deep enough into the plication sleeve to pass the internal detent step member.

Figure 69A:
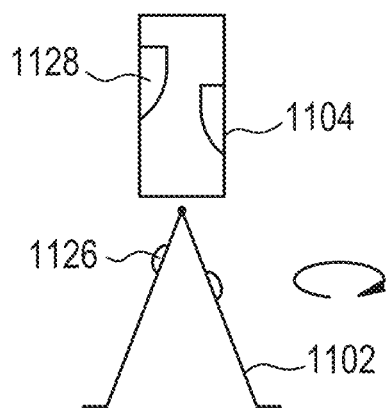
Figure 69B:
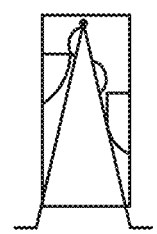

FIGS. 69A and 69B are a two-part illustration of a plan view of another preferred embodiment of a spiral or rifled plication sleeve and plicator cell combination. FIG. 69A shows plication sleeve having internal spiral detent stops for engaging a matching locking element on the arms of the plication diamond cell. FIG. 69B shows plication sleeve after rotatably sliding over the plication cell, causing the plication cell to compress, and locking into place once the locking element of the plication cell arms has passed deep enough into the plication sleeve to pass the internal spiral detent step member.

Figure 70A:
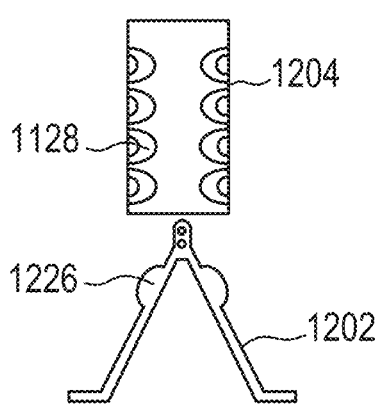
Figure 70B:
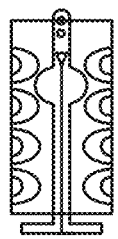

FIGS. 70A and 70B are a two-part illustration of a plan view of one preferred embodiment of a multi-step plication sleeve and plicator cell combination. FIG. 70A shows multi-step plication sleeve having multiple internal detent stops for engaging a matching locking element on the arms of the plication diamond cell. FIG. 70B shows plication sleeve after sliding over the plication cell, causing the plication cell to compress, and locking into place once the locking elements of the plication cell arms have passed deep enough into the plication sleeve to pass one or more, here shown passing four, of the multi-step internal detent step member.

FIG. 71 is a graph illustration and shows a comparison of various tricuspid valve diameters, the calculated circumference, and the calculated repaired size after two (2) 20 mm plications, or three (3) 20 mm plications, or four (4) 20 mm plications.

FIGS. 72A-72C are an illustration of a plan view of a tissue anchor having a floating radiopaque marker. FIG. 72A shows the tissue anchor accessing the annular tissue withe the radiopaque marker at the distal end of the anchor and in contact with the atrial surface of the annular tissue. FIG. 72B shows the tissue anchor advancing into the annular tissue with the radiopaque marker threaded onto the tissue anchor and maintaining position on the atrial surface of the annular tissue. FIG. 72C) shows the tissue anchor completely advanced into the annular tissue such that the tissue anchor and the threaded floating marker are now adjacent, indicating the desired depth, tension, and/or plication of the tissue anchor with respect to the annular tissue.

FIG. 73 is an illustration of a plan view of a tissue anchor having a straight thread and a constant pitch.

FIG. 74 is an illustration of a plan view of a tissue anchor having a straight thread and a variable pitch.

FIG. 75 is an illustration of a plan view of a tissue anchor having a tapered thread and a constant pitch.

FIG. 76 is an illustration of a plan view of a tissue anchor having a variable taper thread and a constant pitch.

Figure 77:
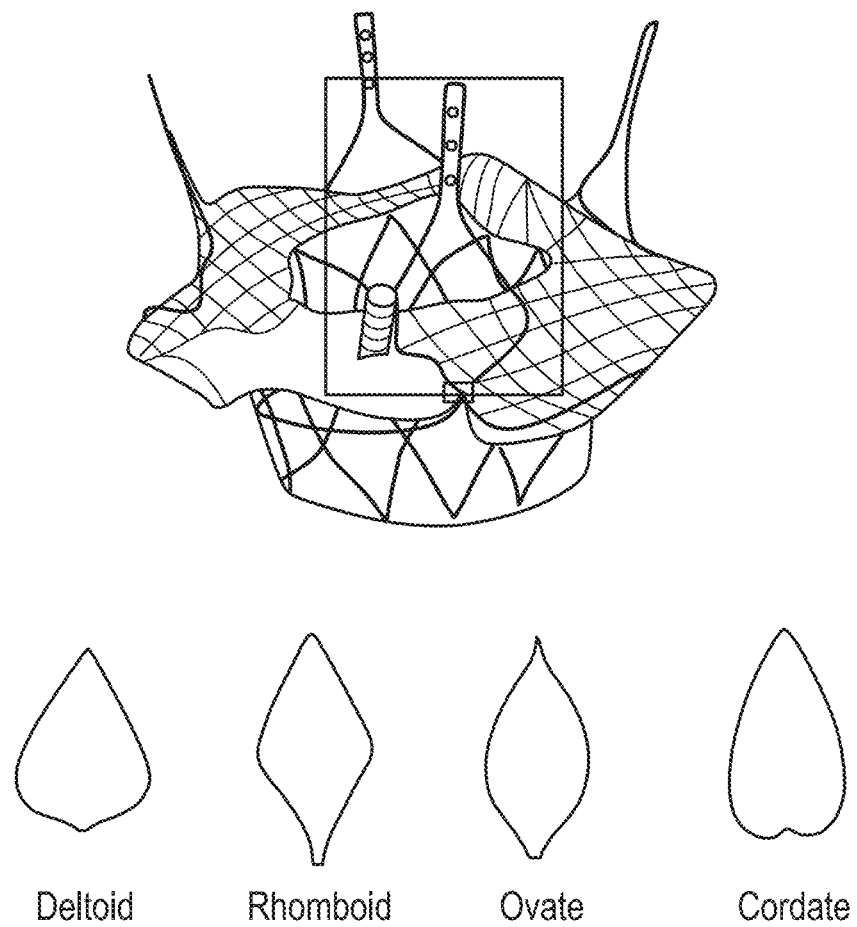

FIG. 77 is an illustration of the various circumferential shapes contemplated as within the scope of the invention for the wire plication cell.

Figure 78:
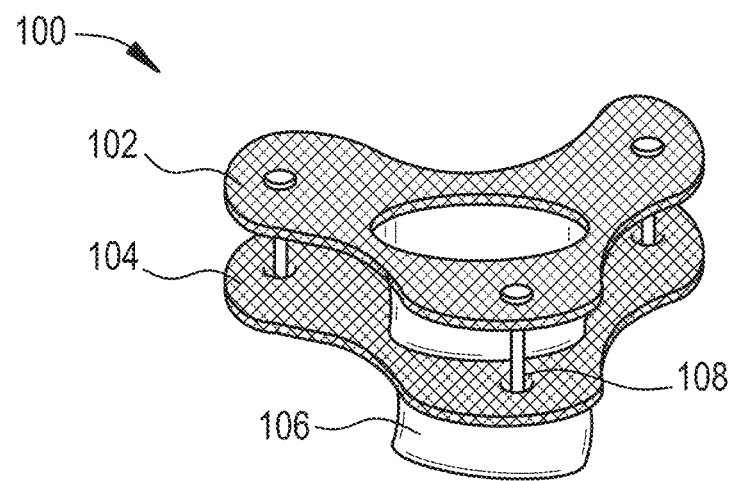

FIG. 78 is an illustration of a perspective view of a three-lobed (trefoil) heart valve prosthesis according to the present invention. FIG. 78 shows a pair of pinned three-lobed sealing collars encircling a collapsible flow control sleeve.

Figure 79:
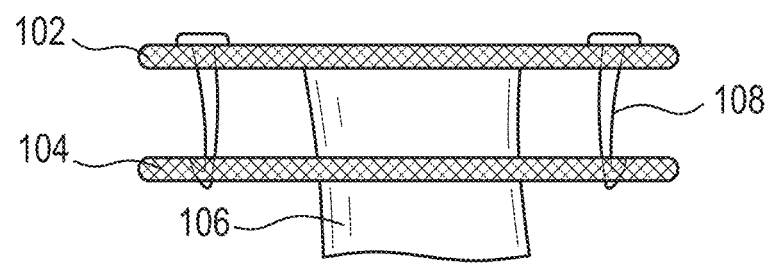

FIG. 79 is an illustration of a plan or side view of a heart valve prosthesis according to the present invention. FIG. 79 shows a pair of pinned three-lobed sealing collars connected to a collapsible flow control sleeve.

Figure 80:
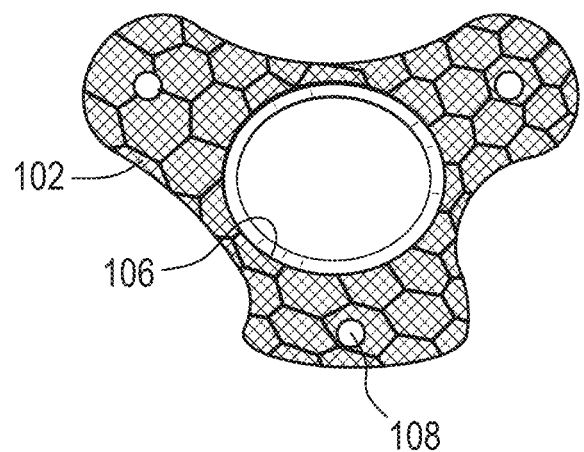

FIG. 80 is an illustration of a top view of a heart valve prosthesis according to the present invention. FIG. 80 shows the supra-annular (top) collar of a pair of pinned three-lobed sealing collars encircling a collapsible flow control sleeve.

Figure 81:
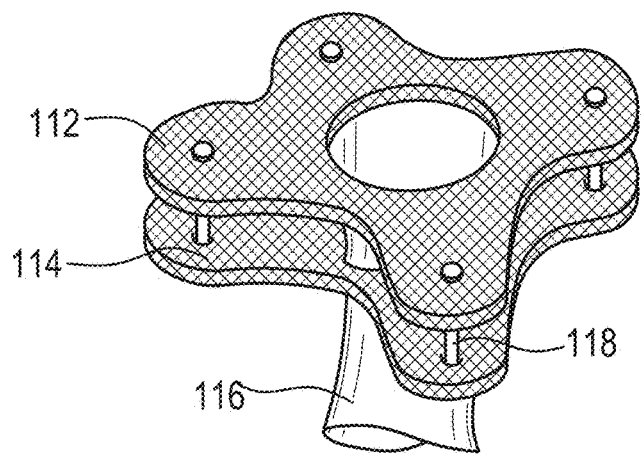

FIG. 81 is an illustration of a perspective view of a four-lobed (quatrefoil) heart valve prosthesis according to the present invention. FIG. 81 shows a pair of pinned four-lobed sealing collars encircling a collapsible flow control sleeve.

Figure 82:
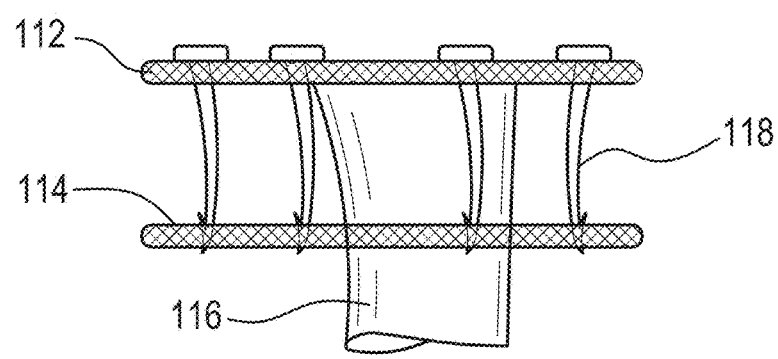

FIG. 82 is an illustration of a plan or side view of a heart valve prosthesis according to the present invention. FIG. 82 shows a pair of pinned four-lobed sealing collars connected to a collapsible flow control sleeve.

Figure 83:
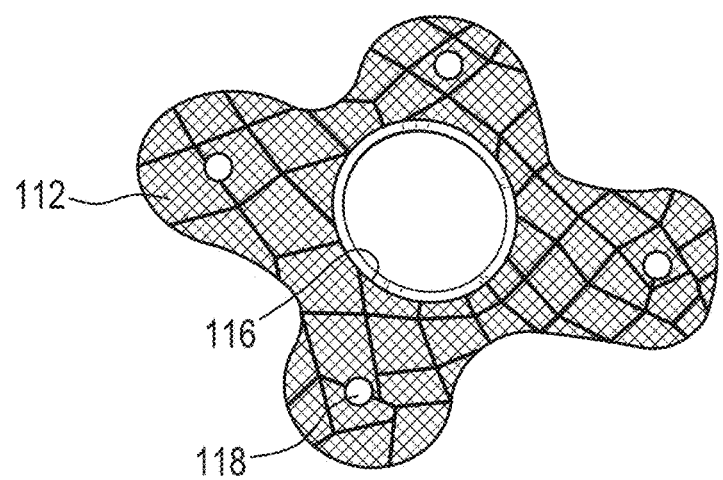

FIG. 83 is an illustration of a top view of a heart valve prosthesis according to the present invention. FIG. 83 shows the supra-annular (top) collar of a pair of pinned four-lobed sealing collars encircling a collapsible flow control sleeve.

Figure 84:
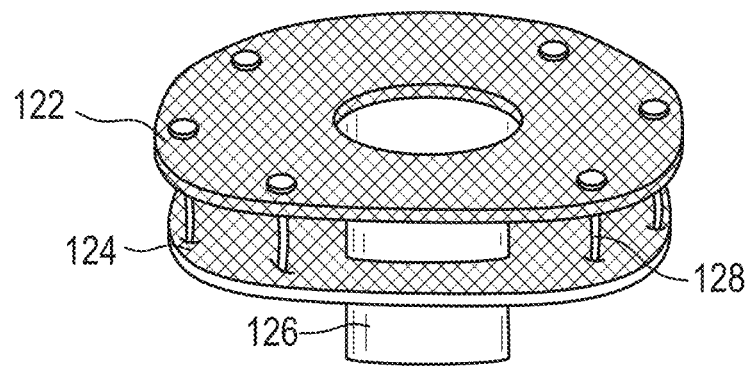

FIG. 84 is an illustration of a perspective view of a circular or ellipsoidal-shaped heart valve prosthesis according to the present invention. FIG. 84 shows a pair of pinned circular or ellipsoidal-shaped sealing collars encircling a collapsible flow control sleeve.

Figure 85:
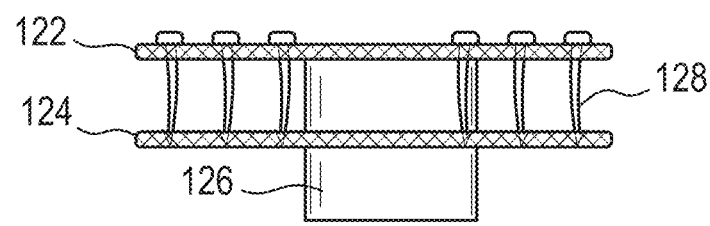

FIG. 85 is an illustration of a plan or side view of a circular or ellipsoidal-shaped heart valve prosthesis according to the present invention. FIG. 85 shows a pair of pinned circular or ellipsoidal-shaped sealing collars connected to a collapsible flow control sleeve.

Figure 86:
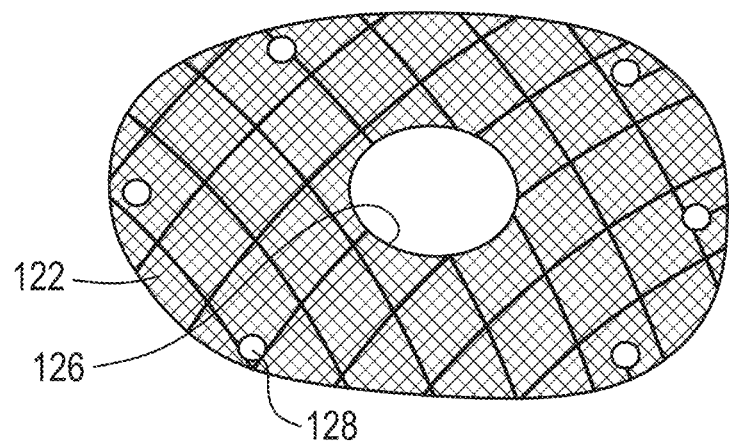

FIG. 86 is an illustration of a top view of a circular or ellipsoidal-shaped heart valve prosthesis according to the present invention. FIG. 86 shows the supra-annular (top) collar of a pair of pinned circular or ellipsoidal-shaped sealing collars encircling a collapsible flow control sleeve.

Figure 87:
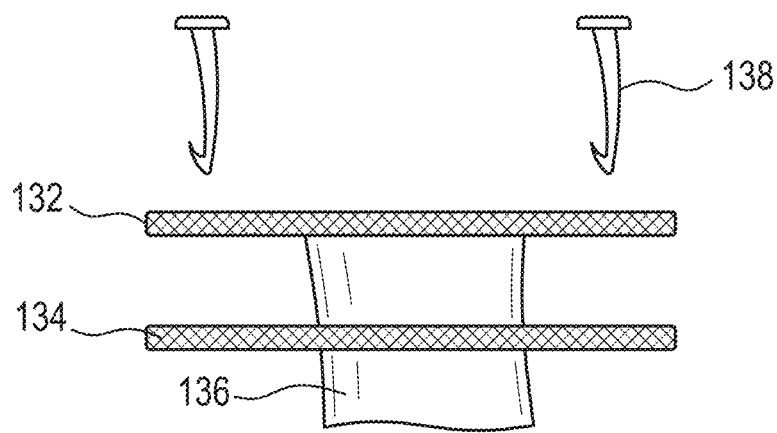

FIG. 87 is an illustration of a plan or side view of a heart valve prosthesis according to the present invention. FIG. 87 shows pinning members prior to deployment by insertion or piercing into a pair of sealing collars connected to a collapsible flow control sleeve.

Figure 88:
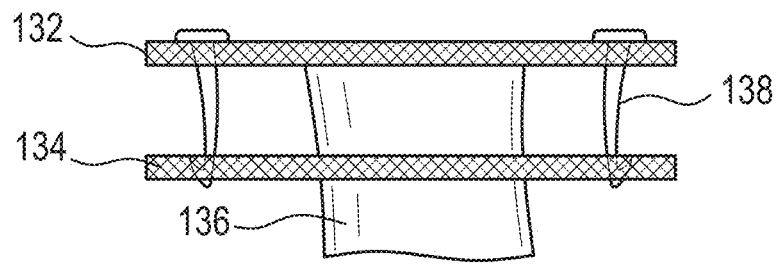

FIG. 88 is an illustration of a plan or side view of a heart valve prosthesis according to the present invention. FIG. 88 shows pinning members after deployment by insertion or piercing into a pair of sealing collars connected to a collapsible flow control sleeve.

Figure 89:
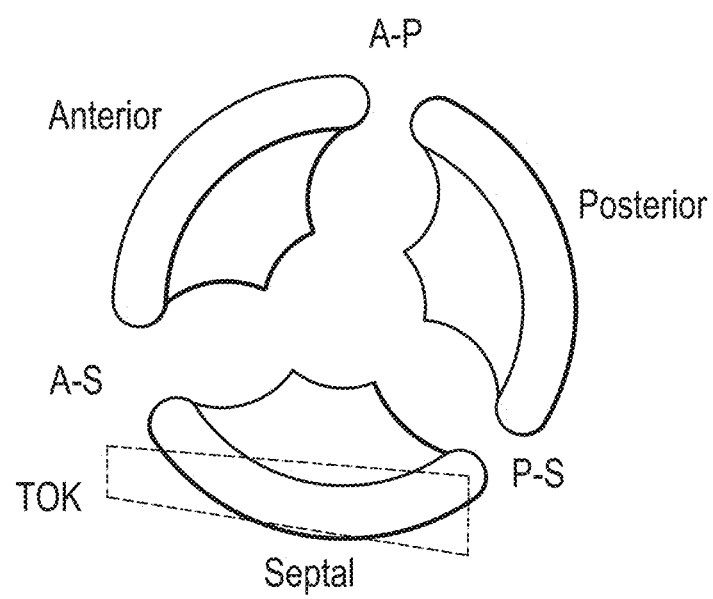

FIG. 89 is an illustration of a top view of a native tricuspid valve for planning pinning locations. FIG. 89 shows the annulus segments—anterior, posterior and septal, the leaflets extending from the annular plane down into the ventricle, the commissures or gaps between the segments—Antero-posterior, Posterio-septal, Anteroseptal, and the triangle of Koch electrical conduction avoidance zone.

Figure 90:
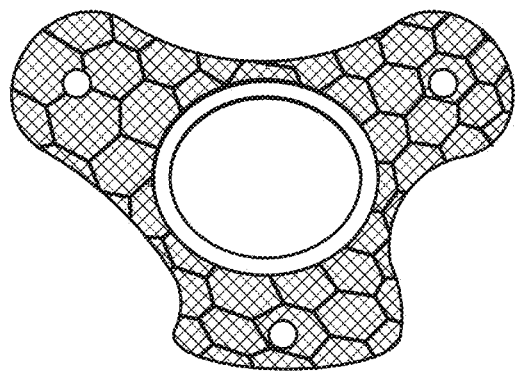

FIG. 90 is an illustration of a top view of a three-lobed, or trefoil, heart valve prosthesis according to the present invention and shows a non-limiting example of pin placement using three fastener pins.

Figure 91:
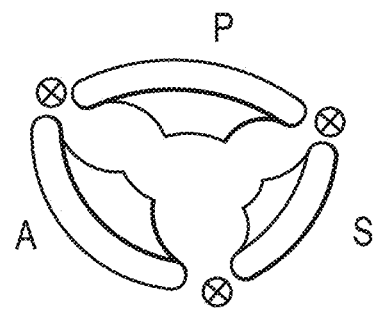

FIG. 91 is an illustration of a top view of a native tricuspid valve and shows an example of pin location for a three fastener deployment into the commissures, A-P, A-S and P-S.

Figure 92:
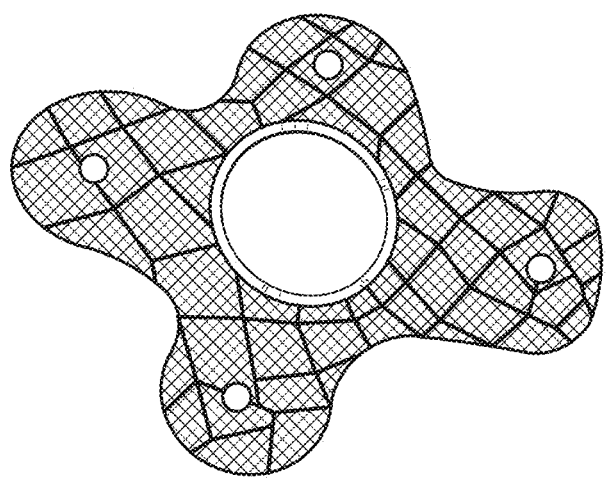

FIG. 92 is an illustration of a top view of a four-lobed, or quatrefoil, heart valve prosthesis according to the present invention and shows a non-limiting example of pin placement using four fastener pins.

Figure 93:
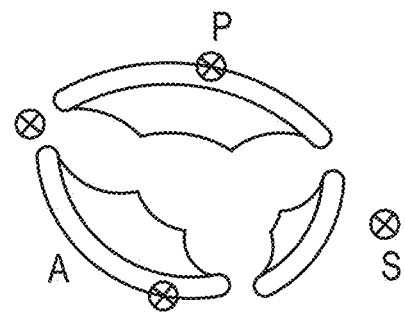

FIG. 93 is an illustration of a top view of a native tricuspid valve and shows an example of pin location for a four fastener deployment into the posterior annulus, into the anterior annulus, into the A-P commissure, and into heart tissue adjacent the septal region.

Figure 94:
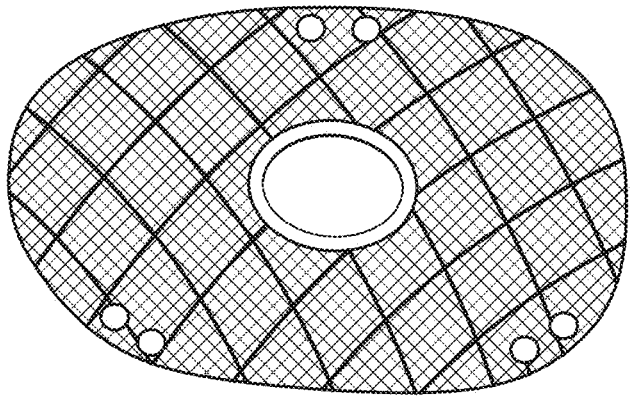

FIG. 94 is an illustration of a top view of a circular or ellipsoidal heart valve prosthesis according to the present invention and shows a non-limiting example of pin placement using six fastener pins.

Figure 95:
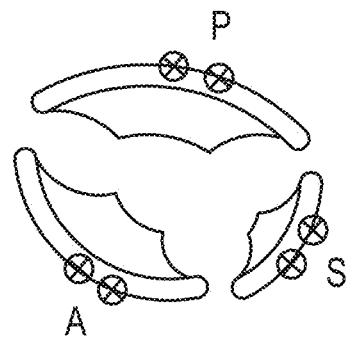

FIG. 95 is an illustration of a top view of a native tricuspid valve and shows an example of pin location for a six fastener deployment into the posterior annulus, into the anterior annulus, and into the septal annulus.

Figure 96:
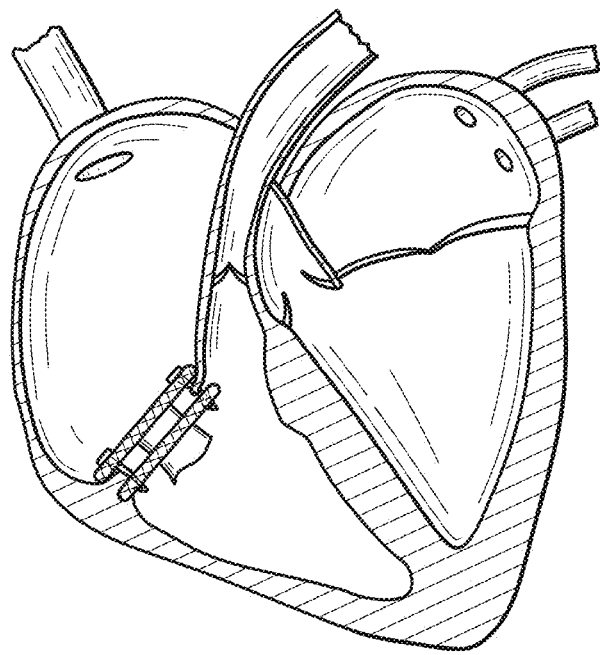

FIG. 96 is an illustration of a plan or side view of a heart valve prosthesis according to the present invention deployed into the tricuspid annulus. FIG. 96 shows an atrial-side annulus sealing collar and a ventricular-side annulus sealing collar pinned by fastener pins that have been inserted, pierced, etc. into the pair of sealing collars to capture native tricuspid tissue on or near the annulus and to sandwich the native tissue between the top and bottom sealing collars. FIG. 96 also shows the top/atrial-side sealing collar and the bottom/ventricular-side sealing collar connected to a collapsible flow control sleeve that provides a reciprocating closable channel from right atrium to right ventricle.

Figure 97:
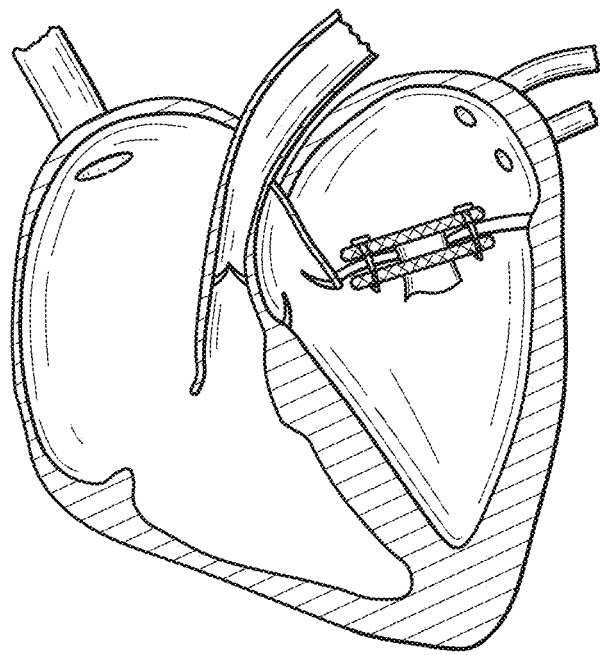

FIG. 97 is an illustration of a plan or side view of a heart valve prosthesis according to the present invention deployed into the mitral annulus. FIG. 97 shows an atrial-side annulus sealing collar and a ventricular-side annulus sealing collar pinned by fastener pins that have been inserted, pierced, etc. into the pair of sealing collars to capture native mitral tissue on or near the annulus and to sandwich the native mitral tissue between the top and bottom sealing collars. FIG. 97 also shows the top/atrial-side sealing collar and the bottom/ventricular-side sealing collar connected to a collapsible flow control sleeve that provides a reciprocating closable channel from left atrium to left ventricle.

Figure 98:
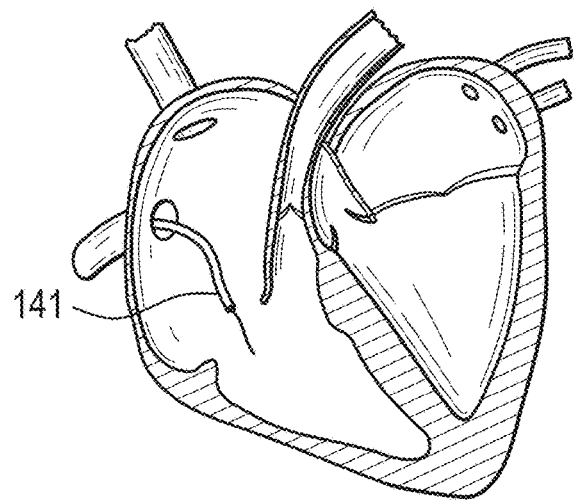

FIG. 98 is an illustration of a cross-sectional view of a heart. FIG. 98 shows a Step 1 of 4 of a time sequence illustration of a transcatheter delivery of a heart valve prosthesis according to the present invention where a steerable catheter is introduced into the heart.

Figure 99:
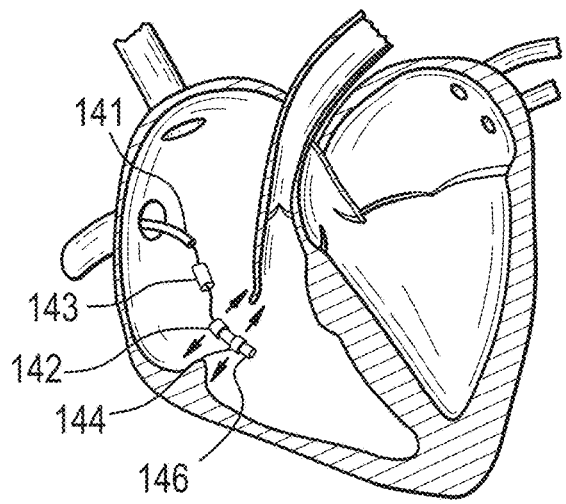

FIG. 99 is an illustration of a cross-sectional view of a heart. FIG. 99 shows a Step 2 of 4 of a time sequence illustration of a transcatheter delivery of a heart valve prosthesis according to the present invention where a compressed device capsule is delivered to its deployment position.

Figure 100:
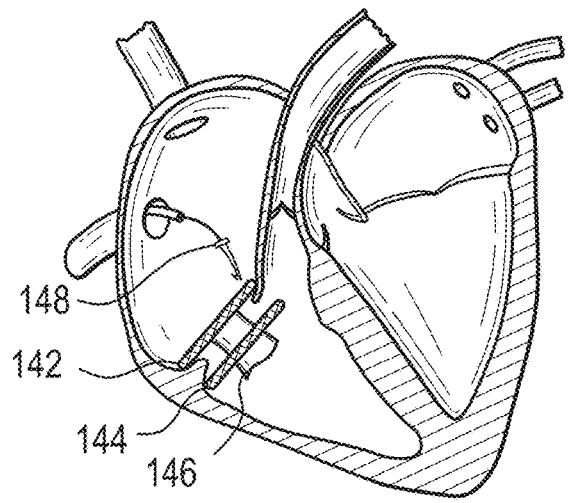

FIG. 100 is an illustration of a cross-sectional view of a heart. FIG. 100 shows a Step 3 of 4 of a time sequence illustration of a transcatheter delivery of a heart valve prosthesis according to the present invention where a compressed device capsule has been expanded to its working size with an atrial side sealing collar and a ventricle side sealing collar positioned to capture annulus or adjacent tissue. FIG. 100 also shows catheter tool delivering a first fastener pin.

Figure 101:
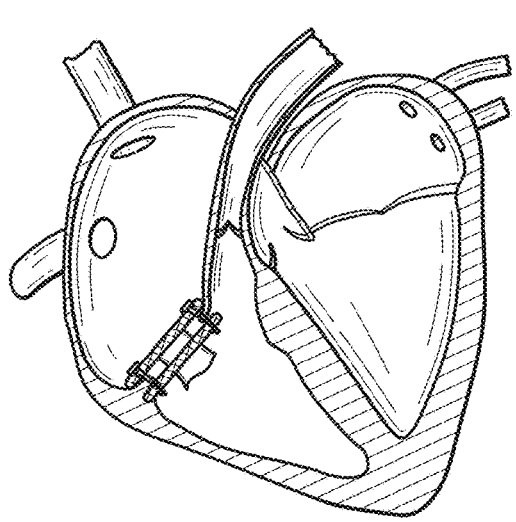

FIG. 101 is an illustration of a cross-sectional view of a heart. FIG. 101 shows a Step 4 of 4 of a time sequence illustration of a transcatheter delivery of a heart valve prosthesis according to the present invention where fastener pins have been installed and the top and bottom sealing collars have been cinched together to secure the prosthesis to annular tissue by compressive sandwiching and/or by direct tissue anchoring.

Figure 102:
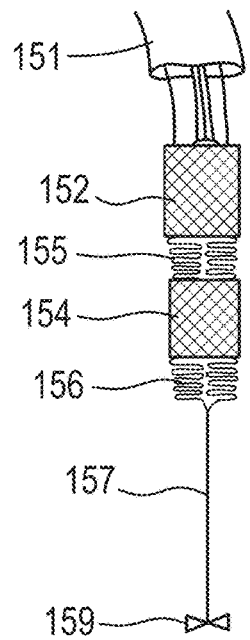

FIG. 102 is an illustration of a side view of a transcatheter prosthetic valve device. FIG. 102 shows a Step 1 of 8 of a time sequence illustration of a transcatheter delivery of a heart valve prosthesis according to the present invention where a steerable catheter is introduced into the heart, a temporary ventricular tether has been anchored within the heart, and a compressed device capsule has been expelled over-wire from the transcatheter lumen for delivery to the annulus target location.

Figure 103:
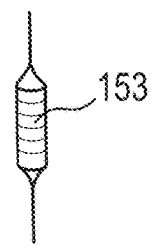

FIG. 103 is an illustration of a balloon expansion device that is delivered over-wire to an internal working channel within the compressed device capsule where air or fluid is delivered to the inner chamber of the balloon expansion device to expand in sequence various expandable segments of the compressed device capsule.

Figure 104:
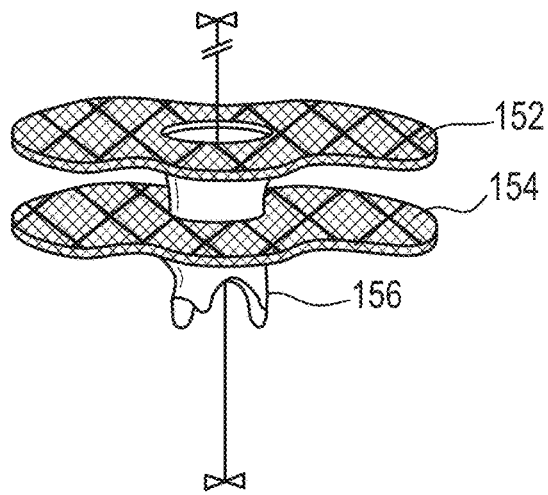

FIG. 104 is an illustration of a side perspective view of an expanded transcatheter prosthetic valve device. FIG. 104 shows a Step 2 of 8 of a time sequence illustration of a transcatheter delivery of a heart valve prosthesis according to the present invention where an expanded transcatheter prosthetic valve device is delivered over-wire to its target deployment location/position.

Figure 105:
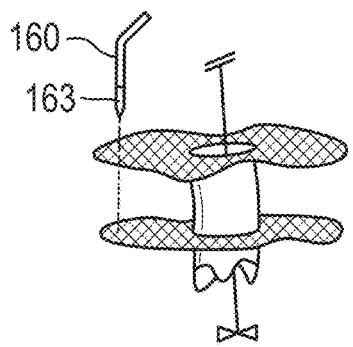

FIG. 105 is an illustration of a side perspective view of an expanded transcatheter prosthetic valve device. FIG. 105 shows a Step 3 of 8 of a time sequence illustration of a transcatheter delivery of a heart valve prosthesis according to the present invention where a compressed device capsule has been expanded to its working size with an atrial side sealing collar and a ventricle side sealing collar positioned to capture annulus or adjacent tissue. FIG. 105 also shows catheter tool targeting a first fastener pin for delivery.

Figure 106:
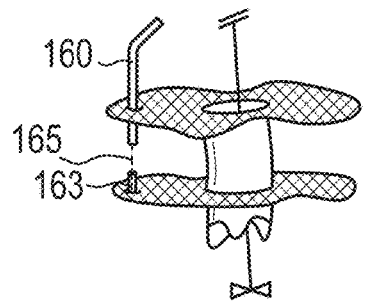

FIG. 106 is an illustration of a side perspective view of an expanded transcatheter prosthetic valve device. FIG. 106 shows a Step 4 of 8 of a time sequence illustration of a transcatheter delivery of a heart valve prosthesis according to the present invention where a compressed device capsule has been expanded to its working size with an atrial side sealing collar and a ventricle side sealing collar positioned to capture annulus or adjacent tissue. FIG. 106 also shows pin delivery tool delivering a first fastener pin through the atrial side sealing collar and attaching it to the ventricular side sealing collar.

Figure 107:
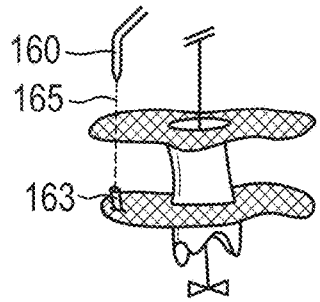

FIG. 107 is an illustration of a side perspective view of an expanded transcatheter prosthetic valve device. FIG. 107 shows a Step 4 of 8 of a time sequence illustration of a transcatheter delivery of a heart valve prosthesis according to the present invention where a pin delivery tool is disengaged from the pin anchored in the ventricular sealing collar and a securement wire is paid out from the pin delivery tool.

Figure 108:
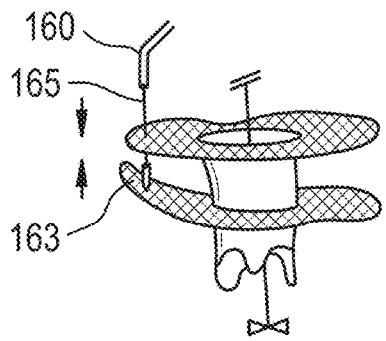

FIG. 108 is an illustration of a side perspective view of an expanded transcatheter prosthetic valve device. FIG. 108 shows a Step 5 of 8 of a time sequence illustration of a transcatheter delivery of a heart valve prosthesis according to the present invention where the securement wire is tensioned to draw the ventricular sealing collar towards the atrial sealing collar.

Figure 109:
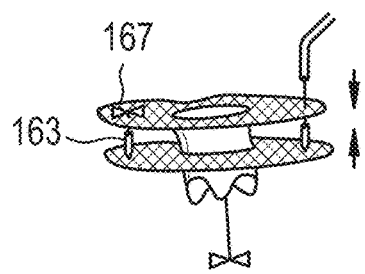

FIG. 109 is an illustration of a side perspective view of an expanded transcatheter prosthetic valve device. FIG. 109 shows a Step 5 of 8 of a time sequence illustration of a transcatheter delivery of a heart valve prosthesis according to the present invention where a pin delivery tool delivers one or more pin fasteners and attaches them to the ventricular sealing collar, where a securement wire is paid out and then tensioned to draw the upper and lower sealing collars together.

Figure 110:

FIG. 110 is an illustration of a side perspective view of a transcatheter prosthetic valve device after it has been mounted within the annulus and the temporary over-wire delivery tether has been unsecured and withdrawn.

Figure 111:
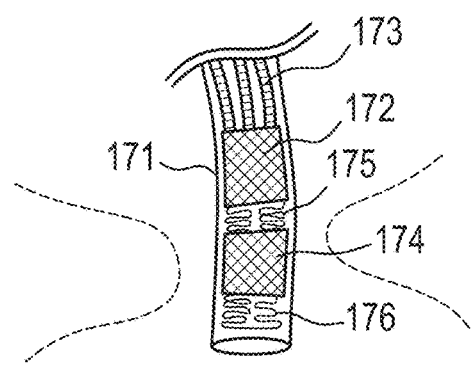

FIG. 111 is an illustration of a cross-sectional view of a transcatheter prosthetic valve device that has been compressed within the lumen of a delivery catheter. FIG. 111 shows Step 1 of 5 of a time sequence illustration wherein the compressed capsule/payload of the valve is delivered to the native annulus of a heart valve.

Figure 112:
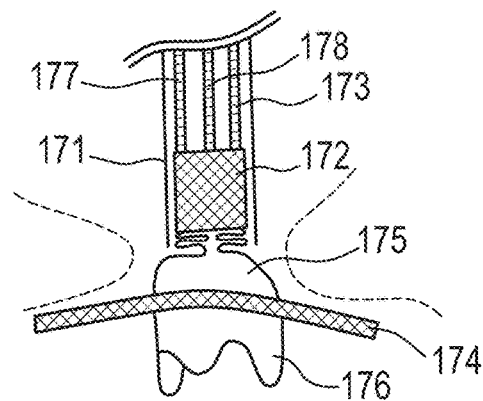

FIG. 112 is an illustration of a cross-sectional view of a transcatheter prosthetic valve device that has been compressed within the lumen of a delivery catheter and is partially expelled from the catheter. FIG. 112 shows Step 2 of 5 of a time sequence illustration wherein the compressed capsule/payload of the valve is delivered to the native annulus of a heart valve, and the sub-annular collar is expanded within the ventricle just below the native annulus.

Figure 113:
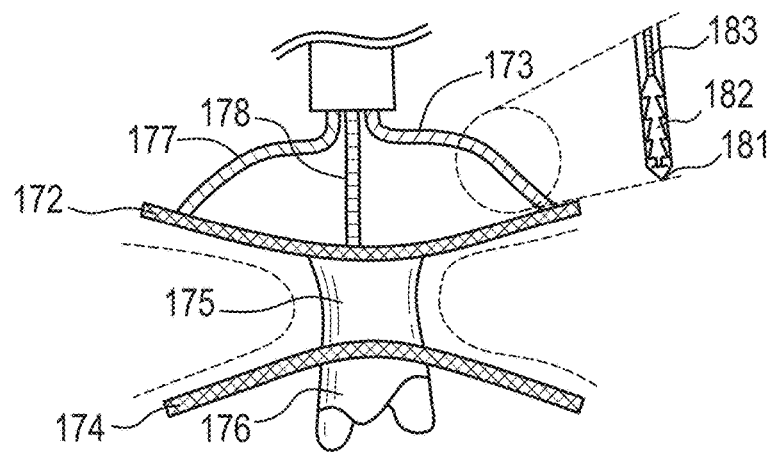

FIG. 113 is an illustration of a cross-sectional view of a transcatheter prosthetic valve device that has been expelled within the lumen of a delivery catheter. FIG. 113 shows Step 3 of 5 of a time sequence illustration wherein the prosthetic valve device is delivered to the native annulus of a heart valve, the sub-annular collar has been expanded within the ventricle just below the native annulus, and the supra-annular collar is expanded within the atrium just above the native annulus.

Figure 114:
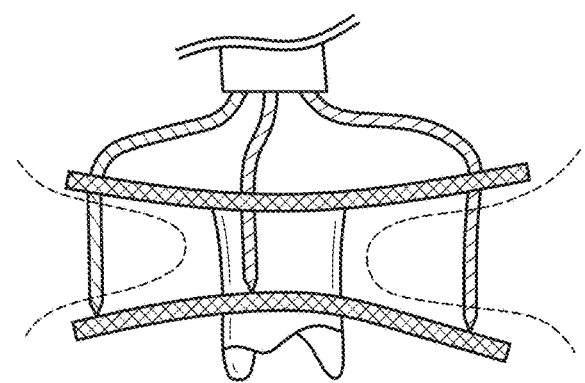

FIG. 114 is an illustration of a cross-sectional view of a transcatheter prosthetic valve device that has been expelled within the lumen of a delivery catheter. FIG. 114 shows Step 4 of 5 of a time sequence illustration wherein the prosthetic valve device is delivered to the native annulus of a heart valve, with a subannular collar on the ventricular side of the native annulus and a supra-annular collar on the atrial side of the native annulus, and where three steerable pin delivery catheters are shown after piercing the supra-annular collar and advancing the end of the pin delivery tool to an attachment location on the sub-annular collar.

Figure 115:
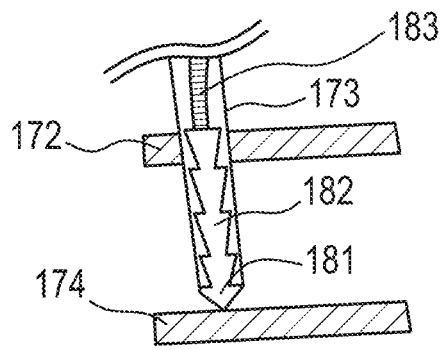

FIG. 115 is an illustration of a cross-sectional detailed view of a distal end of a pin delivery catheter. FIG. 115 shows Step 5(a) of 5(a)-(d) of a time sequence illustration where steerable pin delivery catheter is advanced, extended across the supra-annular collar and positioned just above the anchoring location on the sub-annular collar.

Figure 116:
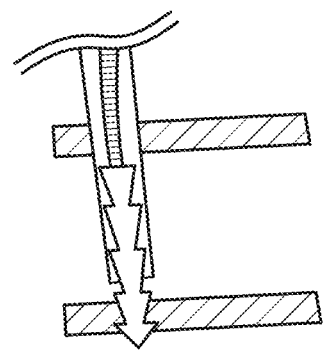

FIG. 116 is an illustration of a cross-sectional detailed view of a distal end of a pin delivery catheter. FIG. 116 shows Step 5(b) of 5(a)-(d) of a time sequence illustration where steerable pin delivery catheter is advanced, extended across the supra-annular collar and the anchoring point or tip is advanced to penetrate the cover material and the wire frame of the sub-annular collar at the anchoring location on the sub-annular collar.

Figure 117:
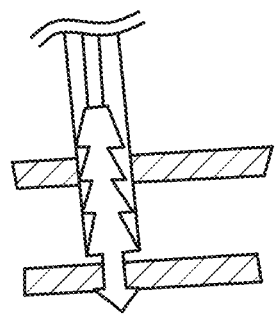

FIG. 117 is an illustration of a cross-sectional detailed view of a distal end of a pin delivery catheter. FIG. 117 Step 5(c) of 5(a)-(d) of a time sequence illustration where steerable pin delivery catheter is advanced, extended across the supra-annular collar, the anchoring point or tip has penetrated the cover material and wire frame of the sub-annular collar at the anchoring location on the sub-annular collar, and steerable delivery catheter is withdrawn to bring the top and bottom collars together, compressing and capturing the annular tissue located between the collars.

Figure 118:
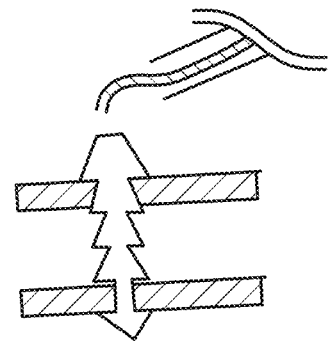

FIG. 118 is an illustration of a cross-sectional detailed view of a distal end of a pin delivery catheter. FIG. 118 Step 5(d) of 5(a)-(d) of a time sequence illustration where steerable pin delivery catheter is advanced, extending across the supra-annular collar, the anchoring point or tip has penetrated the cover material and wire frame of the sub-annular collar at the anchoring location on the sub-annular collar, steerable delivery catheter has closed the distance and brought the top and bottom collars together, compressing and capturing the annular tissue located between the collars, and where the external sheath of of the steerable delivery catheter is withdrawn, exposing anchoring flanges to lock the top supra-annular collar in place, maintaining the tensioned, compression of the collars on the native annulus tissue captured between the collars.

Figure 119:
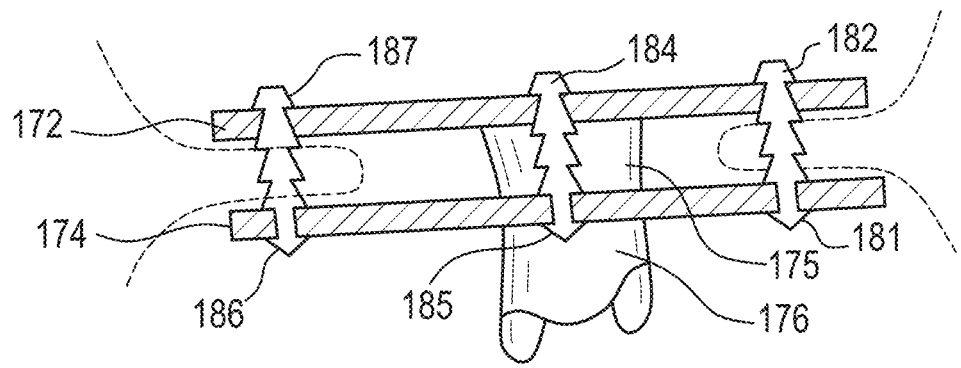

FIG. 119 is an illustration of a partial cross-sectional side view of a prosthetic valve device with three locking pins mounted between the two collars. FIG. 119 shows steerable pin delivery catheter extending across the supra-annular collar, the anchoring point or tip has penetrated the cover material and wire frame of the sub-annular collar at the anchoring location on the sub-annular collar, the top and bottom collars are together, compressing and capturing the annular tissue located between the collars, and the anchoring flanges lock the top supra-annular collar in place, maintaining the tensioned, compression of the collars on the native annulus tissue captured between the collars.

Figure 120:
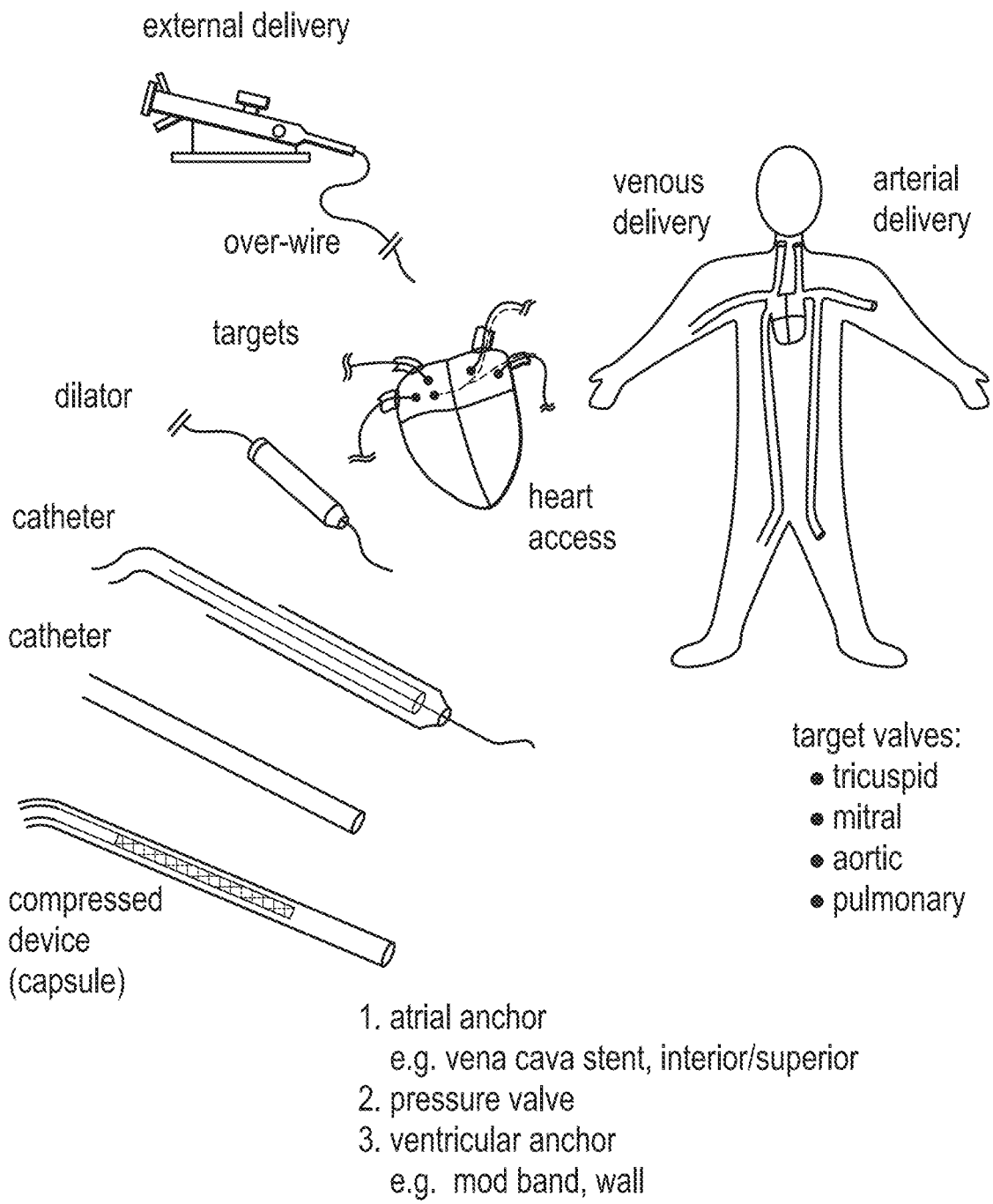

FIG. 120 is an illustration showing that the device(s) can be delivered over wire, using a dilator, and catheter using the traditional venous and arterial access techniques for the heart.

Figure 121:
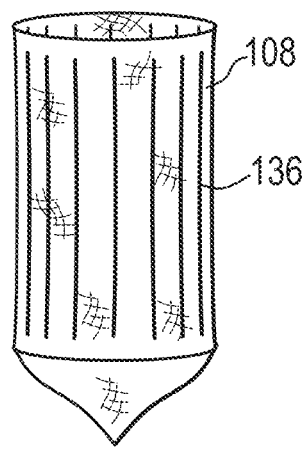

FIG. 121 is an illustration showing that the pliant conduit may be fitted with longitudinal filaments, or ribs, that are integrated within the fabric or material of the pliant conduit to provide additional mechanical support to the pliant conduit if necessary.

Figure 122:
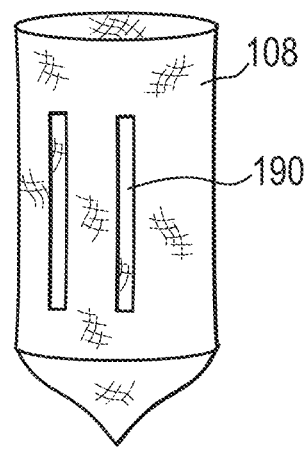

FIG. 122 is an illustration showing additional length-wise mechanical supports may also be in the form of one or more batons or rigid members.

Figure 123:
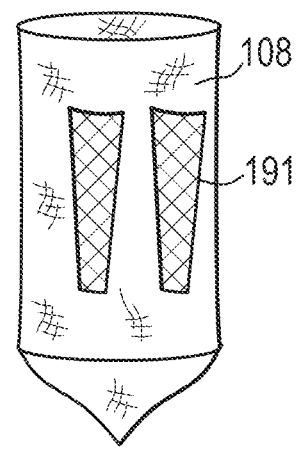

FIG. 123 is an illustration showing additional length-wise mechanical supports may also be in the form of one or more panels.

Figure 124:
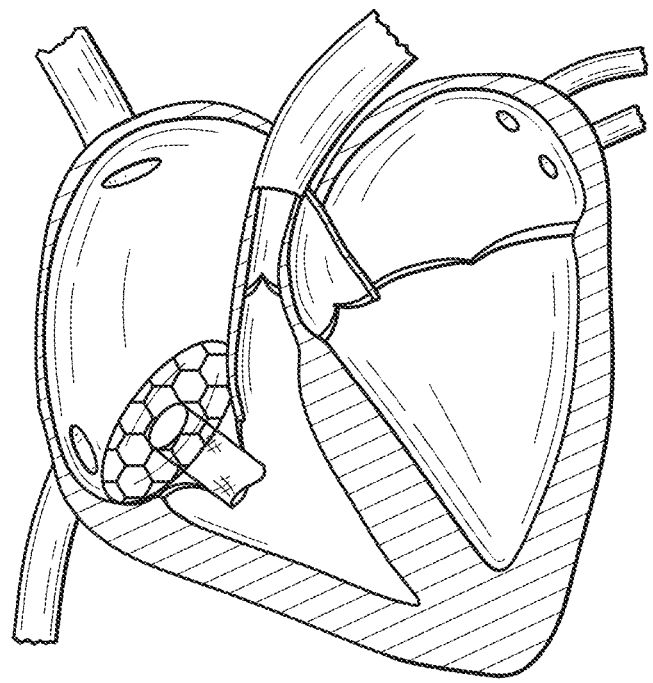

FIG. 124 is a cross-sectional illustration of the heart and shows an embodiment having a covered annular mesh attached to the atrial floor with the opening of a tube valve integrated into the mesh, where the tube is papillary length.

Figure 125:
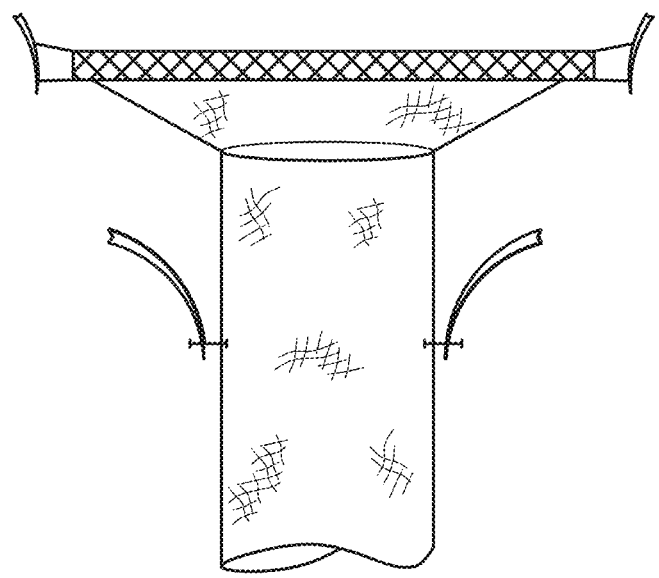

FIG. 125 is a cross-sectional illustration and shows an embodiment having the tube stitched to the native leaflets.

Figure 126:
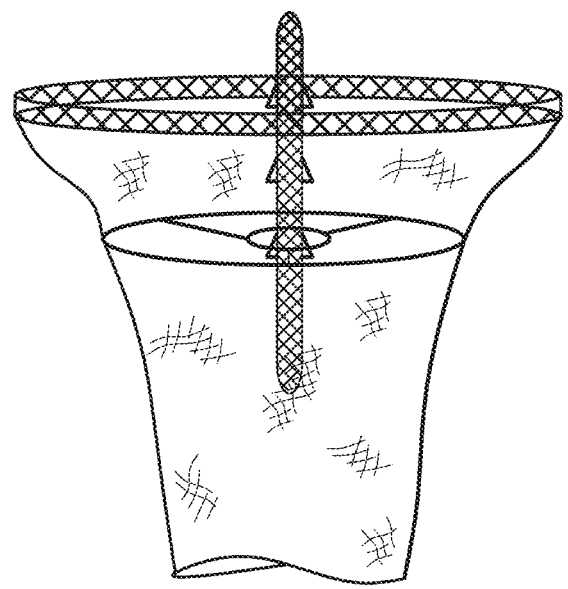

FIG. 126 is a cross-sectional illustration and shows an embodiment having an adjustable post height, where the annular ring has a hub, and the hub engages self-locking pegs or pin, and where the tube is adjustably mounted to travel with the post/frame.

Figure 127:
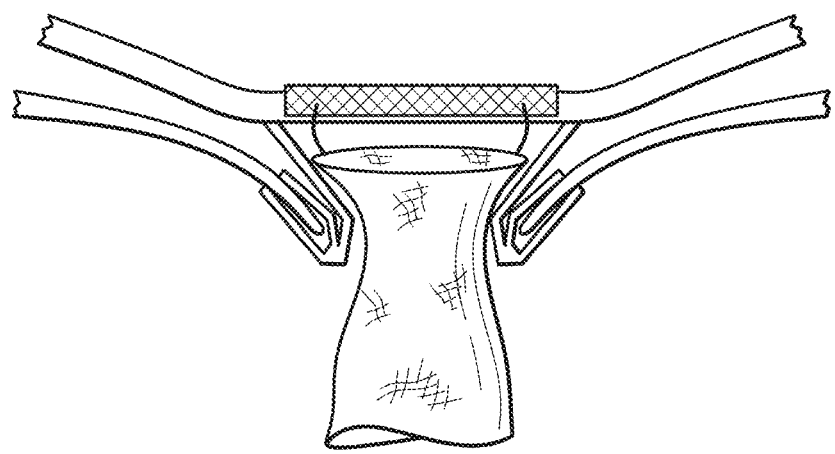

FIG. 127 is a cross-sectional illustration and shows an embodiment having clips for capturing leaflets where the clips are attached to an atrial plate, and an hourglass shaped tube is mounted above and below the annular plane.

Figure 128:
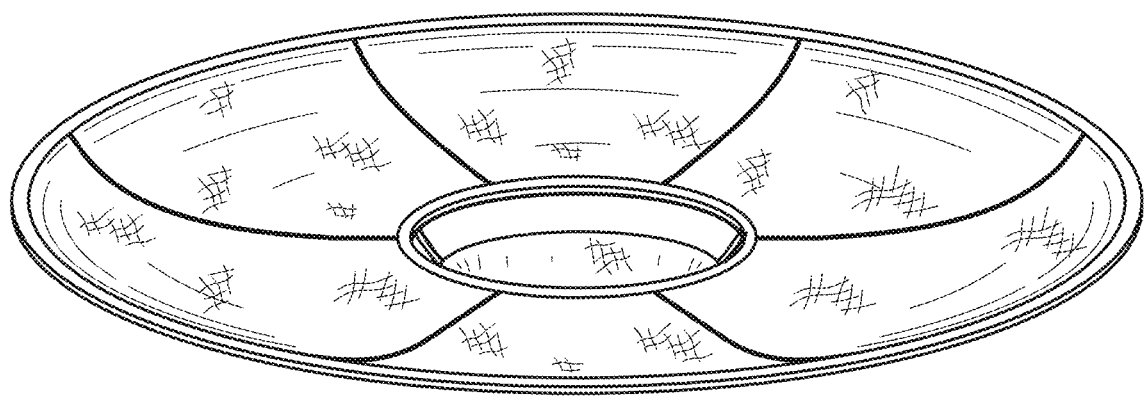

FIG. 128 is a top perspective view illustration of FIG. 127.

Figure 129:
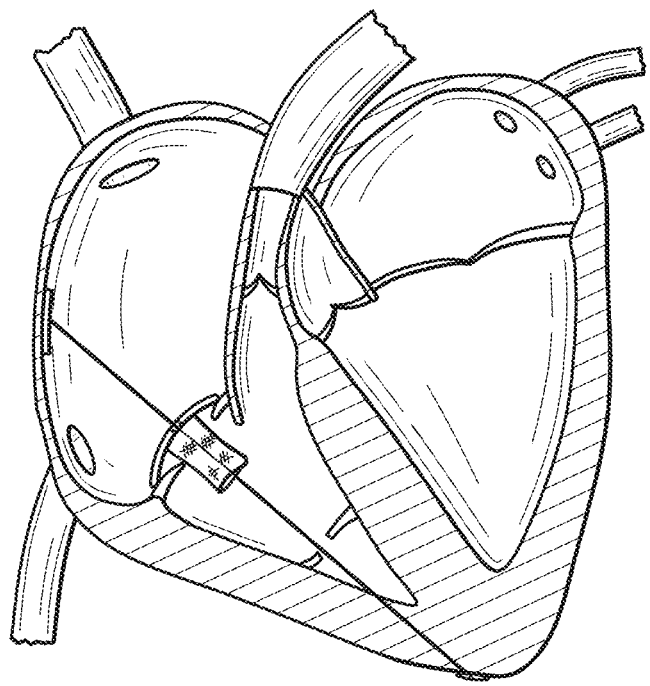

FIG. 129 is cross-sectional illustration and show an embodiment having a spanning tether between a pad on the atrial ceiling and a toggle or anchor outside the pericardium, with the tube valve mounted on a flexing frame that is adjustably positioned in a tensioned, sealing conformation at the annulus.

Figure 130:
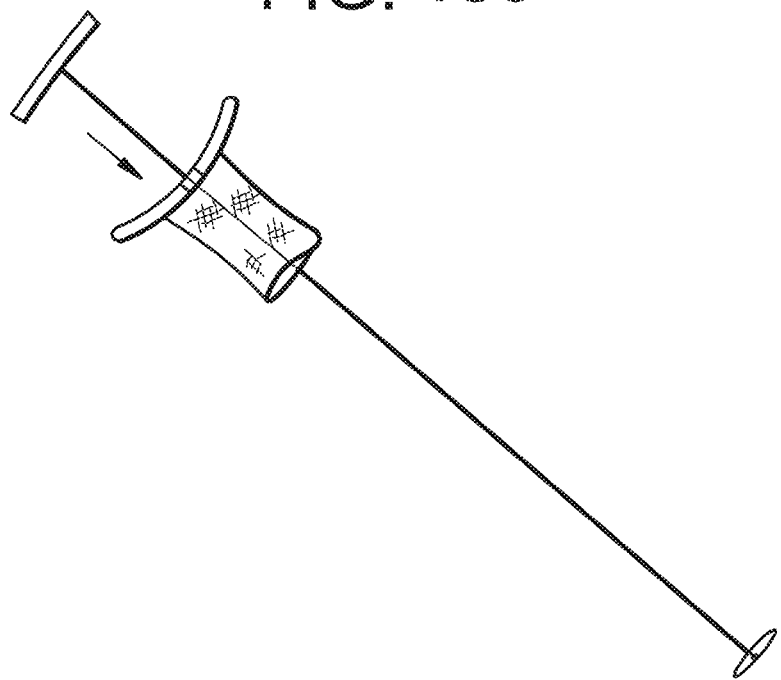

FIG. 130 is a cross sectional illustration showing the valve compressed into a sealing position.

Figure 131:
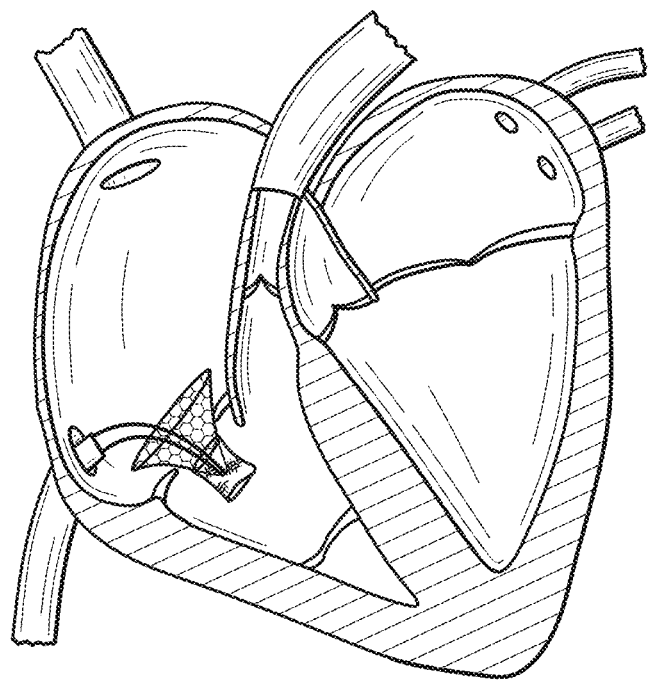

FIG. 131 is a cross-sectional illustration of the heart and shows an embodiment mounting from within the IVC, where the structure extends conically from below the annulus to above the annulus and provides sealing on the annular floor, with the valve mounted on the structure starting at the annular plane and extending as a short "leaflet-length" tube into the ventricle.

Figure 132:
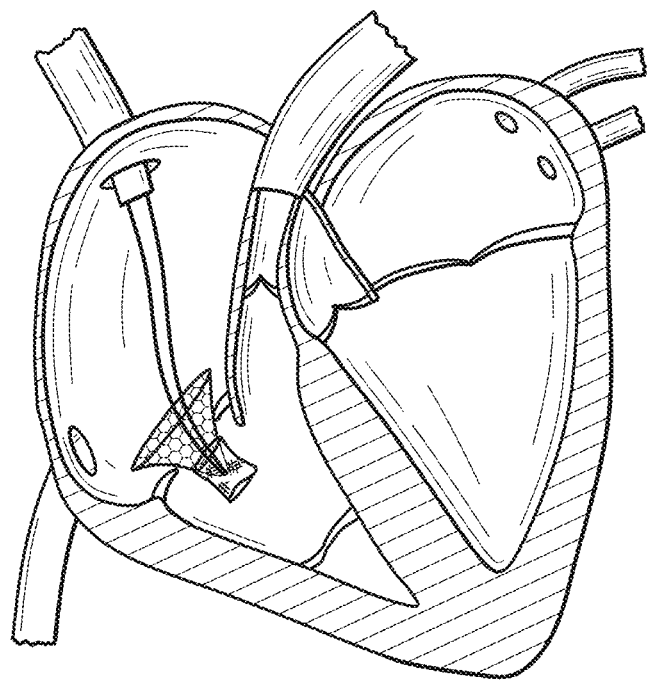

FIG. 132 is a cross-sectional illustration of the heart and shows an embodiment mounting from within the SVC, where the structure extends conically from below the annulus to above the annulus and provides sealing on the annular floor, with the valve mounted on the structure starting at the annular plane and extending as a short "leaflet-length" tube into the ventricle.

Figure 133:
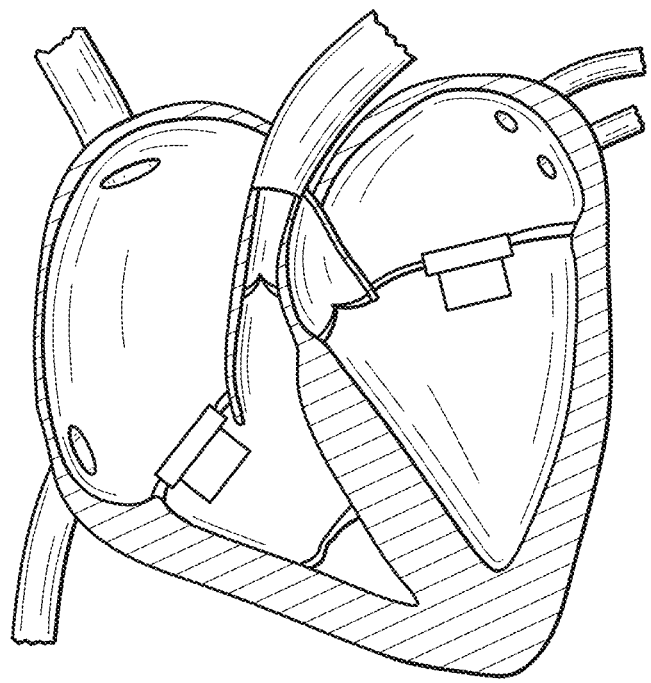

FIG. 133 is a cross-sectional illustration of the heart and shows an embodiment having a screw-in anchored annular frame and a short tube-valve.

Figure 134:
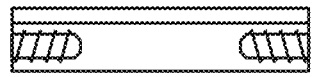

FIG. 134 is a plan illustration of the side of the annular stent frame having screws.

Figure 135:
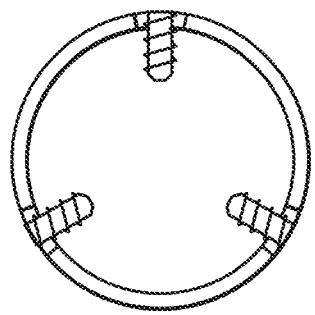

FIG. 135 is a top view and shows the screws within the internal aperture of the annular frame prior to be screwed in and deployed into the annular fibrous tissue.

Figure 136:
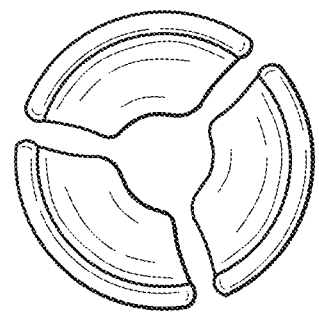

FIG. 136 is a top view of the native tricuspid and shows target location for screws.

Figure 137:
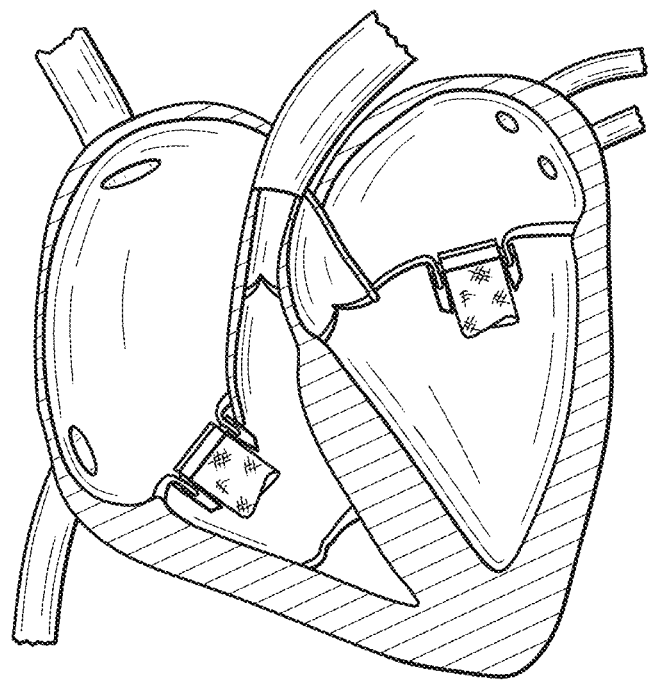

FIG. 137 is a cross-sectional illustration of the heart and shows an embodiment having (magnetic) leaflet clips for mounting the tube-valve and annular ring frame.

Figure 138:
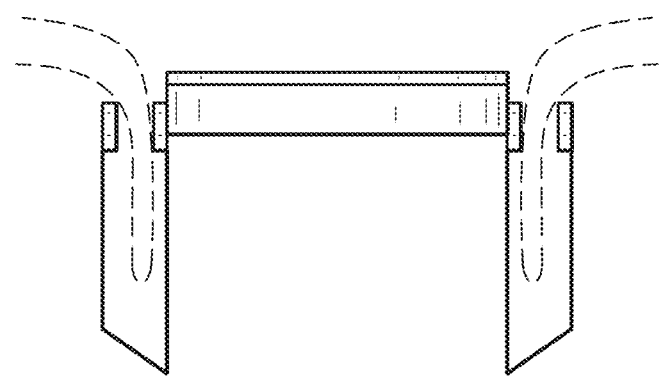

FIG. 138 is a cross-sectional illustration of the heart and shows how the leaflets would be placed within wire-form pockets.

Figure 139:
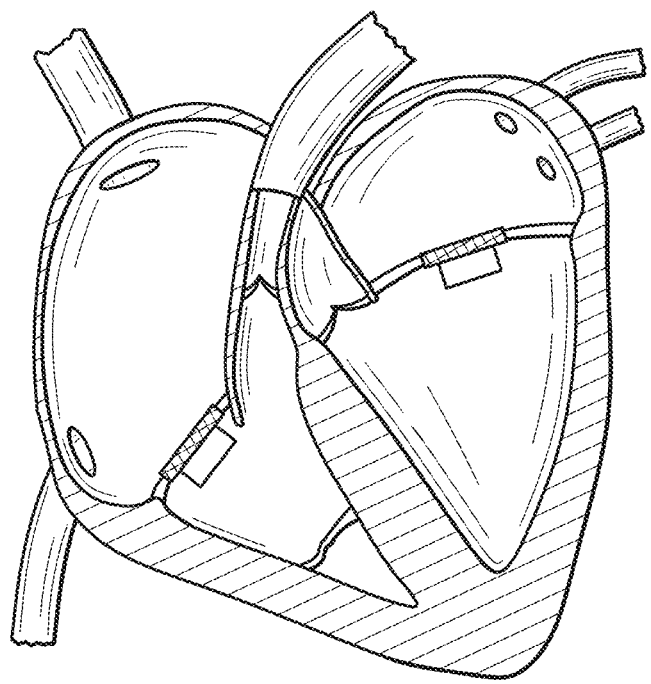

FIG. 139 is a cross-sectional illustration of the heart and shows an embodiment having anchor barbs on an expandable annular stent frame.

Figure 140:
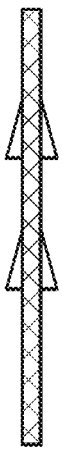

FIG. 140 shows before balloon expansion where the barbs go from laying flat against the stent body to deploying into the fibrous annular tissue upon expanding of the stent frame.

Figure 141:
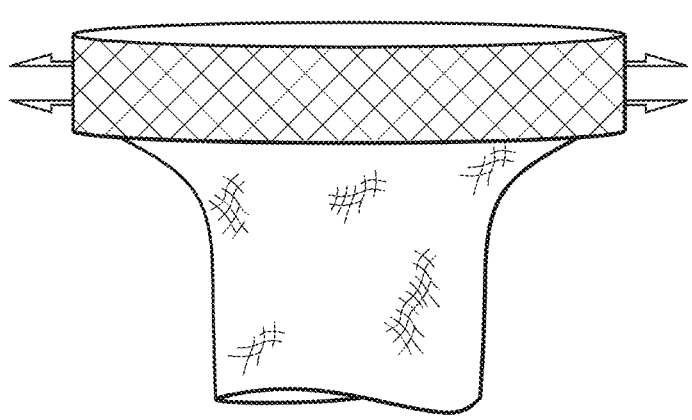

FIG. 141 shows after balloon expansion where the barbs go from laying flat against the stent body to deploying into the fibrous annular tissue upon expanding of the stent frame.

Figure 142:
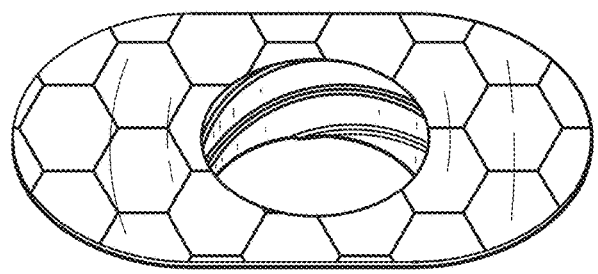

FIG. 142 is an illustration of a two-piece screw-in embodiment having an outer atrial cuff that has a central threaded aperture that allows an externally threaded mounting ring to be deployed within the aperture.

Figure 143:
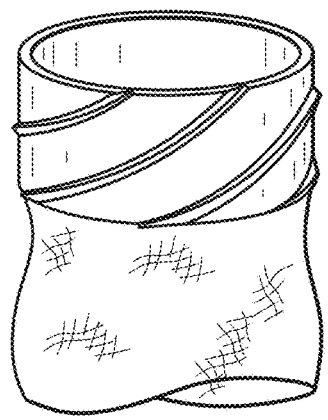

FIG. 143 is an illustration of an externally threaded mounting ring for deploying within the aperture of FIG. 142 and shows the tube-valve attached to the bottom edge of the threaded mounting ring.

Figure 144:
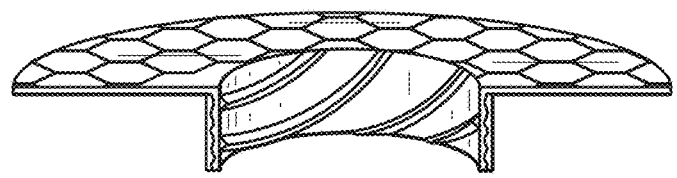

FIG. 144 is a cross-sectional illustration and shows the plate of the atrial cuff and the internal screw threads of the aperture/mounting ring receiver.

Figure 145:
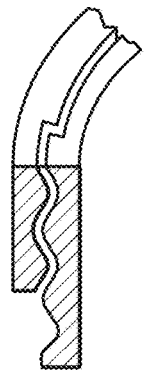

FIG. 145 is an illustration of a snap-locking mechanism to lock the mounting ring in place within the receiver.

Figure 146:

FIG. 146 is an illustration of a screw-type locking mechanism for securing the mounting ring within the threaded receiver.

Figure 147:
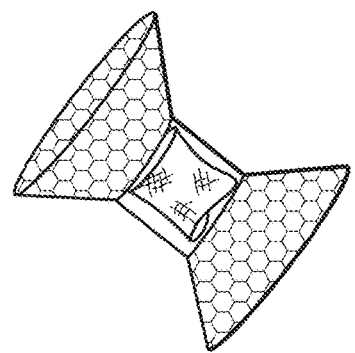

FIG. 147 is an illustration of an embodiment having an hourglass shaped wire-form structure that is deployed to extend partially into both the atrium and the ventricle with the tube-valve mounted within the central tubular chamber between the two divergent conical frame members.

Figure 148:
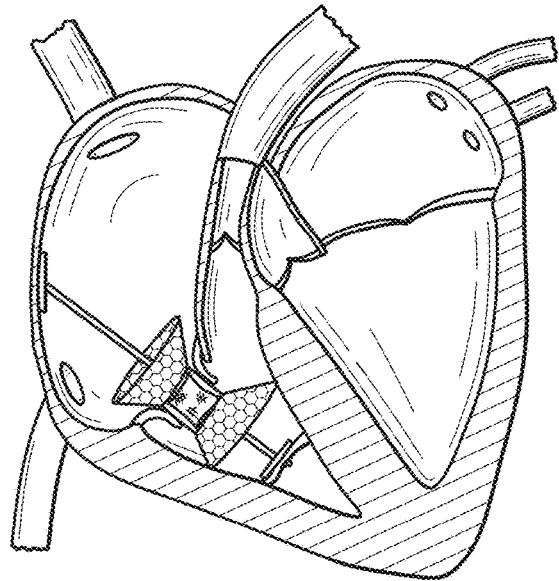

FIG. 148 is a cross-sectional illustration of the heart and shows an embodiment having an hourglass tube-valve deployed in the tricuspid valve annulus.

Figure 149:
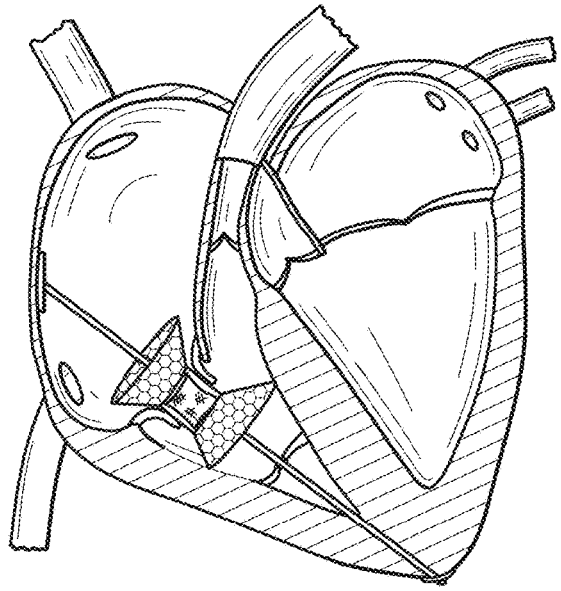

FIG. 149 shows optional tethers than can be used with the hourglass embodiment.

Figure 150:
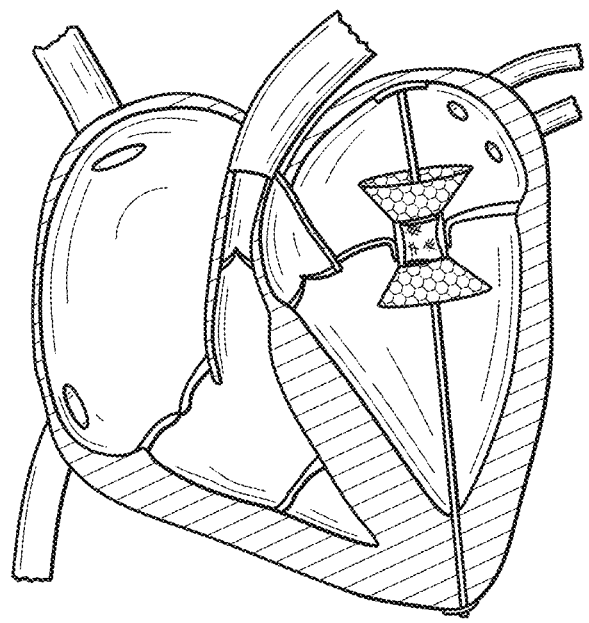

FIG. 150 is a cross-sectional illustration of the heart and shows an embodiment having an hourglass tube-valve deployed in the mitral valve annulus.

Figure 151:
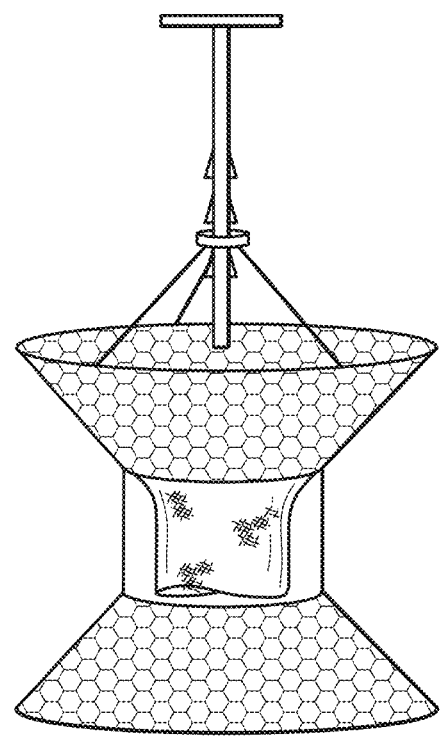

FIG. 151 is an illustration that shows the hourglass embodiment used in conjunction with the tensioning atrial rod.

DETAILED DESCRIPTION OF THE INVENTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Rather, these embodiments are provided so that this disclosure will be thorough and complete, and will fully convey the scope of the invention to those skilled in the art. Like numbers refer to like elements throughout. As used herein the term "and/or" includes any and all combinations of one or more of the associated listed items.

The terminology used herein is for the purpose of describing particular embodiments only and is not intended to limit the full scope of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal subparts. As will be understood by one skilled in the art, a range includes each individual member.

DEFINITIONS

Transcatheter

In the description and claims herein, the term "transcatheter" is used to define the process of accessing, controlling, and delivering a medical device or instrument within the lumen of a catheter that is deployed into a heart chamber, as well as an item that has been delivered or controlled by such as process. Transcatheter access is known to include via femoral artery and femoral vein, via brachial artery and vein, via carotid and jugular, via intercostal (rib) space, and via sub-xyphoid.

Wire Frame or Flange or Collar

In the description and claims herein, the terms "frame" or "flange or "collar" refers to flange, disk, band, ring, hem, rim, or belt that is a substantially flat cone shaped braided or laser-cut wire frame covered with a biocompatible material and having a central aperture. An atrial frame or collar is located in the atrium on the atrial floor and is used to direct blood into the sleeve attached to the aperture and seal against blood leakage around the sleeve. A ventricular frame or collar is located in the ventricle immediately below the native annulus and is used to prevent regurgitant leakage during systole, to prevent dislodging of the device during systole, to sandwich or compress the native annulus or adjacent tissue against the atrial collar, and to attach to a mid-section of the sleeve/conduit. The frames may be formed from braided or laser-cut Nitinol and as such may be compressed for transcatheter delivery and may be expandable as a self-expandable shape memory element or using a transcatheter expansion balloon. Some embodiments may have both an atrial collar and a ventricular collar, whereas other embodiments within the scope of the invention include prosthetic valves having either a single atrial collar or a single ventricular collar.

Sleeve

In the description and claims herein, the term "collapsible flow control sleeve" refers to a tube or conduit of flexible material that is open to blood flowing during diastole from atrium to ventricle, and that closes from systolic ventricular pressure applied to the outer surface. Repeated opening and closing in sequence can be described as "reciprocating." The tube is form of pinch valve but is not a valve in the tradition sense having no internal leaflets.

Tissue Anchor

In the description and claims herein, the term "tissue anchor" or "plication tissue anchor" or "secondary tissue anchor", or "dart" or "pin" refers to a fastening device that connects the upper atrial frame to the native annular tissue, usually at or near the periphery of the collar. The anchor may be positioned to avoid piercing tissue and just rely on the compressive force of the two plate-like collars on the captured tissue, or the anchor, itself or with an integrated securement wire, may pierce through native tissue to provide anchoring, or a combination of both. The anchor may have a specialized securement mechanism, such as a pointed tip with a groove and flanged shoulder that is inserted or popped into a mated aperture or an array of mated apertures that allow the anchor to attach, but prevent detachment when the aperture periphery locks into the groove near the flanged shoulder. The securement wire may be attached or anchored to the collar opposite the pin by any attachment or anchoring mechanisms, including a knot, a suture, a wire crimp, a wire lock having a cam mechanism, or combinations.

Support Post

The term "support post" refers to a rigid or semi-rigid length of material such as Nitinol or PEEK, that may be mounted on a spoked frame and that runs axially, or down the center of, or within a sewn seam of—, the flexible sleeve. The sleeve may be unattached to the support post, or the sleeve may be directly or indirectly attached to the support post.

In the description that follows, the term "body channel" is used to define a blood conduit or vessel within the body. Of course, the particular application of the prosthetic heart valve determines the body channel at issue. An aortic valve replacement, for example, would be implanted in, or adjacent to, the aortic annulus. Likewise, a tricuspid or mitral valve replacement will be implanted at the tricuspid or mitral annulus. Certain features of the present invention are particularly advantageous for one implantation site or the other. However, unless the combination is structurally impossible, or excluded by claim language, any of the heart valve embodiments described herein could be implanted in any body channel.

The term "lumen" refers to the inside of the cylinder tube. The term "bore" refers to the inner diameter.

Displacement—The volume of fluid displaced by one complete stroke or revolution.

Ejection fraction is a measurement of the percentage of blood leaving your heart each time it contracts. During each heartbeat pumping cycle, the heart contracts and relaxes. When your heart contracts, it ejects blood from the two pumping chambers (ventricles)

As a point of further definition, the term "expandable" is used herein to refer to a component of the heart valve capable of expanding from a first, delivery diameter to a second, implantation diameter. An expandable structure, therefore, does not mean one that might undergo slight expansion from a rise in temperature, or other such incidental cause. Conversely, "non-expandable" should not be interpreted to mean completely rigid or a dimensionally stable, as some slight expansion of conventional "non-expandable" heart valves, for example, may be observed.

Force—A push or pull acting upon a body. In a hydraulic cylinder, it is the product of the pressure on the fluid, multiplied by the effective area of the cylinder piston.

Prosthetic Valve

The term prosthesis or prosthetic encompasses both complete replacement of an anatomical part, e.g. a new mechanical valve replaces a native valve, as well as medical devices that take the place of and/or assist, repair, or improve existing anatomical parts, e.g. native valve is left in place. For mounting within a passive assist cage, the invention contemplates a wide variety of (bio)prosthetic artificial heart valves. Contemplated as within the scope of the invention are ball valves (e.g. Starr-Edwards), bileaflet valves (St. Jude), tilting disc valves (e.g. Bjork-Shiley), stented pericardium heart-valve prosthesis' (bovine, porcine, ovine) (Edwards line of bioprostheses, St. Jude prosthetic valves), as well as homograft and autograft valves. For bioprosthetic pericardial valves, it is contemplated to use bioprosthetic aortic valves, bioprosthetic mitral valves, bioprosthetic tricuspid valves, and bioprosthetic pulmonary valves.

Septomarginal Trabecula Also Known as Moderator Band

The septomarginal trabecula of the right ventricle, originally termed the moderator band because it was thought to limit the lateral expansion of the chamber, is a muscular thickening extending from the interventricular septum to the base of the anterior papillary muscle. One of the main functions of the septomarginal trabecula is to convey the right branch of the atrioventricular bundle of the conducting system. The septomarginal trabecula also functions to form the anteroinferior border between the superior, smooth outflow tract of the ventricle and the trabeculated inflow tract. At its septal attachment, it may be continuous with the supraventricular crest.

Frame Structure

Preferably, the frame is made from superelastic metal wire, such as Nitinol (TM) wire or other similarly functioning material. The material may be used for the frame/stent, for the collar, and/or for anchors. It is contemplated as within the scope of the invention to use other shape memory alloys such as Cu—Zn—Al—Ni alloys, Cu—Al—Ni alloys, as well as polymer composites including composites containing carbon nanotubes, carbon fibers, metal fibers, glass fibers, and polymer fibers. It is contemplated that the frame may be constructed as a braided wire frame or as a laser cut wire frame. Such materials are available from any number of commercial manufacturers, such as Pulse Systems. Laser cut wire frames are preferably made from Nickel-Titanium (Nitinol (TM)), but also without limitation made from stainless steel, cobalt chromium, titanium, and other functionally equivalent metals and alloys, or Pulse Systems braided frame that is shape-set by heat treating on a fixture or mandrel.

One key aspect of the frame design is that it be compressible and when released have the stated property that it return to its original (uncompressed) shape. This requirement limits the potential material selections to metals and plastics that have shape memory properties. With regards to metals, Nitinol has been found to be especially useful since it can be processed to be austenitic, martensitic or super elastic. Martensitic and super elastic alloys can be processed to demonstrate the required compression features.

Laser Cut

One possible construction of the wire frame envisions the laser cutting of a thin, isodiametric Nitinol tube. The laser cuts form regular cutouts in the thin Nitinol tube.

Secondarily the tube is placed on a mold of the desired shape, heated to the Martensitic temperature and quenched. The treatment of the wire frame in this manner will form a device that has shape memory properties and will readily revert to the memory shape at the calibrated temperature.

Braided Wire

A frame can be constructed utilizing simple braiding techniques. Using a Nitinol wire—for example, a 0.012" wire—and a simple braiding fixture, the wire is wound on the braiding fixture in a simple over/under braiding pattern until an isodiametric tube is formed from a single wire. The two loose ends of the wire are coupled using a stainless steel or Nitinol coupling tube into which the loose ends are placed and crimped. Angular braids of approximately 60 degrees have been found to be particularly useful. Secondarily, the braided wire frame is placed on a shaping fixture and placed in a muffle furnace at a specified temperature to set the wire frame to the desired shape and to develop the martensitic or super elastic properties desired.

Tethers

The tethers are made from surgical-grade materials such as biocompatible polymer suture material. Non-limiting examples of such material include ultra-high-molecular weight polyethylene (UHMWPE), 2-0 exPFTE(polytetrafluoroethylene) or 2-0 polypropylene. In one embodiment the tethers are inelastic. It is also contemplated that one or more of the tethers may optionally be elastic to provide an even further degree of compliance of the valve during the cardiac cycle.

Tines-Anchors-Tines/Barbs

The device can be seated within the valvular annulus through the use of tines or barbs. These may be used in conjunction with, or in place of one or more tethers. The tines or barbs are located to provide attachment to adjacent tissue. Tines are forced into the annular tissue by mechanical means such as using a balloon catheter. In one non-limiting embodiment, the tines may optionally be semi-circular hooks that upon expansion of the wire frame body, pierce, rotate into, and hold annular tissue securely. Anchors are deployed by over-wire delivery of an anchor or anchors through a delivery catheter. The catheter may have multiple axial lumens for delivery of a variety of anchoring tools, including anchor setting tools, force application tools, hooks, snaring tools, cutting tools, radio-frequency and radiological visualization tools and markers, and suture/thread manipulation tools. Once the anchor(s) are attached to the moderator band, tensioning tools may be used to adjust the length of tethers that connect to an implanted valve to adjust and secure the implant as necessary for proper functioning. It is also contemplated that anchors may be spring-loaded and may have tether-attachment or tether-capture mechanisms built into the tethering face of the anchor(s). Anchors may also have in-growth material, such as polyester fibers, to promote ingrowth of the anchors into the myocardium.

In one embodiment, where a prosthetic valve may or may not include a ventricular collar, the anchor or dart is not attached to a lower ventricular collar but is attached directly into annular tissue or other tissue useful for anchoring.

Tube and/or Cover Material—Biological Tissue—

The tissue used herein is a biological tissue that is a chemically stabilized pericardial tissue of an animal, such as a cow (bovine pericardium) or sheep (ovine pericardium) or pig (porcine pericardium) or horse (equine pericardium). Preferably, the tissue is bovine pericardial tissue. Examples of suitable tissue include that used in the products Dura-guard®, Peri-Guard®, and Vascu-Guard®, all products currently used in surgical procedures, and which are marketed as being harvested generally from cattle less than 30 months old. Other patents and publications disclose the surgical use of harvested, biocompatible animal thin tissues suitable herein as biocompatible "jackets" or sleeves for implantable stents, including for example, U.S. Pat. No. 5,554,185 to Block, U.S. Pat. No. 7,108,717 to Design & Performance-Cyprus Limited disclosing a covered stent assembly, U.S. Pat. No. 6,440,164 to Scimed Life Systems, Inc. disclosing a bioprosthetic valve for implantation, and U.S. Pat. No. 5,336,616 to LifeCell Corporation discloses acellular collagen-based tissue matrix for transplantation.

Polymers

In one preferred embodiment, the conduit may optionally be made from a synthetic material such a polyurethane or polytetrafluoroethylene.

Where a thin, durable synthetic material is contemplated, e.g. for a covering, synthetic polymer materials such expanded polytetrafluoroethylene or polyester may optionally be used. Other suitable materials may optionally include thermoplastic polycarbonate urethane, polyether urethane, segmented polyether urethane, silicone polyether urethane, silicone-polycarbonate urethane, and ultra-high molecular weight polyethylene. Additional biocompatible polymers may optionally include polyolefins, elastomers, polyethylene—glycols, polyethersulphones, polysulphones, polyvinylpyrrolidones, polyvinylchlorides, other fluoropolymers, silicone polyesters, siloxane polymers and/or oligomers, and/or polylactones, and block co-polymers using the same.

Polyamides (PA)

PA is an early engineering thermoplastic invented that consists of a "super polyester" fiber with molecular weight greater than 10,000. It is commonly called Nylon. Application of polyamides includes transparent tubing's for cardiovascular applications, hemodialysis membranes, and also production of percutaneous transluminal coronary angioplasty (PTCA) catheters.

Polyolefin

Polyolefins include polyethylene and polypropylene are the two important polymers of polyolefins and have better biocompatibility and chemical resistance. In cardiovascular uses, both low-density polyethylene and high-density polyethylene are utilized in making tubing and housings. Polypropylene is used for making heart valve structures.

Polyesters

Polyesters includes polyethylene-terephthalate (PET), using the name Dacron. It is typically used as knitted or woven fabric for vascular grafts. Woven PET has smaller pores which reduces blood leakage and better efficiency as vascular grafts compared with the knitted one. PET grafts are also available with a protein coating (collagen or albumin) for reducing blood loss and better biocompatibility [39]. PET vascular grafts with endothelial cells have been searched as a means for improving patency rates. Moreover, polyesters are widely preferred material for the manufacturing of bioabsorbable stents. Poly-L-lactic acids (PLLA), polyglycolic acid (PGA), and poly(D, L-lactide/glycolide) copolymer (PDLA) are some of the commonly used bioabsorbable polymers.

Polytetrafluoroethylene

Polytetrafluoroethylene (PTFE) is synthetic fluorocarbon polymer with the common commercial name of Teflon by Dupont Co. Common applications of PTFE in cardiovascular engineering include vascular grafts and heart valves. PTFE sutures are used in the repair of mitral valve for myxomatous disease and also in surgery for prolapse of the anterior or posterior leaflets of mitral valves. PTFE is particularly used in implantable prosthetic heart valve rings. It has been successfully used as vascular grafts when the devices are implanted in high-flow, large-diameter arteries such as the aorta. Problem occurs when it is implanted below aortic bifurcations and another form of PTFE called elongated-PTFE (e-PTFE) was explored. Expanded PTFE is formed by compression of PTFE in the presence of career medium and finally extruding the mixture. Extrudate formed by this process is then heated to near its glass transition temperature and stretched to obtain microscopically porous PTFE known as e-PTFE. This form of PTFE was indicated for use in smaller arteries with lower flow rates promoting low thrombogenicity, lower rates of restenosis and hemostasis, less calcification, and biochemically inert properties.

Polyurethanes

Polyurethane has good physiochemical and mechanical properties and is highly biocompatible which allows unrestricted usage in blood contacting devices. It has high shear strength, elasticity, and transparency. Moreover, the surface of polyurethane has good resistance for microbes and the thrombosis formation by PU is almost similar to the versatile cardiovascular biomaterial like PTFE. Conventionally, segmented polyurethanes (SPUs) have been used for various cardiovascular applications such as valve structures, pacemaker leads and ventricular assisting device.

Covered Wire Frame Materials

Drug-eluting wire frames are contemplated for use herein. DES basically consist of three parts: wire frame platform, coating, and drug. Some of the examples for polymer free DES are Amazon Pax (MINVASYS) using Amazonia CroCo (L605) cobalt chromium (Co—Cr) wire frame with Paclitaxel as an antiproliferative agent and abluminal coating have been utilized as the carrier of the drug. BioFreedom (Biosensors Inc.) using stainless steel as base with modified abluminal coating as carrier surface for the antiproliferative drug Biolimus A9. Optima (CID S.r.I.) using 316 L stainless steel wire frame as base for the drug Tacrolimus and utilizing integrated turbostratic carbofilm as the drug carrier. VESTA sync (MIV Therapeutics) using GenX stainless steel (316 L) as base utilizing microporous hydroxyapatite coating as carrier for the drug Sirolimus. YUKON choice (Translumina) used 316 L stainless steel as base for the drugs Sirolimus in combination with Probucol.

Biosorbable polymers may also be used herein as a carrier matrix for drugs. Cypher, Taxus, and Endeavour are the three basic type of bioabsorbable DES. Cypher (J&J, Cordis) uses a 316 L stainless steel coated with polyethylene vinyl acetate (PEVA) and poly-butyl methacrylate (PBMA) for carrying the drug Sirolimus. Taxus (Boston Scientific) utilizes 316 L stainless steel wire frames coated with translute Styrene Isoprene Butadiene (SIBS) copolymer for carrying Paclitaxel which elutes over a period of about 90 days. Endeavour (Medtronic) uses a cobalt chrome driver wire frame for carrying zotarolimus with phosphorylcholine as drug carrier. BioMatrix employing S-Wire frame (316 L) stainless steel as base with polylactic acid surface for carrying the antiproliferative drug Biolimus. ELIXIR-DES program (Elixir Medical Corp) consisting both polyester and polylactide coated wire frames for carrying the drug novolimus with cobaltchromium (Co—Cr) as base. JACTAX (Boston Scientific Corp.) utilized D-lactic polylactic acid (DLPLA) coated (316 L) stainless steel wire frames for carrying aclitaxel. NEVO (Cordis Corporation, Johnson & Johnson) used cobalt chromium (Co—Cr) wire frame coated with polylactic-co-glycolic acid (PLGA) for carrying the drug Sirolimus.

Examples of preferred embodiments of the reciprocating pressure conduit valve include the following details and features.

EXAMPLE

One preferred embodiment of a tethered transcatheter valve is a heart valve substitute or successor comprising a pliant tubular conduit that is mounted on a resilient annular or ventricular frame, wherein the pliant tubular conduit is a reciprocating mechanical member that is compressed by pressurized working fluid, blood, within the ventricle during systole, and wherein the frame includes plication tissue anchors for capturing and anchoring annular tissue with tissue anchors. Importantly, this heart valve substitute has no leaflets and does not have a traditional valve configuration. Additionally, the device can be delivered to the ventricle compressed within a catheter and expelled from the catheter to be deployed without open heart surgery.

Example

In another preferred embodiment of a transcatheter valve, comprises: (i) a atrial sealing frame and wherein the atrial frame optionally includes secondary plication tissue anchors for capturing and anchoring annular tissue with tissue anchors, and (ii) a ventricular sealing collar/flange/frame, each of said atrial and ventricular frame connected to (iii) a collapsible flow control sleeve that provides a reciprocating closable channel from a heart atrium to a heart ventricle, each of said frames comprised of a pair of flat conical shaped braided or laser-cut wire frame covered with a biocompatible material and each having a central aperture, the collapsible flow control sleeve connected at an upper end to an inner perimeter of the central aperture of the atrial sealing frame, the collapsible flow control sleeve connected at a middle section to an inner perimeter of the central aperture of the ventricular sealing frame, and the collapsible flow control sleeve extending beyond the central aperture of the ventricular sealing frame and having a lower end positioned with the ventricle of the heart, (iv) at least one folding tab member attached to the atrial sealing frame, and (v) from 2-12 tissue anchors connected to the folding tab(s), wherein the collapsible flow control sleeve defines a channel therein, said channel having a volume that ranges from 1.57 mL-18.84 mL, said sleeve having an average radius of 4.0-16.5 mm and an average height of 20-60 mm, said sleeve comprised of decellularized pericardium or polymer, said sleeve having top end, a bottom end, an internal surface, and an external surface, said sleeve is compressible under a pressure of 50-160 mm Hg on the external surface to close the channel, and said sleeve is expandable under a pressure of 40-80 mm Hg on the internal surface to open the channel, the collars have an average side length of 5-20 mm, an aperture having an average expanded diameter of 30-35 mm, and a perimeter having an average expanded diameter/circumference of 40-60 mm, said collars having a cover; and optional one-piece rigid or semi-rigid axial post disposed with the lumen of the sleeve to support the length-wise integrity of the flexible sleeve.

Example

In another preferred embodiment of a transcatheter valve, there is provided a feature wherein the sleeve is shaped as a conic cylinder, said top end having a diameter of 30-35 mm and said bottom end having a diameter of 8-20 mm.

Example

In another preferred embodiment of a transcatheter valve, there is provided a feature wherein the cover is comprised of polyester, polyethylene terephthalate, decellularized pericardium, or a layered combination thereof.

Example

In another preferred embodiment of a transcatheter valve, there is provided a feature wherein the nitinol frame supports a gel ring, wherein the gel ring is comprised of an expandable material enclosed within an outer sealing membrane, wherein the expandable material is a swellable powder within a polymeric matrix, a swellable polymeric matrix, or a swellable polymeric liquid.

Example

In another preferred embodiment of a transcatheter valve, there is provided a feature wherein the nitinol frame supports a deflatable ring, wherein the deflatable ring is comprised of a toroid-shaped sealed compartment having a valve, said sealed compartment Tillable with a biocompatible liquid or gas, wherein upon removal of some or all of the biocompatible liquid or gas, the deflatable ring has a reduced diameter, and wherein upon removal of some or all of the biocompatible liquid or gas, the top spacer segment of the cylinder has a reduced height and the collar is compressed in the direction of the top wire frame.

Example

In another preferred embodiment of a transcatheter valve, there is provided a feature wherein the sleeve has an hourglass (hyperboloid) shape from top end to bottom end.

Example

In another preferred embodiment of a transcatheter valve, there is provided a feature wherein the bottom end of the sleeve has a sinusoidal edge, and wherein one or more sections of the sleeve edge may be secured to one or more rigid support posts.

Example

In another preferred embodiment of a transcatheter valve, there is provided a feature wherein the atrial frame comprises a threaded structure, wherein the threaded structure allows for a simple circular screw-type deployment of the device into a native annulus to aid in sealing and sizing of the top collar into the native annulus.

Example

In a preferred embodiment of the invention, there is also provided a method of controlling flow of bodily fluid within an enclosed cavity of a human body, said enclosed cavity having a reciprocating pressure differential, the method comprising the steps: (i) delivering the transcatheter prosthetic medical device described herein, to the enclosed cavity within the human body; (ii) arranging the prosthetic medical device whereby the sleeve and sleeve channel are arranged parallel to a flow of fluid entering the enclosed cavity; (iii) expanding a top frame above an entrance to the enclosed cavity to mount the top end of the sleeve within the entrance, whereby the top flange applies an compression force and seals the entrance, and expanding the bottom frame below the entrance to the enclosed cavity to position the bottom end of the sleeve within the enclosed cavity; and (iv) anchoring the medical device using tissue anchor(s) to adjacent tissue, wherein bodily fluid arriving at the enclosed cavity is diverted into the channel of the sleeve; wherein the reciprocating pressure differential comprises a low pressure state and a high pressure state; wherein bodily fluid flows into the channel to the enclosed cavity during the low pressure state, and wherein bodily fluid is prevented from flowing into the channel to the enclosed cavity during the high pressure state, wherein the high pressure state exerts a force on the external surface of the sleeve and reversibly collapses the channel.

Example

The transcatheter prosthetic heart valve may be percutaneously delivered using a transcatheter process via the carotid, but both carotid, femoral, sub-xyphoid, and intercostal access across the chest wall. The device is delivered via catheter to the right or left atrium and is expanded from a compressed shape that fits with the internal diameter of the catheter lumen. The compressed pinch valve is loaded external to the patient into the delivery catheter and is then pushed out of the catheter when the capsule arrives to the atrium. The cardiac treatment technician visualizes this delivery using available imaging techniques such as fluoroscopy or ultrasound, and in a preferred embodiment the pinch valve self-expands upon release from the catheter since it is constructed in part from shape-memory material, such as Nitinol®, a nickel-titanium alloy used in biomedical implants.

In another embodiment, the valve may be constructed of materials that requires balloon-expansion after the capsule has been ejected from the catheter into the atrium.

Once the atrial collar/frame and the conduit sleeve are expanded to their functional diameter, they are deployed into the native annulus. The optional ventricular collar is expanded below the annulus forming a layered stack with the collars on top and bottom and the native annulus in the middle. It is also contemplated that an optional support post may be deployed within the lumen or within the seam, of the sleeve. Once the frame is deployed about the tricuspid annulus, fasteners secure the device about the native annulus. Additional fastening of the device to a moderator band mounting may be performed, and the deployment is complete. Further adjustments using hemodynamic imaging techniques are contemplated as within the scope of the invention in order to ensure the device is secure, is located and oriented as planned, and is functioning as a substitute or successor to the native tricuspid valve.

Example

In a preferred example of the invention, there is provided a method for securing a transcatheter heart valve prosthesis within a heart, the transcatheter heart valve prosthesis comprising a atrial sealing collar and a ventricular sealing collar, each of said collars connected to a collapsible flow control sleeve that provides a reciprocating closable channel from a heart atrium to a heart ventricle, each of said collars comprised of a substantially flat braided or laser-cut wire frame covered with a biocompatible material and each having a central aperture, the collapsible flow control sleeve connected at an upper end to an inner perimeter of the central aperture of the atrial sealing collar, the collapsible flow control sleeve connected at a middle section to an inner perimeter of the central aperture of the ventricular sealing collar, and the collapsible flow control sleeve extending beyond the central aperture of the ventricular sealing collar and having a lower end positioned with the ventricle of the heart, the method comprising the steps: (i) piercing the atrial sealing collar of the transcatheter heart valve prosthesis using a pin delivery tool; (ii) anchoring a pin into the ventricular sealing collar of the transcatheter heart valve prosthesis using the pin delivery tool; (iii) detaching the pin from the pin delivery tool and withdrawing the pin delivery tool, said pin having a securement wire attached thereto, the securement wire disposed within an inner lumen of the pin delivery tool, wherein the securement wire is revealed by withdrawal of the pin delivery tool, and wherein the pin delivery tool is withdrawn above the atrial sealing collar; (iv) tensioning the securement wire to draw the ventricular sealing collar toward the atrial sealing collar by reducing the length of the securement wire between the sealing collars; (v) fastening the securement wire to the atrial sealing collar and trimming the securement wire to disconnect the securement wire from the pin delivery tool; and (vi) repeating steps (i)-(v) to deploy from 2-12 pins and securement wires in the transcatheter heart valve prosthesis.

Example

In a preferred embodiment of the invention, there is also provided a method of controlling flow of bodily fluid within an enclosed cavity of a human body, said enclosed cavity having a reciprocating pressure differential, the method comprising the steps: (i) delivering the transcatheter prosthetic medical device, to the enclosed cavity within the human body; (ii) arranging the prosthetic medical device whereby the sleeve and sleeve channel are arranged parallel to a flow of fluid entering the enclosed cavity; (iii) expanding a top collar above an entrance to the enclosed cavity to mount the top end of the sleeve within the entrance, whereby the top collar applies an compression force and seals the entrance, and expanding the bottom collar below the entrance to the enclosed cavity to position the bottom end of the sleeve within the enclosed cavity; (iv) anchoring the sleeve to a rigid or semi-rigid axial tether disposed within the lumen of the sleeve; wherein bodily fluid arriving at the enclosed cavity is diverted into the channel of the sleeve; wherein the reciprocating pressure differential comprises a low pressure state and a high pressure state; wherein bodily fluid flows into the channel to the enclosed cavity during the low pressure state, and wherein bodily fluid is prevented from flowing into the channel to the enclosed cavity during the high pressure state, wherein the high pressure state exerts a force on the external surface of the sleeve and reversibly collapses the channel.

Example

In one preferred embodiment, a tricuspid pinch valve has an open framed annular collar having 2-12 radial bracket supports within the circumference of the atrial collar. Attached to the open framed collar is an axial post that extends into the ventricle and functions to provide structural support to the sleeve and the device, wherein the axial post is axially disposed within the pliant conduit sleeve. The axial post may be rigid or may be flexible and is attached at the top, e.g. proximal end to the open framed collar at a central tether mount. Center tether mount is held in place with 2-12 radial bracket supports that are connected to or extend from the inner circumferential surface of atrial collar to the center of the collar where the central tether mount is located. Axial post is fastened at the ventricular (bottom) or distal end with 2-8 conduit sleeve tethers. It is contemplated that the tricuspid pinch valve may be a standalone with no further tethering to ventricular tissue, or the tricuspid pinch valve may be anchored to the septomarginal trabecula, or moderator band, of the right ventricle using a pre-attached moderator band anchor/mount.

The open-framed annular collar has an open framework that permits blood from the right atrium to flow directly past the tricuspid annulus during diastole (ventricular infilling), bypassing the native valve. During ventricular compression, systole, the pliant conduit sleeve flattens (collapses) and is pinched closed due to the intraventricular pressure created by the heart. The axial post helps to maintain longitudinal integrity while permitting the axial flattening across the diameter of the conduit. The open frame collar, and both annular collars are collapsible and expandable allowing delivery via catheter, and it may be a stent structure or similar circular frame. The prosthetic valve device may be anchored solely using the compressed annular collars and/or may be anchored using the axial post when the axial post is mounted at its distal end to the moderator band by one or more suitable anchor devices such as surgical clips, clamps, and so forth. The distal end of the axial post can be allowed to "float", serving primarily as a longitudinal support for the pliant conduit sleeve or the distal end of the axial post may also be fastened to the bottom or distal end of the pliant conduit sleeve using 2-8 conduit sleeve tethers that connect the distal portion and/or edge of the pliant conduit to the axial post. Collars, radial bracket supports, central tether mount, axial post, conduit sleeve tethers, and the moderator band anchor/mount may be constructed, in whole or in part, of suitable metal, polymeric, or composite materials including nickel-titanium alloy, cobalt-chromium alloy, high cycle fatigue tolerant polymers including composites containing glass fiber, polymer fiber, carbon fiber, metal fiber, carbon nanotube fiber, and composites containing polymer filler materials.

Example

The transcatheter prosthetic heart valve may be percutaneously delivered using a transcatheter process via the carotid, but both carotid, femoral, sub-xyphoid, and intercostal access across the chest wall. Pinned annular collar pinch valve device is delivered via catheter to the right or left atrium and is expanded from a compressed capsule shape that fits with the internal diameter of the catheter lumen. The compressed pinch valve is loaded external to the patient into the delivery catheter and is then pushed out of the catheter when the capsule arrives to the atrium. The cardiac treatment technician visualizes this delivery using available imaging techniques such as fluoroscopy or ultrasound, and in a preferred embodiment the pinch valve self-expands upon release from the catheter since it is constructed in part from shape-memory material, such as Nitinol®, a nickel-titanium alloy used in biomedical implants. In another embodiment, the pinch valve may be constructed of materials that requires balloon-expansion after the capsule has been ejected from the catheter into the atrium. Once the atrial collar and the conduit sleeve are expanded to their functional diameter, they are deployed into the native annulus. Then the ventricular collar is expanded below the annulus forming a layered stack with the collars on top and bottom and the native annulus in the middle. It is also contemplated that the axial post may be deployed within the lumen of the sleeve. Once the top and bottom collars are deployed about the tricuspid annulus, the pin fasteners secure the top and bottom collars about the native annulus. Additional fastening the axial post to a moderator band mounting may be performed, and the deployment is complete. Further adjustments using hemodynamic imaging techniques are contemplated as within the scope of the invention in order to ensure the device is secure, is located and oriented as planned, and is functioning as a substitute or successor to the native tricuspid valve.

Drawings

Referring now to the drawings, the feature numbers provided in each drawing refer to features in that drawing, regardless of whether a feature number is re-used elsewhere in this document, it should be understood for example that feature 102 of Figure A is referred to as A-102, and feature 102 in Figure B is referred to as B-102, and that the features a not necessary identical and reference should be made to each drawing individually.

Figure 1:
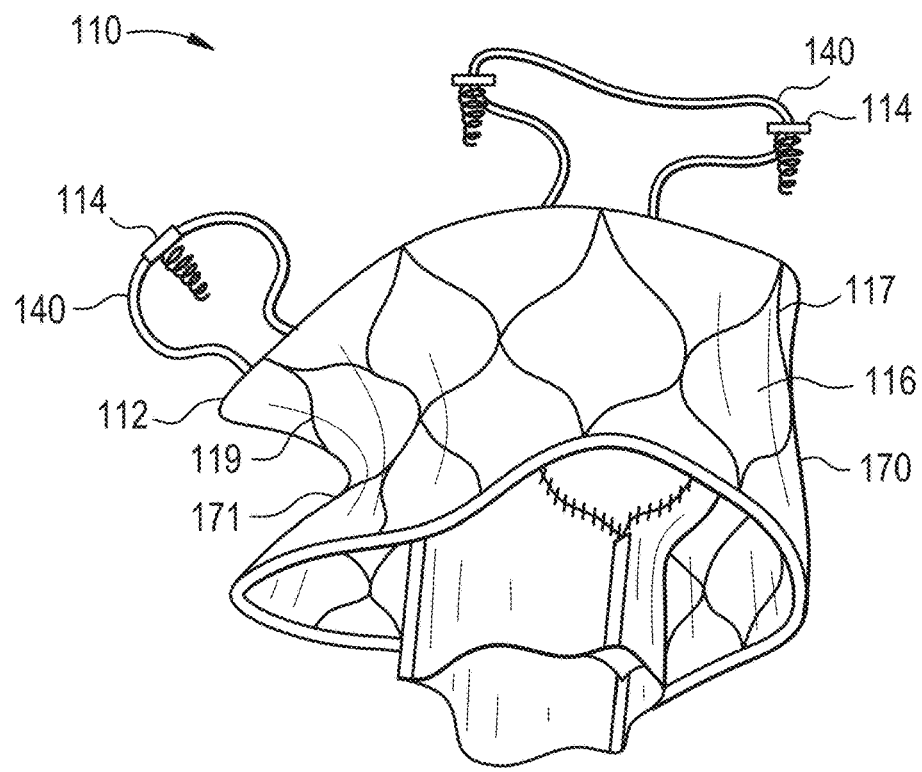
FIG. 1 is an illustration in a perspective view from below of a heart valve prosthesis according to the present invention with a valve frame having an atrial cuff component.

FIG. 1 is an illustration in a perspective view from below of a heart valve prosthesis 110 according to the present invention with a valve frame 116 having an atrial cuff/flange component 112. FIG. 1 shows folding wire tabs 140 having a tissue anchors 114 for accessing annular tissue through the biocompatible material 118 (not visible) covering the valve frame 116. The wire frame 116 is preferably an open cell structure with substantially vertical diamond shaped cells 117 creating a collar or cylinder and has flared horizontal or angled diamond shaped cells 119 forming the atrial cuff or flange component. FIG. 1 shows flow control sleeve 120, aka "tube valve", having three panels supported by one or more rigid support members 122.

Septal Wall

In a preferred embodiment, valve frame 116 has a flat, septal wall 170 on one side (septum-facing side) and an annular channel 171 on the other side. The septal wall 170 allows for annular sealing without compressing sensitive septal tissue, Triangle of Koch, that would interfere with electrical conductivity within the heart, and specifically, the A-V node. Importantly, the folding tab(s) and tissue anchor(s) are positioned to avoid anchoring and tissue damage in this sensitive region.

Annular Channel

The annular channel 171 defines a supra-annular atrial-side flange and a subannular ventricular-side flange separated by a concavity or furrow, into which the native annulus is captured. This structure sandwiches the native annulus between the atrial flange and the ventricular flange and provide sealing against regurgitation, stability during systole, and tissue ingrowth for long-term performance.

Flow Control Sleeve

The flow control sleeve 120 is shown as a three-panel collapsible tube valve mounted on a three-arch wire frame forming a lumen that has a triangular cross section. The lack of a traditional "leaflet valve" reduces stenosis and calcification. By using a tube, which is by default in an open position, blood flow can travel from atrium to ventricle without a barrier, only closing when, during ventricular systole, the intra-ventricular pressure exerts closing pressure on the exterior surface of the panels of the three-panel collapsible tube valve. This is in contrast to traditional leaflet valves where hemodynamic pressure forces open closed leaflets (closed by default) to allow blood to fill from atrium to ventricle but posing a barrier and increasing stenosis and calcification of the implant.

Figure 2:
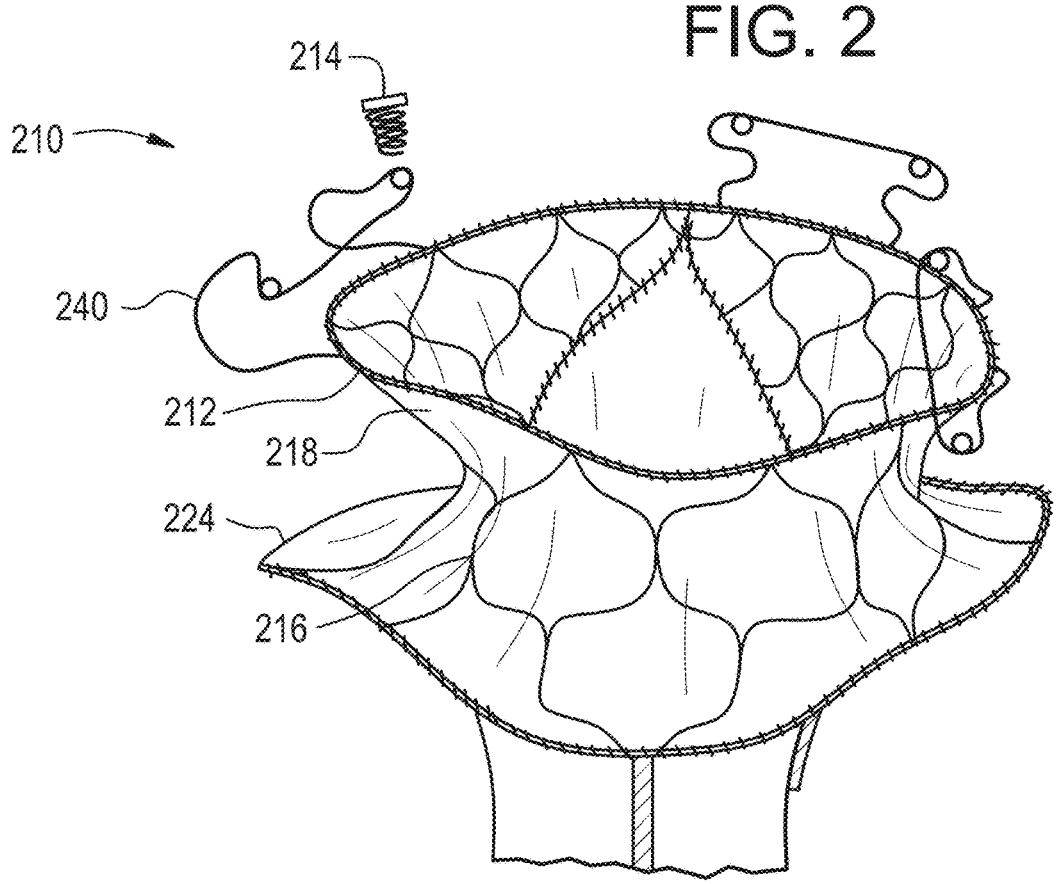
FIG. 2 is an illustration in a perspective view from above of a heart valve prosthesis having according to the present invention with a valve frame having an atrial cuff component and a ventricular cuff component.

FIG. 2 is an illustration in a perspective view from above of a heart valve prosthesis 210 having according to the present invention with a valve frame 216 having both an atrial cuff component 212 and a ventricular cuff component 224. FIG. 2 shows folding wire tabs 240 for mounting tissue anchors 214 to secure the valve 210 to annular tissue, through the biocompatible material 218 covering the valve frame 216. In this embodiment, a biocompatible mesh disk can be deployed after the valve has been positioned in the valve annulus, allowing a larger sealing mesh disk to be used for greater sealing. By delivering the mesh disk separately, the circumference of the opening of the atrial flange can be uniform across patient types. This also allows a valve to have a diameter of, for example, 40 mm, while delivering a sealing disk having a diameter of, e.g. 60 mm. This significantly reduces the amount of material that is required to be delivered down a transcatheter delivery catheter. The Nitinol folding tabs are used to secure the mesh disk against the atrial flange. Further, the ability of the heat-treated Nitinol folding tabs to be elongated away from the main body of the valve, is another feature to accommodate the limited delivery space within the transcatheter delivery catheter. This is especially important for a valve repair or replacement for a valve such as the tricuspid valve, which requires the delivery of a very large valve in pathological conditions. By staging, or segmenting, the inventive valve herein, the problem of fitting a large valve in a small transcatheter delivery catheter is addressed.

Figure 3:
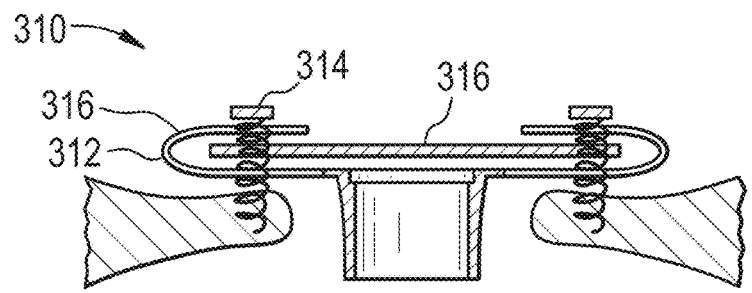
FIG. 3 is an illustration in a plan view of a heart valve prosthesis having according to the present invention with a valve frame having an atrial flange/cuff component and without a ventricular cuff component.

FIG. 3 is an illustration in a plan view of a heart valve prosthesis 310 having according to the present invention with a valve frame 316 having an atrial flange/cuff component 312 and without a ventricular cuff component. FIG. 3 shows tissue anchors 314 accessing annular tissue through the biocompatible material 316 covering the valve frame 316.

Figure 4:
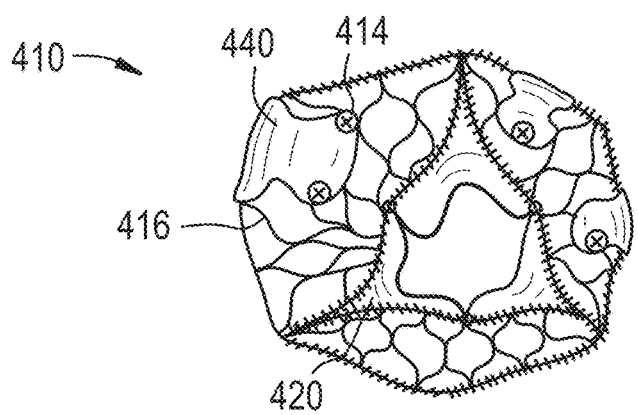
FIG. 4 is an illustration in a top view of a heart valve prosthesis according to the present invention.

FIG. 4 is an illustration in a top view of a heart valve prosthesis 410 according to the present invention. FIG. 4 shows folding tabs 440 having tissue anchors 414 folded over a valve frame 416 encircling a collapsible flow control sleeve 420.

Figure 5:
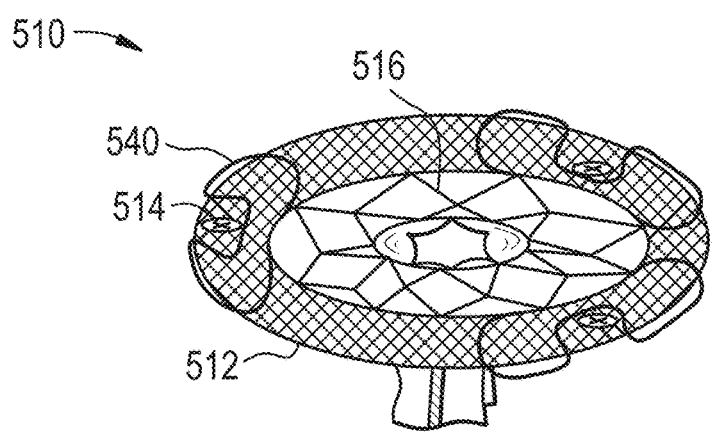
FIG. 5 is an illustration in a perspective view from the top of a heart valve prosthesis according to the present invention.

FIG. 5 is an illustration in a perspective view from the top of a heart valve prosthesis 510 according to the present invention. FIG. 5 shows a valve prosthesis 510 with a valve frame 516 having an atrial cuff 512 and 3 topologically diverse folding wire tabs 540 with tissue anchors 514 for mounting the heart valve prosthesis 510 to the annular tissue.

Figure 6:
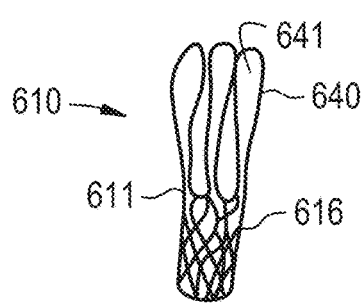
FIG. 6 is an illustration in a plan view of a heart valve prosthesis according to the present invention.

FIG. 6 is an illustration in a plan view of a heart valve prosthesis 610 according to the present invention. FIG. 6 shows a valve prosthesis 610 in a radially compressed configuration 611 where the shape memory folding tabs 640 are in a confined configuration 641 and are elongated out of the main body, or annular portion, of the valve wire frame 616.

Figure 7:
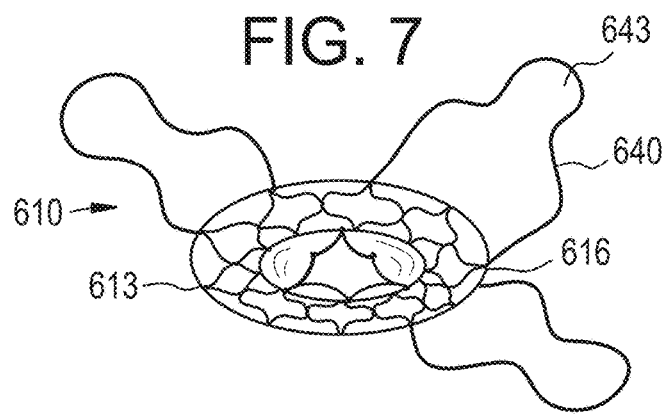
FIG. 7 is an illustration in a plan view of a heart valve prosthesis according to the present invention.

FIG. 7 is an illustration in a plan view of a heart valve prosthesis 610 according to the present invention. FIG. 7 shows a valve prosthesis 610 in a radially expanded, partially uncompressed, configuration 613 where the shape memory folding tabs 640 are in a partially unconfined configuration 643 and are shown elongated out of the main body, or annular portion, of the valve wire frame 616.

Figure 8:
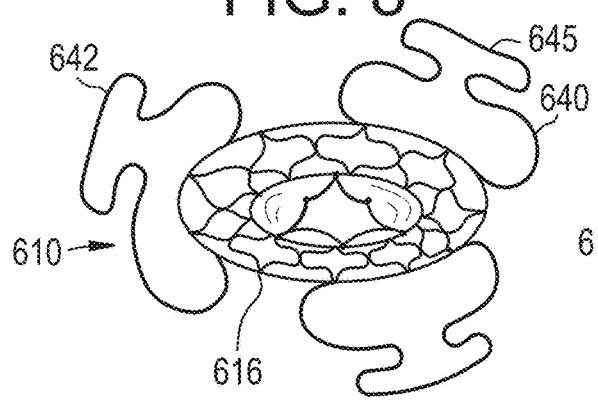
FIG. 8 is an illustration in a plan view of a heart valve prosthesis according to the present invention.

FIG. 8 is an illustration in a plan view of a heart valve prosthesis 610 according to the present invention. FIG. 8 shows a valve prosthesis in a radially expanded, fully uncompressed, configuration 615 where the shape memory folding tabs are in a final, unconfined, shape-memory configuration 645 and are shown elongated out of the main body, or annular portion, of the valve wire frame 616.

FIG. 9 is an illustration in a plan view of a heart valve prosthesis 610 according to the present invention. FIG. 9 shows a valve prosthesis 610 in a radially expanded, fully uncompressed, configuration 615 where the shape memory folding tabs are in a final, unconfined, shape-memory configuration 645 and are shown elongated out of the main body, or annular portion, of the valve wire frame 616. FIG. 9 shows biocompatible mesh ring 650 mounted over the valve wire frame 616 to cover the flared or horizontal diamond-shaped cells 619 of the atrial flange portion 612 and to overlap and cover a lower, bottom portion 644 of the shape memory folding tabs 640. Upper, top portion 642 of folding tabs 640 are shown in an unfolded, or open configuration.

FIG. 10 is an illustration in a plan view of a heart valve prosthesis 610 according to the present invention. FIG. 10 shows a valve prosthesis in a radially expanded, fully uncompressed, configuration 615 where the shape memory folding tabs 640 are in a final, unconfined, shape-memory configuration 645 and are shown with an upper, top portion 642 of the tabs 640 folded inwards towards the main body, or annular portion, 617, 619 of the valve wire frame 616. FIG. 10 shows biocompatible mesh ring 650 mounted over the flared or horizontal diamond-shaped cells 619 of the atrial flange portion 612 to cover both, the diamond-shaped cells 619 of atrial flange portion 612, and to overlap and cover the lower, bottom portion 644 of the shape memory folding tabs 640, with the upper, top portion 642 of the shape memory folding tab 640 folded over and sandwiching or covering, a portion of the biocompatible mesh ring 650.

FIG. 11 is an illustration in a top view of a shape memory folding tab in a final, unconfined, shape-memory configuration. FIG. 11 shows folding tab 1140 having an upper, top portion 1142 in the center, and a lower, bottom portion 1144 on the left and right as connecting limbs 1146, 1147 that attach to the main body or annular portion of the wire frame.

FIG. 12 is an illustration in a front view of a shape memory folding tab 1140 in a final, unconfined, shape-memory configuration. FIG. 12 shows folding tab having an upper, top portion 1142 in the center, and a lower, bottom portion 1144 on the left and right as connecting limbs 1146, 1147 that attach to the main body or annular portion of the wire frame.

FIG. 13 is an illustration in a perspective view of a shape memory folding tab 1140 in a final, unconfined, shape-memory configuration 1145. FIG. 13 shows folding tab 1140 having an upper, top portion 1142 in the center, and a lower, bottom portion 1144 on the left and right as connecting limbs 1146, 1147 that attach to the main body or annular portion 1119 of the wire frame 1116.

FIG. 14 is an illustration in a plan view of a shape memory folding tab 1140 in a compressed and elongated, or confined, shape-memory configuration 1141. FIG. 14 shows folding tab 1140 having an upper, top portion 1142 in the center, and a lower, bottom portion 1144 on the left and right as connecting limbs 1146, 1147 that attach to the main body or annular portion 1119 of the wire frame 1116.

FIG. 15 is an illustration in a plan view of a valve prosthesis wire frame 1516 in a radially expanded, fully uncompressed, configuration where the shape memory folding tabs 1540 are in a final, unconfined, shape-memory configuration and are shown with an upper, top portion 1542 of the tabs folded inwards towards the main body, or annular portion 1519, of the valve wire frame 1516.

FIG. 16 is an illustration in a top view of another preferred embodiment of a wire-minimized one-diamond valve prosthesis wire frame 1616 in a radially expanded, fully uncompressed, configuration where the shape memory folding tabs 1640 are in a final, unconfined, shape-memory configuration and are shown with an upper, top portion 1642 of the tabs folded inwards towards the main body, or annular portion 1619, of the valve wire frame 1616.

FIG. 17 is an illustration in a top view of another preferred embodiment of a one-diamond-height wire-minimized complete valve prosthesis 1710 having (i) a wire frame 1716 in a radially expanded, fully uncompressed, configuration where the shape memory folding tabs 1740 are in a final, unconfined, shape-memory configuration and are shown with an upper, top portion 1742 of the tabs folded inwards towards the main body, or annular portion 1719, of the valve wire frame 1716, (ii) biocompatible mesh disk 1750 mounted on the annular portion 1719 of the wire frame and across the lower, bottom portion 1744, i.e. across the support arms 1746, 1747, of the folding tabs 1740, and under the folded-over upper, top portion 1742 of the folding tabs 1740, and (iii) three-panel collapsible tube valve 1720 mounted within the axial, center aperture 1715 of the wire frame 1716.

FIG. 18 is an illustration in a plan view of another preferred embodiment of a single flange valve prosthesis 1810 having (i) a wire frame 1816 in a radially expanded, fully uncompressed, configuration where the shape memory folding tabs 1840 are in a final, unconfined, shape-memory configuration and are shown with an upper, top portion 1842 of the tabs folded inwards towards the main body, or annular portion 1819, of the valve wire frame 1816, where the wire frame is comprised of an atrial flange only, (ii) biocompatible mesh disk 1850 mounted on the annular portion 1819 of the wire frame 1816 and across the lower, bottom portion 1844, i.e. across the support arms of the folding tabs 1840, and under the folded-over upper, top portion 1842 of the folding tabs 1840, and (iii) three-panel collapsible tube valve 1820 mounted within the axial, center aperture 1815 (not visible) of the wire frame 1816.

FIG. 19 is an illustration in a perspective view of a wire frame 1816 in a radially expanded, fully uncompressed, configuration where the shape memory folding tabs 1840 are in a final, unconfined, shape-memory configuration and are shown with an upper, top portion 1842 of the tabs folded inwards towards the main body, or annular portion 1819, of the valve wire frame 1816, where the wire frame is comprised of an atrial flange only.

FIG. 20 is an illustration of a three-panel collapsible tube valve 1820 for mounting within the axial, center aperture 1815 of the wire frame 1816.

FIG. 21 is an illustration in a perspective view of a biocompatible mesh disk 1850 for mounting on the annular portion 1819 of the wire frame 1816 and across the lower, bottom portion 1844, i.e. across the support arms of the folding tabs 1840, and under the folded-over upper, top portion 1842 of the folding tabs 1840.

FIG. 22 is an illustration in a plan view of a compressed valve prosthesis 2210 within a delivery catheter 2230, having (i) a wire frame 2216 in a radially compressed configuration where the shape memory folding tabs 2240 are in a confined, elongated shape-memory configuration attached to the main body, or annular portion 2219, of the valve wire frame 2216, which is further connected to the three-panel collapsible tube valve 2220 mounted on the axial, center aperture of the wire frame 2216.

FIG. 23 is an illustration in an exploded view of another preferred embodiment of a single flange valve prosthesis 2310 having (i) a wire frame 2316 in a radially expanded, fully uncompressed, configuration where the shape memory folding tabs 2340 are in a final, unconfined, shape-memory configuration and are shown with an upper, top portion 2342 of the tabs folded inwards towards the main body, or annular portion 2319, of the valve wire frame 2316, where the wire frame 2316 is comprised of an atrial flange only, (ii) biocompatible mesh disk 2350 mounted on the annular portion 2319 of the wire frame 2316 and across the lower, bottom portion 2344, i.e. across the support arms 2346, 2347, of the folding tabs 2340, and under the folded-over upper, top portion 2342 of the folding tabs, and (iii) three-panel collapsible tube valve 2320 mounted within the axial, center aperture of the wire frame 2316.

FIG. 24 is an illustration in an exploded view of another preferred embodiment of a single flange valve prosthesis 2410 having (i) a wire frame 2416 in a radially expanded, fully uncompressed, configuration where the shape memory folding tabs 2440 are in a final, unconfined, shape-memory configuration and are shown with an upper, top portion 2442 of the tabs folded inwards towards the main body, or annular portion 2419, of the valve wire frame, where the wire frame 2416 is comprised of an atrial flange only, (ii) biocompatible mesh disk 2450 mounted on the annular portion 2419 of the wire frame and across the lower, bottom portion 2444, i.e. across the support arms 2446, 2447, of the folding tabs, and under the folded-over upper, top portion 2442 of the folding tabs, a (iii) three-panel collapsible tube valve 2420 mounted within the axial, center aperture of the wire frame, and (iv) a second biocompatible mesh 2452 mounted below the wire frame.

FIGS. 25A-25C is an illustration of a plan view of a tissue anchor 2514 having a floating radiopaque marker 2513. FIG. 25A shows the tissue anchor 2514 accessing the annular tissue with the radiopaque marker 2513 at the distal end of the anchor 2514 and in contact with the atrial surface of the annular tissue. FIG. 25B shows the tissue anchor 2514 advancing into the annular tissue with the radiopaque marker 2513 threaded onto the tissue anchor and maintaining position on the atrial surface of the annular tissue. FIG. 25C shows the tissue anchor 2514 completely advanced into the annular tissue such that the tissue anchor 2514 and the threaded floating marker 2513 are now adjacent, indicating the desired depth, tension, and/or plication of the tissue anchor with respect to the annular tissue.

FIG. 26 is an illustration of a plan view of a tissue anchor 2614 having a straight thread and a constant pitch.

FIG. 27 is an illustration of a plan view of a tissue anchor 2714 having a straight thread and a variable pitch.

FIG. 28 is an illustration of a plan view of a tissue anchor 2814 having a tapered thread and a constant pitch.

FIG. 29 is an illustration of a plan view of a tissue anchor 2914 having a variable taper thread and a constant pitch.

FIG. 30 is an illustration of a plan view of an alignment system according to the present invention. FIG. 30 shows a pair of imaging transceivers, e.g. fluoro, providing illumination along the axis of the dart delivery catheter/lumen with the three radiopaque targeting sights in x- and y-axis alignment.

FIG. 31 is an illustration of a plan view of dart delivery catheter of an alignment system according to the present invention. FIG. 31 shows that guide wires and radiopaque markers can be delivered using a single steerable catheter.

FIG. 32 is an illustration of a plan view of the spoke system with spoke-release guide wires of an alignment system according to the present invention.

FIG. 32 shows how the spoke system is used to torque the valve into proper position within the native annulus of a tricuspid or mitral valve.

FIG. 33 is an illustration of a plan view of a compressed transcatheter prosthetic valve within the steerable catheter of an alignment system according to the present invention. FIG. 33 shows nose cone housing part of the valve to allow for stepped, section by section delivery of the valve.

FIG. 34 is an illustration of a plan view of the compressed transcatheter valve partially expelled by extension of the nose cone to release the atrial side collar. FIG. 34 shows spoke attached to the atrial side of the atrial sealing collar.

FIG. 35 is an illustration of a plan view of a nose cone fully extended releasing the ventricular sealing collar in the second stage of the staged delivery. FIG. 35 shows how the spokes can be used to torque the valve into proper alignment prior to pin/dart anchoring.

FIG. 36 is an illustration of a plan view of a deployed valve of an alignment system according to the present invention. FIG. 36 shows how release of the spoke guide wire releases the spoke from the atrial sealing collar.

FIG. 37 is an illustration of a plan view of the dart catheter or lumen that is used to deliver the radiopaque markers and the anchoring dart according to the present invention.

FIG. 38 is an illustration of a perspective view of a valve with alignment system having imaging, radiopaque markers, and catheter dart deployment according to the present invention.

FIGS. 39A-39C are illustrations of a plan view of a time sequence according to the present invention.

FIG. 40 is an illustration of a plan view of another embodiment of a target sight aligning mechanism according to the present invention FIG. 41 is an illustration of a plan view of a time-sequence of a dart/pin being deployed thru the upper collar, then anchoring into the lower collar/flange according to the present invention.

FIG. 42 is an illustration of a perspective view of a valve having an irregular shaped (circumference) tailored to a patient's specific anatomy according to the present invention.

FIG. 43 is an illustration of a perspective view of a three-lobed, double-flanged (collared) annulus spanning valve according to the present invention FIG. 44 is an illustration of a plan view of an example of a radiography apparatus, e.g. fluoro, for performing imaging in real time on a patient who is receiving a transcatheter valve according to the present invention FIG. 45 is an illustration of a plan view of a cardiologist, surgeon, or interventionalist highlighting the difficulty in blind pinning through a first collar, then through captured tissue, and finally affixing to a lower collar according to the present invention.

FIG. 46 is an illustration of a plan view of a valve according to the present invention before deployment of the pins/darts, and after installation of the pins/darts.

FIG. 47 is an illustration of an exploded view of a transcatheter valve according to the present invention. FIG. 47 shows an example of one of the plurality of pinning paths that are used to secure the atrial collar to the ventricular collar and capture the annular tissue therebetween.

FIG. 48 is an illustration of a series in three parts showing alignment mechanism and method.

FIG. 49 is an illustration of a perspective top view of a heart valve prosthesis according to the present invention having a flange-integrated plication cell 102, sleeve plicator 104, and screw-type tissue anchors 106. FIG. 49 shows a valve frame 108 having an atrial cuff component 110, the atrial cuff or flange 110 having a plication gap 112 formed from a plication cell 102 that is integrated with, or integral to, the diamond cells of the flange 110, and extending from the circumferential edge of the atrial flange 110, creating an over-sized diamond cell, the plication cell 102 having a first arm 114 and a second arm 116, with a plication tissue anchor 106 mounted on each arm of the plication cell 102 on either side of the plication gap 112. FIG. 49 shows a pair of screw-type tissue anchors 106 accessing annular tissue 103.

FIG. 50 is an illustration of a perspective top view of a heart valve prosthesis according to the present invention having a flange-integrated plication cell 102, sleeve plicator 104, and screw-type tissue anchors 106. FIG. 50 shows a valve frame 108 having an atrial cuff component 110, the atrial cuff or flange 110 having a closed plication cell 102 formed from the folding or compression of the plication cell 102 using a plicator device 104, e.g. a sleeve, that confines, compresses, folds the first arm 114 and the second arm 116 of the plication cell 102 together. FIG. 50 shows that by closing the plication gap 112 with the action of the plicator device 104 on the cell 102, the plication tissue anchor 106 that is mounted on each arm 114, 116 of the plication cell 102 on either side of the plication gap 112 causes the annular tissue 103 to fold and plicate, and reduces the circumference of the native annulus. This ability to cinch or plicate the native annular tissue around a limited number of standard sizes of prosthetic valves reduces the problem of fitting each prosthesis to each patient's specific anatomy, simplifying the procedure for the cardiac interventionalist/physician.

FIG. 51 is an illustration of a perspective top view of a heart valve prosthesis according to the present invention having a flange-integrated plication cell 202, coil plicator 204, and post-type tissue anchors 206. FIG. 51 shows a valve frame 208 having an atrial cuff component 210, the atrial cuff or flange 210 having a plication gap 212 formed from a plication cell 202 that is integrated with, or integral to, the diamond cells of the flange 210, and extending from the circumferential edge of the atrial flange 210, creating an over-sized diamond cell, the plication cell 202 having a first arm 214 and a second arm 216, with a plication tissue anchor 206 mounted on each arm 214, 216 of the plication cell 202 on either side of the plication gap 212. FIG. 51 shows post-type tissue anchors 206 accessing and anchoring annular tissue 203.

FIG. 52 is an illustration of a perspective top view of a heart valve prosthesis according to the present invention having a flange-integrated plication cell 202, coil plicator 204, and post-type tissue anchors 206. FIG. 52 shows a valve frame 208 having an atrial cuff component 210, the atrial cuff or flange 210 having a closed plication cell 202 formed from the folding or compression of the plication cell 202 using a plicator 204, e.g. a coil, that confines, compresses, folds the first arm 214 and the second arm 216 of the plication cell 202 together. FIG. 52 shows that by closing the plication gap 212 with the action of the plicator device 204 on the cell 202, the plication tissue anchor 206 that is mounted on each arm 214, 216 of the plication cell 202 on either side of the plication gap 212 causes the annular tissue to fold and plicate, and reduces the circumference of the native annulus. This ability to cinch or plicate the native annular tissue around a limited number of standard sizes of prosthetic valves reduces the problem of fitting each prosthesis to each patient's specific anatomy, simplifying the procedure for the cardiac interventionalist/physician.

FIG. 53 is an illustration of a perspective top view of a heart valve prosthesis according to the present invention having a peripheral plication cell 302, coil plicator 304, and screw-type tissue anchors 306. FIG. 53 shows a valve frame 308 having an atrial cuff component 310, the atrial cuff or flange 310 having a plication gap 312 formed from an independent plication cell 302 extending from the peripheral edge 318 of the atrial flange 310, the independent plication cell 302 having a first arm 314 and a second arm 316, with a plication tissue anchor 306 mounted on each arm 314, 316 of the plication cell 302 on either side of the plication gap 312. FIG. 53 shows a pair of screw-type tissue anchors 306 accessing annular tissue 303.

FIG. 54 is an illustration of a perspective top view of a heart valve prosthesis according to the present invention having a peripheral/independent plication cell 302, coil plicator 304, and screw-type tissue anchors 306. FIG. 54 shows a valve frame 308 having an atrial cuff component 310, the atrial cuff or flange 310 having a closed plication cell 302 formed from the folding or compression of the independent plication cell 302 using a plicator 304, e.g. a coil or helical member, that confines, compresses, folds the first arm 314 and the second arm 316 of the plication cell 302 together. FIG. 54 shows that by closing the plication gap 312 with the plicator device 304, the plication tissue anchor 306 that is mounted on each arm 314, 316 of the plication cell 302 on either side of the plication gap 312 causes the annular tissue 303 to fold and plicate, and reduces the circumference of the native annulus 303. This ability to cinch or plicate the native annular tissue 303 around a limited number of standard sizes of prosthetic valves reduces the problem of fitting each prosthesis to each patient's specific anatomy, simplifying the procedure for the cardiac interventionalist/physician.

FIG. 55 is an illustration of a perspective top view of a heart valve prosthesis according to the present invention having a peripheral/independent plication cell 402, sleeve plicator 404, and post-type tissue anchors 406. FIG. 55 shows a valve frame 408 having an atrial cuff component 410, the atrial cuff or flange 410 having a plication gap 412 formed from an independent plication cell 402 extending from the peripheral edge 418 of the atrial flange 410, the independent plication cell 402 having a first arm 414 and a second arm 416, with a plication tissue anchor 406 mounted on each arm 414, 416 of the plication cell 402 on either side of the plication gap 412. FIG. 55 shows post-type tissue anchors 406 accessing and anchoring annular tissue 403.

FIG. 56 is an illustration of a perspective top view of a heart valve prosthesis according to the present invention having a peripheral plication cell 402, sleeve plicator 404, and post-type tissue anchors 406. FIG. 56 shows a valve frame 408 having an atrial cuff component 410, the atrial cuff or flange 410 having a closed plication cell 402 formed from the folding or compression of the independent plication cell 402 using a plicator 404, e.g. a sleeve, that confines, compresses, folds the first arm 414 and the second arm 416 of the plication cell 402 together. FIG. 56 shows that by closing the plication gap 412 with the plicator device 404, the plication tissue anchor 406 that is mounted on each arm 414, 416 of the plication cell 402 on either side of the plication gap 412 causes the annular tissue 403 to fold and plicate, and reduces the circumference of the native annulus. This ability to cinch or plicate the native annular tissue around a limited number of standard sizes of prosthetic valves reduces the problem of fitting each prosthesis to each patient's specific anatomy, simplifying the procedure for the cardiac interventionalist/physician.

FIG. 57 is an illustration in a perspective view from above of a heart valve prosthesis according to the present invention with a peripheral plication cell 502, a coil plicator 504, and screw-type tissue anchors 506, connected to a valve frame 508 having an atrial cuff component 510 and a ventricular cuff component 520. FIG. 57 shows plication cell 502 having a first and second arms 514, 516 on which plication tissue anchors 506 are mounted to secure the valve to annular tissue. The tissue anchors 506 are shown spread apart in a non-plicated configuration, and may directly engage annular tissue, or optionally, through a biocompatible disk material covering the atrial flange 510 of the valve frame 508, where the biocompatible disk is different from the biocompatible material covering the diamond cells of the wire frame 508.

FIG. 58 is an illustration in a perspective view from above of a heart valve prosthesis according to the present invention with a peripheral plication cell 502, a coil plicator 504, and screw-type tissue anchors 506, connected to a valve frame 508 having an atrial cuff component 510 and a ventricular cuff component 520. FIG. 58 shows the coil plicator 504 folding or compressing the plication cell 502 by winding around the first and second arms 514, 516. The folding together of the arms 514, 516 of the plication cell 502 draws the already-anchored tissue anchors 506 together, closing the plication gap 512, which plicates, or pinches together, annular tissue, shortening the annular circumference.

FIG. 59 is an illustration in a perspective view from below of a heart valve prosthesis according to the present invention with a flange-integrated plication cell 602, a sleeve plicator 604, and screw-type tissue anchors 606, connected to a valve frame 608 having an atrial cuff component 610 and a ventricular cuff component 620. FIG. 59 shows plication cell 602 having a first and second arms 614, 616 on which plication tissue anchors 606 are mounted to secure the valve to annular tissue. The tissue anchors 606 may directly engage annular tissue, or optionally, through a biocompatible disk material covering the atrial flange 610 of the valve frame 608, where the biocompatible disk is different from the biocompatible material covering the diamond cells of the wire frame. Three-panel flow control sleeve, tube valve, 624 is shown mounted within the central axial aperture of the valve and is shown reinforced with three (3) vertical support posts mounted between the panels.

FIG. 60 is an illustration in a perspective view from below of a heart valve prosthesis according to the present invention with a flange-integrated plication cell 602, a sleeve plicator 604, and screw-type tissue anchors 606, connected to a valve frame having an atrial cuff component 610 and a ventricular cuff component 620. FIG. 60 shows the sleeve plicator 604 folding or compressing the plication cell 602 by sliding down and over the first and second arms 614, 616 to compress the plication cell 602. The folding of the arms 614, 616 of the plication cell 602 draws the already-anchored tissue anchors 606 together, which plicates, or pinches together, annular tissue, shortening the annular circumference. Three-panel flow control sleeve, tube valve, 624 is shown mounted within the central axial aperture of the valve.

FIG. 61 is an illustration of a detailed view of a plication cell 702 with a sleeve plicator 704 and post-type tissue anchors 706. FIG. 61 shows the plication cell 702 prior to engagement with the annular tissue 703, and prior to compression of the plication cell 702 by sliding the sleeve 704 down and over the arms 714, 716 of the plication cell 702.

FIG. 62 is an illustration of a detailed view of a plication cell 702 with a sleeve plicator 704 and post-type tissue anchors 706. FIG. 62 shows the plication cell 702 after engagement of the posts 706 into the annular tissue 703, and after the compression of the plication cell 702 by sliding the sleeve 704 down and over the arms 714, 716 of the plication cell 702.

FIG. 63 is an illustration of a detailed view of a plication cell 802 with a sleeve plicator 804 and screw-type tissue anchors 806. FIG. 63 shows the plication cell 802 prior to engagement with the annular tissue 803, and prior to compression of the plication cell 802 by sliding the sleeve 804 down and over the arms 814, 816 of the plication cell 802.

FIG. 64 is an illustration of a detailed view of a plication cell 802 with a sleeve plicator 804 and screw-type tissue anchors 806. FIG. 64 shows the plication cell 802 after engagement of the screws 806 into the annular tissue 803, and after the compression of the plication cell 802 by sliding the sleeve 804 down and over the arms 814, 816 of the plication cell 802.

FIG. 65 is an illustration of a top view of a native tricuspid valve. FIG. 65 shows septal region of the annulus at bottom, posterior region of the annulus at right and anterior region of the annulus at left. FIG. 65 shows in a non-limiting preferred embodiment, three preferred locations for plicating and/or for performing tissue anchoring.

FIG. 66 is an illustration of a perspective view from the top of a plicator delivery tool 905 that is accessing the plication diamond cells 902 of an implanted transcatheter prosthetic valve through a delivery catheter 903. FIG. 66 shows three plicator sleeves 904 mounted in ready-position on the top of their plication cells 902. FIG. 66 shows three plication cells 902 framed by screw-type plication tissue anchors 906.

FIG. 67 is an illustration of a perspective view from the top of a plicator delivery tool 905 that has deployed the plication tissue anchors 906 into the annular tissue, and then has compressed the plication cells 902 into the plication sleeves 904. FIG. 67 shows three plicator sleeves 904 that have been mounted over their plication cells 902. FIG. 67 shows the closing of the three plication cells 902 and the plication of the annular tissue by the pairing or merging movement of the fixed screw-type plication tissue anchors 906. FIG. 67 shows withdrawal of the plicator delivery tool 905 back into the catheter 903.

FIGS. 68A and 68B are a two-part illustration of a plan view of one preferred embodiment of a plication sleeve 1004 and plicator cell 1002 combination. FIG. 68A shows plication sleeve 1004 having internal detent stops 1028 for engaging a matching locking element 1026 on the arms of the plication diamond cell 1002. FIG. 68B shows plication sleeve 1004 after sliding over the plication cell 1002, causing the plication cell 1002 to compress, and locking into place once the locking element 1026 of the plication cell 1002 arms has passed deep enough into the plication sleeve 1004 to pass the internal detent step member 1028.

FIGS. 69A and 69 are a two-part illustration of a plan view of another preferred embodiment of a spiral or rifled plication sleeve 1104 and plicator cell 1102 combination. FIG. 69A shows plication sleeve 1104 having internal spiral detent stops 1128 for engaging a matching locking element 1126 on the arms of the plication diamond cell 1102. FIG. 69B shows plication sleeve 1104 after rotatably sliding over the plication cell 1102, causing the plication cell 1102 to compress, and locking into place once the locking element 1126 of the plication cell 1102 arms has passed deep enough into the plication sleeve 1104 to pass the internal spiral detent step member 1128.

FIGS. 70A and 70B are a two-part illustration of a plan view of one preferred embodiment of a multi-step plication sleeve 1204 and plicator cell 1202 combination. FIG. 70A shows multi-step plication sleeve 1204 having multiple internal detent stops 1228 for engaging a matching locking element 1226 on the arms of the plication diamond cell 1202. FIG. 70B shows plication sleeve 1204 after sliding over the plication cell 1202, causing the plication cell 1202 to compress, and locking into place once the locking elements 1226 of the plication cell 1202 arms have passed deep enough into the plication sleeve 1204 to pass one or more, here shown passing four, of the multi-step internal detent step member 1228.

FIG. 71 is a graph illustration and shows a comparison of various tricuspid valve diameters, the calculated circumference, and the calculated repaired size after two (2) 20 mm plications, or three (3) 20 mm plications, or four (4) 20 mm plications. FIG. 71 show that the normal, healthy average diameter of a tricuspid valve is 28 mm+/−5 mm, or a range from 23-33 mm. Using the formula for calculating the circumference of an approximately circular valve, (2)×(pi)×(radius), or also (pi)×(diameter), the circumference of various valve diameters is shown. At 40 mm the diameter is 125 mm, at 50 mm the diameter is 157 mm, at 60 mm the diameter is 188 mm, and at 70 mm the diameter is 220. Tricuspid diameters of 40-70 mm represent typical values for unhealthy or pathological/diseased tricuspid valves.

In FIG. 71, the three right-hand columns represent the amount of reduction in tricuspid circumference from deploying two (2), three (3), or four (4) plication cells of the present invention. In this example, each plication reduces annular circumference by 10 mm. Thus, deploying two 10 mm plication cells would reduce the annulus by 20 mm, three by 30 mm, and four by 40 mm, respectively. Thus, it can be seen that by choosing the number of plication cells, the physician can reduce annular circumference by one entire valve size, e.g. from a 60 mm to a 50 mm, or from a 50 mm to a 40 mm. This allows for a combination of annular plication and valve replacement previously unavailable. Further, the ability to correctly "size" a valve to a target circumference, provides a physician with the ability to deploy graduated treatment levels, avoiding the trauma that occurs when a patient is prematurely fitted with a, e.g. 40 mm valve, when their pre-operative condition was a 70 mm regurgitant tricuspid. Instead, a physician can reduce valvular diameter to a degree that is tailored to each individual patient condition, but without requiring a manufacturer to produce a commercially non-viable number, e.g. 30, of different sizes of valves.

FIGS. 72A-72C is an illustration of a plan view of a tissue anchor having a floating radiopaque marker. FIG. 72A shows the tissue anchor accessing the annular tissue withe the radiopaque marker at the distal end of the anchor and in contact with the atrial surface of the annular tissue. FIG. 72B shows the tissue anchor advancing into the annular tissue with the radiopaque marker threaded onto the tissue anchor and maintaining position on the atrial surface of the annular tissue. FIG. 72C shows the tissue anchor completely advanced into the annular tissue such that the tissue anchor and the threaded floating marker are now adjacent, indicating the desired depth, tension, and/or plication of the tissue anchor with respect to the annular tissue.

FIG. 73 is an illustration of a plan view of a tissue anchor having a straight thread and a constant pitch.

FIG. 74 is an illustration of a plan view of a tissue anchor having a straight thread and a variable pitch.

FIG. 75 is an illustration of a plan view of a tissue anchor having a tapered thread and a constant pitch.

FIG. 76 is an illustration of a plan view of a tissue anchor having a variable taper thread and a constant pitch.

FIG. 77 is an illustration of the various circumferential shapes contemplated as within the scope of the invention for the wire plication cell. In non-limiting embodiments, the wire plication cell is an open, non-covered, compressible wire cell. It is contemplated that the cell must accommodate the motion of the plicator device to advance over or around the cell and compress the cell, and accordingly, it is contemplated that the distal aspect of the cell is pointed. The two arms that extend proximally from the edge of the flange out to the distal point are contemplated as having a curved shape, or they may have a straight, linear shape. When the cell has a curved shape, it is contemplated in some preferred embodiments as having a deltoid shape, an oblate shape, a cordate shape, or a curved rhomboid shape. When the cell has a linear shape, it is contemplated in a preferred embodiment as having a diamond shape, or an angular rhomboid shape.

In this non-limiting embodiment, the method for deploying the valve herein comprises the steps: method for securing a transcatheter heart valve prosthesis within a heart, the method comprising the steps of, in order: (i) advancing a procedure guide wire into a ventricle of a heart; (ii) advancing a 22 Fr-34 Fr steerable catheter over the procedure guide wire to deliver a compressed transcatheter heart valve prosthesis to an atrium of the ventricle of the heart; (iii) advancing the catheter to the valve annulus and releasing the self-expanding atrial sealing collar from within the catheter; (iv) anchoring at least one wire plication cell to the annular tissue, wherein said anchoring comprises fastening a pair of plication tissue anchors to tissue one or near a native annulus or leaflet, wherein the plication tissue anchors are fastened at least 5 mm apart; and (v) advancing the plicator device onto the at least one wire plication cell to fold the wire plication cell into a confined configuration and bring the pair of plication tissue anchors together.

FIG. 78 is an illustration of a perspective view of a three-lobed (trefoil) heart valve prosthesis 100 according to the present invention. FIG. 78 shows a pair of pinned three-lobed sealing collars 102, 104 encircling a collapsible flow control sleeve 106. Pin fasteners 108 connect supra-annular collar 102 to sub-annular collar 104. The pin fasteners 108 may be placed to avoid piercing native tissue or may be placed to anchor directly through native tissue such as the annulus.

FIG. 79 is an illustration of a plan or side view of a heart valve prosthesis according to the present invention. FIG. 79 shows a pair of pinned three-lobed sealing collars 102, 104 connected to a collapsible flow control sleeve 106. Pin fasteners 108 are shown having a flanged head on the upper surface of the supra-annular collar 102 and having a barbed anchor element for piercing the cover material and attached to sub-annular collar 104. Sleeve 106 is shown extending from the supra-annular collar 102, traversing the space between the collars, attaching at a mid-section of the sleeve 106 and continuing to a distal section of sleeve 106 below the annulus and into the ventricle.

FIG. 80 is an illustration of a top view of a heart valve prosthesis according to the present invention. FIG. 80 shows the supra-annular (top) collar 102 of a pair of pinned three-lobed sealing collars encircling a collapsible flow control sleeve 106. The flanged heads of pins 108 are shown. Collar 102 is shown having a wire frame structure that is covered by a biocompatible material.

FIG. 81 is an illustration of a perspective view of a four-lobed (quatrefoil) heart valve prosthesis according to the present invention. FIG. 81 shows a pair of pinned four-lobed sealing collars 112, 114 encircling a collapsible flow control sleeve 116. Pin fasteners 118 connect supra-annular collar 112 to sub-annular collar 114. The pin fasteners 118 may be placed to avoid piercing native tissue or may be placed to anchor directly through native tissue such as the annulus.

FIG. 82 is an illustration of a plan or side view of a heart valve prosthesis according to the present invention. FIG. 82 shows a pair of pinned four-lobed sealing collars 112, 114 connected to a collapsible flow control sleeve 116. Pin fasteners 118 are shown having a flanged head on the upper surface of the supra-annular collar 112 and having a barbed anchor element for piercing the cover material and attached to sub-annular collar 114. Sleeve 116 is shown extending from the supra-annular collar 112, traversing the space between the collars, attaching at a mid-section of the sleeve 116 and continuing to a distal section of sleeve 116 below the annulus and into the ventricle.

FIG. 83 is an illustration of a top view of a heart valve prosthesis according to the present invention. FIG. 83 shows the supra-annular (top) collar 112 of a pair of pinned four-lobed sealing collars encircling a collapsible flow control sleeve 116. The flanged heads of pins 118 are shown. Collar 112 is shown having a wire frame structure that is covered by a biocompatible material.

FIG. 84 is an illustration of a perspective view of a circular or ellipsoidal-shaped heart valve prosthesis according to the present invention. FIG. 84 shows a pair of pinned circular or ellipsoidal-shaped sealing collars 122, 124 encircling a collapsible flow control sleeve 126. Pin fasteners 128 connect supra-annular collar 122 to sub-annular collar 124. The pin fasteners 128 may be placed to avoid piercing native tissue or may be placed to anchor directly through native tissue such as the annulus.

FIG. 85 is an illustration of a plan or side view of a circular or ellipsoidal-shaped heart valve prosthesis according to the present invention. FIG. 85 shows a pair of pinned circular or ellipsoidal-shaped sealing collars 1224, 124 connected to a collapsible flow control sleeve 126. Pin fasteners 128 are shown having a flanged head on the upper surface of the supra-annular collar 122 and having a barbed anchor element for piercing the cover material and attached to sub-annular collar 124. Sleeve 126 is shown extending from the supra-annular collar 122, traversing the space between the collars, attaching at a mid-section of the sleeve 126 and continuing to a distal section of sleeve 126 below the annulus and into the ventricle.

FIG. 86 is an illustration of a top view of a circular or ellipsoidal-shaped heart valve prosthesis according to the present invention. FIG. 86 shows the supra-annular (top) collar 122 of a pair of pinned circular or ellipsoidal-shaped sealing collars encircling a collapsible flow control sleeve 126. The flanged heads of pins 128 are shown. Collar 122 is shown having a wire frame structure that is covered by a biocompatible material.

FIG. 87 is an illustration of a plan or side view of a heart valve prosthesis according to the present invention. FIG. 87 shows pinning members 138 prior to deployment by insertion or piercing into a pair of sealing collars 132, 134 connected to a collapsible flow control sleeve 136.

FIG. 88 is an illustration of a plan or side view of a heart valve prosthesis according to the present invention. FIG. 88 shows pinning members 138 after deployment by insertion or piercing into a pair of sealing collars 132, 134 connected to a collapsible flow control sleeve 136.

FIG. 89 is an illustration of a top view of a native tricuspid valve for planning pinning locations. FIG. 89 shows the annulus segments—anterior, posterior and septal, the leaflets extending from the annular plane down into the ventricle, the commissures or gaps between the segments—Antero-posterior, Posterio-septal, Anteroseptal, and the triangle of Koch electrical conduction avoidance zone.

FIG. 90 is an illustration of a top view of a three-lobed, or trefoil, heart valve prosthesis according to the present invention and shows a non-limiting example of pin placement using three fastener pins.

FIG. 91 is an illustration of a top view of a native tricuspid valve and shows an example of pin location for a three fastener deployment into the commissures, A-P, A-S and P-S.

FIG. 92 is an illustration of a top view of a four-lobed, or quatrefoil, heart valve prosthesis according to the present invention and shows a non-limiting example of pin placement using four fastener pins.

FIG. 93 is an illustration of a top view of a native tricuspid valve and shows an example of pin location for a four fastener deployment into the posterior annulus, into the anterior annulus, into the A-P commissure, and into heart tissue adjacent the septal region.

FIG. 94 is an illustration of a top view of a circular or ellipsoidal heart valve prosthesis according to the present invention and shows a non-limiting example of pin placement using six fastener pins.

FIG. 95 is an illustration of a top view of a native tricuspid valve and shows an example of pin location for a six fastener deployment into the posterior annulus, into the anterior annulus, and into the septal annulus.

FIG. 96 is an illustration of a plan or side view of a heart valve prosthesis according to the present invention deployed into the tricuspid annulus. FIG. 96 shows an atrial-side annulus sealing collar and a ventricular-side annulus sealing collar pinned by fastener pins that have been inserted, pierced, etc. into the pair of sealing collars to capture native tricuspid tissue on or near the annulus and to sandwich the native tissue between the top and bottom sealing collars. FIG. 96 also shows the top/atrial-side sealing collar and the bottom/ventricular-side sealing collar connected to a collapsible flow control sleeve that provides a reciprocating closable channel from right atrium to right ventricle.

FIG. 97 is an illustration of a plan or side view of a heart valve prosthesis according to the present invention deployed into the mitral annulus. FIG. 97 shows an atrial-side annulus sealing collar and a ventricular-side annulus sealing collar pinned by fastener pins that have been inserted, pierced, etc. into the pair of sealing collars to capture native mitral tissue on or near the annulus and to sandwich the native mitral tissue between the top and bottom sealing collars. FIG. 97 also shows the top/atrial-side sealing collar and the bottom/ventricular-side sealing collar connected to a collapsible flow control sleeve that provides a reciprocating closable channel from left atrium to left ventricle.

FIG. 98 is an illustration of a cross-sectional view of a heart. FIG. 98 shows a Step 1 of 4 of a time sequence illustration of a transcatheter delivery of a heart valve prosthesis according to the present invention where a steerable catheter 141 is introduced into the heart.

FIG. 99 is an illustration of a cross-sectional view of a heart. FIG. 99 shows a Step 2 of 4 of a time sequence illustration of a transcatheter delivery of a heart valve prosthesis according to the present invention where steerable catheter 141 has delivered a compressed device capsule having compressed supra-annular collar 142, compressed sub-annular collar 144, and compressed/folded sleeve 146 to its deployment position. Balloon device 143 is shown delivered over-wire in a slightly inflated view for illustration purposes only, prior to insertion into the lumen of the compressed device capsule where is it used to expand the compressed elements of the capsule.

FIG. 100 is an illustration of a cross-sectional view of a heart. FIG. 100 shows a Step 3 of 4 of a time sequence illustration of a transcatheter delivery of a heart valve prosthesis according to the present invention where a compressed device capsule has been expanded to its working size with an atrial side sealing collar 142 and a ventricle side sealing collar 144 positioned to capture annulus or adjacent tissue. Sleeve 146 is shown connecting supra-annular collar 142 to sub-annular collar 144 and extending into the ventricle. FIG. 100 also shows catheter tool delivering a first fastener pin 148.

FIG. 101 is an illustration of a cross-sectional view of a heart. FIG. 101 shows a Step 4 of 4 of a time sequence illustration of a transcatheter delivery of a heart valve prosthesis according to the present invention where fastener pins have been installed and the top and bottom sealing collars have been cinched together to secure the prosthesis to annular tissue by compressive sandwiching and/or by direct tissue anchoring.

FIG. 102 is an illustration of a side view of a transcatheter prosthetic valve device. FIG. 102 shows a Step 1 of 8 of a time sequence illustration of a transcatheter delivery of a heart valve prosthesis according to the present invention where a steerable catheter 151 is introduced into the heart, a temporary ventricular tether 157 has been anchored 159 within the heart, and a compressed device capsule having compressed supra-annular collar 152, compressed sub-annular collar 154, and compressed/folded sleeve 155 and 156 has been expelled over-wire from the transcatheter lumen for delivery to the annulus target location.

FIG. 103 is an illustration of a balloon expansion device 153 that is delivered over-wire to an internal working channel within the compressed device capsule where air or fluid is delivered to the inner chamber of the balloon expansion device to expand in sequence various expandable segments of the compressed device capsule.

FIG. 104 is an illustration of a side perspective view of an expanded transcatheter prosthetic valve device. FIG. 104 shows a Step 2 of 8 of a time sequence illustration of a transcatheter delivery of a heart valve prosthesis according to the present invention where an expanded transcatheter prosthetic valve device having supra-annular collar 152, sub-annular collar 154, and sleeve 156 is delivered over-wire to its target deployment location/position.

FIG. 105 is an illustration of a side perspective view of an expanded transcatheter prosthetic valve device. FIG. 105 shows a Step 3 of 8 of a time sequence illustration of a transcatheter delivery of a heart valve prosthesis according to the present invention where a compressed device capsule has been expanded to its working size with an atrial side sealing collar and a ventricle side sealing collar positioned to capture annulus or adjacent tissue. FIG. 105 also shows catheter tool 160 targeting a first fastener pin 163 for delivery.

FIG. 106 is an illustration of a side perspective view of an expanded transcatheter prosthetic valve device. FIG. 106 shows a Step 4 of 8 of a time sequence illustration of a transcatheter delivery of a heart valve prosthesis according to the present invention where a compressed device capsule has been expanded to its working size with an atrial side sealing collar and a ventricle side sealing collar positioned to capture annulus or adjacent tissue. FIG. 106 also shows pin delivery tool 160 delivering a first fastener pin 163 through the atrial side sealing collar and attaching it to the ventricular side sealing collar. Securement wire 165 is shown still attached to pin 163 after pin 163 has been disengaged.

FIG. 107 is an illustration of a side perspective view of an expanded transcatheter prosthetic valve device. FIG. 107 shows a Step 4 of 8 of a time sequence illustration of a transcatheter delivery of a heart valve prosthesis according to the present invention where a pin delivery tool 160 is disengaged from the pin 163 anchored in the ventricular sealing collar and a securement wire 165 is paid out from the pin delivery tool 160.

FIG. 108 is an illustration of a side perspective view of an expanded transcatheter prosthetic valve device. FIG. 108 shows a Step 5 of 8 of a time sequence illustration of a transcatheter delivery of a heart valve prosthesis according to the present invention where the securement wire 165 is tensioned to draw the ventricular sealing collar towards the atrial sealing collar.

FIG. 109 is an illustration of a side perspective view of an expanded transcatheter prosthetic valve device. FIG. 109 shows a Step 5 of 8 of a time sequence illustration of a transcatheter delivery of a heart valve prosthesis according to the present invention where a pin delivery tool 160 delivers one or more pin fasteners 163 and attaches them to the ventricular sealing collar, where a securement wire 165 is paid out and then tensioned to draw the upper and lower sealing collars together.

FIG. 110 is an illustration of a side perspective view of a transcatheter prosthetic valve device after it has been mounted within the annulus, with native annular tissue sandwiched between the top and bottom collars, and the temporary over-wire delivery tether has been unsecured and withdrawn.

FIG. 111 is an illustration of a cross-sectional view of a transcatheter prosthetic valve device that has been compressed within the lumen of a delivery catheter 171. FIG. 111 shows Step 1 of 5 of a time sequence illustration wherein the compressed capsule/payload of the valve with top collar 172, annular sleeve 175, bottom collar 174, and ventricular sleeve 176 are shown compressed within the catheter 171, which has been delivered to the native annulus of a heart valve. Steerable pin delivery tool 173 is shown attached to top collar 172.

FIG. 112 is an illustration of a cross-sectional view of a transcatheter prosthetic valve device that has been compressed within the lumen of a delivery catheter 171 and is partially expelled from the catheter 171. FIG. 112 shows Step 2 of 5 of a time sequence illustration wherein the compressed capsule/payload of the valve comprising top collar 172, annular sleeve 175, bottom collar 174, and ventricular sleeve 176, are delivered to the native annulus of a heart valve, and the sub-annular collar 174 is expanded within the ventricle just below the native annulus, with ventricular sleeve 176 extending into the ventricle.

FIG. 113 is an illustration of a cross-sectional view of a transcatheter prosthetic valve device that has been expelled within the lumen of a delivery catheter 171. FIG. 113 shows Step 3 of 5 of a time sequence illustration wherein the prosthetic valve device is delivered to the native annulus of a heart valve, the sub-annular collar 174 has been expanded within the ventricle just below the native annulus, and the supra-annular collar 172 is expanded within the atrium just above the native annulus. Sleeve 175, 176 traverse the annular space and extends into the ventricle to direct blood flow. Steerable pin delivery tools 173, 177, 178 are shown attached to top collar 172. Inset view shows pinpoint 181, pin body 182, and steerable pin delivery inner catheter 183 within pin delivery tool 173.

FIG. 114 is an illustration of a cross-sectional view of a transcatheter prosthetic valve device that has been expelled within the lumen of a delivery catheter. FIG. 114 shows Step 4 of 5 of a time sequence illustration wherein the prosthetic valve device is delivered to the native annulus of a heart valve, with a subannular collar on the ventricular side of the native annulus and a supra-annular collar on the atrial side of the native annulus, and where three steerable pin delivery catheters are shown after piercing the supra-annular collar and advancing the end of the pin delivery tool to an attachment location on the sub-annular collar.

FIG. 115 is an illustration of a cross-sectional detailed view of a distal end of a pin delivery catheter. FIG. 115 shows Step 5(*a*) of 5(*a*)-(*d*) of a time sequence illustration where steerable pin delivery catheter 173 is advanced, extended across the supra-annular collar 172 and positioned just above the anchoring location on the sub-annular collar 174. Pinpoint 181, pin body 182, and steerable, releasable pin delivery inner catheter 183 are shown within catheter 173.

FIG. 116 is an illustration of a cross-sectional detailed view of a distal end of a pin delivery catheter. FIG. 116 shows Step 5(*b*) of 5(*a*)-(*d*) of a time sequence illustration where steerable pin delivery catheter is advanced, extended across the supra-annular collar and the anchoring point or tip is advanced to penetrate the cover material and the wire frame of the sub-annular collar at the anchoring location on the sub-annular collar.

FIG. 117 is an illustration of a cross-sectional detailed view of a distal end of a pin delivery catheter. FIG. 117 Step 5(*c*) of 5(*a*)-(*d*) of a time sequence illustration where steerable pin delivery catheter is advanced, extended across the supra-annular collar, the anchoring point or tip has penetrated the cover material and wire frame of the sub-annular collar at the anchoring location on the sub-annular collar, and steerable delivery catheter is withdrawn to bring the top and bottom collars together, compressing and capturing the annular tissue located between the collars.

FIG. 118 is an illustration of a cross-sectional detailed view of a distal end of a pin delivery catheter. FIG. 118 Step 5(*d*) of 5(*a*)-(*d*) of a time sequence illustration where steerable pin delivery catheter is advanced, extending across the supra-annular collar, the anchoring point or tip has penetrated the cover material and wire frame of the sub-annular collar at the anchoring location on the sub-annular collar, steerable delivery catheter has closed the distance and brought the top and bottom collars together, compressing and capturing the annular tissue located between the collars, and where the external sheath of of the steerable delivery catheter is withdrawn, exposing anchoring flanges to lock the top supra-annular collar in place, maintaining the tensioned, compression of the collars on the native annulus tissue captured between the collars.

FIG. 119 is an illustration of a partial cross-sectional side view of a prosthetic valve device with three locking pins mounted between the two collars. FIG. 119 shows pin anchor bodies 182, 184, 187 locked into the supra-annular collar, the anchoring points 181, 185, 186 have penetrated the cover material and wire frame of the sub-annular collar at the anchoring location on the sub-annular collar, the top and bottom collars 172, 174 are together, compressing and capturing the annular tissue located between the collars, and the anchoring flanges on pin bodies 182, 184, 187 lock the top supra-annular collar in place, maintaining the tensioned, compression of the collars on the native annulus tissue captured between the collars.

Anchor Deployment

Anchors are deployed by over-wire delivery of an anchor or anchors through a delivery catheter. The catheter may have multiple axial lumens for delivery of a variety of anchoring tools, including anchor setting tools, force application tools, hooks, snaring tools, cutting tools, radio-frequency and radiological visualization tools and markers, and suture/thread manipulation tools. Once the anchor(s) are attached to the moderator band, tensioning tools may be used to adjust the length of tethers that connect to an implanted valve to adjust and secure the implant as necessary for proper functioning. It is also contemplated that anchors may be spring-loaded and may have tether-attachment or tether capture mechanisms built into the tethering face of the anchor(s). Anchors may also have ingrowth material, such as polyester fibers, to promote in-growth of the anchors in the myocardium.

Transcatheter Delivery

Referring now to FIG. 120, FIG. 120 is an illustration showing that the device(s) can be delivered over wire, using a dilator, and catheter using the traditional venous and arterial access techniques for the heart.

During use, the transcatheter delivery apparatus includes a delivery sheath assembly, a handle and an outer stability tube. The delivery sheath assembly defines a lumen and includes a distal capsule and a proximal shaft. The capsule is configured to compressively contain the heart valve prosthesis. The shaft is coupled to the capsule such that longitudinal movement of the shaft is transferred to the capsule. The handle includes a housing and an actuator mechanism. The housing defines a proximal side and a distal side. The actuator mechanism is maintained by the housing and is coupled to the shaft, with the shaft extending distal the distal side of the housing. Further, the actuator mechanism is configured to selectively move the shaft, and thus the capsule, relative to the housing. The outer stability tube is coupled to the housing and is coaxially received over the shaft such that the shaft is slidable relative to the stability tube. Finally, a distal end of the stability tube terminates proximal the capsule in at least a distalmost arrangement of the delivery sheath assembly. With the above in mind, the actuator mechanism is operable to transition the delivery device from a loaded or delivery state to a deployed state. In the loaded state, the capsule encompasses the implantable device to be deployed, e.g. a moderator band anchor, or a prosthetic heart valve. In the deployed state, the capsule is withdrawn from the implant. In this regard, the shaft slides relative to the stability tube in transitioning from the delivery state to the deployed state. In some embodiments, the delivery device is used in conjunction with an introducer device for delivering the implant into the patient's vasculature, with the stability tube serving to isolate the delivery sheath from the introducer device.

The delivery devices described herein can be modified for delivery of balloon-expandable stented heart valves, within the scope of the present disclosure. Delivery of balloon-expandable stented heart valves can be performed percutaneously using modified versions of the delivery devices of the present disclosure. In general terms, this includes providing the transcatheter delivery assembly akin to those described above, along with a balloon catheter and a guide wire.

To access a bodily lumen (e.g., femoral artery) of the patient, an incision is formed in the patient's skin, and the introducer sheath inserted through the incision and into the desired bodily lumen. The valve fluidly closes the connection with the bodily lumen external the patient. The delivery device is then inserted into the bodily lumen via the introducer device. The introducer sheath has an inner diameter greater than that of the outer stability tube and the capsule, such that the capsule can readily be delivered through the bodily lumen, directed to other branches of the patient's vasculature, and then to the implantation site. In this regard, the introducer valve frictionally contacts the outer stability tube, thereby establishing a low friction hemostasis seal around the outer stability tube.

Notably, however, the outer stability tube isolates the delivery sheath assembly and in particular the shaft from the introducer sheath and valve. While the outer stability tube is in physical contact with portions of the introducer device, the delivery sheath assembly does not directly contact the introducer device. Further, the stability tube overtly supports the delivery shaft in traversing the tortuous vasculature, minimizing occurrences of kinks forming in the shaft when moving across the curved portions of the heart.

FIG. 121 is an illustration showing that the pliant conduit 108 may be fitted with longitudinal filaments, or ribs 136, that are integrated within the fabric or material of the pliant conduit to provide additional mechanical support to the pliant conduit if necessary.

FIG. 122 is an illustration showing that the additional length-wise mechanical supports may also be in the form of one or more batons or rigid members that are integrated or sewn into the fabric or material of the pliant conduit 108. Such an engineered collapsible tube has support ridges that provide vertical structural support that does not require the tube material to carry the load, but also allows the flexible tube to elastically, and reciprocally collapse and refill in accordance with the present invention.

FIG. 123 is an illustration showing that the additional length-wise mechanical supports may also be in the form of one or more panels or layered members that are integrated or sewn into the fabric or material of the pliant conduit 108.

FIG. 124 is a cross-sectional illustration of the heart and shows an embodiment having a covered annular mesh attached to the atrial floor with the opening of a tube valve integrated into the mesh, where the tube is papillary length.

FIG. 125 is a cross-sectional illustration and shows an embodiment having the tube stitched to the native leaflets.

FIG. 126 is a cross-sectional illustration and shows an embodiment having an adjustable post height, where the annular ring has a hub, and the hub engages self-locking pegs or pin, and where the tube is adjustably mounted to travel with the post/frame.

FIG. 127 is a cross-sectional illustration and shows an embodiment having clips for capturing leaflets where the clips are attached to an atrial plate, and an hourglass shaped tube is mounted above and below the annular plane.

FIG. 128 is a top perspective view illustration of FIG. 127.

FIG. 129 is cross-sectional illustration and show an embodiment having a spanning tether between a pad on the atrial ceiling and a toggle or anchor outside the pericardium, with the tube valve mounted on a flexing frame that is adjustably positioned in a tensioned, sealing conformation at the annulus.

FIG. 130 is a cross sectional illustration showing the valve compressed into a sealing position.

FIG. 131 is a cross-sectional illustration of the heart and shows an embodiment mounting from within the IVC, where the structure extends conically from below the annulus to above the annulus and provides sealing on the annular floor, with the valve mounted on the structure starting at the annular plane and extending as a short "leaflet-length" tube into the ventricle.

FIG. 132 is a cross-sectional illustration of the heart and shows an embodiment mounting from within the SVC, where the structure extends conically from below the annulus to above the annulus and provides sealing on the annular floor, with the valve mounted on the structure starting at the annular plane and extending as a short "leaflet-length" tube into the ventricle.

FIG. 133 is a cross-sectional illustration of the heart and shows an embodiment having a screw-in anchored annular frame and a short tube-valve.

FIG. 134 is a plan illustration of the side of the annular stent frame having screws.

FIG. 135 is a top view and shows the screws within the internal aperture of the annular frame prior to be screwed in and deployed into the annular fibrous tissue.

FIG. 136 is a top view of the native tricuspid and shows target location for screws.

FIG. 137 is a cross-sectional illustration of the heart and shows an embodiment having (magnetic) leaflet clips for mounting the tube-valve and annular ring frame.

FIG. 138 is a cross-sectional illustration of the heart and shows how the leaflets would be placed within wire-form pockets.

FIG. 139 is a cross-sectional illustration of the heart and shows an embodiment having anchor barbs on an expandable annular stent frame.

FIG. 140 shows before balloon expansion where the barbs go from laying flat against the stent body to deploying into the fibrous annular tissue upon expanding of the stent frame.

FIG. 141 shows after balloon expansion where the barbs go from laying flat against the stent body to deploying into the fibrous annular tissue upon expanding of the stent frame.

FIG. 142 is an illustration of a two-piece screw-in embodiment having an outer atrial cuff that has a central threaded aperture that allows an externally threaded mounting ring to be deployed within the aperture.

FIG. 143 is an illustration of an externally threaded mounting ring for deploying within the aperture of FIG. 142 and shows the tube-valve attached to the bottom edge of the threaded mounting ring.

FIG. 144 is a cross-sectional illustration and shows the plate of the atrial cuff and the internal screw threads of the aperture/mounting ring receiver.

FIG. 145 is an illustration of a snap-locking mechanism to lock the mounting ring in place within the receiver.

FIG. 146 is an illustration of a screw-type locking mechanism for securing the mounting ring within the threaded receiver.

FIG. 147 is an illustration of an embodiment having an hourglass shaped wire-form structure that is deployed to extend partially into both the atrium and the ventricle with the tube-valve mounted within the central tubular chamber between the two divergent conical frame members.

FIG. 148 is a cross-sectional illustration of the heart and shows an embodiment having an hourglass tube-valve deployed in the tricuspid valve annulus.

FIG. 149 shows optional tethers than can be used with the hourglass embodiment.

FIG. 150 is a cross-sectional illustration of the heart and shows an embodiment having an hourglass tube-valve deployed in the mitral valve annulus.

FIG. 151 is an illustration that shows the hourglass embodiment used in conjunction with the tensioning atrial rod.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

Having described embodiments for the invention herein, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

What is claimed:

1. A method for securing a transcatheter heart valve prosthesis within a heart, the transcatheter heart valve prosthesis comprising a supra-annular sealing collar and a sub-annular sealing collar, each of said collars connected to a collapsible flow control sleeve that provides a reciprocating closable channel from a heart atrium to a heart ventricle, each of said collars comprised of a substantially flat braided or laser-cut wire frame covered with a biocompatible material and each having a central aperture, the collapsible flow control sleeve connected at an upper end to an inner perimeter of the central aperture of the supra-annular sealing collar, the collapsible flow control sleeve connected at a middle section to an inner perimeter of the central aperture of the subannular sealing collar, and the collapsible flow control sleeve extending beyond the central aperture of the sub-annular sealing collar and having a lower end positioned with the ventricle of the heart, the method comprising the steps:

(i) piercing the supra-annular sealing collar of the transcatheter heart valve prosthesis using a pin delivery tool;

(ii) anchoring a pin into the sub-annular sealing collar of the transcatheter heart valve prosthesis using the pin delivery tool;

(iii) detaching the pin from the pin delivery tool and withdrawing the pin delivery tool, said pin having a securement wire attached thereto, the securement wire disposed within an inner lumen of the pin delivery tool, wherein the securement wire is revealed by withdrawal of the pin delivery tool, and wherein the pin delivery tool is withdrawn above the supra-annular sealing collar;

(iv) tensioning the securement wire to draw the sub-annular sealing collar toward the supra-annular sealing collar by reducing the length of the securement wire between the sealing collars;

(v) fastening the securement wire to the supra-annular sealing collar and trimming the securement wire to disconnect the securement wire from the pin delivery tool; and (vi) repeating steps (i)-(v) to deploy from 2-12 pins and securement wires in the transcatheter heart valve prosthesis.

2. The method of claim 1, where the step of (ii) anchoring comprises inserting a pin having a pointed end and a groove with a flanged shoulder into an aperture in the subannular sealing collar, said aperture having a diameter equal to or smaller than the diameter of the flanged shoulder, whereby inserting the pointed end of the pin into the aperture temporarily elastically expands the diameter of the aperture and locks the aperture around the groove securing the pin to the sub-annular sealing collar.

3. A transcatheter heart valve replacement, comprising:
(i) a supra-annular sealing collar and (ii) a sub-annular sealing collar, each of said collars connected to (iii) a collapsible flow control sleeve that provides a reciprocating closable channel from a heart atrium to a heart ventricle, each of said collars comprised of a substantially flat braided or laser-cut wire frame covered with a biocompatible material and each having a central aperture, the collapsible flow control sleeve connected at an upper end to an inner perimeter of the central aperture of the supra-annular sealing collar, the collapsible flow control sleeve connected at a middle section to an inner perimeter of the central aperture of the sub-annular sealing collar, and the collapsible flow control sleeve extending beyond the central aperture of the sub-annular sealing collar and having a lower end positioned with the ventricle of the heart, and (iv) from 2-12 fastening pins with securement wires, said fastening pins attached to the subannular sealing collar and said securement wires attached to the supra-annular sealing collar, wherein said fastening pins with securement wires are tensioned to compress native heart annular tissue between the collars to function as a securement and mounting mechanism.

4. The transcatheter heart valve replacement of claim 3, wherein the transcatheter heart valve replacement is compressible and fits when compressed within the internal diameter of a transcatheter implantation catheter having an internal diameter less than 22 Fr (7.33 mm).

* * * * *